(12) United States Patent
Howe et al.

(10) Patent No.: US 11,674,151 B2
(45) Date of Patent: Jun. 13, 2023

(54) TRANSCRIPTION FACTORS TO IMPROVE RESISTANCE TO ENVIRONMENTAL STRESS IN PLANTS

(71) Applicant: Board of Trustees of Michigan State University, East Lansing, MI (US)

(72) Inventors: Gregg A. Howe, East Lansing, MI (US); Marcelo Campos, Lago Norte (BR); Yuki Yoshida, Tokyo (JP)

(73) Assignee: Board of Trustees of Michigan State University, East Lansing, MI (US)

( * ) Notice: Subject to any disclaimer, the term of this patent is extended or adjusted under 35 U.S.C. 154(b) by 651 days.

(21) Appl. No.: 16/323,737

(22) PCT Filed: Aug. 25, 2017

(86) PCT No.: PCT/US2017/048660
§ 371 (c)(1),
(2) Date: Feb. 6, 2019

(87) PCT Pub. No.: WO2018/039590
PCT Pub. Date: Mar. 1, 2018

(65) Prior Publication Data
US 2019/0330653 A1 Oct. 31, 2019

Related U.S. Application Data

(60) Provisional application No. 62/379,773, filed on Aug. 26, 2016.

(51) Int. Cl.
*C12N 15/82* (2006.01)
(52) U.S. Cl.
CPC .................. *C12N 15/8286* (2013.01)
(58) Field of Classification Search
None
See application file for complete search history.

(56) References Cited

U.S. PATENT DOCUMENTS

| 8,735,555 B2 | 5/2014 | Lagarias et al. |
| 2014/0246036 A1 | 9/2014 | Qu et al. |

FOREIGN PATENT DOCUMENTS

| CN | 101899449 A | 12/2010 |
| CN | 103602686 A | 2/2014 |
| WO | WO-2015/124620 A1 | 8/2015 |
| WO | WO-2018039590 A1 | 3/2018 |

OTHER PUBLICATIONS

Melisa Leone et al. (New Phytologist; 204: 355-367; 2014).*
Doerks et al., (TIG, 14:248-250, 1998).*
Smith et al. (Nature Biotechnology, 15:1222-1223, 1997).*
Bork et al. (TIG, 12:425-427, 1996).*
Leone et al. (New Phytologist, 204:355-367, 2014).*
Niu et al. (J Exp bot., 62:2143-2154, 2011).*
Reed et al. (Plant Cell, 5:147-157, 1993).*
"European Application Serial No. 17761766.9, Communication Pursuant to Article 94(3) EPC dated Apr. 6, 2020", 5 pgs.
"European Application Serial No. 17761766.9, Response to Response to Communication pursuant to Rules 161(1) and 162 EPC filed Oct. 22, 2019", 8 pgs.
"International Application Serial No. PCT/US2017/048660, International Preliminary Report on Patentability dated Mar. 7, 2019", 7 pgs.
Boccalandro, H. E., et al., "Phytochrome B Enhances Photosynthesis at the Expense of Water-Use Efficiency in *Arabidopsis*", Plant Physiol 150, (2009), 1083-1092.
Boter, M., et al., "Conserved MYC transcription factors play a key role in jasmonate signaling both in tomato and *Arabidopsis*", Genes Development, 18(13), (2004), 1577-1591.
Campos, M. L., et al., "Rewiring of jasmonate and phytochrome B signalling uncouples plant growth-defense tradeoffs", Nature Communications, 7: Article No. 12570, (2016), 1-10.
Chico, J.-M., et al., "Repression of Jasmonate-Dependent Defenses by Shade Involves Differential Regulation of Protein Stability of MYC Transcription Factors and Their JAZ Repressors in *Arabidopsis*", Plant Cell, 26, (2014), 1967-1980.
Chung, H. S., et al., "A Critical Role for the TIFY Motif in Repression of Jasmonate Signaling by a Stabilized Splice Variant of the JASMONATE ZIM-Domain Protein JAZ10 in *Arabidopsis*", The Plant Cell, 21(1), (2009), 131-145.
Fernandez-Calvo, P., et al., "The *Arabidopsis* bHLH Transcription Factors MYC3 and MYC4 are targets of JAZ repressors and act additively with MYC2 in the activation of jasmonate responses", Plant Cell 23, (2011), 701-715.
Gasperini, D., et al., "Multilayered Organization of Jasmonate Signalling in the Regulation of Root Growth", PLoS Genetics, 11(6): e1005300., (2015), 27 pgs.
Goosens, J., et al., "Change of a conserved amino acid in the MYC2 and MYC3 transcription factors leads to release of JAZ repression and increased activity", New Phytoologist, 206, (2015), 1229-1237.
Hornitschek, P., et al., "Phytochrome interacting factors 4 and 5 control seedling growth in changing light conditions by directly controlling auxin signaling", Plant J., 71, (2012), 699-711.
Kazan, K., et al., "MYC2: The Master in Action", Molecular Plant 6(3), (2013), 686-703.
Lorenzo, O., et al., "Jasmonate-Insensistive1 Encodes a MYC Transcription Factor Essential to Discriminate between Differnt Jasmonate-Regulated Defense Responses in *Arabidopsis*", The Plant Cell, vol. 16, (Jul. 2004), 1938-1950.

(Continued)

*Primary Examiner* — Vinod Kumar
(74) *Attorney, Agent, or Firm* — Schwegman Lundberg & Woessner, P.A.

(57) ABSTRACT

Plants, plant cells, and seeds are described herein that grow well and are resistant to environmental stresses such as drought and insects, where the plants have one or more mutations that reduce or eliminate the interaction of MYC transcription factors with the JAZ proteins. The plants can have an additional mutation that reduces or eliminates the function of the PHYB gene, and/or a heterologous PIF4 transgene or PIF4 expression cassette to improve the growth of the myc mutant plants. Methods of making and using such plants, plant cells, and seeds are also described.

6 Claims, 21 Drawing Sheets
Specification includes a Sequence Listing.

(56) References Cited

OTHER PUBLICATIONS

Major, I. T., "Regulation of growth-defense balance by the Jasmonate Zim-Domain (JAZ)-MYC transcriptional module", The New Phytologist, 215(4), (2017), 1533-1547.

Moreno, J. E., et al., "Ecological modulation of plant defense via phytochrome control of jasmonate sensitivity", Proc Natl Acad Sci U S A 106, (2009), 4935-4940.

Reed, J. W., et al., "Mutations in the Gene for the Red/Far-Red Llight Receptor Phytochrome B Alter Cell Elongation and Physiological Responses Throughout *Arabidopsis* Development", Plant Cell 5, (1993), 147-157.

Smolen, G. A., et al., "Dominant Alleles of the Basic Helix-Loop-Helix Transcription Factor ATR2 Activate Stress-Responsive Genes in *Arabidopsis*", Genetics, 161(3), (2002), 1235-1246.

Yang, D. L., et al., "Plant hormone jasmonate prioritizes defense over growth by interfering with gibberellin signaling cascade", Proc. Natl. Acad. Sci. USA, 109(19), (2012), E1192-E1200.

Zhang, F., et al., "Structural basis of JAZ repression of MYC transcription factors in jasmonate signaling", Nature, 525(7568), (2015), 269-273 (17 pgs.).

"European Application Serial No. 17761766.9, Communication Pursuant to Article 94(3) EPC dated Aug. 25, 2021", 4 pgs.

"European Application Serial No. 17761766.9, Response filed Apr. 13, 2021 to Communication Pursuant to Article 94(3) EPC dated Nov. 26, 2020", 12 pgs.

"European Application Serial No. 17761766.9, Response filed Dec. 31, 2021 to Communication Pursuant to Article 94(3) EPC dated Aug. 25, 2021", 12 pgs.

U.S. Appl. No. 62/359,293, filed Jul. 7, 2016, Rewiring Jasmonate and Phytochrome B Signaling Uncouples Plant Growth-Defense Tradeoffs.

U.S. Appl. No. 62/379,773, filed Aug. 26, 2016, Transcription Factors to Improve Resistance to Environmental Stress in Plants.

"European Application Serial No. 17761766.9, Communication Pursuant to Article 94(3) EPC dated Nov. 26, 2020", 4 pgs.

Frances, Robson, et al., "Jasmonate and Phytochrome Signaling in *Arabidopsis* Wound and Shade Responses are Integrated through JAZ1 Stability", The Plant Cell, (Apr. 1, 2010).

Hoo, Sun Chung, et al., "Top hits on contemporary JAZ an update on jasmonate signaling", (Sep. 1, 2009), 1547-1559.

I, Cerrudo, et al., "Low Red/Far-Red Ratios Reduce *Arabidopsis* Resistance to Botrytis cinerea and Jasmonate Responses via COI1-JAZ1O-Dependent Sal icyl ic Acid-Independent Mechanism", Plant Physiology, vol. 158, Rockville Md USA, ISSN 0032-0889 DOI 10.1104/pp. 112 193359, (Feb. 27, 2012), 2042-2052.

J, M Chico, et al., "Repression of Jasmonate-Dependent Defenses by Shade Involves Differential Regulation of Protein Stability of MYC Transcription Factors and Their JAZ Repressors in *Arabidopsis*", The Plant Cell, (May 1, 2014).

Marcelo, Campos, et al., "Rewiring of jasmonate and phytochrome signalling uncouples plant growth-defense tradeoffs", Nature Communications, (Aug. 30, 2016).

Melisa, Leone, et al., "To grow or defend? Low red far-red ratios reduce jasmonate sensitivity in *Arabidopsis* seedlinas bv promoting DELLA degradation and increasing JAZ10 stability", New Phytologist, vol. 204, (Oct. 1, 2014), 355-367.

"International Application Serial No. PCT/US2017/048660, International Search Report dated Oct. 18, 2017", 6 pgs.

"International Application Serial No. PCT/US2017/048660, Written Opinion dated Oct. 18, 2017", 5 pgs.

I, Cerrudo, et al., "Low Red/Far-Red Ratios Reduce *Arabidopsis* Resistance to Botrytis cinerea and Jasmonate Responses via COI1-JAZ10-Dependent Sal icyl Ic Acid-Independent Mechanism", Plant Physiology, vol. 158, Rockville Md USA, ISSN 0032-0889 DOI; 10.1104/pp. 112 193359, (Feb. 27, 2012), 2042-2052.

Melisa, Leone, et al., "To grow or defend? Low red far-red ratios reduce jasmonate sensitivity in *Arabidopsis* seedlings by promoting DELLA degradation and increasing JAZ10 stability", New Phytologist, vol. 204, (Oct. 1, 2014), 355-367.

"European Application Serial No. 17761766.9, Response filed Aug. 13, 2020 to Communication Pursuant to Article 94(3) EPC dated Apr. 6, 2020", 9 pgs.

"European Application Serial No. 17761766.9, Communication Pursuant to Article 94(3) EPC dated Jul. 22, 2022", 4 pgs.

"European Application Serial No. 17761766.9, Response Filed Dec. 6, 2022 to Communication Pursuant to Article 94(3) EPC dated Jul. 22, 2022", 168 pgs.

"Brazilian Application Serial No. BR1120190038884, Office Action dated Dec. 14, 2022", w English Translation, 7 pgs.

Hoo, Sun Chung, "Top hits in contemporary JAZ: An update on jasmonate signaling", Phytochemistry, (Sep. 1, 2009), vol. 70, No. 13-14, (Sep. 1, 2009), 24 pgs.

* cited by examiner

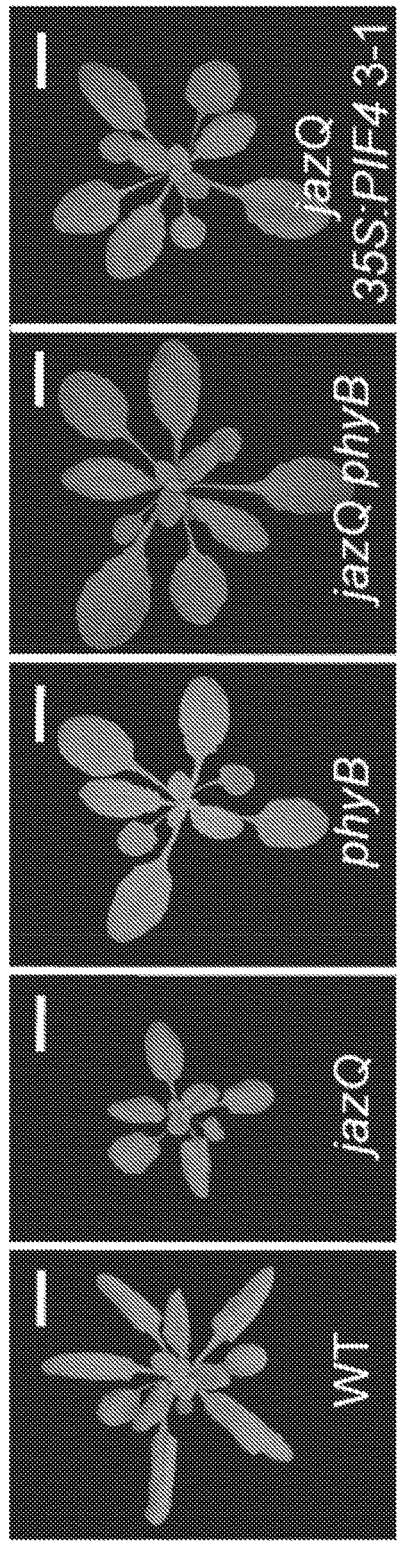
FIG. 5A
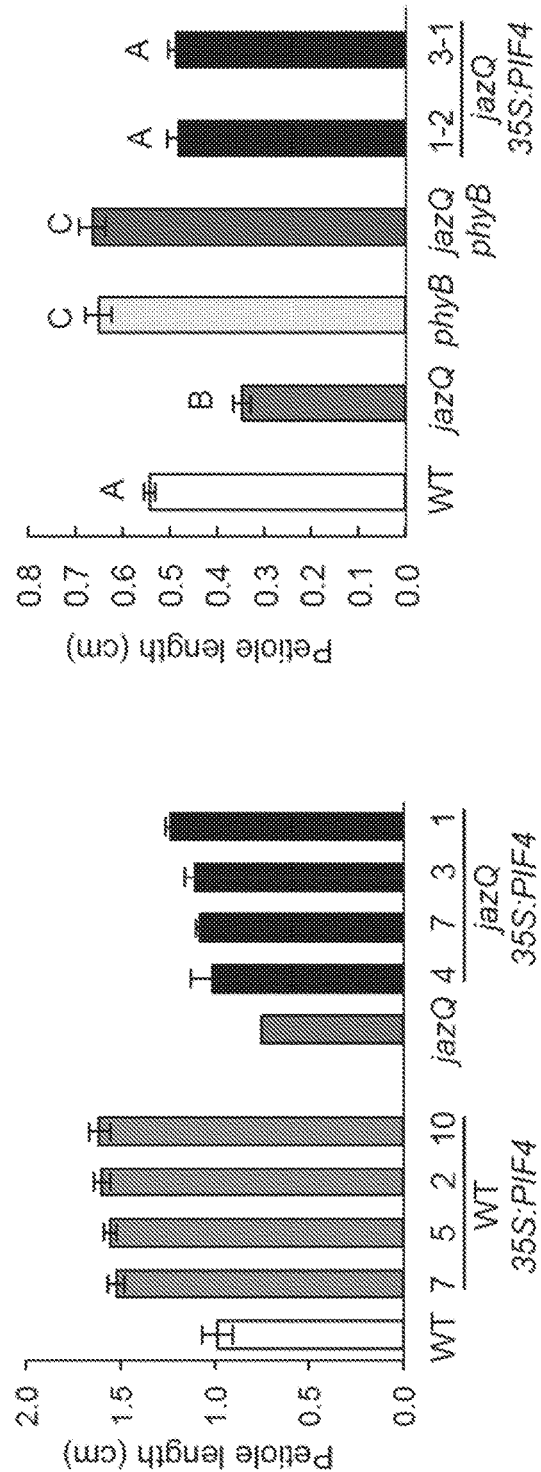
FIG. 5B
FIG. 5C

| AtMYC3 | GDNTVILGWGDGYYKGEEDKEKKR---N----------N-TNTAEQEHRKRVLRELNSLISGG |
| AtMYC4 | NNNTVLLGWGDGYYKGEEEKSRKKKSN----------P--ASAAEQEHRKRVLRELNSLISGG |
| Bradi3g34200 | GAGASLLGWGDGYYKGCDDADKRARQQ-P----TP-ASAAEQEHRKRVLRELNSLIAGG |
| GRMZM2G049229 | ATGASLLGWGDGYYKGCDDDKRRHRPP-L----TP-AAQAEQEHRKRVLRELNSLISGG |
| Os10g42430 | STGASLLGWGDGYYKGCDDDKRRKQR-S-S----TP-AAAAEQEHRKRVLRELNSLIAGA |
| GRMZM2G001930 | ATGASLLGWGDGYYKGCDEDKRRKQK-P-L----TP-SAQAEQEHRKRVLRELNSLISGA |
| Sobic.001G287600 | ATGASLLGWGDGYYKGCDDDKRRKQR-P-L----TP-AAQAEQEHRKRVLRELNSLISGA |
| Camelina sativa | FSGASVLGWGDGYYKGEEDKAKPQRSSS----PFFSTPADQEYRKKVLRELNSLISGG |
| AtMYC2 | FSGASVLGWGDGYYKGEEDKAMPRRRSSS----PFFSTPADQEYRKKVLRELNSLISGG |
| Solyc08g076930 | FSSPSVLGWGDGYYKGEEDKAKRKLSV-S----SP-AYIAEQEHRKKVLRELNSLISGA |
| Solyc08g005050 | FASQVLGWGDGYYKGEEDKNKRGSSSS----AA-NFVAEQEHRKKVLRELNSLISGV |
| AtJAM1 | RSGQVLGWGDGCCREPNEEEESKVVRSYNFNMMGAEETWQDMRKRVLQKLHRL------ |
| AtJAM2 | KAGDLVLCWGDGYCREPKEGEKSEIVRIL---SMGREEETHQTMRKRVLQKIHDLFGG--- |
|  | :* **** ; :*  :           . * ****;;*;; * |

FIG. 6

TRANSCRIPTION FACTORS TO IMPROVE RESISTANCE TO ENVIRONMENTAL STRESS IN PLANTS

This application is a national stage application filed under 35 U.S.C. § 371 from International Application Serial No. PCT/US2017/048660, filed 25 Aug. 2017 and published as jWO 2018/039590 on 1 Mar. 2018, which claims benefit of priority to the filing date of U.S. Provisional Application Ser. No. 62/379,773, filed Aug. 26, 2016, the contents of which are specifically incorporated herein by reference in their entity.

FEDERAL FUNDING

This invention was made with government support under DE-FG02-91ER20021 awarded by the U.S. Department of Energy, and under GM057795 awarded by the National Institutes of Health, and under IOS1139329 awarded by the National Science Foundation. The government has certain rights in the invention.

BACKGROUND OF THE INVENTION

Plants integrate developmental and environmental cues to prioritize the allocation of photosynthetic products to growth, defense and other physiological processes. Investments in defense often suppress growth, whereas rapid growth, such as that triggered by competition for light, attenuates defense.

SUMMARY

In plants, investments in defense often suppress growth, reducing overall biomass yields. For example, dense planting of crops such as corn suppresses the plant immune system through active repression of the jasmonate signaling pathway. As described herein, selected jasmonate and phytochrome gene deletions can unlink growth and defense tradeoffs in plants. As also described herein, selected mutations in transcription factors can obviate jasmonate inhibition and improve plant resistance to environmental stresses, but plants with such transcription factor mutations may not grow optimally. By combining the transcription factor mutations with loss-of-function phytochrome gene mutations can improve plant growth while retaining environmental stress resistance. The resulting phenotype observed in plants includes robust growth and less insect infestation. Such modifications enhance biomass output, and allows crops to be densely planted. Such modified plants can have significant utility in agriculture.

Described herein are plants, plant cells, and plant seeds that can have a PhyB loss-of-function mutation, and (a) a modified MYC nucleic acid encoding a mutant MYC protein comprising at least one mutation within or outside of a JAZ-interacting domain (JID) polypeptide region, (b) a loss-of-function mutation in at least one gene encoding a transcriptional repressor of jasmonic acid response (JAZ) protein; or (c) a combination of (a) and (b).

Also described here are methods of making such plants, plant cells, and seeds. For example, one method can include (a) providing one or more plant cell that has a PhyB loss-of-function mutation; (b) introducing into at least one of the one or more plant cells at least one transgene or expression cassette encoding a mutant MYC nucleic acid segment that encodes a mutant MYC protein to generate one or more transformed plant cells; and (c) generating a plant from the one or more transformed plant cell(s). The mutant MYC nucleic acid can, for example, have a dominant MYC mutation. Such a mutant MYC protein can have reduced binding to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein. JAZ10 protein. JAZ11 protein, JAZ12 protein, JAZ13 protein, or a combination thereof, where for example the binding is reduced by at least 20% compared to a corresponding wild type MYC protein that does not have the MYC mutation(s).

Another exemplary method can include (a) providing one or more plant cells with a loss-of-function mutation in at least one gene encoding a transcriptional repressor of jasmonic acid response (JAZ) protein; (b) introducing into the one or more plant cells a PhyB loss-of-function mutation to generate one or more modified plant cells; and (c) generating a plant from the one or more modified plant cell(s). For example, the method can involve providing one or more plant cells with a loss-of-function mutation in jaz1, jaz3, jaz4-1, jaz9, and jaz10 genes.

Such methods can provide plants that exhibit resistance to environmental stress compared to a wild type plant of the same species under the same environmental conditions.

For example, the modified plants and plants grown from the modified seeds described herein can have 5% less, or 10% less, or 20% less, or 30% less, or 40% less, or 50% less, or 60% less, or 70% less, or 80% less, or 90% less, or 100% less leaf damage from insect feeding than a wild type plant (without the mutations described herein) of the same species grown under the same conditions. In some cases, the modified plants and plants grown from the modified seeds described herein can have at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same conditions.

The modified plants and plants grown from the modified seeds described herein grow as well as or better than wild type plants. For example, the rosette dry weight of the modified plants and plants grown from the modified seeds described herein is about the same as the rosette dry weight of wild type plants (without the genetic modifications described herein) grown for the same time and under the same conditions. For example, the rosette dry weight of the modified plants, and plants grown from the modified seeds, described herein is about 80% to about 120%, or about 90% to about 110% of the rosette dry weight of wild type plants grown for the same time and under the same conditions. In some cases, the average primary root length of the modified plants and plants grown from the modified seeds described herein can be 1.5-fold longer, of 2-fold longer, or 2.3-fold longer, or 2.5-fold longer, or 2.7-fold longer, or 3-fold longer than the average primary root length of wild type plants grown for the same time and under the same conditions.

DESCRIPTION OF FIGURES

FIG. 1A shows a simple model of the jasmonate (JA)-gibberellic acid (GA) signaling network that governs growth and defense against environmental stress. FIG. 1B shows an image of wild-type (WT) and jazQ (jQ) seedlings grown in the absence or presence of 25 µM methyl-jasmonic acid (MJ or MeJA). FIG. 1C graphically illustrates accumulation of glucosinolates in WT (open bar) and jazQ mutant (shaded bar) seedlings. Compound abbreviations: 3MSP=3-methylsulfinylpropylglucosinolate; 4MSB=4-methylsulfinylbutylglucosinolate; 5MSP=5-methylsulfinylpentylyglucosinolate; 4OHI3M=4-hydroxyindol-3-ylmethylglucosinolate; 7MSH=7-methylsulfinylheptylglucosinolate; 4MTB=4-methylthiobutylglucosinolate; 8MSO=8-methylsulfinyloctylglucosinolate; I3M=indol-3-ylmethylglucosinolate; 4MI3M=4-methoxyindol-3-ylmethylglucosinolate; 1MI3M=1-methoxyindol-3-ylmethylglucosinolate; 7MTH=7-methylthioheptylglucosinolate; 8MTO, 8-methylthiooctylglucosinolate. FIG. 1D graphically illustrates anthocyanin accumulation in petioles of 4-week-old plants. FIG. 1E graphically illustrates *Trichoplusia ni* weight after feeding on WT (33 larvae) and mutant jazQ (38 larvae) plants for 10 days. FIG. 1F shows an image of 4-week old soil-grown WT and jazQ plants. Data in all graphs represent the mean±standard error (s.e.) of at least 10 biological replicates. Asterisks in FIGS. 1C, 1D, and 1E denote significant differences between WT and jazQ mutants at P<0.05 (Student's t-test). FIG. 1G is a schematic diagram showing T-DNA insertion lines used for construction of jazQ mutations. The organization of each JAZ gene is depicted by white and grey boxes representing untranslated regions (UTRs) and exons, respectively. The identity and position of the T-DNA insertion is shown. Arrows show the position of primers used to test expression by RT-PCR. FIG. 1H shows a gel illustrating RT-PCR analysis of JAZ gene expression in WT and mutant jazQ seedlings. RNA was obtained from seedlings grown for eight days on plates containing 25 µM MeJA. The ACTIN1 gene (ACT1. At2g37620) was used as a positive control. FIG. 1I graphically illustrates root length of WT, jaz10-1 mutant, and jazQ mutant seedlings grown for eight days on MS medium supplemented with 5, 10 or 25 µM MeJA. Control seedlings were grown in the absence of MeJA (0 µM). Data shown are the mean±s.e. of measurements on at least 12 seedlings per genotype. P-values are shown for two-way ANOVA comparisons (inset). Asterisks represent statistical difference between mutant and WT according to Tukey HSD test (P<0.05). Single asterisks denote a significant difference between mutant and WT, whereas double asterisks denote a significant difference between jaz10-1 and jazQ mutants at a given concentration of MeJA.

FIG. 2A shows images of five week-old WT, jazQ mutant, and sjq11 mutant plants. The sjq11 plants have a mutation in the PHYB gene that suppresses the growth phenotype of jazQ. Hence, jazQ sjq11 mutant plants are about the same size as wild type plants. FIG. 2B illustrates *Trichoplusia ni* weight after feeding for 10 days on WT (31 larvae), mutant jazQ (31 larvae), and mutant sjq11 (37 larvae) plants. Data shown are the mean±standard error (s.e.) of at least 12 independent replicates. FIG. 2C shows images of four week-old plants grown in soil. FIG. 2D graphically illustrates rosette dry weight of WT, mutant jazQ, mutant phyB and mutant jazQ/phyB plants. FIG. 2E graphically illustrates anthocyanin accumulation in petioles of WT, mutant jazQ, mutant phyB and mutant jazQ phyB plants. Data shown in FIG. 2D-2E are the mean±standard error (s.e.) often plants per genotype. FIG. 2F graphically illustrates *T. ni* larval weight after feeding for 10 days on WT (23 larvae), mutant jazQ (29 larvae), and mutant jazQ phyB (27 larvae) plants. Data show the mean larval weight±s.e. of insects reared on 12 plants per host genotype. Capital letters denote statistical differences according to Tukey HSD-test (P<0.05). Scale bars=1 cm. FIG. 2G shows a schematic diagram of the PHYB gene in sjq11. Sequence analysis identified a cytosine (C) to thymine (T) transition that creates a TGA nonsense mutation at the CGA codon for R322. This mutation truncates the PHYB apoprotein in the chromophore-binding GAF domain and is a null mutation. FIG. 2H graphically illustrates the number of days to bolting of wild type, jazQ, and jazQ sjq11 plants. Data show the mean±standard error (s.e.) of at least 12 independent replicates. Letters indicate statistical differences between genotypes (Tukey HSD-test, P<0.05).

FIG. 4A shows a heat map of photosystem II quantum efficiency ($\Phi_{II}$) in response to varying light regimes. Chlorophyll fluorescence values for the indicated mutants were normalized to Col-0. Plants were exposed to three consecutive 16 hr/day light regimes: constant light (day 1, left panel); sinusoidal increase and decrease in light intensity (day 2, middle panel); and sinusoidal light with higher intensity pulses (day 3, right panel). FIG. 4B graphically illustrates the photosynthetic rate in response to increasing light as measured by gas exchange in 6-9 plants per genotype. The inset shows non-linear curve-fitting to model the maximum velocity of Rubisco determined from foliage photosynthetic rates in response to increasing $CO_2$. FIG. 4C graphically illustrates Rubisco concentration in leaves from 54-day-old plants (n=4). FIG. 4D graphically illustrates total chlorophyll concentration in leaves from 54-day-old plants (n=4). FIG. 4E graphically illustrates the thickness of 22-day-old rosette leaves (n=4). Data shown in FIGS. 4B-4E are the mean±s.e., and capital letters indicate statistical difference at P<0.05 (Tukey HSD-test). In d. WT and mutant jazQ phyB means are different at P<0.1.

FIGS. 5A-5E illustrate that overexpression of PIF4 in the mutant jazQ background leads to partial rescue of growth without compromising defense. FIG. 5A shows images of representative 21-d-old plants of the indicated genotype. Two independent T3 lines (#1-2 and #3-1) of jazQ 35S:PIF4 were characterized but only the latter is shown. Scale bars=1 cm. FIG. 5B graphically illustrates petiole length of the third true leaf of independent jazQ 35S:PIF4 T2 lines (n=6 plants per line). T2 lines #1 and #3 are parents of T3 lines #1-2 and #3-1 described in panels c-e below. As a control to demonstrate the expected effects of PIF4 overexpression on petiole length, WT Col-0 plants were also transformed with the 35S:PIF4 transgene. Data for four independent T2 lines is shown. FIG. 5C graphically illustrates petiole length of the third true leaf of 21-d-old jazQ 35S:PIF4 plants compared to WT and mutant jazQ (n=10). FIG. 5D graphically illustrates anthocyanin content in petioles of 21-d-old plants of the indicated genotype (n>10 plants). FIG. 5E graphically illustrates the weight of *T. ni* larvae recovered after 10 d feeding on 12 plants per genotype: WT plants (37 larvae), jazQ mutant plants (31 larvae), jazQ 35:PIF4 #1-2 mutant plants (27 larvae), and jazQ 35:PIF4 #3-1 mutant plants (25 larvae). Data show the mean±s.e. Capitalized letters indicate statistical differences (Tukey HSD-test, P<0.05).

FIG. 6 shows a sequence alignment of the JAZ-interacting domain (JID) from various MYC transcription factors (SEQ ID NOs: 116-128). Underlining identifies those conserved amino acids that interact directly with JAZ9. These amino acid residues are targets for site directed mutagenesis, to generate modified MYC transcription factors that are insensitive to inhibition by JAZ repressors.

FIG. 7A schematically illustrates the domain architecture of *Arabidopsis thaliana* MYC3 (AtMYC3) and two alternative splice forms of *Arabidopsis thaliana* JAZ10 (AtJAZ10). FIG. 7B shows schematic diagrams of X-ray crystal structures of MYC3 in complex with JAZ10's CMID (left) or Jas domain (center), and an overlay of the two structures (see, e.g., Zhang et al., 2017). FIG. 7C shows results of yeast two-hybrid analyses of MED25 and JAZ10.4 (bait) interactions with wild-type MYC3 and MYC3 point mutants (prey, identified at the top). Darker color (blue in the original) denotes protein-protein interaction. Asterisks (*) denote two novel MYC3 mutants that fail to interact with the CMID of JAZ10.4 but retain interaction with the MED25 co-activator. FIG. 7D shows that overexpression of the $MYC3^{D94N}$ dominant transcription factor (but not wild-type MYC3) in the phyB mutant background confers resistance to 5-methyl-tryptophan (5-MT). Plants were grown for 3 weeks in MS medium containing 50 μM 5-methyl-tryptophan or in mock treatment without methyl-tryptophan. FIG. 7E graphically illustrates that overexpression of a dominant MYC2 mutant transcription factor ($MYC2^{D105N/E165K}$) in phyB-9-defective mutant *Arabidopsis* plants reduces primary root inhibition caused by treatment with 5-methyl-tryptophan. As shown, the non-transgenic (NT) phyB-9 mutant plants that do not express the $MYC2^{D105N/E165K}$ protein exhibit smaller primary roots, indicating the presence of 5-methyl-tryptophan has inhibited growth. Transgenic expression of additional wild type MYC2 improves primary root length the phyB-9-defective mutant *Arabidopsis* plants. However, expression of the dominant MYC2 mutant transcription factor ($MYC2^{D105N/E165K}$) provides the best primary root growth in the phyB-9-defective mutant *Arabidopsis* plants.

DETAILED DESCRIPTION

Figure 1A:
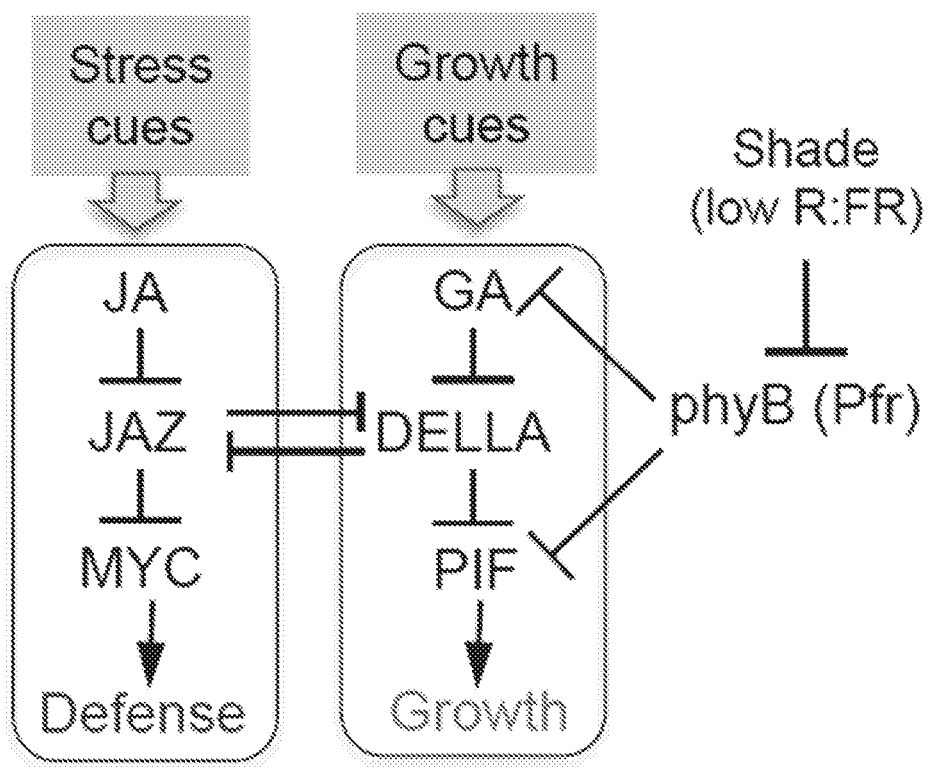
FIGS. 1A-1I illustrate development of a JAZ quintuple mutant (jazQ) that exhibits reduced growth and enhanced defense.

Plants and methods of making such plants are described herein that grow well and are resistant to environmental stresses such as drought and insects. The plants have mutations that reduce or eliminate the expression or function of proteins that modulate jasmonic acid responses (e.g., JAZ genes/proteins). Plants with such mutations are referred to herein as jaz mutants or jaz plants. Such reduction/elimination of jasmonic acid regulatory protein expression and/or function improves the insect resistance (compared to wild type plants) of jaz mutant plants. An additional mutation that reduces or eliminates the function of the PHYB gene improves the growth of jaz mutant plants. Hence, the combination of jaz and phyB loss-of-function mutations provides robustly growing plant lines that are also resistant to insects. Seeds of such jaz and phyB loss-of-function mutants, and methods of making and using such seeds and plants are also described herein.

Plants described herein can have one or more mutations that reduce or eliminate the interaction of MYC transcription factors with the JAZ proteins. MYC2 mediates stress responses through the action of plant stress hormones such as jasmonate (JA). In plant cells containing high levels of jasmonate, MYC transcription factors bind to the promoter region of JA-response genes to promote their transcriptional activation. However, simple overexpression of MYC2 is insufficient to constitutively activate defense responses. This is because MYC transcription factors are strongly repressed by direct binding of members of the JAZ family of repressor proteins. This application describes mutated MYC transcription factors that do not bind JAZ repressor proteins. Such mutations can be dominant MYC mutations. These plants that express mutant MYC proteins are capable of strongly activated defense responses in the presence of JAZ proteins. Such strong defense responses can reduce plant growth. By expressing mutant MYC proteins in a mutant phyB loss-of-function background, the plants exhibit strong defenses against environmental stress and also grow well.

Jasmonic acid and its various metabolites regulate plant responses to abiotic and biotic stresses as well as plant growth and development. The JAZ proteins typically inhibit the activation of defense responses that are controlled by jasmonic acid, and reduce the resistance of plants to environmental stresses such as drought, insects, and other environmental stresses. Reduction or elimination of JAZ functions tends to increase jasmonic acid expression and/or function, increase the activity of MYC transcription factors, and thereby improve drought and insect resistance (compared to wild type plants). Plants that produce mutated MYC proteins unable to bind JAZ proteins are phenotypically similar (increased resistance and reduced growth) to plants in which JAZ function is reduced or eliminated. An additional mutation that reduces or eliminates the function of the PHYB gene improves the growth of the myc mutant plants. Hence, the combination of myc and phyB loss-of-function mutations provides robustly growing plant lines that are also resistant to environmental stresses. Seeds of such myc and phyB loss-of-function mutants, and methods of making and using such seeds and plants are also described herein.

Mutations

Plants and seeds have one or more genomic deletions, insertions, or substitutions in at least part of the MYC. JAZ, and PHYB genes. Such deletions, insertions, or substitutions can be generated by site-specific recombination-mediated methods. The mutations can range in size from one or two nucleotides to thousands of nucleotides (or any value therebetween). Deletions, insertions, and/or substitutions are created at a desired location in the genome. For example, borders (end points) of the deletions, insertions, or substitutions can be at defined locations to control the size of the deletions, insertions, or substitutions.

The mutation(s) can reduce or eliminate expression of endogenous JAZ and/or PhyB genes within plant cells, plants, and seeds. For example, the mutations can eliminate transcription and/or translation of from JAZ and PHYB genes encoding JAZ1, JAZ3, JAZ4, JAZ9. JAZ10, PHYB, and combinations thereof. The mutations can also eliminate transcription and/or translation of from genes related to the JAZ and PHYB genes encoding JAZ1, JAZ3, JAZ4, JAZ9, JAZ10, PHYB, and combinations thereof. For example, transcription and/or translation can be reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the JAZ and/or PhyB mutation(s)).

The mutation(s) can reduce or eliminate MYC protein interaction with one or more JAZ protein. For example, the mutation(s) can reduce or eliminate MYC protein interaction with JAZ1 protein, JAZ2 protein, JAZ3 protein, JAZ4 protein, JAZ5 protein, JAZ6 protein, JAZ7 protein, JAZ8 protein, JAZ9 protein. JAZ10 protein. JAZ11 protein, JAZ12 protein, JAZ13 protein, and combinations thereof. For example, interaction between a MYC protein and a JAZ protein, or binding between such mutant MYC protein and any of such JAZ proteins can be reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the MYC mutation(s)).

Non-limiting examples of methods of introducing a modification into the genome of a plant cell can include microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

For example, nucleases such as zinc finger nucleases (ZFNs), transcription activator like effector nucleases (TALENs), and/or meganucleases can be employed with guide nucleic acid that allows the nuclease to target the genomic MYC. JAZ and PHYB site(s). In some cases of the various aspects described herein, a targeting vector can be used to introduce a deletion or modification of the genomic MYC, JAZ and PHYB chromosomal sites.

A "targeting vector" is a vector generally has a 5' flanking region and a 3' flanking region homologous to segments of the gene of interest. The 5' flanking region and a 3' flanking region can surround a DNA sequence comprising a modification and/or a foreign DNA sequence to be inserted into the gene. For example, the genomic MYC, JAZ and PHYB site(s) can be disrupted by insertion of T-DNA. In another example, the foreign DNA to be inserted may encode a selectable marker, such as an antibiotics resistance gene. Examples for suitable selectable markers include chloramphenicol resistance, gentamycin resistance, kanamycin resistance, spectinomycin resistance (SpecR), neomycin resistance gene (NEO) and hygromycin β-phosphotransferase markers (genes). The 5' flanking region and the 3' flanking region can be homologous to regions within the gene, or such flanking regions can flank the coding region of gene to be deleted, mutated, or replaced with the unrelated DNA sequence. In some cases, the targeting vector does not comprise a selectable marker. DNA comprising the targeting vector and the native gene of interest are contacted under conditions that favor homologous recombination (e.g., by transforming plant cell(s) with the targeting vector).

A typical targeting vector contains nucleic acid fragments of not less than about 0.1 kb nor more than about 10.0 kb from both the 5' and the 3' ends of the genomic locus which encodes the gene to be modified (e.g. the genomic MYC, JAZ and/or PHYB site(s)). These two fragments can be separated by an intervening fragment of nucleic acid that includes the modification to be introduced. When the resulting construct recombines homologously with the chromosome at this locus, it results in the introduction of the modification, e.g. an insertion, substitution, or a deletion of a portion of the genomic MYC. JAZ and/or PHYB site(s).

In some cases, a Cas9/CRISPR system can be used to create a modification in genomic MYC. JAZ and/or PHYB site(s). Clustered regularly interspaced short palindromic repeats (CRISPR)/CRISPR-associated (Cas) systems are useful for, e.g. RNA-programmable genome editing (see e.g., Marraffini and Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010: 45:292-302; Jinek et al. Science 2012 337:815-820; Bikard and Marraffini Curr Opin Immunol 2012 24:15-20; Bikard t al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is available in the art and described, e.g. at Mali et al. Science 2013 339:823-6, which is incorporated by reference herein in its entirety and kits for the design and use of CRISPR-mediated genome editing are commercially available, e.g. the PRECISION X CAS9 SMART NUCLEASE™ System (Cat No. CAS900A-1) from System Biosciences, Mountain View, Calif.

In other cases, a cre-lox recombination system of bacteriophage P1, described by Abremski et al. 1983. *Cell* 32:1301 (1983), Sternberg et al., *Cold Spring Harbor Symposia on Quantitative Biology*, Vol. XLV 297 (1981) and others, can be used to promote recombination and alteration of the genomic MYC. JAZ and/or PHYB site(s). The cre-lox system utilizes the cre recombinase isolated from bacteriophage P1 in conjunction with the DNA sequences (termed lox sites) it recognizes. This recombination system has been effective for achieving recombination in plant cells (U.S. Pat. No. 5,658,772), animal cells (U.S. Pat. Nos. 4,959,317 and 5,801,030), and in viral vectors (Hardy et al., *J. Virology* 71:1842 (1997).

The plant cells, plants, and plant seeds can have genomic mutations that alter one or more amino acids in the encoded MYC, JAZ and/or PHYB proteins. For example, plant cells, plants, and seeds can be modified so that at least one amino acid of a MYC. JAZ and/or PHYB polypeptide is deleted or mutated to reduce the function of MYC JAZ and/or PHYB proteins. In some cases, a conserved amino acid or a conserved domain of the MYC. JAZ and/or PHYB polypeptide is modified. For example, a conserved amino acid or several amino acids in a conserved domain of the MYC, JAZ and/or PHYB polypeptide can be modified to change the physical and/or chemical properties of the conserved amino acid(s). For example, to change the physical and/or chemical properties of the conserved amino acid(s), the amino acid(s) can be deleted or replaced by amino acid(s) of another class, where the classes are identified in the following Table 1.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-$NH_2$), DBU, $A_2$ BU |

TABLE 1-continued

| Classification | Genetically Encoded | Genetically Non-Encoded |
| --- | --- | --- |
| Polar | Q, N, S, T, Y | Cit, AcLys, MSO, hSer |
| Cysteine-Like | C | Pen, hCys, β-methyl Cys |

Different types of amino acids can be in the mutant myc, jazQ and/or phyB polypeptide(s) such as any of those listed in Table 2.

TABLE 2

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| N-Methylglycine (sarcosine) | | MeGly |
| Ornithine | | Orn |
| Citrulline | | Cit |
| N-methylisoleucine | | MeIle |
| Phenylglycine | | Phg |
| Norleucine | | Nle |
| Penicillamine | | Pen |
| Homoarginine | | hArg |
| N-acetyl lysine | | AcLys |
| p-Aminophenylalanine | | Phe(pNH$_2$) |
| N-methylvaline | | MeVal |
| Homocysteine | | hCys |
| Homoserine | | hSer |

For example, modified MYC proteins can have any naturally occurring amino acid within the protein replaced with any of the amino acids listed in Tables 1 or 2. Positions within MYC protein that can have such replacements include, for example, amino acid positions 94, 97, 102, 105, 107, 125, 128, 129, 148, 152, 155, 163, 165, 169, and/or 172.

In some cases, myc, jaz and/or phyB mutations are introduced by insertion of foreign DNA into the gene of interest. For example, this can involve the use of either transposable elements (see, e.g., Parinov et al., Plant Cell 11, 2263-2270 (1999)) or T-DNA. The foreign DNA not only disrupts the expression of the gene into which it is inserted but also acts as a marker for subsequent identification of the mutation. Because some plant introns are small, and because there can be very little intergenic material in plant chromosomes, the insertion of a piece of T-DNA on the order of 5 to 25 kb in length generally produces a dramatic disruption of gene function. If a large enough population of T-DNA-transformed lines is available, one has a very good chance of finding a plant carrying a T-DNA insert within any gene of interest.

Mutations that are homozygous lethal can be maintained in the population in the form of heterozygous plants.

MYC Proteins and Modifications Thereof

The bHLH-type transcription factor (TF) MYC2, together with related members of this family (e.g., MYC3 and MYC4 in *Arabidopsis*), promote myriad plant responses to biotic and abiotic stress (Kazan & Manners, 2013). MYC2 executes biotic and abiotic stress responses primarily through the stress hormones jasmonate and abscisic acid (ABA). For example, in some cases the MYC transcription factors can promote jasmonate-triggered defense responses against pathogen and insect pests. In plant cells containing high levels of jasmonate, MYC transcription factors bind to the promoter region of JA-response genes to promote their transcriptional activation.

Previous studies have shown that simple overexpression of MYC2 from a strong promoter such as the 35S cauliflower mosaic virus promoter is insufficient to constitutively activate defense responses in tomato/potato and *Arabidopsis* (Boter et al., 2004; Lorenzo et al., 2004). The reason for this is now clear: MYC transcription factors are strongly repressed via direct binding by members of the JAZ family of repressor proteins (of which there are thirteen in *Arabidopsis*, JAZ1-JAZ13).

JAZ proteins contain a C-terminal Jas motif that interacts directly with the JAZ-interacting domain (JID) of MYC transcription factors, thus inhibiting transcriptional activation of jasmonate response genes (Fernandez-Calvo et al., 2011; Zhang et al., 2015). Mutated derivatives of MYC2 (e.g. MYC2D105N) and MYC3 (e.g. MYC3D94N) fail to interact with most JAZ proteins, and are capable of activating jasmonate-responsive target genes in the presence of JAZs. This has been demonstrated from co-transfection assays (Goossens el al., 2015) and characterization of an *Arabidopsis* atr2D mutant (which harbors an Asp-to-Asn, MYC3D94N mutation) (Smolen et al., 2002). Based on these findings, it was stated that "Ultimately, the transferability of the Asp-to-Asn amino acid change might facilitate the design of hyperactive transcription factors for plant engineering" (Goossens et al., 2015). However, such mutations do not inhibit interactions with JAZ1 and JAZ10, which are potent repressors of MYC transcription factors.

Depending upon the location of a mutation, some mutations of MYC transcription factors may still be subject to repression by JAZ1 and JAZ10 because these two JAZ proteins harbor a cryptic MYC-interaction domain (CMID). By changing the MYC contact points with the CMID domain, which in some cases may be within the JID domain and in some cases outside of the JID domain, MYC transcription factors are generated that escape repression by all JAZ proteins. Such MYC transcription factors therefore are highly potent in their capacity to promote the expression of JA-response genes (i.e., MYC transcription factors that avoid repression by all JAZs).

This technology is useful not only for design of crops with increased resistance to pests, but also for enhancing the production of plant-derived medicinal compounds. One example is the anti-cancer drug taxol, whose production in taxus cells is promoted by the JA pathway via MYC transcription factors. Engineering of mutant (e.g., dominant mutant) MYC transcription factors into taxus cells could significantly increase taxol production. This same approach can be used to increase the production of any plant compound whose synthesis is controlled by MYC transcription factors (this includes many if not most plant secondary metabolites).

Examples of MYC protein sequences are provided herein that have one or more amino acid mutations, substitutions, replacements, insertions, or deletions within their JAZ-interacting domains (JIDs). In some cases, one or more mutations, substitutions, replacements, insertions, or deletions that are outside of the JAZ-interacting domain (JID) of the MYC proteins provided herein, for example, in regions that may interact with JAZ cryptic MYC-interaction domains (CMIDs).

For example, any of the MYC or MYC-related proteins described herein have at least one amino acid, or at least two amino acids, or at least three amino acids, or at least four amino acids, or at least five amino acid mutations, substitutions, replacements, insertions, or deletions in their JAZ-interacting domains (JIDs) on in regions that interact with JAZ cryptic MYC-interaction domains (CMIDs), or in both JID and CMID-interacting domains of a MYC protein. For example, MYC2 regions that interact with JAZ cryptic MYC-interaction domains (CMIDs) and/or MYC2 JAZ-interacting domains (JID) of a modified MYC protein can have less than 100%, or at less than 99.5%, or at less than 99%, or less than 98%, or at less than 97%, or less than 96%, or less than 95%, or less than 94%, or less than 93%, or less than 92%, or less than 91%, or less than 90% sequence identity with any of the CMID-interacting domains, JID, MYC or MYC related sequences described herein. However, in some cases the modified MYC protein have at least 40%, or at least 50%, or at least 60%, or at least 70%, or at least 80%, or at least 90%, or at least 95%, or at least 97%, or at least 99% sequence identity compared to the MYC or MYC-related sequences described herein.

For example, an *Arabidopsis thaliana* MYC2 sequence is shown below as SEQ ID NO: 1, where the JAZ-interacting domain (JID) is shown in bold and with underlining.

```
  1  MTDYRLQPTM NLWTTDDNAS MMEAFMSSSD ISTLWPPAST
 41  TTTTATTETT PTPAMEIPAQ AGFNQETLQQ RLQALIEGTH
 81  EGWTYAIFWQ PSYDFSGASV LGWGDGYYKG EEDKANPRRR
121  SSSPPFSTPA DQEYRKKVLR ELNSLISGGV APSDDAVDEE
161  VTDTEWFFLV SMTQSFACGA GLAGKAFATG NAVWVSGSDQ
201  LSGSGCERAK QGGVFGMHTI ACIPSANGVV EVGSTEPIRQ
241  SSDLINKVRI LFNFDGGAGD LSGLNWNLDP DQGENDPSMW
281  INDPIGTPGS NEPGNGAPSS SSQLFSKSIQ FENGSSSTIT
321  ENPNLDPTPS PVHSQTQNPK FNNTFSRELN FSTSSSTLVK
361  PRSGEILNFG DEGKRSSGNP DPSSYSGQTQ FENKRKRSMV
401  LNEDKVLSFG DKTAGESDHS DLEASVVKEV AVEKRPKKRG
441  RKPANGREEP LNHVEAERQR REKLNQRFYA LRAVVPNVSK
481  MDKASLLGDA IAYINELKSK VVKTESEKLQ IKNQLEEVKL
521  ELAGRKASAS GGDMSSSCSS IKPVGMEIEV KIIGWDAMIR
561  VESSKRNHPA ARLMSALMDL ELEVNHASMS VVNDLMIQQA
601  TVKMGFRIYT QEQLRASLIS KIG
```

The JAZ-interacting domain (JID) of the SEQ ID NO: 1 *Arabidopsis thaliana* MYC2 protein is shown below as SEQ ID NO:2.

```
 81                YDFSGASV LGWGDGYYKG EEDKANPRRR
121  SSSPPFSTPA DQEYRKKVLR ELNSLISGGV APS
```

In some cases, the MYC2 protein with SEQ ID NO: 1 can have one or more mutations within the JID, and/or one or more mutations outside of the JID region. Thus modified MYC proteins described herein have less than 100% sequence identity to SEQ ID NO: 1 and/or to SEQ ID NO:2.

Several amino acid positions of the MYC2 proteins can be modified, including for example, positions 94, 97, 102, 105, 107, 125, 128, 129, 148, 152, 155, 163, 165, 169, 172, or combinations thereof. MYC2 from different plant species can have variations in sequence. Hence, MYC2 from species other than *Arabidopsis thaliana* can have modifications at positions corresponding to positions 94, 97, 102, 105, 107, 125, 128, 129, 148, 152, 155, 163, 165, 169, and/or 172 from *Arabidopsis thaliana*.

For example, in some cases position 165 of the SEQ ID NO:1 MYC2 sequence can be a lysine rather than a glutamic acid (i.e., an E165K mutation). Such an E165K mutation is a gain-of-function allele of MYC2. The E165K mutation is in the transcriptional activation domain (TAD) of MYC2, which lies outside the JAZ-interacting domain, as described by Gasperini et al. PLOS Genetics 11(6): e1005300 (2015).

Other examples of MYC2 mutations include MYC2 D105N; MYC2 D105N+E165K; MYC2 M172A; MYC2 E165A+M172: and MYC2 L169A mutations.

An *Arabidopsis thaliana* MYC3 sequence is shown below as SEQ ID NO:3, where the JAZ-interacting domain (JID) is shown in bold and with underlining.

```
  1  MNGTTSSINF LTSDDDASAA AMEAFIGTNH HSSLFPPPPQ
 41  QPPQPQFNED TLQQRLQALI ESAGENWTYA IFWQISHDFD
 81  SSTGDNTVIL GWGDGYYKGE EDKEKKKNNT NTAEQEHRKR
121  VIRELNSLIS GGIGVSDESN DEEVTDTEWF FLVSMTQSFV
161  NGVGLPGESF LNSRVIWLSG SGALTGSGCE RAGQGQIYGL
201  KTMVCIATQN GVVELGSSEV ISQSSDLMHK VNNLFNFNNG
241  GGNNGVEASS WGFNLNPDQG ENDPALWISE PTNTGIESPA
281  RVNNGNNSNS NSKSDSHQIS KLEKNDISSV ENQNRQSSCL
321  VEKDLTFQGG LLKSNETLSF CGNESSKKRT SVSKGSNNDE
361  GMLSFSTVVR SAANDSDHSD LEASVVKEAI VVEPPEKKPR
401  KRGRKPANGR EEPLNHVEAE RQRREKLNQR FYSLRAVVPN
441  VSKMDKASLL GDAISYINEL KSKLQQAESD KEEIQKKLDG
481  MSKEGNNGKG CGSRAKERKS SNQDSTASSI EMEIDVKIIG
521  WDVMIRVQCG KKDHPGAREM EALKELDLEV NHASLSVVND
561  LMIQQATVKM GSQFFNHDQL KVALMTKVGE NY
```

The JAZ-interacting domain (JID) of the SEQ ID NO:3 *Arabidopsis thaliana* MYC3 protein is shown below as SEQ ID NO:4.

```
 81  STGDNTVIL GWGDGYYKGE EDKEKKKNNT NTAEQEHRKR
121  VIRELNSLIS GGIGVS
```

In some cases, the MYC3 protein with SEQ ID NO:3 can have one or more mutations within the JID, and/or one or more mutations outside of the JID region. Thus modified MYC proteins described herein have less than 100% sequence identity to SEQ ID NO:3 and/or to SEQ ID NO:4.

Several amino acid positions of the MYC3 proteins can be modified, including for example, positions 94, 97, 102, 105, 107, 125, 128, 129, 148, 152, 155, 163, 165, 169, 172, or combinations thereof. MYC3 from different plant species can have variations in sequence. Hence, MYC3 from species other than *Arabidopsis thaliana* can have modifications at positions corresponding to positions 94, 97, 102, 105, 107, 125, 128, 129, 148, 152, 155, 163, 165, 169, and/or 172 from *Arabidopsis thaliana*.

For example, the glutamic acid at position 148 of the MYC3 protein with SEQ ID NO:3 corresponds to the glutamic acid at position 165 of the MYC2 protein, and can be lysine rather than glutamic acid (E148K) or an alanine rather than glutamic acid (E148A). In addition the aspartic acid at position 94 of the MYC3 protein with SEQ ID NO:3 or SEQ ID NO:4 can be an asparagine (D94N). Modified MYC3 proteins can also have a combination of E148K and D94N mutations.

Other MYC3 modifications can include an MYC3 M155A mutation, an MYC3 L152A mutation, and combinations thereof. The MYC3 M155A mutation, and/or MYC3 L152A mutation can be combined with E148K, E148A, and/or D94N mutation.

An *Arabidopsis thaliana* MYC4 sequence is shown below as SEQ ID NO:5, where the JAZ-interacting domain (JID) is shown in bold and with underlining.

```
  1 MSPTNVQVTD YHLNQSKTDT TNLWSTDDDA SVMEAFIGGG
 41 SDHSSLFPPL PPPPLPQVNE DNLQQRLQAL IEGANENWTY
 81 AVFWQSSHGF AGEDNNNNNT VLLGWGDGYY KGEEEKSRKK
121 KSNPASAAEQ EHRKRVIREL NSLISGGVGG GDEAGDEEVT
161 DTEWFFLVSM TQSFVKGTGL PGQAFSNSDT IWLSGSNALA
201 GSSCERARQG QIYGLQTMVC VATENGVVEL GSSEIIHQSS
241 DLVDKVDTFF NFNNGGGEFG SWAFNLNPDQ GENDPGLWIS
281 EPNGVDSGLV AAPVMNNGGN DSTSNSDSQP ISKLCNGSSV
321 ENPNPKVLKS CEMVNFKNGI ENGQEEDSSN KKRSPVSNNE
361 EGMLSFTSVL PCDSNHSDLE ASVAKEAESN RVVVEPEKKP
401 RKRGRKPANG REEPLNHVEA ERQRREKLNQ RFYSLRAVVP
441 NVSKMDKASL LGDAISYISE LKSKLQKAES DKEELQKQID
481 VMNKEAGNAK SSVKDRKCLN QESSVLIEME VDVKIIGWDA
521 MIRIQCSKRN HPGAKFMEAL KELDLEVNHA SLSVVNDLMI
561 QQATVKMGNQ FFTQDQLKVA LTEKVGECP
```

The JAZ-interacting domain (JID) of the SEQ ID NO:5 *Arabidopsis thaliana* MYC4 protein is shown below as SEQ ID NO:6.

```
 81                 NNNNNT VLLGWGDGYY KGEEEKSRKK
121 KSNPASAAEQ EHRKRVIREL NSLISGGVGG G
```

A comparison of the *Arabidopsis thaliana* MYC4 sequence with SEQ ID NO:5 and the *Arabidopsis thaliana* MYC2 sequence having SEQ ID NO: 1 is shown below.

```
50.2% identity in 630 residues overlap; Score: 1225.0;
Gap frequency: 12.4
Seq1   9 TMNLWTTDDNASMMEAEMSS-
           SDISTLWPPASTTTTTATTETTPTPAMEIPAQAGFNQET
Seq5  20 TTNLWSTDDDASVMEAFIGGGSDHSSLEPPLP-----------PPPLPQV-----
           NEDN
         * *** *** ** ****      ** * **              * *            *

Seq1  68 LQQRLQALIEGTHEGWTYAIFWQPSYDFSGAS-------
           VLGWGDGYYKGEEDKANPRRR
Seq5  63 LQQRLQALIEGANENWTYAVFWQSSHGFAGEDNNNNNTVLLGWGDGYYKGEEEKS--
           RKK
         **********  * **** ***  *   * *               ************ *   *

Seq1 121 SSSPPFSTPADQEYRKKVLRELNSLISGGVAPSDDAVDEEVTDTEWFFLVSMTQSFACGA
Seq5 121 KSNR--
           ASAAEQEHRKPVIRELNSLISGGVGGGDEAGDEEVTDTEWFFLVSMTQSFVKGT
           * *       * ** **  * ***********   *  * *********************

Seq1 181 GLAGKAFATGNAVWVSGSDQLSGSGCERAKQGGVFGMHTIACIPSANGVVEVGSTEPIRQ
Seq5 179 GLPGQAFSNSDTIWLSGSNALAGSSCERARQGQIYGLQTMVCVATENGVVELGSSEIIHQ
         ** * **    * ***  * ** **** **    *    * *     ***** ** * **

Seq1 241 SSDLINKVRILFNFDGGAGDLSGLNWNLDPDQGENDPSMWINDPIGTPGSNEPGNGAPSS
Seq5 239 SSDLVDKVDTFFNFNNGGGEFGSWAFNLNPDQGENDPGLWISEPNGV-----------
           --
         ****  **   ***    *  *   ** ********  **   * *

Seq1 301 SSQLFSKSIQFENGSSSTITENPNLDPTPSPVHSQTQNPKFNNTFSRELNFSTSSSTLVK
Seq5 286 DSGLVAAPVMNNGGNDSTSNSDSQ------PISKLCNGSSVENPNPKVL---------
           --
          * *          * **              *          *       *        *

Seq1 361 PRSGEILNFGDEGKRSSGNPDPSSYSGQTQFENKRKRSMVLNEDKVLSFGDKTAGESDHS
Seq5 329 -KSCEMVNE--KNGIENGQEEDSS--------
           NKKRSPVSNNEEGMLSFTSVLPCDSNH
           ** **        *   **      **     **   ** ***      *
         **
```

-continued
```
Seq1  421 DLEASVVKE-------
          VAVEKRPKKRGRKPANGREEPLNHVEAERQRREKLNQRFYALPA
Seq5  378 DLEASVAKEAESNRVVVEPEKKPRKRGRKPANGREEPLNHVEAERQRREKLNQRFYSLRA
          ****** **        *  ** * ****************************
          ***

Seq1  474 VVPNVSKMDKASLLGDAIAYINELKSKVVKTESEKLQIKNQLEEVKLELAGRKASASGGD
Seq5  438 VVPNVSKMDKASLLGDAISYISELKSKLQKAESDKEELQKQIDVMNKEAGNAKSSVKDRK
          ****************** ** ***** * ** *     *        *   *  *

Seq1  534 MSSSCSSIKPVGMEIEVKIIGWDAMIRVESSKRNHPAARLMSALMDLELEVNHASMSVVN
Seq5  498 CLNQESSVL-
          IEMEVDVKIIGWDAMIRIQCSKRNHPGAKFMEALKELDLEVNHASLSVVN
              **      **  **********   ******  *  * **  * *******
          ****

Seq1  594 DLMIQQATVKMGFRIYTQEQLRASLISKIG
Seq5  557 DLMIQQATVKMGNQFFTQDQLKVALTEKVG
          ************  ** **  * *  * *
```

In some cases, the *Arabidopsis thaliana* MYC4 protein with SEQ ID NO:5 can have one or more mutations within the JID, and/or one or more mutations outside of the JID region. Thus modified MYC4 proteins described herein have less than 100% sequence identity to SEQ ID NO:5 and/or to SEQ ID NO:6.

Several amino acid positions of the MYC proteins can be modified, including for example, positions 94, 97, 102, 105, 107, 125, 128, 129, 148, 152, 155, 163, 165, 167, 169, 170, 172, or combinations thereof. MYC4 from different plant species can have variations in sequence. Hence, MYC4 from species other than *Arabidopsis thaliana* can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the MYC4 protein can vary from those in the corresponding *Arabidopsis thaliana* MYC2 protein by 1-10 positions.

For example, modified MYC4 proteins can have D107N mutations, E163K mutations, M170A mutations, L167A mutations, or combinations thereof. Other MYC proteins can have the same types of mutations but the location can vary. For example, the aspartic acid (D) that is at position 107 of the MYC4 protein with SEQ ID NO:5, at be at different positions in other MYC proteins. For example, such an aspartic acid can be at ±5 positions from position 107. However, such an aspartic acid is readily identified by sequence comparisons such as those illustrated herein because a selected amino acid at a particular position can be aligned via its adjoining sequence with the sequence of a related protein, and even if there are sequence variations between the two proteins the skilled person can find the selected amino acid in the related protein.

Similarly, for example, a selected amino acid at a particular position, such an aspartic acid at position 107 in one protein can readily be identified in another protein as being at position 102 because that aspartic acid it is typically found within a sequence that is conserved between the two proteins. For example an aspartic acid at position 102 or 107 in different proteins can readily be identified because it is at the end of a conserved GWG<u>D</u> (SEQ ID NO: 110) sequence. Other conserved segments of MYC protein sequences are illustrated in the sequence comparisons shown herein, including for example, the DFSG (SEQ ID NO: 111) sequence, the RELNSLISGGV (SEQ ID NO: 112) sequence, the DTEWFFLVSM (SEQ ID NO: 113) sequence, the VVNDLMIQQATVKMG (SEQ ID NO: 114) sequence, and/or the KRGRKPANGREEPLNHVEAERQR-REKLNQRFY (SEQ ID NO: 115) sequence. Such segments of conserved sequences facilitate alignment of related amino acid sequences so that corresponding amino acids can be identified despite position and some sequence variation.

MYC-related proteins can also be modified and expressed in a variety of plants, for example, instead of or in addition to a native MYC protein. An example of a MYC-related protein is a rice (*Oryza sativa*) MYC7E protein, which has at least 47% sequence identity to the MYC2 sequence with SEQ ID NO: 1. This rice MYC7E protein sequence is shown below as SEQ ID NO:7, where the JAZ-interacting domain (JID) is shown in bold and with underlining.

```
  1 MWVLLSPLLT TKNPFHPIPI PTFPLLLFSS SLVGVLFQIK

41 SNLEEEEIEI KSMNLWTDDN ASMMEAFMAS ADLPAFPWGA

81 ASTPPPPPPP PHHHHQQQQQ QVLPPPAAAP AAAAFNQDTL

121 QQRLQSIIEG SRETWTYAIF WQSSIDVSTG ASLLGWGDGY

161 YKGCDDDKRK QRSSTPAAAA EQEHRKRVLR ELNSLIAGAG

201 AAPDEAVEEE VTDTEWFFLV SMTQSFPNGL GLPGQALFAA

241 QPTWIATGLS SAPCDRARQA YTFGLRTMVC LPLATGVLEL

281 GSTDVIFQTG DSIPRIRALF NLSAAAASSW PPHPDAASAD

321 PSVLWLADAP PMDMKDSISA ADISVSKPPP PPPHQIQHFE

361 NGSTSTLTEN PSPSVHAPTP SQPAAPPQRQ QQQQQSSQAQ

401 QGPFRRELNF SDFASNGGAA APPFFKPETG EILNFGNDSS

441 SGRRNPSPAP PAATASLTTA PGSLFSQHTP TLTAAANDAK

481 SNNQKRSMEA TSRASNTNNH PAATANEGML SFSSAPTTRP

521 STGTGAPAKS ESDHSDLEAS VREVESSRVV APPPEAEKRP

561 RKRGRKPANG REEPLNHVEA ERQRREKLNQ RFYALRAVVP

601 NVSKMDKASL LGDAISYINE LRGKLTALET DKETLQSQME

641 SLKKERDARP PAPSGGGDG GARCHAVEIE AKILGLEAMI

681 RVQCHKRNHP AARLMTALRE LDLDVYHASV SVVKDLMIQQ

721 VAVKMASRVY SQDQLNAALY TRIAEPGTAA R
```

A comparison of the rice MYC7E protein sequence having SEQ ID NO:7 with the MYC2 protein sequence having SEQ ID NO:1 is shown below, where the asterisks identify positions that are identical in the two proteins.

```
47.2% identity in 705 residues overlap; Score: 1039.0; Gap frequency:
14.8%
UserSeq1    9 TMNLWTTDDNASMMEAFMSSSDISTL-WPPASTTTTTATT---------ETTPTPAMEIP
UserSeq7   52 SMNLWT-DDNASMMEAFMASADLPAFTWGPASTPPPPPPPPHHHHQQQQQQVLPPPAAAP
              ***** ***********  *     *A  ***                      *    *

UserSeq1   59 AQAGFNQETLQQRLQALIEGTHEGWTYAIFWQPSYDFS-GASVLGWGDGYYKGEEDKANP
UserSeq7  111 AAAAFNQDTLQQRLQSIIEGSRETWTYAIFWQSSIDVSTGASLLGWGDGYYKGCDDDKR-
              *  *** ******* ***  * ******** * * ***  * *** **********  *

UserSeq1  118 RRRSSSPPFSTPADQEYRKKVLRELNSLISGGVAPSDDAVDEEVTDTEWFFLVSMTQSFA
UserSeq7  170 KQRSSTP--AAAAEQEHRKRVLRELNSLIAGAGAAPDEAVEEEVTDTEWFFLVSMTQSFP
               *** *    *  ** ** **********  *   * **  * ** ******************

UserSeq1  178 CGAGLAGKAFATGNAVWVSGSDQLSGSGCERAKQGGVFGMHTIACIPSANGVVEVGSTEP
UserSeq7  228 NGLGLPGQALFAAQPTWIATG--LSSAPCDRARQAYTFGLRTMVCLPLATGVLELGSTDV
                * **  *       *         ** * **       *     *  ***  * ***

UserSeq1  238 IRQSSDLINKVRILFNFDGGAGDLSGLNWNLDPDQGENDPS-MWIND--PIGTGPGSNEPG
UserSeq7  286 IFQTGDSIPRIRALFNLSAAAAS----SWPPHPDAASADPSVLWLADAPPMDMKDSISAA
              * *   *   * *** *      *       **   ***     *   *

UserSeq1  295 NGAPSSSSQLFSKSIQ-FENGSSSTITENPNID---PTPS----PVHSQTQNPKFNNT--
UserSeq7  342 DISVSKPPPPPHQIQHFENGSTSTLTENPSPSVHAPTPSQPAAPPQRQQQQQQSSQAQQ
                *          ** ***** ** ****     ****   *      * *

UserSeq1  345 --FSRELFSTSSST-------LVKPRSGEILNFGDEGKRSSGNRDPSSYSGQTQF----
UserSeq7  402 GPFRRELNFSDFASNGGAAAPPFFKPETGEILNFGNDSSSGRRNPSPAPPAATASLTTAP
                * ****** *           ** *******  **  ****  **

UserSeq1  392 ------------------ENKRKRSMVLNE--------------DKVLSF---------
UserSeq7  462 GSLFSQHTPTLTAAANDAKSNNQKRSMEATSRASNTNNHPAATANEGMLSFSSAPTTRRS
                                 * ****                  ***

UserSeq1  410 ---GDKTAGESDHSDLEASVVKEVA---------VEKRPKKRGRKPANGREEPLNHVEAE
UserSeq7  522 TGTGAPAKSESDHSDLEASVREVESSRVVAPPPEAEKRPRKRGRKPANGREEPLNHVEAE
                 *   ***********            **** ******************

UserSeq1  458 RQRREKLNQRFYALRTAVVPNVSKMDKASLLGFAIAYINELKSKVVKTESEKLQIKNQLEE
UserSeq7  582 RQRREKLNQRFYALRVVPNVSKMDKASLLGDAISYINELRGKLTALETDKETLQSQMES
              ***************  ************* ** ****** *     *   *  *   *

UserSeq1  518 VKLELAGRKASASGGDMSSSCSSIKPVGMEIEVKIIGWDAMIRVESSKRNHPAARLMSAL
UserSeq7  642 LKKERDARPPAPSGG---GGDGGARCHAVEIEAKILGLEAMIRVQCHKRNHPAARLMTAL
               *  *   * **      ***    ** ** **** **** **  * ********** **

UserSeq1  578 MDLELEVNHASMSVVNDLMIQQATVKMGFRIYTQEQLRASLISKI
UserSeq7  699 RELDLDVYHASVSVVKDLMIQQVAVKMASPVYSQDQLNAALYTRI
                * * * ***  *** ****** * **  *   *  * ** *  *
```

The JAZ-interacting domain (JID) of the rice MYC7E protein sequence having SEQ ID NO:7 is shown below as SEQ ID NO:8.

```
121                                  STG ASLLGWGDGY
161       YKGCDDDKRK QRSSTPAAAA EQEHRKRVLR ELNSLIAGA
```

In some cases, the MYC7E protein with SEQ ID NO:7 can have one or more mutations within the JID, and/or one or more mutations outside of the JID region. Thus modified MYC proteins described herein have less than 100% sequence identity to SEQ ID NO:7 and/or to SEQ ID NO:8.

For example, MYC7E from *Oryza sativa* can have modifications at positions 50 corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the endogenous *Oryza sativa* MYC protein can vary from those in the corresponding *Arabidopsis thaliana* MYC2 protein by 1-10 positions.

An example of another MYC protein is a maize (*Zea mays*) MYC4 protein, which has at least 47% sequence identity to the *Arabidopsis* MYC2 sequence with SEQ ID NO:1. This maize MYC4 protein sequence is shown below as SEQ ID NO:9, where the JAZ-interacting domain (JID) is shown in bold and with underlining.

```
  1 MNLWTDDNAS MMEAFMASAD LPTFPWGAPA GGGNSSAAAA
 41 SPPPPQMPAA TAPGFNQDTL QQRLQAMIEG SRETWTYAIF
 81 WQSSLDSATG ASLLGWGDGY YKGCDEDKRK QKPLTPSAQA
121 EQEHRKRVLR ELNSLISGAA AAPDEAVEEE VTDTEWFFLV
161 SMTQSFLNGS GLPGQALFAG QPTWIASGLS SAPCERARQA
201 YNFGLRTMVC FPVGTGVLEL GSTDVVFKTA ESMAKIRSLF
241 GGGAGGGSWP PVQPQAPSSQ QPAAGADHAE TDPSMLWLAD
281 APVMDIKDSL SHPSAEISVS KPPPHPPQIH FENGSTSTLT
321 ENPSPSVHAP PPPPAPAAPQ QRQHQHQNQA HQGPFRRELN
361 FSDFASTPSL AATPPFFKPE SGEILSFGAD SMARRNPSPV
401 PPAATASLTT APGSLFSQHT ATMTAAAAND AKNNNKRSME
441 ATSRASNTNH HPAATANEGM LSFSSAPTTR PSTGTGAPAK
```

```
481 SESDHSDLDA SVREVESSRV VAPPPEAEKR PRKRGRKPAN

521 GREEPLNHVE AERQRREKLN QRFYALRAVV PNVSKMDKAS

561 LLGDAISYIN ELRGKLTSLE TDKETLQTQV EALKKERDAR

601 PPSHSAGLGG HDGGPRCHAV EIDAKILGLE AMIRVQCHKR

641 NHPSARLMTA LRELDLDVYH ASVSVVKDLM IQQVAVKMAS

681 RVYTQDQLSA ALYSRLAEPG SAMGR*
```

A comparison of the maize MYC4 protein sequence having SEQ ID NO:9 with the MYC2 protein sequence having SEQ ID NO: 1 is shown below.

```
47.2% identity in 703 residues overlap; Score: 1048.0; Gap frequency:
13.8%
UserSeq1  10 MNLWTTDDNASMMEAFMSSSDISTL-W-PPASTTTTTATTETTPTPAMEIPAQAGFNQET
UserSeq9   1 MNLMT-DDNASMMEAFMASADLPTFPWGAPAGGGNSSAAAASPPPPQMPAATAPGFNQDT
             *****  ************ *   *   *   **    *         * * *    **** *

UserSeq1  68 LQQRLQALIEGTHEGWTYAIFWQPSYDFS-GASVLGWGDGYYKGEEDKANPRRRSSSPPF
UserSeq9  60 LQQRLQAMIEGSRETWTYAIFWQSSLDSATGASLLGWGDGYYKGCDED---KRKQKPLTP
             *******  ***  * ******** *  *    *** **********  *

UserSeq1 127 STPADQEYRKKVLRELNSLISGGVAPSDDAVDEEVTDTEWFFLVSMTQSFACGAGLAGKA
UserSeq9 117 SAQAEQEHRKRVLRELNSLISGAAAAPDEAVEEEVTDTEWFFLVSMTQSFLNGSGLPGQA
             *  * ** ** ************  *  ** *******************   *  *   *

UserSeq1 187 FATGNAVWVSGSDQLSGSGCERAKQGGVFGMHTIACIPSANGVVEVGSTEPIRQSDLIN
UserSeq9 177 LFAGQPTWIASG--LSSAPCERARQAYNFGLRTMVCFPVGTGVLELGSTDVVFKTAESMA
              *  *    **   * ****  **  *  *    *  *  **  * ***  * * ***

UserSeq1 247 KVRILFNFDGGAGDL--------SGLNWNLDPDQGENDPSM-WIND-PIGT--PGSNEPG
UserSeq9 235 KIRSLFGGGAGGGSWPPVQPQAPSSQQPAAGADHAETDPSMLWLADAPVMDIKDSLSHPS
             * **  **   **        *           *   * ****  * *

UserSeq1 295 NGAPSSSSQLFSKSIQFENGSSSTITENPNLD-----PTPSPV-----HSQTQNPKFNNT
UserSeq9 295 AEISVSKPPPHPPQIHFENGSTSTLTENPSPSVHAPPPPPAPAAPQQRQHQHQNQAHQGP
                *       *  ***** ** ****  *         * *       *  **

UserSeq1 345 FSRELNFSTSSST--------LVKPRSGEILNFG-DEGKRSSGNPDP------------S
UserSeq9 355 FRRELNFSDFASTPSLAATPPFFKPESGEILSFGADSNARRNPSPVPPAATASLTTAPGS
             * ******  **        **  *****  ** *     *                    *

UserSeq1 384 SYSGQT---------QFENKRKRSMVLNE--------------DKVLSF----------
UserSeq9 415 LFSQHTATMTAAAANDAKNNNKRSMEATSRASNTNHHPAATANEGMLSFSSAPTTRPSTG
              * *            * ****                       ***

UserSeq1 410 -GDKTAGESDHSDLEASVVKEVA---------VEKRPKKRGRKPANGREEPLNHVEAERQ
UserSeq9 475 TGAPAKSESDHSDLDASVREVESSRVVAPPPEAEKRPRKRGRKPANGREEPLNHVEAERQ
              *    ********  *** ***         ****  ********************

UserSeq1 460 RREKLNQRFYALRAVVPNVSKMDKASLLGDAIAYINELKSKVVKTESEKLQIKNQLEEVK
UserSeq9 535 RREKLNQRFYALRAVVPNVSKMDKASLLGDAISYINELRGKLTSLETDKETLQTQVEALK
             ********************************  *****    *  * *   *   * *

UserSeq1 520 LELAGRKASASGGDMSSSCSSIKPVGMEIEVKIIGWDAMIRVESSKRNHPAARLMSALMD
UserSeq9 595 KERDARPPSHSAG-LGGHDGGPRCHAVEIDAKILGLEAMIRVQCHKRNHPSARLMTALRE
              *  *    *      * **  **   * * ***** *****   **** ****  * *

UserSeq1 580 LELEVNHASMSVVNDLMIQQATVKMGFRIYTQEQLRASLISKI
UserSeq9 654 LDLDVYHASVSVVKDLMIQQVAVKMASRVYTQDQLSAALYSRL
             * * * *** *** ******  ****  ****** *  * *
```

The JAZ-interacting domain (JID) of the maize MYC4 protein sequence having SEQ ID NO:9 is shown below as SEQ ID NO: 10.

```
 81            ATG ASLLGWGDGY YKGCDEDKRK QKPLTPSAQA
121       EQEHRKRVLR ELNSLISGA
```

In some cases, the maize MYC4 protein with SEQ ID NO:9 can have one or more mutations within the JID, and/or one or more mutations outside of the JID region. Thus modified MYC proteins described herein have less than 100% sequence identity to SEQ ID NO:9 and/or to SEQ ID NO: 10.

For example, such a MYC4 from *Zea mays* can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a maize (*Zea mays*) MYC4-like protein, shown below as SEQ ID NO: 11, where the JAZ-interacting domain (JID) is shown in bold and with underlining.

```
  1 MNLWTDDNAS MMEAFMASAD LPAYPWGAPA GGGNPPPPQM

41 PPAMAMAPGF NQDTLQQRLQ AMIEGSRETW TYAIFWQSSL

81 DAATGASLLG WGDGYYKGCD DDKRRHRPPL TPAAQAEQEH
```

```
121 RKRVLRELNS LISGGASAAP APAPDEAVEE EVTDTEWFFL

161 VSMTQSFLNG SGLPGQALFA GHHTWIAAGL SSAPCDRARQ

201 AYNFGLRTMV CFPVGTGVLE LGSTDVVFQT AETMAKIRSL

241 FGGGPGGGSW PPVQPQAAPQ QQHAAEADQA AETDPSVLWL

281 ADAPVVDIKD SYSHPSAAEI SVSKPPPPPP PPQIHFENGS

321 TSTLTENPSP SVHAPPAPPA PPQRQQQNQG PFRRELNFSD

361 FASNPSLAAA PPFFKPESGE ILSFGVDSNA QRNPSPAPPA

401 SLTTAPGSLF SQSQHTATAA ANDAKNNNNN NKRSMEATSL

441 ASNTNHHPAA AANEGMLSFS SAPTARPSAG TGAPAKSESD

481 HSDLDASVRE VESSRVVAPP PEAEKRPRKR GRKPANGREE

521 PLNHVEAERQ RREKLNQRFY ALRAVVPNVS KMDKASLLGD

561 AISYINELRG KLTSLESDRE TLQAQVEALK KERDARPHPH

601 PAAGLGGHDA GGPRCHAVEI DAKILGLEAM IRVQCHKRNH

641 PSARLMTALR ELDLDVYHAS VSVVKDLMIQ QVAVKMASRM

681 YSQDQLSAAL YSRLAEPGSV MGR
```

The JAZ-interacting domain (JID) of the maize MYC4-like protein sequence having SEQ ID NO:1 is shown below as SEQ ID NO: 12.

```
 81     ATGASLLG WGDGYYKGCD DKRRHRPPL TPAAQAEQEH

121     RKRVLRELNS LISGG
```

A comparison of the *Arabidopsis* MYC4 protein with SEQ ID NO:5 with the *Zea mays* MYC4-like having SEQ ID NO: 11 is shown below.

```
41.5% identity In 689 residues overlap; Score: 710.0; Gap frequency: 19.7%
Seq5   25 STDDDASVMEAFIGGGSDHSSLFPPLPPPPLPQVNEDNLQQRLQALIEGANENWTYAVFW
Seq11  18 SADLPAYPWGAPAGGGNPPPPQMPPAMAMA-
          PGFNQDTLQQRLQAMIEGSRETWTYAIFW
           *  *   *   ***      **        *  * ******* ***  * ****
          **

Seq5   85 QSSHGFAGEDNNNNNTVLLGWGDGYYKGEEEKSRKKKS--
          NPASAAEQHRKRVIRELNS
Seq11  77 QSSLDAA------
          TGASLLGWGDGYYKGCDDDKRRHPPLTPAAQAEQEHRKRVLRELNS
          ***  *         ***********   *    **  *********
          *****

Seq5  143 LISGGVGGG-----
          DEAGDEEVTDTEWFFLVSMTQSFVKGTGLPGQAFSNSDTIWLSGSN
Seq11 131 LISGGASAAPAPDEAVEEEVTDTEWFFLVSMTQSFLNGSGLPGQALFAGHHTWIAAG-
          *****        ***  ****************  ******        *

Seq5  198 ALAGSSCERARQGGQIYGLQTMVCVATENGVVELGSSEIIHQSSDLVDKVDTFFNFNNGGG
Seq11 190 -
          LSSAPCDRARQAYNFGLRTMVCFPVGTGVLELGSTDVVFQTAETMAKIRSLFGGGPGGG
                 *  ****   **  * ****   ** ****     *    *    *
          ***

Seq5  258 EFGSWAFNLNPDQ---------GENDPG-LWI------------
          SEPNGVDSGLVAAP--
Seq11 249 SWPPVQPQAAPQQQHAAEADQAAETDPSVLWLADAPVVDIKDSYSHPSAAEISVSKPPPP
                   * *       *  ** **            * *            *

Seq5  294 -----VMNNGGNDSTSNSDSQP-----------------------------------
          --
Seq11 309 PPPPQIHFENGSTSTLTENPSPSVHAPPAPPAPPQRQQQNQGPFRRELNFSDFASNPSLA
               *  **    *

Seq5  311 -------------ISKLCNGSSVENPNPKVLKSC---------
          EMVNFKNGIEGQEEDS
Seq11 369 AAPPFFKPESGEILSFGVDSNAQRNPSPAPPASLTTAPGSLFSQSQHTATAANDAKNNN
                       *   **  *     *                         *

Seq5  349 SNKKRS-------------PVSNNEEGMLSFTSV------------
          LPCDSNHSDLEASV
Seq11 429 NNNKRSMEATSLASNTNHHPAAAANEGMLSFSSAPTARPSAGTGAPAKSESDHSDLDASV
          * ***              *      ****** *                *   * ****
          ***

Seq5  384 AKEAESNRVVVEP---
          EKKPRKRGRKPANGREEPLNHVEAERQPREKLNQRFYSLRAVVP
Seq11 489 -
          REVESSRVVAPPPEAEKRPRKRGRKPANGREEPLNHVEAERQRREKLNQRFYALRAVVP
               *  **  *** *   ** **********************************
          ******
```

```
Seq5    441 NVSKMDKASLLGDAISYISELKSKLQKAESDKEELQKQIDVMNKEAGNAKSSVKDRKCLN
Seq11   548 NVSKMDKASLLGDAISYINELRGKLTSLESDRETLQAQVEALKKERDARPHPHPAAGLGG
            ****************** **  **    *** * ** *       **

Seq5    501 QESSV--
            LIEMEVDVKIIGWDAMIRIQCSKRNHPGAKFMEALKELDLEVNHASLSVVNDL
Seq11   608 HDAGGPRCHAVEIDAKILGLEAMIRVQCHKRNHPSARLMTALRELDLDVYHASVSVVKDL
                * ** * **** ** ***** *  * ** **** * *** ***
            **

Seq5    559 MIQQATVKMGNQFFTQDQLKVALTEKVGE
Seq11   668 MIQQVAVKMASRMYSQDQLSAALYSRLAE
            ****  ***         ****  **    *
```

In some cases, the MYC4-like protein with SEQ ID NO: 11 can have one or more mutations within the JID, and/or one or more mutations outside of the JID 55 region. Thus modified MYC proteins described herein have less than 100% sequence identity to SEQ ID NO: 11 and/or to SEQ ID NO: 12.

For example, such a *Zea mays* MYC4-like protein can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a *Brachypodium distachyon* MYC4-like protein, shown below as SEQ ID NO: 13, where the JAZ-interacting domain (JID) is shown in bold and with underlining.

```
  1 MNLWTDDNAS MMEAFMASAA DLPTFPWGAA AATPPPPAAV

41 MPQQPAFNQD TLQQRLQAII EGSRETWTYA IFWQSSTDAG

81 AGASLLGWGD GYYKGCDDAD KRARQQPTPA SAAEQEHRKR

121 VLRELNSLIA GGGAAAPDEA VEEEVTDTEW FFLVSMTQSF

161 PNGMGLPGQA LYTRQPTWIA SGLASAPCER ARQAYTFGLR

201 TMVCIPVGTG VLELGATEVI FQTADSLGRI RSLFNLNGGG

241 GGGGAGSSWP PVAPHQQHGG DQAETDPSVL WLTDAPVGDM

281 KESPSVEISV SKPPPPPQIH HFENGSTSTL TENAGPSLHA

321 HQQPATLAPA APPRQNQHPH QLQLQHQQSQ QQQQQQQGPF

361 RRELNFSDFA TNASVTVTPP FFKPESGEIL NFGADSTSRR

401 NPSPAPPAAA ASLTTAPGSL FSQHTATVTA PTNEAKNNPK

441 RSMEATSRAS NTNHHPSATA NEGMLSFSSA PTTRPSTGTG

481 APAKSESDHS DLEASVREVE SSRVVPPPEE KRPRKRGRKP

521 ANGREEPLNH VEAERQRREK LNQRFYALRA VVPNVSKMDK

561 ASLLGDAISY INELRGKMTA LESDKDTLHS QIEALKKERD

601 ARPVAPLSGV HDSGPRCHAV EIEAKILGLE AMIRVQCHKR

641 NHPAAKLMTA LRELDLDVYH ASVSVVKDIM IQQVAVKMPN

681 RVYSQDQLNA ALYSRLAEPG APVPIR
```

The JAZ-interacting domain (JID) of the *Brachypodium distachyon* MYC4-like protein sequence having SEQ ID NO: 13 is shown below as SEQ ID NO: 14.

```
 80                                              G
 81 AGASLLGWGD GYYKGCDDAD KRARQQPTPA SAAEQEHRKR
121 VLRELNSLIA GG
```

In some cases, the *Brachypodium distachyon* MYC4-like protein with SEQ ID NO: 13 can have one or more mutations within the JID, and/or one or more mutations outside of the JID region. Thus modified MYC proteins described herein have less than 100% sequence identity to SEQ ID NO: 13 and/or to SEQ ID NO: 14.

For example, such a MYC4-like from *Brachypodium distachyon* can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Sorghum bicolor* MYC-like protein, shown below as SEQ ID NO: 15, where the JAZ-interacting domain (JID) is shown in bold and with underlining

```
  1 MNLWTDDNAS MMEAFMASAD LPTFPWGATA GGGNSSAAAA

41 TPPPPPQMPA AAMAPGFNQD TLQQRLQAMI EGSSETWTYA

81 IFWQSSLDAA TGASLLGWGD GYYKGCDDDK RKQRPLTPAA

121 QAEQEHRKRV LRELNSLISG AAAAPDEAVE EEVTDTEWFF

161 LVSMTQSFLN GSGLPGQALF AGQPTWIASG LSSAPCERAR

201 QAYNFGLRTM VCFPVGTGVL ELGSTDVVFQ TAESMAKIRS

241 LFGGGAGGGS WPPPQAPSHQ QPAAGPDQAE TDLWLADAPV

281 MDIKDSMSHP SAEISVSKPP PPPPPPQIHF ENASTSTLTE

321 NPSPSVHAAP PQPAPAAAPQ RQHQHQNQAH QGPFRRELNF

361 SDFASTNPSS LAATPPFFKP ESGEILSFGA DSNARRNPSP

401 APPAATASLT TAPGSLFSQH TATMTQAAAA NDAKNNNKRS

441 MEATSRASNT NHHPAATANE GMLSFSSAPT TRPSTGTGAP

481 AKSESDHSDL DASVREVESS RVVAPPPEAE KRPRKRGRKP

521 ANGREEPLNH VEAERQRREK LNQRFYALRA VVPNVSKMDK

561 ASLLGDAISY INELRGKLTS LESDKDTLQA QIEALKKERD

601 ARPPAHAAGL GGHDGGPRCH AVEIDAKILG LEAMIRVQCH

641 KRNHPSARLM TALRELDLDV YHASVSVVKD LMIQQVAVKM

681 ASRIYSQDQL NAALYSRLAE PGSAMGR
```

The JAZ-interacting domain (JID) of the *Sorghum bicolor* MYC-like protein sequence having SEQ ID NO: 15 is shown below as SEQ ID NO: 16.

```
 81          A TGASLLGWGD GYYKGCDDDK RKQRPLTPAA

121 QAEQEHRKRV LRELNSLISG
```

In some cases, the *Sorghum bicolor* MYC-like protein with SEQ ID NO: 15 can have one or more mutations within the JID, and/or one or more mutations outside of the JID region. Thus modified MYC proteins described herein have less than 100% sequence identity to SEQ ID NO: 15 and/or to SEQ ID NO: 16. For example, although any of the amino acids in the SEQ ID NO: 15 or 16 protein be modified, modification of the amino acids in the JAZ-interacting domain (JD), and/or modification of the serine at position 136 of the SEQ ID NO: 15 or at the corresponding position of SEQ ID NO: 16 can be useful to reduce interaction of the MYC-related protein with one or more JAZ proteins.

In other cases, such a *Sorghum bicolor* MYC-like protein can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Camelina sativa* MYC2-like protein, shown below as SEQ ID NO: 17, where the JAZ-interacting domain (JID) is shown in bold and with underlining.

```
  1 MTDYRLQPTM NLWTTDDNAS MMEAFISSSD ISTLWPMATT

41 TTTTTTATTS APATAMDIPA PAGFNQETLQ QRLQALIEGT

81 NEGWTYAIFW QPSYDFSGAS VLGWGDGYYK GEEDKAKPRQ

121 RSSSPPFSTP ADQEYRKKVL RELNSLISGG VAPSDDAVDE

161 EVTDTEWFFL VSMTQSFACG AGLAGRAFST GNAVWVSGSD

201 QLSGSGCERA KQGGVFGMQT IACIPSANGV VEVGSTEQIR

241 QSSDLINKVR VLFNLDGGAG DLSGLDWNLD PDQGENDPSM

281 WINDPIGAPG SNEPGNGAPS SSSQLFSKSI QFENGSSSTI

321 TENPNPDPTP SPVHSQTQNP KFSNNFSREL NFSTSSSTLV

361 KPRSGEILSF GDDGKRGSGN PDPSSYSGQT QFENKRKKSP

401 NEDKVLSFGD KTTGESDASD LEASVVKEVA VEKRPKKRGR

441 KPANGREEPL NXMIYVIHSP NP
```

The JAZ-interacting domain (JID) of the *Camelina sativa* MYC2-like protein sequence having SEQ ID NO:17 is shown below as SEQ ID NO:18.

```
 41                                    QRLQALIEGT

81 NEGWTYAIFW QPSYDFSGAS VLGWGDGYYK GEEDKAKPRQ

121 RSSSPPFSTP ADQEYRKKVL RELNSLISGG
```

In some cases, the *Camelina sativa* MYC2-like protein with SEQ ID NO: 17 can have one or more mutations within the JID, and/or one or more mutations outside of the JID region. Thus modified MYC proteins described herein have less than 100% sequence identity to SEQ ID NO: 17 and/or to SEQ ID NO: 18.

For example, such a *Camelina sativa* MYC2-like protein can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Solanum lycopersicum* MYC2-like protein, shown below as SEQ ID NO: 19, where the JAZ-interacting domain (JID) is shown in bold and with underlining.

```
  1 MTEYSLPTMN LWNNSTSDDN VSMMEAFMSS DLSFWATNNS

41 TSAAVVGVNS NLPHASSNTP SVFAPSSSTS ASTLSAAATV

81 DASKSMPFFN QETLQQRLQA LIDGARETWT YAIFWQSSVV

121 DFSSPSVLGW GDGYYKGEED KAKRKLSVSS PAYIAEQEHR

161 KKVLRELNSL ISGAPPGTDD AVDEEVTDTE WFFLISMTQS

201 FVNGSGLPGQ ALYSSSPIWV AGTEKLAASH CERVRQAQGF

241 GLQTIVCIPS ANGVVELGST ELIVQSSDLM NKVRVLFNFS

281 NDLGSGSWAV QPESDPSALW LTDPSSSGME VRESLNTVQT

321 NSVPSSNSNK QIAYGNENNH PSGNGQSCYN QQQQKNPPQQ

361 QTQGFFTREL NFSEFGFDGS SNRNGNSSVS CKPESGEILN

401 FGDSTKKSAS SANVNLFTGQ SQFGAGEENN NKNKKRSATS

441 RGSNEEGMLS FVSGTVLPSS GMKSGGGGGE DSEHSDLEAS

481 VVKEADSSRV VEPEKRPRKR GRKPANGREE PLNHVEAERQ

521 RREKLNQRFY ALRAVVPNVS KMDKASLLGD AISYINELKS

561 KLQNTESDKE DLKSQIEDLK KESRRPGPPP PPNQDLKMSS

601 HTGGKIVDVD IDVKIIGWDA MIRIQCNKKN HPAARLMAAL

641 MELDLDVHHA SVSVVNDLMI QQATVKMGSR HYTEEQLRVA

681 LTSKIAETH
```

The JAZ-interacting domain (JID) of the *Solanum lycopersicum* MYC2-like protein sequence having SEQ ID NO: 19 is shown below as SEQ ID NO:20.

```
121 FSSPSVLGW GDGYYKGEED KAKRKLSVSS PAYIAEQEHR

161 KKVLRELNSL ISGA
```

A comparison of the *Arabidopsis thaliana* MYC2 sequence having SEQ ID NO: 1 with the *Solanum lycopersicum* MYC2-like protein with SEQ ID NO: 19 is shown below.

```
54.0% identity in 641 residues overlap; Score: 1333.0; Gap frequency:
8.7%
Seq1   27 SSSDISTLWPPASTTTTTATTETTPTPAMEIPAQAGFNQETLQQRLQALIEGTHEGWTYA
Seq19  56 SSNTESVFAPSSSTSASTLSAAATVDASKSMPF---
              FNQETLQQRLQALIDGARETWTYA
          **   *  * **   *      *      *  ************* *  *
          ****
```

```
Seq1    87 IFWQPSY-
           DFSGASVLGWGDGYYKGEEDKANPRRRSSSPPFSTPADQEYRKKVLRELNSL
Seq19  113 IFWQSSVVDFSSPSVLGWGDGYYKGEEDKAKRKLSVSSPAYI--
           AEQEHRKKVLRELNSL
              **** * *** ****************     ***    * **
              ***********

Seq1   146 ISGGVAPSDDAVDEEVTDTEWFFLVSMTQSFACGAGLAGKAFATGNAVWVSGSDQLSGSG
Seq19  171 ISGAPPGTDDADEEVTDTEWFFLISMTQSFVNGSGLPGQALYSSSPIWVAGTEKLAASH
              ***    *****************  ****** * **  *     **  *    *  *

Seq1   206 CEPAKQGGVEGMHTIACIPSANGVVEVGSTEPIRQSSDLINKVRILFNFDGGAGDLSGLN
Seq19  231 CERVPQAQGFGLQTIVCIPSANGVVELGSTELIVQSSDLMNKVRVLFNF---
           SNDLGSGS
              *** *   **  ** ********** **** * ***** **** ****      **

Seq1   266 WNLDPDQGENDPS-MWINDPIGTPGS-
           NEPGNGAPSSSSQLFSKSIQFENGSSSTITENP
Seq19  288 WAVQP---
           ESDPSALWLTDPSSSGMEVRESLNTVQTNSVPSSNSNKQIAYGNENNHPSGN
              *   *     * ***   *  **          *  *     *       *  *

Seq1   324 NLDPTPSPVHSQTQNPKFNNTFSRELNFST-----------
           SSSTLVKPRSGEILNFGDE
Seq19  345 GQSCYNQQQQKNPPQQQTQGFFTRELNFSEFGFDGSSNRNGNSSVSCKPESGEILNFGDS
                         *  ******          **    **   *********

Seq1   373 GKRSSGNPDPSSYSGQTQF------ENKRKR----SMVLNEDKVLSE
           GDKT
Seq19  405 TKKSASSANVNLFTGQSQFGAGEENNNKNKKRSATSRGSNEEGMLSFVSGTVLPSSGMKS
              * *         ** **        ** *      *    **   ***          * *

Seq1   414 AG----ESDHSDLEASVVKE------
           VAVEKRPKKRGRKPANGREEPLNHVEAERQRREK
Seq19  465 GGGGGEDSEHSDLEASVVKEADSSRVVEPEKRPRKRGRKPANGREEPLNHVEAERQRREK
              *          * *********        *    ****
              ****************************

Seq1   464 LNQRFYALRAVVPNVSKMDKASLLGDAIAYINELKSKVVKTESKLQIKNQLEEVKLELA
Seq19  525 LNQRFYALRAVVPNVSKMDKASLLGDAISYINELKSKLQNTESDKEDLKSQIEDLKKESR
              ***************************  ********   ***   *    *  *   *   *

Seq1   524 --
           GRKASASGGDMSSSCSSIKPVGMEIEVKIIGWDAMIRVESSKRNHPAARLMSALMDLE
Seq19  585 RPGPPPPPNQDLKMSSHTGGKIVDVDIDVKIIGWDAMIRIQCNKKNHPAARLMAALMELD
              *           **   * *     *  *********** *  * ******** *** *

Seq1   582 LEVNHASMSVVNDLMIQQATVKMGFRIYTQEQLRASLISKI
Seq19  645 LDVHHASVSVVNDLMIQQATVKMGSRHYTEEOLRVALTSKI
              * * *** **************** * **  ****  * ***
```

In some cases, the *Solanum lycopersicum* MYC2-like protein with SEQ ID NO: 19 can have one or more mutations within the JID, and/or one or more mutations outside of the JID region. For example, *Solanum lycopersicum* MYC2-like proteins can have mutations at positions 132, 190, 194, 197, or combinations thereof. In some cases, the positions of mutations can be at one position on either side of positions 132, 190, 194, or 197. Examples of mutations in *Solanum lycopersicum* MYC2-like proteins include mutations such as D132N, E190K, M197A, L194A, and combinations thereof. Thus modified MYC proteins described herein have less than 100% sequence identity to SEQ ID NO: 19 and/or to SEQ ID NO:20.

In other examples, such a *Solanum lycopersicum* MYC2-like protein can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a *Solanum lycopersicum* protein, shown below as SEQ ID NO:21, where the JAZ-interacting domain (JID) is shown in bold and with underlining.

```
  1 MTDYRLWSNT NTTNTCDDTM MMDSFLSSDP SSFWPASTPN

41 RPTPVNGVGE TMPFFNQESL QQRLQALIDG ARESWAYAIF

81 WQSSVVDFAS QTVLGWGDGY YKGEEDKNKR RGSSSSAANF

121 VAEQEHRKKV LRELNSLISG VQASAGNGTD DAVDEEVTDT

161 EWFFLISMTQ SFVNGNGILPG LAMYSSSPIW VTGTEKLAAS

201 QCERARQAQG FGLQTIVCIP SPESREILNF GDSSKRFSGQ

241 SQLGPGPGLM EENKNENKNK KRSLGSRGNN EEGMLSFVSG

281 VILPTSTMGK SGDSDHSDLE ASVVKEAVVE PEKKPRKGR

321 KPANGREEPL NHVEAERQRR EKLNQRFYEL RSQIECLRKE

361 LTNKGSSNYS ASPPLNQDVK IVDMDIDVKV IGWDAMIRIQ
```

```
401 CSKKNHPAAR LMAALKDLDL DVHHASVSVV NDLMIQQATV

441 KMGSRLYAQE QLRIALTSKI AESR
```

The JAZ-interacting domain (JID) of the *Solanum lycopersicum* MYC-related protein sequence having SEQ ID NO:21 is shown below as SEQ ID NO:22.

```
 81        FAS QTVLGWGDGY YKGEEDKNKR RGSSSSAANF

121 VAEQEHRKKV LRELNSLISG V
```

In some cases, the *Solanum lycopersicum* MYC-related protein with SEQ ID NO:21 can have one or more mutations within the JID, and/or one or more mutations outside of the JID region. For example, such *Solanum lycopersicum* MYC-related proteins can have mutations at positions 98, 161, 165, 168, or combinations thereof. In some cases, the positions of mutations can be at one position on either side of positions 98, 161, 165, or 168. Examples of mutations in *Solanum lycopersicum* MYC2-like proteins include mutations such as D98N, E161K, M168A, L165A, and combinations thereof. Thus modified MYC proteins described herein have less than 100% sequence identity to SEQ ID NO:21 and/or to SEQ ID NO:22.

An example of another MYC-related protein is a *Solanum tuberosum* MYC protein, shown below as SEQ ID NO:23, where the JAZ-interacting domain (JID) is shown in bold and with underlining.

```
  1 MTEYSLPTMN LWNNSTSDDN VSMMEAFMSS DLSFWATTNS

41 TTTNSASAAV VGVNSNLLHT NNNNPSVFPL SSSTSVSAAA

81 AVDATKSMPF FNQETLQQRL QALIDGARET WTYAIFWQSS

121 VVDFSSPSVL GWGDGYYKGE EDKAKRKLAV SSPAYIAEQE

161 HRKXVLRELN SLISGAPAGT DDAVDEEVTD TEWFFLiSMT

201 QSFVNGSGLP GQALYSSSPI WVAGTEKLAA SHCERVRQAQ

241 GFGLQTIVCI PSANGVVELG STELIVESSD LMNKVRVLFN

281 FSNDLGSGSW AVQPESDPSA LWLTEPSSSG MEVRESLNTV

321 QTNSVPSSNS NKQIAYANEN NHQSGNGQSC YNLQQQQNNP

361 PQQQTQGFFT RELNFSEFGF DGSSNRNGNA SLSCKPESGE

401 ILNFGDSTKK SASSANVNLF TGQSQFGAVE ENNNNKNKKR

441 SATSRGSNEE GMLSFVSGTV LPSSGMKSGG GGGEDSEHSD

481 LEASVVKEAD SSRVVEPEKR PRKRGRKPAN GREEPLNHVE

521 AERQRREKLN QRFYALRAMV PNVSKMDKAS LLGDAISYIN

561 ELKSKLQNTE SDKEDLKSQI EDLKKESRRP GPPPPNQDLK

601 IGGKIVDVDI DVKJIGWDAM IGIQCNKKNE PAARLMAALM

641 ELDLDVHHAS VSVVNDLMIQ QATVKMGSRH YTEEQLRVAL

681 KSKIAETPLE SR
```

The JAZ-interacting domain (JID) of the *Solanum tuberosum* MYC protein sequence having SEQ ID NO:23 is shown below as SEQ ID NO:24.

```
121     FSSPSVL GWGDGYYKGE EDKAKRKLAV SSPAYIAEQE

161 HRKKVLRELN SLISGA
```

In some cases, the *Solanum tuberosum* MYC protein with SEQ ID NO:23 can have one or more mutations within the JID, and/or one or more mutations outside of the JID region. Thus modified MYC proteins described herein have less than 1000/sequence identity to SEQ ID NO:23 and/or to SEQ ID NO:24.

For example, such a *Solanum tuberosum* MYC protein with SEQ ID NO:23 can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Solanum tuberosum* MYC protein can vary from those in the corresponding *Arabidopsis thaliana* MYC2 protein by 1-10 positions.

An example of another MYC-related protein is a *Solanum tuberosum* MYC protein, shown below as SEQ ID NO:25, where the JAZ-interacting domain (JID) is shown in bold and with underlining.

```
  1 MTDYRLWSNS NTTNTSDDNM MMDAFLSSDP SSFWPNRTSI

41 SPTPVNGGVG ETMPFFNQES LQQRLQALID GARESWAYAI

81 FWQSSSTSDF ATPSVLGWGD GYYKGEENKN KRRASSSSTN

121 EVAEQEHRKK VLRELNSLIS GVQATGAGSG GDDAVDEEVT

161 DTEWFFLISM TQSFANGNGL PGLAMYSSSP IWVTGTEKLA

201 GSQCERARQA QGFGLQTIVC IPSANGVVEL GSTELIFESS

241 DLMNKVKYLF NFNIDMGSVT GSGSGSCAVH PEPDPSALWL

281 TDPSSSVVEA KDSLINSSSR DVQLVFGNEN SENGTQNQQH

321 SQQTQGFFTK ELNFSGYGFD GSSTRNKNGN SSISCKPETR

361 EILNFGDSSK KSGSLFSGQS QFGPGTGLGL MEENKNNNKK

401 RSLASRGNNE KGMLSFVSGV ILPTSTMGKS GGGGNFDHSD

441 LEASVVKEAI VEPERKPRKR GRKPANGREE PLNHVEAERQ

481 RREKLNQRFY ALRAVVPNVS KMDKASLLGD AIAYINELKS

521 KVQNSDLDKE ELRSQIESLR KELANKGSSN YSSSPPSNQD

561 LKIVDMDIDV KVIGWDAMIR IQCSKKNHPA ARLMAALKDL

601 DLDVHHASVS VVNDLMIQQA TVKMGSRLYA QEQLTIALTS

641 KFAESR
```

The JAZ-interacting domain (JID) of the *Solanum tuberosum* MYC protein sequence having SEQ ID NO:25 is shown below as SEQ ID NO:26.

```
 81       F ATPSVLGWGD GYYKGEENKN KRRASSSSTN

121 FVAEQEHRKK VLRELNSLIS GV
```

In some cases, the *Solanum tuberosum* MYC protein with SEQ ID NO:25 can have one or more mutations within the JID, and/or one or more mutations outside of the JID region. Thus modified MYC proteins described herein have less than 100% sequence identity to SEQ ID NO:25 and/or to SEQ ID NO:26.

An example of another MYC-related protein is a *Catharanthus roseus* MYC2 protein, shown below as SEQ ID NO:27, where the JAZ-interacting domain (JID) is shown in bold and with underlining.

```
  1 MTDYRLQPKM NLWGTTTNTA ASPIITSDDN SSMMEAFMTS
 41 SDPISLWPPS MSVNHHHPPT PTSSAVTTAV DSAKSMPAQP
 81 AFFNQENLQQ RLQTLIDGAR ESWTYAIFWQ SSVVEFAGPS
121 VLGWGDGYYK GEEDKGKRKN SSSASSFAEQ EHRKKVLREL
161 NSLIAGPQGT ADDAVDEEVT DTEWFFLISM TQSFVSGSGL
201 PGQALYNSNP VWVTGAGRLA VSHCDRARQA QSFGLQTLVC
241 IPSANGVVEL GSTELIFQSS DLMNKVRILF NFNNIDLGSS
281 SGPWPENDPS SLWLTDPSPS GVGVKEGVNT NNNTSVQGNS
321 IPSGNKQQLV FGNNDNHPTT STLTDHPGAG AVNSYNNSSQ
361 NAQQPQGSFF TRELNFSEYG FERSSVKNGN CKPESGEILN
401 FGGESVTKKN SVSGNGNLFS VQSQFGAGEE NKNKKRPSPV
441 SRGSNDEGML SFTSGVVLPS TGVVKSSGGG GGGDSDHSDL
481 EASVVKEAES SRVVDPEKRP RKRGRKPANG REEPLNHVEA
521 ERQRREKLNQ RFYALRAVVP NVSKMDKASL LGDAISYINE
561 LKAKLQTTET DKDELKNQLD SLKKELASKE SRLLSSPDQD
601 LKSSNKQSVG NLDMDIDVKI IGREAMIRVQ SSKNNHPAAR
641 VMGALKDLDL ELLHASVSVV NDLMIQQNTV RMGSRFYTQE
681 QLRIALTSRI AGNSMRLLV
```

A comparison of the *Catharanthus roseus* MYC2 protein sequence having SEQ ID NO:27 with the MYC2 protein sequence having SEQ ID NO: 1 is shown below.

```
54.1% identity in 693 residues overlap; Score: 1363.0; Gap frequency: 10.7%
UserSeq1    1 MTDYRLQPTMNLW------------TTDDNASMMEAFMSSSDISTLWPRAST-------T
UserSeq27   1 MTDYRLQPKMNLWGTTTNTAASPITTSDDNSSMMEAFMTSSDPISLWPPSMSVNHHHPPT
              ******** ****   * *** ******* ***    ****              *

UserSeq1   42 TTTATTETTPTPAMEIPAQ-AGFNQETLQQRLQALIEGTHEGWTYAIFWQPSY-DFSGAS
UserSeq27  61 PTSSAVTTAVDSAKSMPAQPAFFNQENLQQRLQTLIDGARESWTYAIFWQSSVVEFAGPS
                *     *       *** *  **** ****** ** *  * ********  *   * *

UserSeq1  100 VLGWGDGYYKGEEDKANPRRRSSSPPFSTPADQEYRKKVLRELNSLISGGVAPSDDAVDE
UserSeq27 121 VLGWGDGYYGEEDKGKRKNSSSASSF---AEQEHRKKVLRELNSLIAGPQGTADDAVDE
              **************       **   *    * ** ************* *      ******

UserSeq1  160 EVTDTEWFFLVSMTQSFACGAGLAGKAFATGNAVWVSGSDQLSGSGCERKQGGVFGMHT
UserSeq27 178 EVTDTEWFFLISMTQSFVSGSGLPGQALYNSNPVWVTGAGRLAVSHCDRARQAQSFGLQT
              ********** ******  * **   *    *  *** *   *   *   **  ** *

UserSeq1  220 IACIPSANGVVEVGSTEPIRQSSDLINKVRILFNFDG-GAGDLSGLNWNLDPDQ-GENDP
UserSeq27 238 LVCIPSANGVVELGSTELIFQSSDLMNKVRILFNFNNIDLGSSSGPWPENDPSSLWLTDP
                ********** ****  * ***** ******** *   *          **     **

UserSeq1  278 S---MWINDPIGTPGSNE-PGNGAPSSSSQLFSKSIQFENGSSSTITENPNLDPTPSPVH
UserSeq27 298 SPSGVGVKEGVNTNNNTSVQGNSIPSGNKQQLVFGNNDHPTTSTLTDHPGAGAVNSYNN
                 *          *  ** **  *         **  *      ** *   *

UserSeq1  334 S-QTQNPKFNNTFSRELNES-------TSSSTLVKPRSGEILNFGDEG--KRSSGNPDPS
UserSeq27 358 SSQNAQQPQGSFFTRELNFSEYGFERSSVKNGNCKPESGEILNFGGESVTKKNSVSGNGN
               * *      *  ******              ** ********    *   *

UserSeq1  384 SYSGQTQE----ENKRKR-----SMVLNEDKVLSF---------------GDKTAGESDH
UserSeq27 418 LFSVQSQFGAGEENKNKKRPSPVSRGSNDEGMLSFTSGVVLPSTGVVKSSGGGGGGDSDH
              * * **    *** *        *    *   ***            *   * ***

UserSeq1  420 SDLEASVVKE------VAVEKRPKKRGRKPANGREEPLNHVEAERQRREKLNQRFYALRA
UserSeq27 478 SDLEASVVKEAESSRVVDPEKPRPKRGRKPANGREEPLNHVEAERQRREKLNQRFYALRA
              **********      *  ****  *********************************

UserSeq1  474 VVPNVSKMDKASLLGDAIAYINELKSKVVKTESEKLQIKNQLEEVKLELAGRKA---SAS
UserSeq27 538 VVPNVSKMDKASLLGDAISYINELKAKLQTTETDKDELKNQLDSLKKELASKESRLLSSP
              ****************** ****** *   ***  * *****    **** *      *

UserSeq1  531 GGDM-SSSCSSIKPVGMEIEVKIIGWDAMIRVESSKRNHPAARLMSALMDLELEVNHASM
UserSeq27 598 DQDLKSSNKQVGNLDMDIDVKIIGREAMIRVQSSKNNHPAARVMGALKDLDLELLHASV
                **  *      *   * *****  ***** *** ****** * ** ** **  ***

UserSeq1  590 SVVNDLMIQQATVKMGFRIYTQEQLRASLISKI
UserSeq27 658 SVVNDLMIQQNTVRMGSRFYTQEQLRIALTSRI
              ********** ** ** * *******  * * *
```

The JAZ-interacting domain (JID) of the *Catharanthus roseus* MYC2 protein sequence having SEQ ID NO:27 is shown below as SEQ ID NO:28.

```
 81                                              FAGPS
121 VLGWGDGYYK GEEDKGKRKN SSSASSFAEQ EHRKKVLREL
161 NSLIAG
```

In some cases, the *Catharanthus roseus* MYC protein with SEQ ID NO:27 can have one or more mutations within the JID, and/or one or more mutations outside of the JID region. Thus modified MYC proteins described herein have less than 100% sequence identity to SEQ ID NO:27 and/or to SEQ ID NO:28.

For example, such a *Catharanthus roseus* MYC protein with SEQ ID NO:27 can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Catharanthus roseus* MYC protein can vary from those in the corresponding *Arabidopsis thaliana* MYC2 protein by 1-10 positions.

PhyB and Modifications of PhyB to Enhance Growth

Although jasmonate and MYC transcription factors are potent activators of defense responses, the jasmonate hormone is also a potent inhibitor of plant growth. Plants cells in which the jasmonate pathway and MYC transcription factors are activated exhibit slow growth and low yield. For example, treatment of taxus cells with exogenous jasmonate is currently used to boost taxol production, but the downside of such treatment is that such cells stop dividing and growing. Also, plants having the dominant atr2D mutant of MYC3 (a D94N missense mutation in the JAZ-interacting domain (JID)) grow very slowly. Hence even if expression of such MYC3 proteins can relieve repression by JAZ proteins and improve the environmental stress resistance of plants, use of such an atr2D mutation by itself may not be particularly useful.

The PhyB gene encodes a regulatory photoreceptor protein (Phytochrome B (PHYB)) that exists in two forms. The two forms are reversibly interconvertible by light, where a Pr form absorbs maximally in the red region of the spectrum and where a Pfr form absorbs maximally in the far-red region. As described herein phyB gene mutations improve plant growth, for example, in myc mutant plants that have increased resistance to environmental challenges such as insects. Plant cells, plants, and seeds from selected plant species can be modified to have loss-of-function phyB mutations to improve cell growth.

One example of an *Arabidopsis thaliana* phytochrome B (PHYB) protein sequence is shown below (SEQ ID NO:30). The codon encoding the arginine (R) at position 322 that is highlighted (in bold and with underlining) is replaced by a termination signal (TGA) in some of the mutant phyB plant lines described herein that have improved plant growth. This genetic mutation in such a mutant phyB is a C→T substitution, causing the arginine codon (CGA) to become a termination codon (TGA). Hence, mutant phyB plant lines with phyB loss of function mutations (e.g., deletions) exhibit improved plant growth, for example, when present in a mutant jaz genetic background.

```
   1 MVSGVGGSGG GRGGGRGGEE EPSSSHTPNN RRGGEQAQSS
  41 GTKSLRPRSN TESMSKAIQQ YTVDARLHAV FEQSGESGKS
  81 FDYSQSLKTT TYGSSVPEQQ ITAYLSRIQR GGYIQPFGCM
 121 IAVDESSFRI IGYSENAREM LGIMPQSVPT LEKPEILAMG
 161 TDVRSLFTSS SSILLERAFV AREITLLNPV WIHSKNTGKP
 201 FYAILHRIDV GVVIDLEPAR TEDPALSIAG AVQSQKLAVR
 241 AISQLQALPG GDIKLLCDTV VESVRDLTGY DRVMVYKFHE
 281 DEHGEVVAES KRDDLEPYIG LHYPATDIPQ ASRFLFKQNR
 321 VRMIVDCNAT PVLVVQDDRL TQSMCLVGST LRAPHGCHSQ
 361 YMANMGSIAS LAMAVIINGN EDDGSNVASG RSSMRLWGLV
 401 VCHHTSSRCI PFPLRYACEF LMQAFGLQLN MELQLALQMS
 441 EKRVLRTQTL LCDMLLRDSP AGIVTQSPSI MDLVKCDGAA
 481 FLYHGKYYPL GVAPSEVQIK DVVEWLLANH ADSTGLSTDS
 521 LGDAGYPGAA ALGDAVCGMA VAYITKRDFL FWFRSHTAKE
 561 IKWGGAKHHP EDKDDGQRMH PRSSFQAFLE VVKSRSQPWE
 601 TAEMDAIHSL QLILRDSFKE SEAAMNSKVV DGVVQPCRDM
 641 AGEQGIDELG AVAREMVPLI ETATVPIFAV DAGGCINGWN
 681 AKIAELTGLS VEEAMGKSLV SDLIYKENEA TVNKLLSRAL
 721 RGDEEKNVEV KLKTFSPELQ GKAVFVVVNA CSSKDYLNNI
 761 VGVCFVGQDV TSQKIVMDKF INIQGDYKAI VHSPNPLIPP
 801 IFAADENTCC LEWNMAMEKL TGWSRSEVIG KMIVGEVFGS
 841 CCMLKGPDAL TKFMIVLHNA IGGQDTDKFP FPFFDRNGKF
 881 VQALLTANKR VSLEGKVIGA FCFLQIPSPE LQQALAVQRR
 921 QDTECFTKAK ELAYICQVIK NPLSGMRFAN SLLEATDLNE
 961 DQKQLLETSV SCEKQISRIV GDMDLESIED GSFVLKREEF
1001 FLGSVINAIV SQAMFLLRDR GLQLIRDIPE EIKSIEVFGD
1041 QIRIQQLLAE FLLSIIRYAP SQEWVEIHLS QLSKQMADGF
1081 AAIRTEFRMA CPGEGLPPEL VRDMFHSSRW TSPEGLGLSV
1121 CRKILKLMNG EVQYIRESER SYFLIILELP VPRKRPLSTA
1151 SGSGDMMLMM PY
```

A chromosomal DNA sequence for the *Arabidopsis thaliana* phytochrome B (PHYB) protein with SEQ ID NO:30 is shown below as SEQ ID NO:31.

```
   1 CTTCAATTTA TTTTATTGGT TTCTCCACTT ATCTCCGATC
  41 TCAATTCTCC CCATTTTCTT CTTCCTCAAG TTCAAAATTC
  81 TTGAGAATTT AGCTCTAGCA GAATTCGTCT CCGATAACTA
 121 GTGGATGATG ATTCACCCTA AATCCTTCCT TGTCTCAAGG
 161 TAATTCTGAG AAATTTCTCA AATTCAAAAT CAAACGGCAT
 201 GGTTTCCGGA GTCGGGGGTA GTGGCGGTGG CCGTGGCGGT
 241 GGCCGTGGCG GAGAAGAAGA ACCGTCGTCA AGTCACACTC
 281 CTAATAACCG AAGAGGAGGA GAACAAGCTC AATCGTCGGG
```

```
 321 AACGAAATCT CTCAGACCAA GAAGCAACAC TGAATCAATG
 361 AGCAAAGCAA TTCAACAGTA CACCGTCGAC GCAAGACTCC
 401 ACGCCGTTTT CGAACAATCC GGCGAATCAG GGAAATCATT
 441 CGACTACTCA CAATCACTCA AAACGACGAC GTACGGTTCC
 481 TCTGTACCTG AGCAACAGAT CACAGCTTAT CTCTCTCGAA
 521 TCCAGCGAGG TGGTTACATT CAGCCTTTCG GATGTATGAT
 561 CGCCGTCGAT GAATCCAGTT TCCGGATCAT CGGTTACAGT
 601 GAAAACGCCA GAGAATGTT AGGGATTATG CCTCAATCTG
 641 TTCCTACTCT TGAGAAACCT GAGATTCTAG CTATGGGAAC
 681 TGATGTGAGA TCTTGTTCA CTTCTTCGAG CTCGATTCTA
 721 CTCGAGCGTG CTTTCGTTGC TCGAGAGATT ACCTTGTTAA
 761 ATCCGGTTTG GATCCATTCC AAGAATACTG GTAAACCGTT
 801 TTACGCCATT CTTCATAGGA TTGATGTTGG TGTTGTTATT
 841 GATTTAGAGC CAGCTAGAAC TGAAGATCCT GCGCTTTCTA
 881 TTGCTGGTGC TGTTCAATCG CAGAAACTCG CGGTTCGTGC
 921 GATTTCTCAG TTACAGGCTC TTCCTGGTGG AGATATTAAG
 961 CTTTTGTGTG ACACTGTCGT GGAAAGTGTG AGGGACTTGA
1001 CTGGTTATGA TCGTGTTATG GTTATAAGT TTCATGAAGA
1041 TGAGCATGGA GAAGTTGTAG CTGAGAGTAA ACGAGATGAT
1081 TTAGAGCCTT ATATTGGACT GCATTATCCT GCTACTGATA
1121 TTCCTCAAGC GTCAAGGTTC TTGTTTAAGC AGAACCGTGT
1161 CCGAATGATA GTAGATTGCA ATGCCACACC TGTTCTTGTG
1201 GTCCAGGACG ATAGGCTAAC TCAGTCTATG TGCTTGGTTG
1241 GTTCTACTCT TAGGGCTCCT CATGGTTGTC ACTCTCAGTA
1281 TATGGCTAAC ATGGGATCTA TTGCGTCTTT AGCAATGGCG
1321 GTTATAATCA ATGGAAATGA AGATGATGGG AGCAATGTAG
1361 CTAGTGGAAG AAGCTCGATG AGGCTTTGGG GTTTGGTTGT
1401 TTGCCATCAC ACTTCTTCTC GCTGCATACC GTTTCCGCTA
1441 AGGTATGCTT GTGAGTTTTT GATGCAGGCT TTCGGTTTAC
1481 AGTTAAACAT GGAATTGCAG TTAGCTTTGC AAATGTCAGA
1521 GAAACGCGTT TTGAGAACGA AGACACTGTT ATGTGATATG
1561 CTTCTGCGTG ACTCGCCTGC TGGAATTGTT ACACAGAGTC
1601 CCAGTATCAT GGACTTAGTA AAATGTGACG GTGCAGCATT
1641 TCTTTACCAC GGGAAGTATT ACCCGTTGGG TGTTGCTCCT
1681 AGTGAAGTTC AGATAAAGA TGTTGTGGAG TGGTTGCTTG
1721 CGAATCATGC GGATTCAACC GGATTAAGCA CTGATAGTTT
1761 AGGCGATGCG GGGTATCCCG GTGCAGCTGC GTTAGGGGAT
1801 GCTGTGTGCG GTATGGCAGT TGCATATATC ACAAAAAGAG
1841 ACTTTCTTTT TTGGTTTCGA TCTCACACTG CGAAAGAAAT
1881 CAAATGGGGA GGCGCTAAGC ATCATCCGGA GGATAAAGAT

1921 GATGGGCAAC GAATGCATCC TCGTTCGTCC TTTCAGGCTT
1961 TTCTTGAAGT TGTTAAGAGC CGGAGTCAGC CATGGGAAAC
2001 TGCGGAAATG GATGCGATTC ACTCGCTCCA GCTTATTCTG
2041 AGAGACTCTT TTAAAGAATC TGAGGCGGCT ATGAACTCTA
2081 AAGTTGTGGA TGGTGTGGTT CAGCCATGTA GGGATATGGC
2121 GGGGGAACAG GGGATTGATG AGTTAGGTGC AGTTGCAAGA
2161 GAGATGGTTA GGCTCATTGA GACTGCAACT GTTCCTATAT
2201 TCGCTGTGGA TGCCGGAGGC TGCATCAATG GATGGAACGC
2241 TAAGATTGCA GAGTTGACAG GTCTCTCAGT TGAAGAAGCT
2281 ATGGGGAAGT CTCTGGTTTC TGATTTAATA TACAAAGAGA
2321 ATGAAGCAAC TGTCAATAAG CTTCTTTCTC GTGCTTTGAG
2361 AGGTATATTC AGTTCTTCAG CTATGTTGTA TCTGCGGTGT
2401 ATATACCAAT TCGCGGGTAT TTGATTATTT TGTTGCATTT
2441 GGCAATGCAG GGGACGAGGA AAAGAATGTG GAGGTTAAGC
2481 TGAAAACTTT CAGCCCCGAA CTACAAGGGA AAGCAGTTTT
2521 TGTGGTTGTG AATGCTTGTT CCAGCAAGGA CTACTTGAAC
2561 AACATTGTCG GCGTTTGTTT TGTTGGACAA GACGTTACTA
2601 GTCAGAAAAT CGTAATGGAT AAGTTCATCA ACATACAAGG
2641 AGATTACAAG GCTATTGTAC ATAGCCCAAA CCCTCTAATC
2681 CCGCCAATTT TGCTGCTGA CGAGAACACG TGCTGCCTGG
2721 AATGGAACAT GGCGATGGAA AAGCTTACGG GTTGGTCTCG
2761 CAGTGAAGTG ATTGGGAAAA TGATTGTCGG GGAAGTGTTT
2801 GGGAGCTGTT GCATGCTAAA GGGTCCTGAT GCTTTAACCA
2841 AGTTCATGAT TGTATTGCAT AATGCGATTG GTGGCCAAGA
2881 TACGGATAAG TTCCCTTTCC CATTCTTTGA CCGCAATGGG
2921 AAGTTTGTTC AGGCTCTATT GACTGCAAAC AAGCGGGTTA
2961 GCCTCGAGGG AAAGGTTATT GGGGCTTTCT GTTTCTTGCA
3001 AATCCCGAGC CCTGAGCTGC AGCAAGCTTT AGCAGTCCAA
3041 CGGAGGCAGG ACACAGAGTG TTTCACGAAG GCAAAAGAGT
3081 TGGCTTATAT TTGTCAGGTG ATAAAGAATC CTTTGAGCGG
3121 TATGCGTTTC GCAAACTCAT TGTTGGAGGC CACAGACTTG
3161 AACGAGGACC AGAAGCAGTT ACTTGAAACA AGTGTTTCTT
3201 GCGAGAAACA GATCTCAAGG ATCGTCGGGG ACATGGATCT
3241 TGAAAGCATT GAAGACGGGT GAGTATAGTT AGAATTTATC
3281 TAGAAGCTAG TTTTGCTTAC TTCACAAAAT GTGACCAAAT
3321 CCCAAATTTT GTTTTTTCA TTGATCAGTT CATTTGTGCT
3361 AAAGAGGGAA GAGTTTTTCC TTGGAAGTGT CATAAACGCG
3401 ATTGTAAGTC AAGCGATGTT CTTATTAAGG GACAGAGGTC
3441 TTCAGCTGAT CCGTGACATT CCCGAAGAGA TCAAATCAAT
3481 AGAGGTTTTT GGAGACCAGA TAAGGATTCA ACAGCTCCTG
3521 GCTGAGTTTC TGCTGAGTAT AATCCGGTAT GCACCATCTC
```

```
3561 AAGAGTGGGT GGAGATCCAT TTAAGCCAAC TTTCAAAGCA

3601 AATGGCTGAT GGATTCGCCG CCATCCGCAC AGAATTCAGG

3641 TACATTTCAT TGTTCCCGCT GTTGTCTCCA CATATCCATA

3681 ACCAAAATTA TGCAATCCGG TTTTTTTGGT TCCTTATTTT

3721 GTACATAAAG AAAATGAATT TGGTTTGGTT AATTACGAAT

3761 TTGATTTAGG CGTTTAAAGA ATTTGAGGTT TTAACCAATT

3801 CACTATTTGT TTTGGTTATT GTTTAGTTGG AACCTAGATT

3841 AGTTTGATTT TTGTATTCGG TTTAGTCGAC TTGGGAACTT

3881 TTAGACACAT CCATAGGCCT AGAATTAGCA GTCAAGGAAT

3921 GTAATGTTTT CAAATTGATG AAAACCAGCT CAAAAGTGTA

3961 AAACTTGGGT TTCATGTGTT GGTGTCTTTG TTATGTCTTT

4001 ATTCGTTGTT TGCAGAATGG CGTGTCCAGG TGAAGGTCTG

4041 CCTCCAGAGC TAGTCCGAGA CATGTTCCAT AGCAGCAGGT

4081 GGACAAGCCC TGAAGGTTTA GGTCTAAGCG TATGTCGAAA

4121 GATTTTAAAG CTAATGAACG GTGAGGTTCA ATACATCCGA

4161 GAATCAGAAC GGTCCTATTT CCTCATCATT CTGGAACTCC

4201 CTGTACCTCG AAAGCGACCA TTGTCAACTG CTAGTGGAAG

4241 TGGTGACATG ATGCTGATGA TGCCATATTA GTCACACTTC

4281 AGTTGGTATG AGAGTTTGTA TCATTGTATG AGTGTTTGTG

4321 TGTCTAACGA CGTCGGAGGA GGATAGAAAG TTTTTTTTTT

4361 GTTTCCGGTG AGATTAGTAG AGAAGAGGGA GATTATTTGC

4401 GTTCAGCTCA GCTCGCCGGA AAAAAACGT  AACAGTAGTT

4441 GTAGAGAATT TCAAGACTTT TGTTTGTGCT GTGTAAATTG

4481 ACAACTCCGA GAGAAACAAA ACAATGAGAT AAGAAGAGAG

4081 CATATTAATC GATGACCAAT CCTTTTAATT
```

Chromosomal sequences that encode phytochrome B and/or phytochrome B-related polypeptides from many plant types and species can be modified to reduce or eliminate the expression and/or function of the encoded polypeptide. For example, chromosomal sequences encoding phytochrome B and/or phytochrome B-related polypeptides from agriculturally important plants such as alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of one or more encoded phytochrome B and/or phytochrome B-related polypeptides.

In some cases, more than one gene or chromosomal segment encoding a phytochrome B and/or phytochrome B-related polypeptide can be modified to reduce or eliminate the expression and/or function of the encoded protein(s).

The following are examples of "phytochrome B-related" proteins and nucleic acids that can be modified to reduce or eliminate the expression and/or function thereof, and thereby generate plants with improved growth.

An uncharacterized *Zea mays* protein referred to as LOC100383702 (NCBI accession no. NP_001169810.1 (GI: 293335473) has significant sequence identity to the *Arabidopsis thaliana* PHYB protein with SEQ ID NO:30, as illustrated by the sequence comparison shown below. Domains of sequence homology are identified by asterisks below the sequence comparisons.

```
73.1% identity in 1139 residues overlap; Score: 4271.0; Gap
frequency: 0.9%
Seq30    22 PSSSHTPNNRRGGEQAQSSGTKSLRPRSNTESMSKAIQQYTVDARLHAVFEQSGESGKSF
Seq32    18 PEAPRHAHHHHHSQSSGGSTSRAGGGAAATESVSKAVAQYTLDARLHAVFEQSGASGRSF
            *                *         *** ***  *** ************ **
            **

Seq30    82 DYSQSLKTTTYGSSVPEQQITAYLSRIQRGGYIQPFGCMIAV-
             DESSFRIIGYSENAPEM
Seq32    78 DYSQSLRAPPTPSS--
             EQQIAAYLSRIQRGGHIQPFGCTLAVADDSSFRLLAFSENSPDL
            ******        **  **** ********** ****** ** * ****    ***

Seq30   141 LGIMPQ-SVPTLEK--
             PEILAMGTDVRSLFTSSSSILLERAFVAREITLLNPVWIHSKNT
Seq32   136 LDLSPHHSVPSLDSSAPPHVSLGADARLLFSPSSAVLLERAFAAREISLLNPIWIHSRVS
            *  *   *** *    *       * *  ** **  ******* ****  **** ****

Seq30   198 GKPFYAILHRIDVGVVIDLEPARTEDPALSIAGAVQSQKLAVRAISQLQALPGGDIKLLC
Seq32   196 SKPFYAILHRIDVGVVIDLEPARTEDPALSIAGAVQSQKLAVRAISRLQALPGGDVKLLC
             *********************************************** ********** ********
            ****

Seq30   258 DTVVESVRDLTGYDRVMVYKFHEDEHGEVVAESKRDDLEPYIGLHYPATDIPQASRFLFK
Seq32   256 DTVVEHVRELTGYDRVMVYRFHEDEHGEVVAESRRDNLEPYLGLHYPATDIPQASRFLFR
            ***** ** ********** *************  ** **** ****************

Seq30   318 QNRVRMIVDCNATPVLVVQDDRLTQSMCLVGSTLRAPHGCHSQYMANMGSIASLAMAVII
Seq32   316 QNRVRMIADCHATPVRVIQDPGLSQPLCLVGSTLRAPHGCHAQYMANMGSIASLVMAVII
            ******* ** **** * ** *  *   ************** ************* ********
            *****
```

```
Seq30   378  NGNEDDGSNVASGRSS-
             MRLWGLVVCHHTSSRCIPFPLRYACEFLMQAFGLQLNMELQLA
Seq32   376  SSGGDDEQTGRGGISSAMKLWGLVVCHHTSPRCIPFPLRYACEFLMQAFGLQLNMELQLA
                  **      *  **  * **********
                            ******************************

Seq30   437  LQMSEKRVLRTQTLLCDMLLRDSPAGIVTQSPSIMDLVKCDGAAFLYHGKYYPLGVAPSE
Seq32   436  HQLSEKHILRTQTLLCDMLLRDSPTGIVTQSPSIMDLVKCDGAALYYHGKYYPLGVTPTE
              * ***  ****************** ******************** ********** **

Seq30   497  VQIKDVVEWLLANHADSTGLSTDSLGDAGYPGAAALGDAVCGMAVAYITKRDFLFWFRSH
Seq32   496  SQIKDIIEWLTVFHGDSTGLSTDSLADAGYLGAAALGEAVCGMAVAYITPSDYLFWFRSH
              ****  ***  *  * ********* ****  ******* **********    *
              *******

Seq30   557  TAKEIKWGGAKHHPEDKDDGQRMHPRSSFQAFLEVVKSRSQPWETAEMDAIHSLQLILRD
Seq32   556  TAKEIKWGGAKHHPEDKDDGQRMHPRSSFKAFLEVVKSRSLPWENAEMDAIHSLQLILRD
             ****************************  ********** *** **************
             ***************

Seq30   617  SFKES-
             EAAMNSKVVDGVVQPCRDMAGEQGIDELGAVAREMVRLIETATVPIFAVDAGGC
Seq32   616  SFRDAAEGTNNSKAIVNGQVQLRELE-
             LRGINELSSVAREMVRLIETATVPIFAVDTDGC
             **   *   ***        *     ** **  ********************
             **

Seq30   676  INGWNAKIAELTGLSVEEAMGKSLVSDLIYKENEATVNKLLSRALRGDEEKNVEVKLKTF
Seq32   675  INGWNAKIAELTGLSVEEAMGKSLVNDLIFKESEATVEKLLSRALRGEEDKNVEIKLKTF
             ************************* *** *** ***** *********** *  **** ****
             *****

Seq30   736  SPELQGKAVFVVVNACSSKDYLNNIVGVCFVGQDVTSQKIVMDKFINIQGDYKAIVHSPN
Seq32   735  GSEQSKGPIFVVVNACSSRDYTQNIVGVCFVGQDVTGQKVVMDKFVNIQGDYKAIVHNPN
              *    *  ********* **  *********** *** ****** ************* ***
              **

Seq30   796  PLIPPIFAADENTCCLEWNMAMEKLTGWSRSEVIGKMIVGEVFGSCCMLKGPDALTKFMI
Seq32   795  PLIPPIFASDENTSCSEWNTAMEKLTGWSRGEVVGKFLIGEVFGNCCRLKGPDALTKFMV
             ********  ****  * *** ***********  ** ***   ******   ***********

Seq30   856  VLHNAIGGQDTDKFPFPFFDRNGKFVQALLTANKRVSLEGKVIGAFCFLQIPSPELQQAL
Seq32   855  IIHNAIGGQDYEKFPFSFFDKNGKYVQALLTANTRSKMDGKSIGAFCFLQIASTEIQQAF
              ********   **** *** ***  ********  *      ** ********  *  *   *  *

Seq30   916  AVQRRQTECFTKAKELAYICQVIKNPLSGMRFANSLLEATDLNEDQKQLLETSVSCEKQ
Seq32   915  EIQRQQEKKCYARMKELAYICQEIKNPLSGIRFTNSLLQMTDLNDDQRQFLETSSACEKQ
              ** *  *     ** ******** ******* ***  ** **** ** *** *****
              ****

Seq30   976  ISRIVGDMDLESIEDGSFVLKREEFFLGSVINAIVSQAMFLLRDRGLQLIRDIPEEIKSI
Seq32   975  MSKIVKDASLQSIEDGSLVLEQSEFSLGDVMNAVVSQAMLLLRERDLQLIRDIPDEIKDA
              * **  *   ********* *   ** ** *  *  ********* ***  ********** ***

Seq30   1036 EVFGDQIRIQQLLAEFLLSIIRYAPSQE-
             WVEIHLSQLSKQMADGFAAIRTEFRMACPGE
Seq32   1035 SAYGDQCRIQQVLADFLLSMVRSAPSENGWVEIQVRPNVKQNSDGTNTELFIFRFACPGE
                *** ****  ** **** * *  ***    * * **   **           *    *****
                *****

Seq30   1095 GLPPELVRDMFHSSRWTSPEGLGLSVCRKILKLMNGEVQIRESERSYFLIILELPVPR
Seq32   1095 GLPADVVQDMFSNSWSTQEGVGLSTCRKILKLMGGEVQYIRESERSFFLIVLEQPQPR
             ***    * ***    *  ** *** *** ********** ********* *** ** *
             **
```

This PHYB-related *Zea mays* protein referred to as LOC100383702 (NCBI accession no. NP_001169810.1 (GI: 293335473) has the following sequence (SEQ ID NO:32).

```
  1   MASGSRATPT RSPSSARPEA PRHAHHHHHS QSSGGSTSRA
 41   GGGAAATESV SKAVAQYTLD ARLHAVFEQS GASGRSFDYS
 81   QSLRAPPTPS SEQQIAAYLS RIQRGGHIQP FGCTLAVADD
121   SSFRLLAFSE NSPDLLDLSP HHSVPSLDSS APPHVSLGAD
161   ARLLFSPSSA VLLERAFAAR EISLLNPIWI HSRVSSKPFY
201   AILHRIDVGV VIDLEPARTE DPALSIAGAV QSQKLAVRAI
241   SRLQALPGGD VKLLCDTVVE HVRELTGYDR VMVYRFHEDE
281   HGEVVAESRR DNLEPYLGLH YPATDIPQAS RFLFRQNRVR
321   MIADCHATPV RVIQDPGLSQ PLCLVGSTLR APHGCHAQYM
361   ANMGSIASLV MAVIISSGGD DEQTGRGGIS SAMKLWGLVV
401   CHHTSPRCIP FPLRYACEFL MQAFGLQLNM ELQLAHQLSE
```

```
 441 KHILRTQTLL CDMLLRDSPT GIVTQSPSIM DLVKCDGAAL
 481 YYHGKYYPLG VTPTESQIKD IIEWLTVFHG DSTGLSTDSL
 521 ADAGYLGAAA LGEAVCGMAV AYITPSDYLF WFRSHTAKEI
 561 KWGGAKHHPE DKDDGQRMHP RSSFKAFLEV VKSRSLPWEN
 601 AEMDAIHSLQ LILRDSFRDA AEGTNNSKAI VNGQVQLREL
 641 ELRGINELSS VAREMVRLIE TATVPIFAVD TDGCINGWNA
 681 KIAELTGLSV EEAMGKSLVN DLIFKESEAT VEKLLSRALR
 721 GEEDKNVEIK LKTFGSEQSK GPIFVVVNAC SSRDYTQNIV
 761 GVCFVGQDVT GQKVVMDKFV NIQGDYKAIV HNPNPLIPPI
 801 FASDENTSCS EWNTAMEKLT GWSRGEVVGK FLIGEVFGNC
 841 CRLKGPDALT KFMVIIHNAI GGQDYEKFPF SFFDKNGKYV
 881 QALLTANTRS KMDGKSIGAF CFLQIASTEI QQAFEIQRQQ
 921 EKKCYARMKE LAYICQEIKN PLSGIRFTNS LLQMTDLNDD
 961 QRQFLETSSA CEKQMSKIVK DASLQSIEDG SLVLEQSEFS
1001 LGDVMNAVVS QAMLLLRERD LQLIRDIPDE IKDASAYGDQ
1041 CRIQQVLADF LLSMVRSAPS ENGWVEIQVR PNVKQNSDGT
1081 NTELFIFRFA CPGEGLPADV VQDMFSNSQW STQEGVGLST
1121 CRKILKLMGG EVQYIRESER SFFLIVLEQP QPRPAAGREI
1161 V
```

A codon encoding the arginine at position 320 of the SEQ ID NO:32 protein is equivalent to the codon encoding the arginine at position 322 of the SEQ ID NO:30 protein; a mutant phyB with a sequence encoding the first 319 amino acids of SEQ ID NO:32 can have a C→T substitution, causing the arginine codon (CGA) at position 320 to become a termination codon (TGA).

A cDNA encoding the SEQ ID NO:32 protein is available as NCBI accession number NM_001176339.1 (GI: 293335472), and a chromosomal segment encoding the SEQ ID NO:32 protein is on *Zea mays* chromosome 1 at NC_024459.1 (50023180 . . . 50034310), sequence available as NCBI accession number NC_024459.1 (GI:662250330).

A *Zea mays* protein referred to as phytochromeB1 (NCBI accession no. DAA45039.1 (GI:414866482) has significant sequence identity to the *Arabidopsis thaliana* PHYB protein with SEQ ID NO:30, as illustrated by the sequence comparison shown below. Domains of sequence homology are identified by asterisks below the sequence comparison.

```
73.1% identity in 1139 residues overlap; Score: 4270.0; Gap
frequency: 0.9%
Seq30    22 PSSSHTPNNRRGGEQAQSSGTKSLRPRSNTESMSKAIQQYTVDARLHAVFEQSGESGKSF
Seq33    18 PEAPRHAHHHHHSQSSGGSTSRAGGGAAATESVSKAVAQYTLDARLHAVFEQSGASGRSF
              *         *            *** ***  *** ************ **
            **

Seq30    82 DYSQSLKTTTYGSSVPEQQITAYLSRIQRGGYIQPFGCMIAV-
                DESSFRIIGYSENAPEM
Seq33    78 DYSQSLRAPPTPSS--
                EQQIAAYLSRIQRGGHIQPFGCTLAVADDSSFRLLAFSENSPDL
            ******     **  **** **********  ******  * * ****      ***

Seq30   141 LGIMPQ-SVPTLEK--
                PEILAMGTDVRSLFTSSSSILLERAFVAREITLLNPVWIHSKNT
Seq33   136 LDLSPHHSVPSLDSSAPPHVSLGALARLLFSPSSAVLLERAFAAREISLLNPIWIHSRVS
             *   *  *** *    *     * * ** ** ****** **** **** ****

Seq30   198 GKPFYAILHRIDVGVVIDLEPARTEDPALSIAGAVQSQKLAVRAISQLQALPGGDIKLLC
Seq33   196 SKPFYAILHRIDVGVVIDLEPARTEDPALSIAGAVQSQKLAVRAISRLQALPGGDVKLLC
             ************************************************* ********
            ****

Seq30   258 DTVVESVRDLTGYDRVMVYKFHEDEHGEVVAESKRDDLEPYIGLHYPATDIPQASRFLFK
Seq33   256 DTVVEHVRELTGYDRVMVYRFHEDEHGEVVAESRRDNLEPYLGLHYPATDIPQASRFLFR
            ***** ** ********** ************* **** ******************

Seq30   318 QNRVRMIVDCNATPVLVVQDDRLTQSMCLVGSTLRAPHGCHSQYMANMGSIASLAMAVII
Seq33   316 QNPVRMIADCHATPVRVIQDPGLSQPLCLVGSTLRAPHGCHAQYMANMGSIASLVMAVII
            ** ***** ** **** * **   * * *************** ************
            *****

Seq30   378 NGNEDDGSNVASGRSS-
                MRLWGLVVCHHTSSRCIPFPLRYACEFLMQAFGLQLNMELQLA
Seq33   376 SSGGDDEQTGRGGISSAMKLWGLVVCHHTSPRCIPFPLPYACEFLMQAFGLQLNMELQLA
             **      * ** * **********
            *****************************

Seq30   437 LQMSEKRVLRTQTLLCDMLLRDSPAGIVTQSPSIMDLVKCDGAAFLYHGKYYPLGVAPSE
Seq33   436 HQLSEKHILRTQTLLCDMLLRDSPTGIVTQSPSIMDLVKCDGAALYYHGKYYPLGVTPTE
             * ***   ******************* ********************** *** *  **

Seq30   497 VQIKDVVEWLLANHADSTGLSTDSLGDAGYPGAAALGDAVCGMAVAYITKRDFLFWFRSH
Seq33   496 SQIKDIIEWLTVFHGDSTGLSTDSLADAGYLGAAALGEAVCGMAVAYITPSDYIFWFRSH
              **** ***   * ******** ****  ********* ***************  *
            *******
```

```
Seq30   557 TAKEIKWGGAKHHPEDKDDGQRMHPRSSFQAFLEVVKSRSQPWETAEMDAIHSLQLILRD
Seq33   556 TAKEIKWGGAKHHPEDKDDGQRMHPRSSFKAFLEVVKSRSLPWENAEMDAIHSLQLILRD
            ******************************* ********* ***
            ***************

Seq30   617 SFKES-
            EAAMNSKVVDGVVQPCRDMAGEQGIDELGAVAREMVRLIETATVPIFAVDAGGC
Seq33   616 SFRDAAEGTNNSKAIVNGQVQLRELE-
            LRGINELSSVAREMVRLIETATVPIFAVDTDGC
            **  *  ***       *       ** ** *******************
            **

Seq30   676 INGTRNAKIAELTGLSVEEAMGKSLVSDLIYKENEATVNKLLSRALRGDEEKNVEVKLKTF
Seq33   675 INGWNAKIAELTGLSVEEAMGKSLYNDLIFKESEATVEKLLSRALRGEEDKNVEIKLKTF
            *** ******************* * ** **** ********* **** ****
            *****

Seq30   736 SPELQGKAVFVVVNACSSKDYLNNIVGVCFVDQDVTSQKLIVMDKFINIQGDYKAIVHSPN
Seq33   735 GSEQYKGPIFVVVNACSSRDYTQNIVGVCFVGQDVTGQKVVMDKFVNIQGDYKAIVHNPN
             *   *   ********* **  ******** **** ** ***** *********** **
                **

Seq30   796 PLIPPIFAADENTCCLEWNMAMEKLTGWSREVIGKMIVGEVFGSCCMLKGPDALTKFMI
Seq33   795 PLIPPIFASDENTSCSEWNTAMEKLTGWSRGEVVGKFLIGEVFGNCCRLKGPDALTKFMV
            ******** **** * *** ********** ** **   ***** ** ***********

Seq30   856 VLHNAIGGQDTDKFPFPFFDRNGKFVQALLTANKRVSLEGKVIGAFCFLQIPSPELQQAL
Seq33   855 IIHNAIGGQYEKPPFSFFDKNGKYVQALLTANTRSKMDGKSIGAFCFLQTASTEIQQAF
             ********   * ** *** *** ******* *   ** * ******* *  * ***

Seq30   916 AVQRRQTECFTKAKELAYICQVIKNPLSGMRFANSLLEATDLNEDQKQLLETSVSCEKQ
Seq33   915 EIQRQQEKKCYARMKELAYICQEIKNPLSGIRFTNSLLQMTDLNDDQRQFLETSSACEKQ
             * *  *      ******** ******** ** **** * ****  ** ****  ****
            ****

Seq30   976 ISRIVGDMDLESIEDGSFVLKREEFFLGSVINAIVSQAMFLLPDRGLQLIRDIPEEIKSI
Seq33   975 MSKIVKDASLQSIEDGSLVLEQEFSLGDVMNAVVSQAMLLLRERDLQLIRDIPDEIKDA
             * *    * ****** ** * **  *  *  ****** ***  * *********  ***

Seq30  1036 EVFGQIRIQQLLAEFLLSIIRYAPSQE-
            WVEIHLSQLSKQMADGFAAIRTEFRMACPGE
Seq33  1035 SAYGDQCRIQQVIADFLLSMVRSAPSENGWVEIQVRPNVYQNSDGTNTELFIFRFACPGE
              *     **** * ****  *  ***     ***  *  *       ** *    *****
            *****

Seq30  1095 GLPPELVRDMFHSSRWTSPEGLGLSVCRKILKLMNGEVQYIRESERSYFLIILELPVPR
Seq33  1095 GLPADVVQDMFSNSQWSTQEGVGLSTCRKILKLMGGEVQYIRESERSFFLIVLEQPQPR
            ***    *** * * **  *** *** ******** *********** *** ** * *
            **
```

This PHYB-related *Zea mays* protein referred to as phytochromeB1 (NCBI accession no. DAA45039.1 (GI: 414866482) has the following sequence (SEQ ID NO:33).

```
   1 MASGSRATPT RSPSSARPEA PRHAHHHHHS QSSGGSTSRA
  41 GGGAAATESV SKAVAQYTLD ARLHAVFEQS GASGRSFDYS
  81 QSLRAPPTPS SEQQIAAYLS RIQRGGHIQP FGCTLAVADD
 121 SSFRLLAFSE NSPDLLDLSP HESVPSLDSS APPHVSLGAD
 161 ARLLFSPSSA VLLERAFAAR EISLLNPIWI HSRVSSKPFY
 201 AILHRIDVGV VIDLEPARTE DPALSIAGAV QSQKLAVRAI
 241 SRLQALPGGD VKLLCDTVVE AVRELTGYDR VMVYRFHEDE
 281 HGEVVAESRR DNLEPYLGLH YPATDIPQAS RFLFRQNRVR
 321 MIADCHATPV RVIQDPGLSQ PLCLVGSTLR APHGCHAQYM
 361 ANMGSIASLV MAVIISSGGD DEQTGRGGIS SAMKLWGLVV
 401 CHHTSPRCIP FPLRYACEFL MQAFGLQLNM ELQLAHQLSE
 441 KHILRTQTLL CDMLLRDSPT GIVTQSPSIM DLVKCDGAAL
 481 YYHGKYYPLG VTPTESQIKD IIEWLTVFHG DSTGLSTDSL
 521 ADAGYLGAAA LGEAVCGMAV AYITPSDYLF WFRSHTAKEI
 561 KWGGAKHHPE DKDDGQRMHP RSSFKAFLEV VKSRSLPWEN
 601 AEMDAIHSLQ LILRDSFRDA AEGTNNSKAI VNGQVQLREL
 641 ELRGINELSS VAREMVRLIE TATVPIFAVD TDGCINGWNA
 681 KIAELTGLSV EEAMGKSLVN DLIFKESEAT VEKLLSRALR
 721 GEEDKNVEIK LKTFGSEQYK GPIFVVVNAC SSRDYTQNIV
 761 GVCFVGQDVT GQKVVMDKFV NIQGDYKALV HNPNPLIPPI
 801 FASDENTSCS EWNTAMEKLT GWSRGEVVGK FLIGEVFGNC
 841 CRLKGPDALT KFMVIIHNAI GGQDYEKFPF SFFDKNGKYV
 881 QALLTANTRS KMDGKSIGAF CFLQIASTEI QQAFEIQRQQ
 921 EKKCYARMKE LAYICQEIKN PLSGIRFTNS LLQMTDLNDD
 961 QRQFLETSSA CERQMSKIVK DASLQSIEDG SLVLEQSEFS
1001 LGDVMNAVVS QAMLLLRERD LQLIRDIPDE IKDASAYGDQ
```

```
1041 CRIQQVLADF LLSMVRSAPS ENGWVEIQVR PNVKQNSDGT

1081 NTELFIFRFA CPGEGLPADV VQDMFSNSQW STQEGVGLST

1121 CRKILKLMGG EVQYIRESER SFFLIVLEQP QPRPAAGREI

1161 V
```

A codon encoding the arginine at position 320 of the SEQ ID NO:33 protein is equivalent to the codon encoding the arginine at position 322 of the SEQ ID NO:30 protein. A codon encoding the arginine at position 320 of the SEQ ID NO:33 protein can be changed to a termination codon. Hence, the PHYB-related *Zea mays* protein referred to as phytochromeB1 (NCBI accession no. DAA45039.1 (GI: 414866482) with sequence SEQ ID NO:33) can be inactivated in a manner similar to the PhyB loci described above.

A chromosomal segment encoding the SEQ ID NO:33 protein is on *Zea mays* chromosome 1 at NC_024459.1 (50023180 . . . 50034310), sequence available as NCBI accession number NC_024459.1 (GI:662250330).

A *Zea mays* protein referred to as phytochromeB2 (NCBI accession no. NP_001168077.1 (GI:293336623) has significant sequence identity to the *Arabidopsis thaliana* PHYB protein with SEQ ID NO:30, as illustrated by the sequence comparison shown below. Domains of sequence homology are identified with asterisks below the sequence comparison.

```
72.3% identity in 1135 residues overlap; Score: 4203.0; Gap
frequency: 0.9%
Seq30    26 HTPNNRRGGEQAQSSGTKSLRPRSNTESMSKAIQQTVDARLHAVFEQSGESGKSFDYSQ
Seq34    24 HHHSQSSGGSTSRAGAGGGGGGAAATESVSKAVAQYNLDARLHAVFEQSGASGRSFDYSQ
            *   **              *** ***  ** ************* **
            ******

Seq30    86 SLKTTTYGSSVPEQQITAYLSRIQRGGYIQPFGCMIAV-
            DESSFRIIGYSENAREMLGIM
Seq34    84 SLRAPPTPSS--
            EQQIAAYLSRIQRGGHIQPLGCTLAVADDSSFRLLAFSENAADLLDLS
            **        **  **** ********** *** ** ** * ****    ****   *

Seq30   145 PQ-SVPTLEKPEI--
            LAMGTDVRSLFTSSSSILLERAFVAREITLLNPVWIHSKNTGKPF
Seq34   142 PHHSVPSLDSVALPPVSLGADARLYFSPSSAVLLERAFAAREISLLNPLWIHSRASSKPF
            *  *** *             *  *   **  ****** **** **** ****
            ***

Seq30   202 YAILHRIDVGVVIDLEPARTEDPALSIAGAVQSQKLAVRAISQLQALPGGDIKLLCDTVV
Seq34   202 YAILHRIDVGVVIDLEPARTEDPALSIAGAVQSQLAVPAISRLQALPGGDVKLLCDTVV
            ********************************** ********
            ********

Seq30   262 ESVRDLTGYDRVMVYKFHEDEHGEVVAESKRDDLEPYIGLHYPATDIPQASRFLFKQNRV
Seq34   262 EHVRELTGYDRVMVYKFHEDEHGEVVAESRRDNLEPYLGLHYPATDIPQASRFLFQQNRV
            * ** ************************ ** **** ****************
            ****

Seq30   322 RMIVDCNATPVLVVQDDRLTQSMCLVGSTLRAPHGCHSQMANMGSIASLAMAVIIN-
            GN
Seq34   322 RMIADCHAIPVRVIQDPGLSQQLCLVGSTLRAPHGCHAQYMANMGSIASLVMAVIISSGG
            *** ** * ** * **   ************** *  * ******** ***** *

Seq30   381 EDDGSNVASGRSSMRLWGLVVCHHTSSRCIPFPLRYACEFLMQAFGLQLNMELQLALQMS
Seq34   382 DDERTGRGAISSSMKLWGLVVCHHTSPRCIPFPLRYACEFLMQAFGLQLNMELQLAHQLS
            *          *** ********** ********************************  **

Seq30   441 EKRVLRTQTLLCDMLLRDSPAGIVTQSPSIMDLVKCDGAAFLYHGKYYPLGVAPSEVQIK
Seq34   442 EKHILRTQTLLCDMLLRDSPAGIITQSPSVMDLVKCDGAALYYRGKYYPLGVTPTESQIK
            ** ******************** ***** **********  * ********  *  *
            ***

Seq30   501 DVVEWLLANHADSTGLSTDSLGDAGYPGAAALGDAVCGMAVAYITKRDELFWFRSHTAKE
Seq34   502 DIIEWLTVCHGDSTGLSTDSLADAGYLGAVALGDAVCGMAVAYITPSDYLFWFRSHTAKE
            * ***   *  ********** ****  ********************  *  ******
            **********

Seq30   561 IKWGGAKHHPEDKDDGQRMHPRSSFQAFLEVVKSRSQPWETAEMDAIHSLQLILRDSFKE
Seq34   562 IKWGGAKHHPEDKDDGQRMHPRSSFKAFLEVVKSRSLSWENAEMDAIHSLQLILRDSFRD
            *************************  ********     ******************

Seq30   621 S-
            EAAMNSKVVDGVVQPCRDMAGEQGIDELGAVAREMVRLIETATVPIFAVDAGGCINGW
Seq34   622 AAEGTSNSKAIVNGQRQLGELE-
            LRGINELSSVAREMVRLIETATVPIFAVDTDGCINGW
            *    ***                  ** **  ******************

Seq30   680 NAKIAELTGLSVEEAMGKSLVSDLIYKENEATVNKLLSRALRGDEEKNVEVKLKTFSPEL
Seq34   681 NAKIAELTGLSVEEAMGKSLVNDLIFKECDDIVEKLLSRALRGEEDKNVEIKLKTFGSEQ
            ******************** *** **    ** ******** * ****  **** *  *
```

```
Seq30   740  QGKAVFVVVNACSSKDYLNNIVGVCFVGQDVTSQKIVMDKFINIQGDYKAIVHSPNPLIP
Seq34   741  SKGAIFVIVNACSSRDYTQNIVGVCFVGQDVTGQKVVMDKFINIQGDYKAIVHNPNPLLP
             * ** ****** **  ************* **  ***************** *****

Seq30   800  PIFAADENTCCLEWNMMEKLTGWSRSEVIGKMIVGEVFGSCCMLKGPDALTKFMIVLHN
Seq34   801  PIFASDENTSCSEWNTAMEKLTGWSREEVVGKFLIGEVFGNCCRLKGPDALTKFMVVIHN
             **** **** * ***  ********** ** **     ***** ** *********** *
             **

Seq30   860  AIGGQDTDKFPPPFFDRNGKFVQALLTANKRVSLEGKVIGAFCFLQIPSPELQQALAVQR
Seq34   861  AIEGHDSEKFPFSFFDKNGKYWALLTANTRSKMDGKSIGAFCFLQIASAEIQQAFEIQR
             ** * *  **** *** ***  ********  *   ** *********  *   * ***
             **

Seq30   920  RQDTECFTKAKELAYICQVIKNPLSGMRFANSLLEATDLNEDQKQLLETSVSCEKQISRI
Seq34   921  QQEKKCYARMKELAYICQEIKNPLSGIRFTNSLLQMTDLNDDQRQFLETSSACEKQMSKI
              *   *     ******** ****** ** ****  ****  ** ***** ******  **

Seq30   980  VGDMDLESIEDGSFVLKREEFFLGSVINAIVSQAMFLLRDRGLQLIRDIPEEIKSIEVFG
Seq34   981  VKDASLKSIEDGSLVLEKSEFSLGDVMNAVVSQTMSLLRERDLQLIRDIPDEIKDASAYG
             * *   ******* ** ** **** * * **** * **** * ******** ***    *

Seq30  1040  DQIRIQQLLAEFLLSIIPYAPSQE-
             WVEIHLSQLSKQMADGFAAIRTEFRMACPGEGLPP
Seq34  1041  DQFRIQQVLADFLLSMAQSAPSENGWVEIQVRPNVKQNYDGTDTELFIFRFACPGEGLPA
             ** **** ** ****   * ***   ****        **      **  *********
             ********

Seq30  1099  ELVRDMFHSSRWTSPEGLGLSVCRKILKLMNGEVQYIRESERSYFLIILELPVPR
Seq34  1101  DIVQDMFSNSQWSTQEGVGLSTCRKILKLMGGEVQYIRESERSFFLIVLELPQPR
              * ***  *  ** *** **** ********* ********** *** **** **
```

This PHYB-related *Zea mays* protein referred to as phytochromeB2 (NCBI accession no. NP_001168077.1 (GI: 293336623) has the following sequence (SEQ ID NO:34).

```
   1  MASDSRPPKR SPSARRVAPR AAEEHHSQSS GGSTSRAGAG
  41  GGGGGAAATE SVSKAVAQYN LDARLHAVFE QSGASGRSFD
  81  YSQSLRAPPT PSSEQQIAAY LSRIQRGGHI QPLGCTLAVA
 121  DDSSFRLLAF SENAADLLDL SPHHSVPSLD SVALPPVSLG
 161  ADARLYFSPS SAVLLERAFA AREISLLNPL WIHSRASSKP
 201  FYAILHRIDV GVVIDLEPAR TEDPALSIAG AVQSQKLAVR
 241  AISRLQALPG GDVKLLCDTV VEHVRELTGY DRVMVYKFHE
 281  DEHGVVAES RRDNLEPYLG LHYPATDIPQ ASRFLFQQNR
 321  VRMIADCHAI PVRVIQDPGL SQQLCLVGST LRAPHGCHAQ
 361  YMANMGSIAS LVMAVIISSG GDDERTGRGA ISSSMKLWGL
 401  VVCHHTSPRC IPFPLRYACE FLMQAFGLQL NMELQLAHQL
 441  SEKHILRTQT LLCDMLLRDS PAGIITQSPS VMDLVKCDGA
 481  ALYYRGKYYP LGVTPTESQI KDIIEWLTVC HGDSTGLSTD
 521  SLADAGYLGA VALGDAVCGM AVAYITPSDY LFWFRSHTAK
 561  EIKWGGAKHE PEDKDDGQRM HPRSSFKAFL EVVKSRSLSW
 601  ENAEMDAIHS LQLILRDSFR DAAEGTSNSK AIVNGQRQLG
 641  ELELRGINEL SSVAREMVRL IETATVPIFA VDTDGCINGW
 681  NAKIAELTGL SVEEAMGKSL VNDLIFKECD DIVEKLLSRA
 721  LRGEEDKNVE IKLKTFGSEQ SKGAIFIVVN ACSSRDYTQN
 761  IVGVCFVGQD VTGQKVVMDK FINIQGDYKA IVHNPNPLLP
 801  PIFASDENTS CSEWNTAMEK LTGWSREEVV GKFLIGEVFG
 841  NCCRLKGPDA LTKFMVVIHN AIEGHDSEKF PFSFFDKNGK
 881  YVQALLTANT RSKMDGKSIG AFCFLQIASA EIQQAFEIQR
 921  QQEKKCYARM KELAYICQEI KNPLSGIRFT NSLLQMTDLN
 961  DDQRQFLETS SACEKQMSKI VKDASLKSIE DGSLVLEKSE
1001  FSLGDVMNAV VSQTMSLLRE RDLQLIRDIP DEIKDASAYG
1041  DQFRIQQVLA DFLLSMAQSA PSENGWVEIQ VRPNVKQNYD
1081  GTDTELFIFR FACPGEGLPA DIVQDMFSNS QWSTQEGVGL
1121  STCRKILKLM GGEVQYIRES ERSFFLIVLE LPQPRLAAGR
1161  ENQLIC
```

A codon encoding the arginine at position 322 of the SEQ ID NO:34 protein is equivalent to the codon encoding the arginine at position 322 of the SEQ ID NO:30 protein. A codon encoding the arginine at position 322 of the SEQ ID NO:34 protein 50 can be changed to a termination codon. Hence, the PHYB-related *Zea mays* protein referred to as phytochromeB2 (NCBI accession no. NP_001168077.1 (GI: 293336623) with sequence SEQ ID NO:34) can be inactivated in a manner similar to the PhyB loci described above.

A cDNA encoding the SEQ ID NO:34 protein is available as NCBI accession number NM_001174606.1 (GI: 293336622), and a chromosomal segment encoding the SEQ ID NO:32 protein is on *Zea mays* chromosome 9 at NC_024467.1 (135245613 . . . 135251739, complement), sequence available as NCBI accession number NC_024467.1 (GI:662248440).

A *Glycine max* protein referred to as phytochrome B (NCBI accession no. NP_001240097 XP_003533157; NP_001240097.1 (GI:358248221)) has significant sequence identity to the *Arabidopsis thaliana* PHYB protein with SEQ ID NO:30, as illustrated by the sequence comparison shown below. Domains of sequence homology are identified with asterisks below the sequence comparison.

```
77.4% identity in 1109 residues overlap; Score: 4478.0; Gap
frequency: 1.1%

Seq30    49 SNTESMSKAIQQYTVDARLHAVFEQSGESGKSFDYSQSLKTTTYGSSVPEQQITAYLSRI
Seq35    33 NNIDSMSKAIAQYTEDARLHAVFEQSGESGRSFNYSESIRIAS--
                ESVPEQQITAYLVKI
            *  ****** *** *************** ** ** *        ************

Seq30   109 QRGGYIQPFGCMIAVDESSFRIIGYSENAREMLGIMPQSVPTLEKPE--
                ILAMGTDVRSL
Seq35    91 QRGGFIQPFGSMIAVDEPSFRILGYSDNARDMLGITPQSVPSLDDKNDAAFALGTDVRAL
            **** ***** ****** **** **** *** **** **** *         * ******

Seq30   167 FTSSSSILLERAFVAREITLLNPVWIHSKNTGKPFYAILHRIDVGVVIDLEPARTEDPAL
Seq35   151 FTHSSALLLEKAFSAREISLMNPIWIHSRTSGKPFYGILHRIDVGIVIDLEPARTEDPAL
            ** **  *** ** **** * ** ****    ***** ********
            **************

Seq30   227 SIAGAVQSQKLAVRAISQLQALPGGDIKLLCDTVVESVRDLTGYDRVMVYKFHEDEHGEV
Seq35   211 SIAGAVQSQKLAVRAISQLQSLPGGDVKLLCDTVVESVRELTGYDRVMVYKFHEDEHGEV
            ********************  ***** ************* *****************
            ********************

Seq30   287 VAESKRDDLEPYIGLHYPATDIPQASRFLFKQNRVRMIVDCNATPVLVVQDDRLTQSMCL
Seq35   271 VSESKRPDLEPYIGLHYPATDIRQASRELFKQNRVRMIVDCHASAVRVVQDEALVQPLCL
            * **** *************** **** ************   *  * ****  *  *
            **

Seq30   347 VGSTLRAPHGCHSQYMANMGSIASLAMAVIINGNEDDGSNVASGRSSMRLWGLVVCHHTS
Seq35   331 VGSTLRAPHGCHAQYMANMGSIASLVMAVIINGNDEEG---
                VGGRSSMRLWGLVVCHHTS
            ************ ************ ********  *
            *****************

Seq30   407 SRCIPFPLRYACEFLMQAFGLQLNMELQLALQMSEKRVLRTQTLLCDMLLRDSPAGIVTQ
Seq35   388 ARCIPFPLRYACEFLMQAFGLQLNMELQLAAQSLEKRVLRTQTLLCDMLLRDSPTGIVTQ
             ***************************** *  ****************** *****
            *****

Seq30   467 SPSIMDLVKCDGAAFLYHGKYYPLGVAPSEVQIKDVVEWLLANHADSTGLSTDSLGDAGY
Seq35   448 SPSIMDLVKCDGAALYFQGNYYPLGVTPTEAQIRDIIEWLLAFHGDSTGLSTDSLGDAGY
            **************  *  * ****** * ** ** *****  * **************
            ***************

Seq30   527 PGAAALGDAVCGMAVAYITKRDFLFWFRSHTAKEIKWGGAKHHPEDKDDGQRMHPRSSFQ
Seq35   508 PGAASLGDAVCGMAVAYITEKDFLFWFRSHTAKEIKWGGAKHHPEDKDDGQRMHPRSSFK
            ****  *************  ************************************ *

Seq30   587 AFLEVVKSRSQPWETAEMDAIHSLQLILRDSFKESEAAMNSKVVDGVVQPCRDMAGEQGI
Seq35   568 AFLEVVKSRSLPWENAEMDAIHSLQLILRDSFKDAEHRNSKAVVD----
                PHVSEQELQGV
            ********** *** ******************  *   ***  **           **

Seq30   647 DELGAVAREMVRLIETATVPIFAVDAGGCINGWNAKIAELTGLSVEEAMGKSLVSDLIYK
Seq35   624 DELSSVAREMVRLIETATAPIFAVDVDGHVNGWNAKVSELTGLPVEEAMGKSLVHDLVFK
            *** ************** ****** *   *****  ***** *********  ** *

Seq30   707 ENEATVNKLLSRALRGDEEKNVEVKLKTFSPELQGKAVFVVVNACSSKDYLNNIVGVCFV
Seq35   684 ESEETMNKLLSRALKGEEDKNVEIKMRTFGPEHQNKAVFLVVNACSSKDFTNNVVGVCFV
            * *  ********* *  *****  ** **  * **** ********    * *****
            ******

Seq30   767 GQDVTSQKIVMDKFINIQGDYKAIVHSPNPLIPPIFAADENTCCLEWNMAMEKLTGWSRS
Seq35   744 GQDVTGQKIVMDKFINIQGDYKAIVHSPNPLIPPIFASDDNTCCLEWNTAMEKLTGWGRV
            *****  ******************************  ******** ******* *

Seq30   827 EVIGKMIVGEVFGSCCMLKGPDALTKFMIVLHNAIGGQDTDKFPFPFFDRNGKFVQALLT
Seq35   804 DVIGKMLVGEVFGSCCQLKGSDSITKFMIVLHNALGGQDTDKFPFSFLDRHGKYVQTFLT
             ***** *********  *** * *********  ********** * ** ** **  *
            **

Seq30   887 ANKRVSLEGKVIGAFCFLQIPSPELQQALAVQRRQDTECFTKAKELAYICQVIKNPLSGM
Seq35   864 ANKRVNMEGQIIGAFCFLQIMSPELQQALKAQRQQEKNSFGRMKELAYICQGVKNPLSGI
            *****  **  *********  *******   ** *   *    *********  *****
            ******

Seq30   947 RFANSLLEATDLNEDQKQLLETSVSCEKQISRIVGDMDLESIEDGSFVLKREEFFLGSVI
Seq35   924 RFTNSLLEATSLTNEQKQFLETSVACEKQMLKIIRDVDLESIEDGSLELEKGEFLLGNVI
            ** *******  *  *** ***** **** *  * ***********  * *  **** **
            **
```

```
Seq30  1007  NAIVSQAMFLLRDRGLQLIRDIPEEIKSIEVFGDQIRIQQLLAEFLLSIIRYAPSQE-
              WV
Seq35   984  NAVVSQVMLLLRERNLQLIRDIPEEIKTLAVYGDQLRIQQVLSDFLLNIVRYAPSPDGWV
              ** *** * *** * ************   * *** **** *  *** * *****
              **
Seq30  1066  EIHLSQLSKQMADGFAAIRTEFRMACPGEGLPPELVRDMFHSSRWTSPEGLGLSVCRKIL
Seq35  1044  EIHVRPRIKQISDGLTLLHAEFRMVCPGEGLPPELIQDMFNNSRWGTQEGLGLSMSRKIL
              ***     ** **      **** ********** *** ***    ******
              ****
Seq30  1126  KLMNGEVQYIRESERSYFLIILELPVPRK
Seq35  1104  KLMNGEVQYIREAERCYFYVLLELPVTRR
              ************ ** **    ***** *
```

This PHYB-related *Glycine max* protein referred to as phytochrome B (NCBI accession no. NP_001240097 XP_003533157; NP_001240097.1 (GI:358248221)) has the following sequence (SEQ ID NO:35).

```
   1  MASASGAANS SVPPPQIHTS RTKLSHHSSN NNNNIDSMSK
  41  AIAQYTEDAR LHAVFEQSGE SGRSFNYSES IRIASESVPE
  81  QQITAYLVKI QRGGFIQPFG SMIAVDEPSF RILGYSDNAR
 121  DMLGITPQSV PSLDDKNDAA FALGTDVRAL FTHSSALLLE
 161  KAFSAREISL MNPIWIHSRT SGKPFYGILH RIDVGIVIDL
 201  EPARTEDPAL SIAGAVQSQK LAVRAISQLQ SLPGGDVKLL
 241  CDTVVESVRE LTGYDRVMVY KFHEDEHGEV VSESKRPDLE
 281  PYIGLHYPAT DIPQASRFLF KQNRVRMIVD CHASAVRVVQ
 321  DEALVQPLCL VGSTLRAPHG CHAQYMANMG SIASLVMAVI
 361  INGNDEEGVG GRSSMRLWGL VVCHHTSARC IPFPLRYACE
 401  FLMQAFGLQL NMELQLAAQS LEKRVLRTQT LLCDMLLRDS
 441  PTGIVTQSPS IMDLVKCDGA ALYFQGNYYP LGVTPTEAQI
 481  RDIIEWLLAF HGDSTGLSTD SLGDAGYPGA ASLGDAVCGM
 521  AVAYITEKDF LFWFRSHTAK EIKWGGAKHH PEDKDDGQRM
 561  HPRSSFKAFL EVVKSRSLPW ENAEMDAIHS LQLILRDSFK
 601  DAEHRNSKAV VDPHVSEQEL QGVDELSSVA REMVRLIETA
 641  TAPIFAVDVD GHVNGWNAKV SELTGLPVEE AMGKSLVHDL
 681  VFKESEETMN KLLSRALKGE EDKNVEIKMR TFGPEHQNKA
 721  VFLVVNACSS KDFTNNVVGV CFVGQDVTGQ KIVMDKFINI
 761  QGDYKAIVAS PNPLIPPIFA SDDNTCCLEW NTAMEKLTGW
 801  GRVDVIGKML VGEVFGSCCQ LKGSDSITKF MIVLHNALGG
 841  QDTDKFPFSF LDRHGKYVQT FLTANKRVNM EGQIIGAFCF
 881  LQIMSPELQQ ALKAQRQQEK NSFGRMKELA YICQGVKNPL
 921  SGIRFTNSLL EATSLTNEQK QFLETSVACE KQMLKIIRDV
 961  DLESIEDGSL ELEKGEFLLG NVINAVVSQV MLLLRERNLQ
1001  LIRDIPEEIK TLAVYGDQLR IQQVLSDFLL NIVRYAPSPD
1041  GWVEIHVRPR IKQISDGLTL LHAEFRMVCP GEGLPPELIQ
1081  DMFNNSRWGT QEGLGLSMSR KILKLMNGEV QYIREAERCY
1121  FYYLLELPVT RRSSKKC
```

A codon encoding the arginine at position 306 of the SEQ ID NO:35 protein is equivalent to the codon encoding the arginine at position 322 of the SEQ ID NO:30 protein. A codon encoding the arginine at position 306 of the SEQ ID NO:35 protein can be changed to a termination codon. Hence, the PHYB-related *Glycine max* protein referred to as phytochrome B (NCBI accession no. NP_001240097 XP_003533157; NP_001240097.1 (GI:358248221)) with sequence SEQ ID NO:35) can be inactivated in a manner similar to the PhyB loci described above.

A cDNA encoding the SEQ ID NO:35 protein is available as NCBI accession number NM_001253168.1 (GI: 358248220), and a chromosomal segment encoding the SEQ ID NO:35 protein is on *Glycine max* chromosome 9 at NC_016096.2 (2960478 . . . 2966704, complement), sequence available as NCBI accession number NC_016096.2 (G1:952545307).

Another *Glycine max* protein referred to as phytochrome B (NCBI accession no. ACJ61499.1 (GI:214011498)) also has significant sequence identity to the *Arabidopsis thaliana* PHYB protein with SEQ ID NO:30, as illustrated by the sequence comparison shown below. Domains of sequence homology are identified with asterisks below the sequence comparison.

```
77.5% identity in 1104 residues overlap; Score: 4466.0; Gap
frequency: 1.1%
Seq30   54  MSKAIQQYTVDARLHAVFEQSGESGKSFDYSQSLKTTTYGSSVPEQQITAYLSRIQRGGY
Seq36    1  MSKAIAQYTEDARLHAVFEQSGESGRSFNYSESIRIAS--
            ESVPEQQITAYLVKIORGGF
            ***** *** *************** ** ** *        *********** *****

Seq30  114  IQPFGCMIAVDESSFRIIGYSENAREMLGIMPQSVPTLEKPE--
            ILAMGTDVRSLFTSSS
Seq36   59  IQPFGSMIAVDEPSFRILGYSDNARDMLGITPQSVPSLDDKNDAAFALGTDVRALFTHSS
            ***** ****** **** **** *** **** ****** *        * ***** ***
            **

Seq30  172  SILLERAFVAREITLLNPVWIHSKNTGKPFYAILHRIDVGVVIDLEPARTEDPALSIAGA
Seq36  119  ALLLEKAFSAREISLMNPIWIHSRTSGKPFYGILHPIDVGIVIDLEPAPTEDPALSIAGA
             *** ** **** * ** ****   ****** *** **** *******  **********
            ******************
```

```
Seq30    232 VQSQKLAVRAISQLQALPGGDIKLLCDTVVESVRDLTGYDRVMVYKFHEDEHGEVVAESK
Seq36    179 VQSOKLAVRAISQLQSLPGGDVKLLCDTVVESVRELTGYDRVMVYKFHEDEHGEVVSESK
             *************** ***** ************* ***********************
             ***

Seq30    292 RDDLEPYIGLHYPATDIPQASRFLFKQNRVRMIVDCNATPVLVVQDDRLTQSMCLVGSTL
Seq36    239 RPDLEPYIGLHYPATDIPQASRFLEKQNRVRMIVDCHASAVRVVQDEALVQPLCLVGSTL
             * ********************* ************   *  *** *  *  *******
             *******

Seq30    352 RAPHGCHSQYMANMGSIASLAMAVIINGNEDDGSNVASGRSSMRLWGLVVCHHTSSRCIP
Seq36    299 RAPHGCHAQYMANMGSIASLVMAVIINGNDEEG---
             VGGRSSMRLWGLVVCHHTSARCIP
             ******* ************ ********     *    ******************
             ****

Seq30    412 FPLRYACEFLMQAFGLQLNMELQLALQMSEKRVLRTQTLLCDMLLRDSPAGIVTQSPSIM
Seq36    356 FPLRYACEFLMQAFGLQLNMELQLAAQSLEKRVLRTQTLLCDMLLRDSPTGIVTQSPSIM
             ************************* *  ******************* **********
             **********

Seq30    472 DLNKCDGAAFLYHGKYYPLGVAPSEVQIKDVVEWLLANHADSTGLSTDSLGDAGYPGAAA
Seq36    416 DLNKCDGAALYFQGNYYPLGVTPTEAQIRDIIEWLLAFHGDSTGLSTDSLGDAGYPGAAS
             *********  *   ****** * *  ** * ***** * *******************

Seq30    532 LGDAVCGMAVAYITKRDFLEWFRSHTAKEIKWGGAKHHPEDKDDGQRMHPRSSFQAFLEV
Seq36    476 LGDAVCGMAVAYITEKDFLFWFRSHTAKEIKWGGAKHHPEDKDDGQRMHPRSSFKAFLEV
             ************** **** ********************************** ****
             *****

Seq30    592 VKSRSQPWETAEMDAIHSLQLILRDSFKESEAAMNSKVVDGVVQPCRDMAGEQGIDELGA
Seq36    536 VKSRSLPWENAEMDAIHSLQLILRDSFKDAEHRNSKAVVD----
             PHVSEQELQGVDELSS
             ***** *** ***************** *     *** *      ** ***

Seq30    652 VAREMVRLIETATVPIFAVDAGGCINGWNAKIAELTGLSVEEAMGKSLVSDLIYKENEAT
Seq36    592 VAREMVRLIETATAPIFAVDVDGHVNGWNAKVSELTGLPVEEAMGKSLVHDLVFKESEET
             ************* ****** **  ****** ****** ********* ** ** **

Seq30    712 VNKLLSRALRGDEEKNVEVKLKTFSPELQGKAVFVVVNACSSKDYLNNIVGVCFVGQDVT
Seq36    652 MNKLLSRALKGEEDKNVEIKMRTFGPEHQNKAVFLVVNACSSKDFTNNVVGVCFVGQDVT
              ******** * ** **** * ***  **  **** ******* ** ************
             ***********

Seq30    772 SQKIVMDKFINIQGDYKAIVHSPNPLIPPIFAADENTCCLEWNMAMEKLTGWSRSEVIGK
Seq36    712 GQKIVMDKFINIQGDYKAIVHSPNPLIPPIFASDDNTCCLEWNTAMEKLTGWGRVDVIGK
              ******************************  *********  ****** *  *** *
             ****

Seq30    832 MIVGEVFGSCCMLKGPDALTKFMIVLHNAIGGQDTDKFPFPFFDRNGKFVQALLTANKRV
Seq36    772 MLVGEVFGSCCQLKGSDSITKFMIVLHNALGGQDTDKFPFSFLDRHGKYVQTFLTANKRV
             * ********* *** *  ********** ********* * ** ** ** ********
             *******

Seq30    892 SLEGKVIGAFCFLQIPSPELQQALAVQRRQDTECFTKAKELAYICQVIKNPLSGMRFANS
Seq36    832 NMEGQIIGAFCFLQIMSPELQOALKKRQQEKNSFGRMKELAYICQGVKNPLSGIRFTNS
              * *  ********* ****** *   ** *         ****** ******* ** *
             **

Seq30    952 LLEATDLNEDQKQLLETSVSCEKQISRIVGDMDLESIEDGSFVLKREEFFLGSVINAIVS
Seq36    892 LLEATSLTNEQKQFLETSVACEKQMLKIIRDVDLESIEDGSLELEKGEFLLGNVINAVVS
             *****  *  *** *****  ***        *********      **  * *** **
             **

Seq30   1012 QAMFLLRDRGLQLIRDIPEEIKSIEVFGDQIRIQOLLAEFLLSIIRYAPSQE-
             WVEIHLS
Seq36    952 QVMLLLRERNLQLIRDIPEEIKTLAVYGDQLRIQQVLSDFLLNIVRYAPSPDGWVEIHVR
             * * ** * ************ *   *** **** * * ***  * ****    *****

Seq30   1071 QLSKQMADGFAAIRTEFRMACPGEGLPPELVRDMFHSSRWTSPEGLGLSVCRKILKLMNG
Seq36   1012 PRIKQISDGLTLLHAEFRMVCPGEGLPPELIQDMFNNSRWGTQEGLGLSMSRKILKLMNG
              * ** * **      **** *********  *** **** * ******  ********
             *********

Seq30   1131 EVQYIRESERSYFLIILELPVPRK
Seq36   1072 EVQYIRRAERCYFYVLLELPVTRR
             ******  ** ** ***** *  *
```

This PHYB-related *Glycine max* protein referred to as phytochrome B (NCBI accession no. ACJ61499.1 (GI: 214011498)) has the following sequence (SEQ ID NO:36)

```
  1  MSKAIAQYTE DARLEAVFEQ SGESGRSFNY SESIRIASES
 41  VPEQQITAYL VKIQRGGFIQ PFGSMIAVDE PSFRILGYSD
 81  NARDMLGITP QSVPSLDDKN DAAHALGTDV RALFTHSSAL
121  LLEKAFSARE ISLMNPIWIH SRTSGKPFYG ILHRIDVGIV
161  IDLEPARTED PALSIAGAVQ SQKLAVRAIS QLQSLPGGDV
201  KLLCDTVVES VRELTGYDRV MVYKFHEDEH GEVVSESKRP
241  DLEPYIGLHY PATDIPQASR FLFKQNRVRM IVDCHASAVR
281  VVQDEALVQP LCLVGSTLRA PHGCHAQYMA NMGSIASLVM
321  AVIINGNDEE GVGGRSSMRL WGLVVCHHTS ARCIPFPLRY
361  ACEFLMQAFG LQLNMELQLA AQSLEKRVLR TQTLLCDMLL
401  RDSPTGIVTQ SPSIMDLVKC DGAALYFQGN YYPLGVTPTE
441  AQIRDIIEWL LAFHGDSTGL STDSLGDAGY PGAASLGDAV
481  CGMAVAYITE KDFLFWFRSH TAKEIKWGGA KHHPEDKDDG
521  QRMHPRSSFK AFLEVVKSRS LPWENAEMDA IHSLQLILRD
561  SFKDAEHRNS KAVVDPHVSE QELQGVDELS SVAREMVRLI
601  ETATAPIFAV DVDGHVNGWN AKVSELTGLP VEEAMGKSLV
641  HDLVFKESEE TMNKLLSRAL KGEEDKNVEI KMRTFGPEHQ
681  NKAVFLVVNA CSSKDFTNNV VGVCFVGQDV TGQKIVMDKF
721  INIQGDYKAI VHSPNPLIPP IFASDDNTCC LEWNTAMEKL
761  TGWGRVDVIG KMLVGEVFGS CCQLKGSDSI TKFMIVLHNA
801  LGGQDTDKFP FSFLDRHGKY VQTFLTANKR VNMEGQIIGA
841  FCFLQIMSPE LQQALKAQRQ QEKNSFGRMK ELAYICQGVK
881  NPLSGIRFTN SLLEATSLTN EQKQFLETSV ACEKQMLKII
921  RDVDLESIED GSLELEKGEF LLGNVINAVV SQVMLLLRER
961  NLQLIRDIPE EIKTLAVYGD QLRIQQVLSD FLLNIVRYAP
1001 SPDGWVEIHV RPRIKQISDG LTLLHAEFRM VCPGEGLPPE
1041 LIUMFMNSR WGTQEGLGLS MSRKILKLMN GEVQYIREAE
1081 RCYFYVLLEL PVTRRSSKKC
```

A codon encoding the arginine at position 269 of the SEQ ID NO:36 protein is equivalent to the codon encoding the arginine at position 322 of the SEQ ID NO:30 protein. A codon encoding the arginine at position 269 of the SEQ ID NO:36 protein can be changed to a termination codon. Hence, the PHYB-related *Glycine max* protein referred to as phytochrome B (NCBI accession no. ACJ61499.1 (GI: 214011498) with sequence SEQ ID NO: 36) can be inactivated in a manner similar to the PhyB loci described above.

A chromosomal segment encoding the SEQ ID NO:36 protein is on *Glycine max* chromosome 9, and also at NC_016096.2 (2960478 . . . 2966704, complement), with a sequence available as NCBI accession number NC_016096.2 (GI:952545307).

An *Oryza sativa* protein referred to as phytochrome B (NCBI accession no. AFK31004.1 (GI:388458276)) has significant sequence identity to the *Arabidopsis thaliana* PHYB protein with SEQ ID NO:30, as illustrated by the sequence comparison shown below. Domains of sequence homology are identified with asterisks below the sequence comparison.

```
75.6% identity in 1113 residues overlap; Score: 4309.0; Gap
frequency: 1.3%
Seq30    52 ESMSKAIQQYTVDARLHAVFEQGESGKSFDYSQSLKTTTYGSSVPEQQTAYLSRIQRG
Seq37    56 ESVSKAVAQYTLDARLHAVFEQSGASGRSFDYTQSLRASPTPSS--
                EQQIAAYLSRIQRG
            ** *** *** ************ ** **** ***     ** ****
                *********

Seq30   112 GYIQPFGCMIAV-DESSFRIIGYSENAREMLGIMPQ-SVPTLEK---
                PEILAMGTDVRSL
Seq37   114 GHIQPFGCTLAVADDSSFRLLAYSENTADLLDLSPHHSVPSLDSSAVPPPVSLGADARLL
            * ****** ** * **** ****    *   * *** *      * *     * * **

Seq30   167 FTSSSSILLERAFVAREITLLNPVWIHSKNTGKPFYAILHRIDVGVVIDLEPARTEDPAL
Seq37   174 FAPSSAVLLERAFAAREISLLNPLWIHSRVSSKPFYAILHRIDVGVVIDLEPARTEDPAL
            * ** ****** **** **** ****
                ***************************

Seq30   227 SIAGAVQSQKLAVRAISQLQALPGGDIKLLCDTVVESVRDLTGYDRVMVYKFHEDEHGEV
Seq37   234 SIAGAVQSQKLAVRAISRLQALPGGDVKLLCDTVVEHVRELTGYDRVMVYRFHEDEHGEV
            ***************** ******** ********* ** ********** *********
                *********

Seq30   287 VAESKRDDLEPYIGLHYPATDIPQASRELFKQNRVRMIVDCNATPVLVVQDDRLTQSMCL
Seq37   294 VAESRRNNLEPYIGLHYPATDIPQASRFLFRQNRVRMIADCEAAPVRVIQDPALTQPLCL
            **** *  ******************* *** ******* **  ** *  **  * ***
            **

Seq30   347 VGSTLRAPHGCHSQYMANMGSIASLAMAVIINGNEDDGSNVASGR--
                SSMRLWGLVVCHH
Seq37   354 VGSTLRSPHGCHAQYMANMGSIASLVMAVIISSGGDDDHNIARGSIPSAMKLWGLVVCHH
            ****** ***** ************ ***** **    **  *  *   *
                *********
```

```
Seq30   405 TSSRCIPFPLRYACEFLMQAFGLQLNMELQLALQMSEKRVLRTQTLLCDMLLRDSPAGIV
Seq37   414 TSPRCIPFPLRYACEFLMQAFGLQLNMELQLAHQLSEKHILRTQTLLCDMLLRDSPTGIV
            ** ************************** *** ***************
            ***

Seq30   465 TQSPSIMDLVKCDGAAFLYHGRYYPLGVAPSEVQIKDVVEWLLANHADSTGLSTDSLGDA
Seq37   474 TQSPSIMDLVKCDGAALYYHGKYYPLGVTPTEVQIKDIIEWLTMCHGDSTGLSTDSLADA
            **************** *** ****** * ****** ***  * **********
            **

Seq30   525 GYPGAAALGDAVCGMAVAYITKRDFLFWFRSHTAKEIKWGGAKHHPEDKDDGQRMHPRSS
Seq37   534 GYPGAAALGDAVSGMAVAYITPSDYLFWFRSHTAKEIKWGGAKHHPEDKDDGQRMHPRSS
            ************ ******** * *
            ************************************

Seq30   585 FQAFLEVVKSRSQPWETAEMDAIHSLQLILRDSFKES-EAAMNSK-
                VVDGVVVQPCRDMAG
Seq37   594 FKAFLEVVKSRSLPWENAEMDAIHSLQLILRDSFRDSAEGTSNSKAIVNGQVQ--
                LGELE
            * ********** *** ****************  * *   *** * * **

Seq30   643 EQGIDELGAVAREMVRLIETATVPIFAVDAGGCINGWNAKIAELTGLSVEEAMGKSLVSD
Seq37   652 LRGIDELSSVAREMVRLIETATVPIFAVDTDGCINGWNAKVAELTGLSVEEAMGKSLVND
             *****  ******************** *********** *****************

Seq30   703 LIYKENEATVNKLLSRALRGDEEKNVEVKLKTFSPELQGKAVFVVVNACSSKDYLNNIVG
Seq37   712 LIFKESEETVNKLLSRALRGDEDKNVEIKLKTFGPEQSKGPIFVIVNACSSRDYTKNIVG
            ** ** * ************** ****  ****** **      ** ****** **
            ****

Seq30   763 VCFVGQDVTSQKIVMDKFINIQGDYKAIVHSPNPLIPPIFAADENTCCLEWNMAMEKLTG
Seq37   772 VCFVGQDVTGQKVVMDKFINIQGDYKAIVHNPNPLIPPIFASDENTCCSEWNTAMEKLTG
            ********* ** ***************** ********* ****** *** *******
            *******

Seq30   823 WSRSEVIGKMIVGEVFGSCCMLKGPDALTKFMIVLHNAIGGQDTDKFPFPFFDRNGKFVQ
Seq37   832 WSRGEVVGKLLVGEVFGNCCRLKGPDALTKFMIVLHNAIGGQDCEKFPFSFFDKNGKYVQ
            *** ** ** ****** ** ********************** * **** *** *** **
            **

Seq30   883 ALLTANKRVSLEGKVIGAFCFLQIPSPELQQALAVQRRQDTECFTKAKELAYICQVIKNP
Seq37   892 ALLTANTRSRMDGEAIGAFCFLQIASPELQQAFEIQRHHEKKCYARMKELAYIYQEIKNP
            ****** *   *   ********* *******   ** *   *     ****** * ****
            ****

Seq30   943 LSGMRFANSLLEATDLNEDQKQLLETSVSCEKQISRIVGDMDLESIEDGSFVLKREEFFL
Seq37   952 LNGIRFTNSLLEMTDLKDDQRQFLETSTACEKQMSKIVKDASLQSIEDGSLVLEKGEFSL
            * * ** *****  ***  **   *** *****  *** *  * ****** ***    ***

Seq30  1003 GSVINAIVSQAMFLLRDRGLQLIRDIPEEIKSIEVFGDQIRIQQLLAEFLLSIIRYAPSQ
Seq37  1012 GSVMNAVVSQVMIQLRERDLQLIRDIPDEIKEASAYGDQYRIQQVLCDFLLSMVRFAPAE
            *** ** *** *  ** * ******** ***    ****  ****  ***** * *  *

Seq30  1063 E-
                WVEIHLSQLSKQMADGFAAIRTEFRMACPGEGLPPELVRDMFHSSRWTSPEGLGLSVC
Seq37  1072 NGWVEIQVRPNIKQNSDGTDTMLFLFRRFACPGEGLPPEIVQDMFSNSRWTTQEGIGLSIC
              ****    **  **    **  ** ********** * *** * ****  **  ****

Seq30  1122 RKILKLMNGEVQYIRESERSYFLIILELPVPRK
Seq37  1132 RKILKLMGGEVQYIRESERSFFHIVLELPQPQQ
            ******* ************ *  * **** *
```

This PHYB-related *Oryza sativa* protein referred to as phytochrome B (NCBI accession no. AFK31004.1 (GI: 388458276)) has the following sequence (SEQ ID NO:37).

```
   1  MASGSRATPT RSPSSARPAA PRAQHHHSQS SGGSTSRAGG
  41  GGGGGGGGGG GAAAAESVSK AVAQYTLDAR LHAVFEQSGA
  81  SGRSFDYTQS LRASPTPSSE QQIAAYLSRI QRGGHIQPFG
 121  CTLAVADDSS FRLLAYSENT ADLLDLSPHH SVPSLDSSAV
 161  PPPVSLGADA RLLFAPSSAV LLERAFAARE ISLLNPLWIH
 201  SRVSSKPFYA ILHRIDVGVV IDLEPARTED PALSIAGAVQ
 241  SQKLAVRAIS RLQALPGGDV KLLCDTVVEH VRELTGYDRV
 281  MVYRFHEDEH GEVVAESRRN NLEPYIGLHY PATDIPQASR
 321  FLFRQNRVRM IADCHAAPVR VIQDPALTQP LCLVGSTLRS
 361  PHGCHAQYMA NMGSIASLVM AVIISSGGDD DHNIARGSIP
 401  SAMKLWGLVV CHHTSPRCIP FPLRYACEFL MQAFGLQLNM
 441  ELQLAHQLSE KHILRTQTLL CDMLLRDSPT GIVTQSPSIM
 481  DLVKCDGAAL YYHGKYYPLG VTPTEVQIKD IIEWLTMCHG
 521  DSTGLSTDSL ADAGYPGAAA LGDAVSGMAV AYITPSDYLF
```

```
 561  WFRSHTAKEI KWGGAKHHPE DKDDGQRMHP RSSFKAFLEV

601  VKSRSLPWEN AEMDAIHSLQ LILRDSFRDS AEGTSNSKAI

641  VNGQVQLGEL ELRGIDELSS VAREMVRLIE TATVPIFAVD

681  TDGCINGWNA KVAELTGLSV EEAMGKSLVN DLIFKESEET

721  VNKLLSRALR GDEDKNVEIK LKTFGPEQSK GPIFVIVNAC

761  SSRDYTKNIV GVCFVGQDVT GQKVVMDKFI NIQGDYKAIV

801  HNPNPLIPPI FASDENTCCS EWNTAMEKLT GWSRGEVVGK

841  LLVGEVFGNC CRLKGPDALT KFMIVLHNAI GGQDCEKFPF

881  SFFDKNGKYV QALLTANTRSRMDGEAIGAF CFLQIASPEL

921  QQAFEIQRHH EKKCYARMKE LAYIYQEIKN PLNGIRFTNS

961  LLEMTDLKDD QRQFLETSTA CEKQMSKIVK DASLQSIEDG

1001  SLVLEKGEFS LGSVMNAVVS QVMIQLRERD LQLIRDIPDE

1041  IKEASAYGDQ YRIQQVLCDF LLSMYRFAPA ENGWVEIQVR

1081  PNIKQNSDGT DTMLFLFRFA CPGEGLPPEI VQDMFSNSRW

1121  TTQEGIGLSI CRKILKLMGG EVQYIRESER SFFHIVLELP

1181  QPQQAASRGT S
```

A codon encoding the arginine at position 329 of the SEQ ID NO:37 protein is equivalent to the codon encoding the arginine at position 322 of the SEQ ID NO:30 protein. A codon encoding the arginine at position 329 of the SEQ ID NO:37 protein can be changed to a termination codon. Hence, PHYB-related Oryza sativa protein referred to as phytochrome B (NCBI accession no. AFK31004.1 (GI: 388458276) with sequence SEQ ID NO:37) can be inactivated in a manner similar to the PhyB loci described above.

A chromosomal segment encoding the SEQ ID NO:37 protein is on Oryza sativa chromosome 3 at NC_029258.1 (11020017 . . . 11028186), sequence available as NCBI accession number NC_029258.1 (GI:996703430).

Chromosomal sites encoding any of the conserved amino acids and conserved domains illustrated by the sequence comparisons shown above can be deleted or mutated to reduce the activity of the proteins described herein.

For example, a wild type plant can express PHYB polypeptides or PHYB-related polypeptides with at least 70%, or at least 75%, or at least 80%, or at least 85%, or at least 90%, or at least 95%, or at least 97%, or at least 98%, or at least 99% sequence identity to any of SEQ ID NOs:30, 32, 33, 34, 35, 36, or 37.

However, the mutant phyB plant cells, plants, and/or seeds with reduced PHYB function and improved plant growth can have mutations that delete at least a portion of the phyB loci or that delete at least a portion of phyB-related loci (so that PHYB function is reduced or lost altogether). Mutant phyB plant cells, plants, and/or seeds with reduced PHYB function and improved plant growth can express mutant phyB and/or mutant phyB-related polypeptides that have reduced activity. Such PHYB and/or PHYB-related polypeptides that have reduced PHYB activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37. In other words, mutations can delete or modify chromosomal PhyB or PhyB-related chromosomal sites so that a truncated polypeptide, a highly mutated polypeptide, or no polypeptide is expressed.

The mutant PHYB and/or PHYB-related can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved PhyB and/or PhyB-related domain or the entire endogenous PHYB and/or PHYB-related gene, loci, or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be used are shown in Tables 1 and 2.

Pif4

As described herein, overexpression of PIF4 can improve myc mutant plant growth without compromising defense against insects. Hence, the mutant plants described herein can also express PIF4, for example, by transformation of plants having a myc, myc-related phyB, and/or phyB-related mutant genomic background with an expression cassette or expression vector that encodes PIF4.

One example of an Arabidopsis thaliana PIF4 protein sequence is shown below as SEQ ID NO:38.

```
  1  MEHQGWSFEE NYSLSTNRRS IRPQDELVEL LWRDGQVVLQ

41  SQTHREQTQT QKQDHHEEAL RSSTFLEDQE TVSWIQYPPD

81  EDPFEPDDFS SHFFSTMDPL QRPTSETVKP KSSPEPPQVM

121  VKPKACPDPP PQVMPPPKFR LTNSSSGIRE TEMEQYSVTT

161  VGPSHCGSNP SQNDLDVSMS HDRSKNIEEK LNPNASSSSG

201  GSSGCSFGKD IKEMASGRCI TTDRKRKRIN HTDESVSLSD

241  AIGNKSNQRS GSNRRSRAAE VHNLSERRRR DRINERMKAL

281  QELIPHCSKT DKASILDEAI DYLKSLQLQL QVMWMGSGMA

321  AAAASAPMMF PGVQPQQFIR QIQSPVQLPR FPVMDQSAIQ

361  NNPGLVCQNP VQNQIISDRF ARYIGGFPAM QAATQPMEML

401  RFSSPAGQQS QQPSSVPTKT TDGSRLDH
```

A cDNA that encodes the SEQ ID NO:38 PIF4 protein can have nucleotide sequence SEQ ID NO:39, shown below.

```
  1  ACTTTCTGTC TGTACCCAAA AGAAGTAATG AACCTCTCTC

41  ATCTTCTTCT TCTCTGTTTC TTTCATGTTT TGTGAGTTGT

81  TTCTCAACAA TTTTCTGGTC TCTTAGAGTG AGAGGAGAGA

121  GATAGAGAGT TGTGTTGGGC GTGGAACTTG GACTAGTTCC

161  ACATATCAGG TTATATAGAT CTTCTCTTTC AACTTCTGAT

201  TCGTCCAGAA GCTTTCCTAA TCTGAGATCT GACATGGAAC

241  ACCAAGGTTG GAGTTTTGAG GAGAATTATA GTTTGTCCAC
```

-continued

```
 281 TAATAGAAGA TCTATCAGGC CACAAGATGA ACTAGTGGAG
 321 TTATTATGGC GAGATGGACA AGTGGTTCTG CAGAGCCAAA
 361 CTCATAGAGA ACAAACCCAA ACCCAGAAAC AAGATCATCA
 401 TGAAGAAGCC CTAAGATCCA GCACCTTTCT TGAAGATCAA
 441 GAAACTGTCT CTTGGATCCA ATACCCTCCA GATGAAGACC
 481 CATTCGAACC CGACGACTTC TCCTCCCACT TCTTCTCAAC
 521 CATGGATCCC CTCCAGAGAC CAACCTCAGA GACGGTTAAG
 561 CCTAAGTCCA GTCCTGAACC TCCTCAAGTC ATGGTTAAGC
 601 CTAAGGCCTG TCCTGACCCT CCTCCTCAAG TCATGCCTCC
 641 TCCAAAATTT AGGTTAACAA ATTCATCATC GGGGATTAGG
 681 GAAACAGAAA TGGAACAGTA CTCGGTAACG ACCGTTGGAC
 721 CTAGCCATTG CGGAAGCAAC CCATCACAGA ACGATCTCGA
 761 TGTCTCAATG AGTCATGATC GAAGCAAAAA CATAGAAGAA
 801 AAGCTTAATC CGAACGCAAG TTCCTCATCA GGTGGCTCCT
 841 CTGGTTGCAG CTTTGGCAAA GATATCAAAG AAATGGCTAG
 881 TGGAAGATGC ATCACAACCG ACCGTAAGAG AAAACGTATA
 921 AATCACACTG ACGAATCTGT ATCTCTATCA GATGCAATCG
```

-continued

```
 961 GTAACAAGTC GAACCAACGA TCAGGATCAA ACCGAAGGAG
1001 TCGAGCAGCT GAAGTTCATA ATCTCTCCGA AGGAGGAGG
1041 AGAGATAGGA TCAATGAGAG AATGAAGGCT TTGCAAGAAC
1081 TAATACCTCA CTGCAGTAAA ACTGATAAAG CTTCGATTTT
1121 AGACGAAGCC ATAGATTATT TGAAATCACT TCAGTTACAG
1161 CTTCAAGTGA TGTGGATGGG GAGTGGAATG GCGGCGGCGG
1201 CGGCTTCGGC TCCGATGATG TTCCCCGGAG TTCAACCTCA
1241 GCAGTTCATA CGTCAGATAC AGAGCCCGGT ACAGTTACCT
1281 CGATTTCCGG TTATGGATCA GTCTGCAATT CAGAACAATC
1321 CCGGTTTAGT TTGCCAAAAC CCGGTACAAA ACCAGATCAT
1361 CTCCGACCGG TTTGCTAGAT ACATCGGTGG GTTCCCACAC
1401 ATGCAGGCCG CGACTCAGCC GATGGAGATG TTGAGATTTA
1441 GTTCACCGGC GGGACAGCAA AGTCAACAAC CGTCGTCTGT
1481 GCCGACGAAG ACCACCGACG GTTCTCGTTT GGACCACTAG
1521 GTTGGTGAGC CACTTTTTTA CTTCCTTATT TTTGGTATGT
```

-continued

```
1561 TTCTTTTTTA TATCTATCTT TCTGAACATA CTTAAAACGT
1601 TCAAGGATGT ATTATTATAG AGTAAACGTG CAACTTCATT
1641 ACGTTATTTT CTGTATATGT GAGTTTATGT ATGTCAAAAT
1681 GACATGATGA GATTTTTTGT AAACAACATC TTAAAAACAG
1721 GACATGTGAT TTTTGTAATC GTAAAAA
```

Nucleic acids from a variety of plant types that encode PIF4 and/or PIF4-related polypeptides can be transformed into plants as transgenes. For example, such nucleic acids that encode PIF4 and/or PIF4-related polypeptides can be incorporated into expression cassettes or expression vectors that are introduced into selected plant cells, for example, plant cells with a mutant myc, JAZ, and/or phyB genetic background. Plant lines can be generated from the plant cells.

A PIF4-related protein from *Zea mays* referred as a putative HLH DNA-binding domain superfamily protein (NCBI accession no. NP_001146660.1 (GI:226502090)) has substantial homology to the *Arabidopsis thaliana* PIF4 SEQ ID NO:38 protein sequence, as illustrated below. Domains of sequence homology are identified with asterisks below the sequence comparison.

```
63.6% identity in 99 residues overlap; Score: 316.0; Gap frequency:
0.0%
Seq38  224 RKRKRINHTDESVSLSDAIGNKSNQRSGSNRRSRAAEVHNLSERRRRDRINERMKALQEL
Seq40  218 RRSGKRKHNDATDAEDVGLECEPAQRTTTAKRRAAQVHNLSERRRRDRINEKMKKLQEL
           *    * *           **     * *** ***************
           *******

Seq38  234 IPHCSKTDKASILDEAIDYLKSLQLQLQVMWMGSGMAAA
Seq40  278 IPHCNKADKASMLDEAIEYLKSLQLQLQVVWMGGGIAAA
           **** * **** ***** *********** *** * ***
```

The *Zea mays* protein referred as a putative HLH DNA-binding domain superfamily protein (NCBI accession no. NP_001146660.1 (GI:226502090)) has the following sequence (SEQ ID NO:40).

```
  1 MQTAIEHACS VVECAATARA AMDMSHYIPD WSSSMGDTFA
 41 PLGGEDDDGL IELMWRNGHV VMQAQAPRKP PRPDDDEAAA
 81 AQAQAWFQYP VEERADLFSE LFGEAQAAVG GARGEAARQS
121 IRMMPPPPPP PRPAQAPREE KACPGDGGTA TATDGAGSSV
161 LTVVSSLCGS NGNHVQATAP GDVARARDVL MVTSSSTTRS
201 RSCTTKSEQP GPGPGAARRS GKRKHNDATD AEDVGLECEP
241 AQRTTTAKRR RAAQVHNLSE RRRRDRINEK MKALQELIPH
281 CNKADKASML DEAIEYLKSL QLQLQVVWMG GGIALAGVHQ
321 RTMVAAPGRP PHVASLPASA PDLYTRYLAV DHLPPPPLVP
361 PPRTAAAMGL YPRQNPVPAT SSPSFRTTEN TRKLWQA
```

A cDNA encoding the *Zea mays* protein referred as a putative HLH DNA-binding domain superfamily protein (NCBI accession no. NP_001146660.1 (GI:226502090); SEQ ID NO:38) has the following nucleotide sequence (SEQ ID NO:41).

```
   1 CCTTGCCCTG CTGCAACTTG AACCTCCTGG CAGCTCCTGT
  41 TTCAGGCAGG CAGCAAGTAG GGAAGAGGCT CTGCAGATCA
  81 GTTCCATGCA GACAGCGATC GAGCACGCCT GCTCGGTGGT
 121 GGAATGCGCT GCGACAGCCC GAGCCGCCAT GGACATGAGC
 161 CACTACATCC CCGATTGGAG CAGCAGCATG GGAGACACCT
 201 TCGCGCCACT GGGCGGCGAG GACGACGACG GGCTCATCGA
 241 GCTCATGTGG CGCAACGGCC ACGTGGTCAT GCAGGCCCAG
 281 GCGCCGCGGA AGCCGCCGAG ACCCGACGAC GACGAGGCGG
 321 CGGCGGCGCA GGCGCAGGCG TGGTTCCAGT ACCCGGTGGA
 361 GGAGAGGGCC GACCTCTTCT CGGAGCTCTT CGGGGAGGCG
 401 CAGGCGGCCG TCGGCGGCGC GCGCGGGGAG GCCGCGCGCC
 441 AGAGTATCCG GATGATGCCG CCGCCGCCGC CGCCGCCGAG
 481 GCCCGCGCAA GCGCCGCGGG AGGAGAAGGC GTGCCCGGGA
 521 GACGGCGGCA CGGCGACGGC GACGGACGGC GCCGGCTCGT
 561 CCGTGCTCAC GGTCGTGTCC AGCCTCTGCG GGAGCAACGG
 601 CAACCACGTG CAGGCGACGG CGCCGGGGGA CGTCGCCAGG
 641 GCCCGCGACG TGCTGATGGT GACCTCGTCG TCGACGACGC
```

```
-continued
 681 GTTCCAGGTC ATGCACCACC AAGAGCGAGC AGCCGGGTCC
 721 CGGGCCCGGC GCTGCCCGCC GGAGCGGCAA GAGGAAGCAT
 761 AACGACGCCA CCGATGCCGA GGACGTGGGG CTGGAGTGCG
 801 AGCCGGCGCA GAGGACGACG ACTGCCAAGC GGCGCCGCGC
 841 CGCGCAAGTC CACAACCTCT CGGAGCGGAG GAGACGGGAC
 881 AGGATCAACG AGAAGATGAA GGCCCTGCAG GAACTCATAC
 921 CCCACTGCAA CAAAGCGGAC AAGGCGTCGA TGCTGGACGA
 961 GGCGATCGAG TACCTCAAGT CGCTGCAGCT CCAGCTGCAG
1001 GTGGTGTGGA TGGGCGGCGG CATCGCGGCG GCGGGGGTGC
1041 ACCAGCGGAC GATGGTGGCC GCGCCCGGGC GTCCTCCCCA
1081 CGTGGCTTCC CTGCCGGCGT CGGCGCCCGA CCTCTATACG
1121 CGCTACCTCG CCGTCGACCA CCTGCCGCCA CCGCCCTTGG
1161 TGCCACCGCC ACGCACGGCG GCGGCGATGG GCTTGTACCC
1201 GCGCCAGAAC CCCGTGCCGG CGACGTCGTC TCCTTCCTTC
1241 CGAACGACCG AAAATACGCG AAAACTATGG CAAGCCTGAG
1281 ATTCAGATCC GGGGTATGGT GACCAGCTGA TGGGTCATCT
1321 AGCTGCATGC ATGTGTGTAT GTGTTGGTAG TATGGTTAAG
1361 CCTTGACAGA GACTTGTGAT CGAGACCGAG ATCGACCGAT
1401 AGGCCGTCAC TTCTTTTTTC TTCCATCTTT CAGTTTTTGG
1441 TTGATAGGCC GGAGTGTAAT TTGACCAGTG GTCGAGATTT
1481 GTCAAGCGAC AC
```

A PIF4-related protein from *Glycine max* referred as a transcription factor PIF4 (NCBI accession no. XP_006575634.1 (GI:571442111)) has substantial homology to the *Arabidopsis thaliana* PIF4 SEQ ID NO:38 protein sequence, as illustrated below. Domains of sequence homology are identified with asterisks below the sequence comparison.

```
41.7% identify in 240 residues overlap; Score: 357.0; Gap frequency:
7.5%
Seq38  139 EKLNPNASSSSGGSSGCSFGKDIKEMASGRCITTD-
           RKRKRINHTDESVSLSDAIGNKSN
Seq42  291 EMIELTVTSSGGSGSTGIGRTCSLSTRDHGQKRKGTEEEALEEQSEDTELKSADGNKAS
           *       ******    *                               *   *  * ***

Seq38  248 QRSGSNRRSRAAEVHNLSERRRRDRINERMKALQELIPHCSKTDKASILDEAIDYLKSLQ
Seq42  351 QRTRSSRRNPAAEVHNQSERRRRDPINEKMRTLQQLIPNSNKTDKASMLEEAIEYLKSLQ
           **  * ** *******  ********** * **  ***  ****** * ***
           ******

Seq38  308 LQLQVMWMGSGMAAAAASKPMMFPGANVQPQQF----IRQIQSPVQLPRFPVMDQSAIQN--
Seq42  411 FQLQVMWMGGGMTPVMFPGIQHYMSQMGMGMGAPSLPSIHNPMQLPKVPHDQAMSVLQIP
            *******  **                           *  ***  *

Seq38  362 NPGLVCQNPV----------
           QNQIISDRFARYIGGFPHMQAATQPMEMLRFSSPAGQQSQ
Seq42  471 NQNLMCQNPVLGAFNYQNQMQNPCLPEQYARYMG-
           YHLMQNASQPMNVFRYGSQAVQHSQ
           *  * *****            **      *** *   ** * ***    *   * *
           **
```

The PIF4-related protein from *Glycine max* referred as a transcription factor PIF4 (NCBI accession no. XP_006575634.1 (GI:571442111)) has the following sequence (SEQ ID NO:42).

```
  1 MNNSIPGWDF ESDTCLTNQR KLIGPDQELV ELLWKNGQVV
 41 MHNQTHRKTL GNSSNLRQVQ KSDQSVLRSS GPYGNSSNLD
 81 QEDAAPWVQF PLEDPLEQDF CSNLLSELPT CEFESYKPIR
121 QLEEEKFAKF FASGTPHHPT TSSSQPLPPN MKPSCIQGLQ
161 GNPIPMPAPR FHGPDSSQKI HDFGASRKVL NFPQFSTPRN
201 NVPSAPGITQ FREKTTANMS QSEAREYSVI TVGSSHCGSN
241 HIPQEQDVSR ISSTGVWATT NNNTTLSAEP EAVRDYVQRP
```

```
281 ICPKSGQGKS EMIELTVTSS SGGSGSTGIG RTCSLSTRDH

321 GQKRKGTEEE ALEEQSEDTE LKSADGNKAS QRTRSSRRNR

361 AAEVHNQSER RRRDRINEKM RTLQQLIPMS NKTDKASMLE

401 EAIEYLKSLQ FQLQVMWMGG GMTPVMFPGI QHYMSQMGMG

441 MGAPSLPSIH NPMQLPKVPH DQAMSVLQIP NQNLMCQNPV

481 LGAFNYQNQM QNPCLPEQYA RYMGYELMQN ASQPMNVFRY

521 GSQAVQHSQT MIAPGNNSSG PMSGTANIDD ADSGKAGSST

561 FN
```

A cDNA encoding the PIF4-related protein from *Glycine max* referred as a transcription factor PIF4 (NCBI accession no. XP_006575634.1 (GI:571442111); SEQ ID NO:42) is shown below as SEQ ID NO: 43.

```
   1 GACCCCGTTT TCAACTGGTC CCGTGTTCCT TCATTTGATG

41 CCACATGTGC AGCTAGCCAT GTTTTTCTCG CTGTTGACGA

81 GCACAATATA TAATAAATAC CATTTTTTTC ATGCCATATT

121 TGCTCTCTTC TCTCTTTGTA CTAATAACTT GGATCTATGC

161 CACTGTCCTT CTCCTTGTTA AAAACTGTGC CACACGTCTG

201 TCACCAAACT CCCTAAGCAG AAGAAGCACA TGTTCAGAGG

241 GAGTTTTGTT TCATCAGTCT CTAGCTAGCA TATATTTCTA

281 GCTTCTATTC AACAAGTTGC AAAAAACAGA CTTTGCCTTA

321 ACCAAAAGAA AATCTGTTTT TACCTTAACT CAGACAACTC

361 GTTTGGTGAA CCATGAACAA CAGTATTCCT GGTTGGGATT

401 TTGAGAGTGA TACATGTCTC ACCAACCAAA GAAAGCTCAT

441 AGGGCCGGAC CAAGAACTTG TAGAGCTCCT ATGGAAAAAT

481 GGGCAAGTAG TTATGCACAA CCAAACACAT AGGAAGACAC

521 TTGGGAATTC ATCTAACTTG AGACAGGTGC AGAAAAGTGA

561 TCAATCAGTA TTAAGGTCTA GCGGTCCCTA TGGAAACTCA

601 AGCAACTTGG ATCAAGAAGA TGCCGCCCCA TGGGTCCAAT

641 TCCCACTTGA GGACCCATTG GAACAAGATT TTTGTTCAAA

681 CCTTTTATCT GAACTACCAA CTTGTGAATT TGAATCTTAC

721 AAGCCAATCA GGCAATTGGA AGAGGAAAAG TTTGCCAAAT

761 TTTTTGCTTC CGGTACCCCC CATCATCCTA CAACTTCAAG

801 TTCACAACCA CTACCACCTA ACATGAAACC CTCATGTATT

841 CAGGGACTCC AAGGGAATCC TATTCCTATG CCAGCTCCAA

881 GATTTCATGG TCCTGATTCA TCTCAGAAAA TCCATGACTT

921 TGGAGCATCA CGAAAGGTTC TAAATTTTCC TCAGTTTTCA

961 ACACCCCGTA ATAATGTTCC ATCAGCACCT GGTATTACAC

1001 AGTTTAGAGA GAAAACTACT GCTAACATGT CACAAAGTGA

1041 GGCTAGAGAG TACTCAGTGA TCACAGTTGG TTCAAGTCAC

1081 TGTGGCAGCA ATCACATCCC TCAGGAGCAA GATGTAAGCA

1121 GGATTTCAAG CACTGGTGTT TGGGCCACTA CTAATAATAA

1161 TACTACTTTA TCTGCTGAGC CTGAAGCTGT CAGAGATTAT

1201 GTCCAAAGAC CGATTTGTCC TAAGAGTGGC CAAGGAAAAT

1241 CAGAGATGAT TGAACTAACT GTGACTTCAT CTTCCGGTGG

1281 CTCGGGAAGT ACTGGTATCG GAAGAACCTG TTCCCTATCA

1321 ACAAGAGATC ATGGCCAAAA GAGAAAAGGG ACAGAAGAAG

1361 AAGCGTTAGA GGAACAAAGT GAGGACACAG AACTTAAATC

1401 AGCTGATGGA AACAAGGCTT CTCAGCGGAC GAGGTCTTCC

1441 AGAAGGAACC GTGCAGCAGA AGTGCATAAT CAATCAGAAA

1481 GGAGAAGAAG AGATAGGATC AACGAGAAGA TGAGGACATT

1521 GCAGCAACTG ATACCTAATA GTAACAAGAC AGACAAAGCA

1561 TCAATGTTAG AAGAGGCAAT CGAATACTTG AAATCACTTC

1601 AGTTTCAGCT TCAGGTTATG TGGATGGGGG GTGGCATGAC

1641 ACCAGTGATG TTCCCAGGAA TTCAGCACTA TATGTCACAA

1681 ATGGGTATGG GAATGGGTGC ACCTTCTTTG CCTTCCATTC

1721 ACAACCCGAT GCAATTGCCA AAAGTGCCAC ATGATCAAGC

1761 CATGTCTGTG CTTCAGATAC CAAACCAGAA TTTAATGTGT

1801 CAAAATCCAG TTTTGGGTGC CTTTAACTAC CAAAACCAGA

1841 TGCAGAACCC GTGCCTTCCA GAACAATATG CACGTTACAT

1881 GGGTTACCAT CTTATGCAAA ATGCCTCTCA GCCTATGAAT

1921 GTGTTCAGAT ATGGTTCCCA AGCAGTGCAA CACAGTCAAA

1961 CGATGATTGC ACCAGGCAAT AATAGCAGCG GACCCATGAG

2001 TGGAACAGCT AATATTGATG ATGCTGACAG TGGCAAAGCG

2041 GGTTCTTCCA CCTTTAATTG AATAGTGAAT AGCAATACCT

2081 TAAAATTACT CAATTGGGGG AATTACCTAA TGGAGTACGT

2121 CAATCCTCAC AAGCACCAAT ATGTGCTCCA ATTTTATGTA

2161 G
```

A PIF4-related protein from *Oryza sativa* referred as a transcription factor PIF4 isoform X3 (NCBI accession no. XP_015618080.1 (GI: 1002309425)) has substantial homology to the *Arabidopsis thaliana* PIF4 SEQ ID NO:38 protein sequence, as illustrated below. Domains of sequence homology are identified with asterisks below the sequence comparison.

36.8% identity in 323 residues overlap; Score: 322.0; Gap frequency: 8.4%

```
Seq38   25 DELVELLWRDGQWLQSQTHREQTQTQKQDHHEEALRSSTFLEDQETVSWIQYPPDEDPF
Seq44   24 DGLVELLWCNGHVVMQSQAPRKPPRPEKT-----TAAAAAAMAEDESASWFQYPVD-
           DVL
              ******  *  ** ***   *          *    *   ** *** * *

Seq38   85 EPDDFSSHFFSTMDPLQRPTSETVKPKSSPEPPQVMVKPKACPDPPPQVMPPPKFRLTNS
Seq44   78 EKDLFTE-
           LFGEMTAAGGGGGDVRRAACKEERGAVAAFQSRMMPPPWPARGKAEFGDVDD
           * * *     * *                       *    *         **     *

Seq38  145 SSGIRETEMEQY------------SVTTVGPSHCGSNPSQND-
           LDVSMSHDRSKNIEEKL
Seq44  137 VCGVSEVVMAKMDGAAAAETVGESSMLTIGSSICGSNHVQTPPVGNGKAGAGTAGAARRA
             *  *                    *    * ****  *

Seq38  192 NPNAS--SSSGGSSGCSFGKDIKEMASGRCITTDRKR----
           KRINHTDESVSLSDAIGNK
Seq44  197 HDTATVASSSMRSRSCTAKAEPRDVAAAGVGGKRKQRGGAAMESGSPSEDVEFESAAATC
              *  ***  *  *       *                *           * *   *

Seq38  246 SN-
           QRSGSNRRSRAAEVHNLSERRRRDRINERMKALQELIPHCSKTDKASILDEAIDYLK
Seq44  257 SPAQKTTTAKRRRAAEVHNLSERRRRDRINEKMKALQELIPHCNKTDKASMLDEAIEYLK
              *   *  * ****************** *********** ******  ***** ***
           ***

Seq38  305 SLQLQLQVMWMGSGMAAAAASAP
Seq44  317 SLQLQLQMMWMGGGMAPPAVMFP
           ****** **** ***   *  *
```

This PIF4-related protein from *Oryza sativa* referred as a transcription factor PIF4 isoform X3 (NCBI accession no. XP_015618080.1 (GI:1002309425)) has the following sequence (SEQ ID NO:44).

```
  1 MNQFVPDWNT TSMGDGFAPL GEDDGLVELL WCNGHWMQS
 41 QAPRKPPRPE KTTAAAAAAM AEDESASWFQ YPVDDVLEKD
 81 LFTELFGEMT AAGGGGGDVR RAACKEERGA VAAFQSRMMP
121 PPWPARGKAE FGDVDDVCGV SEWMAKMDG AAAAETVGES
161 SMLTIGSSIC GSMHVQTPPV GNGKAGAGTA GAARRAHDTA
201 TVASSSMRSR SCTAKAEPRD VAAAGVGGKR KQRGGAAMES
241 GSPSEDVEFE SAAATCSPAQ KTTTAKRRRA AEVHNLSERR
281 RRDRINEKMK ALQELIPHCN KTDKASMLDE AIEYLKSLQL
321 QLQMMWMGGG MAPPAVMFPA AGVHQYMQRM GAVGMGPPHM
361 ASLPRMPPFM APPPAAYQSS PVYSMADPYA RCLAVDHLQP
401 PPPMFRREY
```

A cDNA encoding the PIF4-related protein from *Oryza sativa* referred as a transcription factor PIF4 isoform X3 (NCBI accession no. XP_015618080.1 (GI: 1002309425); SEQ ID NO:44) has the following sequence (SEQ ID NO:45).

```
   1 GCGAGTCCTC TTCCTGCCCT GCCCTGCCCT GCCCTGCATT
  41 CTTTCTTTCT CCACCAGGGG AATCCAGTTC ACCCCCAGTG
  81 CTGCTTCTGC TGCTGCTTCT GCATCATCTT GCCCTGTTAA
 121 AAAGACACAG TGCCCTTGTT CTTTCGCAGT TGCAACTAGC
 161 ATCTCCTCCT CTACTTGTAC TCACTTCACA CCTCAGCTCA
```

```
-continued
 201 GCTCAGCTCA TCTCCTGTCA TCTCAGCTCA AAGAGAAAGA
 241 GCTGAAGGTG TAAGCTGATC ACCAGGAAGC AGAGGCTTTT
 281 TTTCAGATTA CAGTTATCTG AAACAACCAA CTTCAGAATC
 321 AATCAGCAAA GGTAGAAACA AGACAGAGCT GCTGTGCTTC
 361 TGTGATTAAT TAGGGTTGTT AATGCCATGA ACCAGTTCGT
 401 CCCTGATTGG AACACCACCA GCATGGGCGA CGGCTTTGCG
 441 CCATTAGGCG AAGACGACGG GCTCGTCGAG CTGCTATGGT
 481 GCAATGGCCA CGTCGTCATG CAGAGCCAGG CGCCGCGGAA
 521 GCCGCCGAGG CCGGAGAAGA CGACGGCGGC GGCGGCGGCG
 561 GCGATGGCGG AGGATGAGTC GGCGTCGTGG TTTCAGTACC
 601 CGGTCGACGA CGTGCTTGAG AAGGACCTGT TCACCGAGCT
 641 GTTCGGCGAA ATGACGGCGG CCGGCGGCGG CGGCGGCGAC
 681 GTCCGCAGGG CGGCGTGCAA GGAGGAGCGC GGCGCGGTCG
 721 CCGCGTTCCA GAGCAGGATG ATGCCGCCGC CGTGGCCGGC
 761 GAGGGGGAAG CGGGAGTTCG GTGACGTCGA CGACGTGTGC
 801 GGCGTCTCGG AGGTCGTCAT GGCGAAGATG GACGGGGCGG
 841 CGGCGGCGGA GACGGTCGGC GAGTCATCGA TGCTGACAAT
 881 CGGGTCGAGC ATCTGCGGGA GCAACCACGT CCAGACGCCG
 921 CCGGTGGGGA ACGGGAAGGC CGGCGCCGGC ACCGCCGGCG
 961 CCGCCAGAAG GGCGCACGAC ACGGCGACGG TGGCGTCGTC
1001 GTCGATGAGG TCGAGGTCCT GCACCGCCAA GGCCGAGCCG
1041 CGCGACGTCG CAGCCGCCGG CGTCGGCGGC AAGCGGAAGC
1081 AGCGCGGCGC CGCCGCCATG GAGTCCGGGA GCCCCAGCGA
```

```
      -continued
1121 GGACGTGGAG TTCGAGTCCG CCGCCGCAAC GTGCTCGCCG

1161 GCGCAGAAGA CGACGACGGC GAAGCGGCGG CGCGCCGCCG

1201 AGGTGCACAA CCTCTCCGAG AGGAGGAGAA GAGATAGGAT

1241 CAATGAGAAG ATGAAAGCAT TACAGGAGCT CATACCTCAC

1281 TGCAACAAAA CGGACAAAGC ATCGATGCTG GATGAAGCGA

1321 TCGAGTATCT CAAGTCACTG CAGCTCCAGC TACAGATGAT

1361 GTGGATGGGC GGCGGAATGG CGCCGCCGGC GGTGATGTTC

1401 CCGGCGGCGG GCGTGCACCA GTACATGCAG CGGATGGGCG

1441 CCGTCGGGAT GGGCCCACCA CACATGGCGT CCCTGCCGAG

1481 GATGCCGCCG TTCATGGCGC CGCCGCCGGC CGCCGTGCAG

1521 AGCTCGCCGG TGGTCAGCAT GGCCGACCCC TACGCCCGCT

1561 GCCTCGCCGT CGACCACCTC CAGCCACCGC CTCCGATGTT

1601 TCGACGCGAA TACTAGGGAA GGAACTAATA TCAAATAATA

1641 GAAGGGGTGA GCCTTCGAAT CGAGATCGTC TAGCCCACCA

1681 CCTTATAGAG CTAGCCGGAA GGCCCTCGAG CGTTTCTCAT

1721 ATTTTCAGTT TCCTAAGAGT TTTTTTTTT
```

Expression cassettes and expression vectors can include a nucleic acid segment encoding a PIF4 protein where the nucleic acid segment is operably linked to a promoter. The nucleic acid segment can encode a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42, or 44. For example, the Pif4 nucleic acid segment can have at least 70% sequence identity, or at least 80° % sequence identity, or at least 85% sequence identity, or at least 90% sequence identity, or at least 95% sequence identity, or at least 97% sequence identity, or at least 98% sequence identity, or at least 99% sequence identity to any of nucleic acid sequences identified as SEQ ID NO: 38, 40, 42, or 44.

As stated, expression cassettes and expression vectors can include a nucleic acid segment encoding a PIF4 protein where the nucleic acid segment is operably linked to a promoter. Promoters provide for expression of mRNA from the PIF4 nucleic acids. The promoter can be heterologous to the PIF4 nucleic acid segment. In other words, such a heterologous promoter is not naturally linked to such a PIF4 nucleic acid segment. Instead, some expression cassettes and expression vectors have been recombinantly engineered to include a PIF4 nucleic acid segment operably linked to a heterologous promoter. A PIF4 nucleic acid is operably linked to the promoter, for example, when it is located downstream from the promoter.

A variety of promoters can be included in the expression cassettes and/or expression vectors. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoters can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. A strong promoter for heterologous DNAs can be advantageous because it provides for a sufficient level of gene expression for easy detection and selection of transformed cells and provides for a high level of gene expression when desired. In some cases, the promoter within such expression cassettes/vectors can be functional during plant development or growth.

Expression cassettes/vectors can include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), Adh1 (Walker et al., *Proc. Natl. Acad. Sci. USA*. 84:6624-6628 (1987)), sucrose synthase (Yang et al., *Proc. Natl. Acad Sci. USA*. 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology*. 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are available to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A PIF4 nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI21 or pBI221). Typically, these plasmids are constructed to have multiple cloning sites having specificity for different restriction enzymes downstream from the promoter. The PIF4 nucleic acids can be subcloned downstream from the promoter using restriction enzymes and positioned to ensure that the DNA is inserted in proper orientation with respect to the promoter so that the DNA can be expressed as sense or antisense RNA. Once the PIF4 nucleic acid is operably linked to a promoter, the expression cassette so formed can be subcloned into a plasmid or other vector (e.g., an expression vector).

In some embodiments, a cDNA clone encoding a PIF4 protein is isolated or obtained from a selected plant type. In other embodiments, cDNA clones from other species (that encode a PIF4 protein) are isolated from selected plant tissues. For example, the nucleic acid encoding a PIF4 protein can be any nucleic acid with a coding region that hybridizes to SEQ ID NO:39 and that has PIF4 activity. In another example, the PIF4 nucleic acid can encode a PIF4 protein with at least 90% sequence identity to SEQ ID NO:38. Using restriction endonucleases, the entire coding sequence for the PIF4 nucleic acid is subcloned downstream of the promoter in a 5' to 3' sense orientation.

jazQ Mutations

A quintet of JAZ transcriptional repressor genes can be modified to improve insect resistance in plants. The quintet of JAZ transcriptional repressor genes can encode JAZ1, JAZ3, JAZ4, JAZ9. JAZ10, and/or related proteins. Reduction or deletion of genes that encode JAZ1, JAZ3. JAZ4, JAZ9, JAZ10, and/or related proteins can provide insect resistance to plants.

JAZ1 proteins are repressors of the jasmonic acid signaling pathway. One example, of an *Arabidopsis thaliana* jasmonate-zim-domain protein 1 (JAZ1) protein sequence is shown below (SEQ ID NO:48).

```
  1 MSLFPCEASN MDSMVQDVKP TNLFPRQPSF SSSSSSLPKE
 41 DVLKMTQTTR SVKPESQTAP LTIFYAGQVI VFNDFSAEKA
 81 KEVINLASKG TANSLAKNQT DIRSNIATIA NQVPHPRKTT
121 TQEPIQSSPT PLTELPIARR ASLHRFLEKR KDRVTSKAPY
161 QLCDPAKASS NPQTTGNMSW LGLAAEI
```

A chromosomal DNA sequence for the *Arabidopsis thaliana* jasmonate-zim-domain protein 1 (JAZ1) protein with SEQ ID NO:48 is shown below as SEQ ID NO:49.

```
  1 ATATTGGAGG TAGGAAGAAG AACTCTGCAA CCAAACCAAC
 41 CAACCCCAAA GCCAAACAAA GTTTTATAGA GACCTTCCAT
121 TTCTCCCTCT CGTGAGAAAC GCAATTTGCA GAGAAGCAAC
201 AGCAACAACA AGAAGAAGAA GAAAAAGATT TGAGATTACT
241 TTGTATCGAT TTAGCTATTC GAGAAACTCT TGCCGTTTGA
281 AAGTTTTAAT TGTTAAAGAT GTCGAGTTCT ATGGAATGTT
321 CTGAGTTCGT CGGTAGCCGG AGATTTACTG GGAAGAAGCC
361 TAGCTTCTCA CAGACGTGTA GTCGATTGAG TCAGTATCTA
401 AAAGAGAACG GTAGCTTTGG AGATCTGAGC TTAGGAATGG
441 CATGCAAGCC TGATGTCAAT GGTAAGAAAC CTTCTCTTTC
481 TCCTAGATCC ACTTCTTTTT TCGTTTTCTC TGTTTTTTAT
521 TTCTTGAATC TTGATCTTGA AAACTTTTCA AGAAAATTTT
561 GAATCGATTT CAAAGAAATT AGGGAGAGTT AGTTTGCTAA
601 ATTTTGACAT AGAAAATGAT TGGAGAGAGT TCTAACTTTT
641 GGATCATATA TATTTGCAGG AACTTTAGGC AACTCACGTC
681 AGCCGACAAC AACCATGAGT TTATTCCCTT GTGAAGCTTC
721 TAACATGGAT TCCATGGTTC AAGATGTTAA ACCGACGAAT
761 CTGTTTCCTA GGCAACCAAG CTTTTCTTCC TCATCTTCCT
801 CTCTTCCAAA GGAAGATGTT TTGAAAATGA CACAGACTAC
841 CAGATCTGTG AAACCAGAGT CTCAAACTGC ACCATTGACT
881 ATATTCTACG CCGGGCAAGT GATTGTATTC AATGACTTTT
921 CTGCTGAGAA AGCCAAAGAA GTGATCAACT TGGCGAGCAA
961 AGGCACCGCT AATAGCTTAG CCAAGAATCA AACCGATATC
1001 AGAAGCAACA TCGCTACTAT CGCAAACCAA GTTCCTCATC
1041 CAAGAAAAAC CACAACACAA GAGCCAATCC AATCCTCCCC
1081 AACACCATTG ACAGAACTTC CTATTGCTAG AAGAGCTTCA
1121 CTTCACCGGT TCTTGGAGAA GAGAAAGGAC AGAGTTACGT
1161 CAAAGGCACC ATACCAATTA TGCGATCCAG CCAAAGCGTC
1201 TTCAAACCCT CAAACCACAG GCAACATGTC GTGGCTCGGT
1241 TTAGCAGCTG AAATATGAAT GCTAACCACC CTCAAGCCGT
1281 ACCAAGAAAT TCTTTTGACG ACGTTGCTTC AAGACAAGAT
1321 ATAAAAGCTC CTATCTTCAT GCTTTTTGAT TTAAGATACA
1361 AACTACTCAA TGATTAGGAA ACTTCATATA TTTGTATGTA
1401 TTGATTAGTG ATCAATTATT GTTAGTATTC GTTATAGTCT
1441 GTTTTTCTAC TAGTTATTGT CGCCTGTCTA AATCCCCTTG
1481 CTATGGGTTA TCTCAAAATT AGTTTCGTAT GTAACTAATT
1521 TTGTAAGAAC AATAATTTTT GTTGACGAAC CATACTATCA
1561 AATACTCTAA ATTATATCTT GATAAATCTA CCTATCAGGT
1601 AAGTAGG
```

JAZ3 is also a repressor of jasmonate responses, and it is targeted by the SCF(COI1) complex for proteasome degradation in response to jasmonate. One example, of an *Arabidopsis thaliana* jasmonate-zim-domain protein 3 (JAZ3) protein sequence is shown below (SEQ ID NO:50).

```
  1 MERDFLGLGS KNSPITVKEE TSESSRDSAP NRGMNWSFSN
 41 KVSASSSQFL SFRPTQEDRH RKSGNYHLPH SGSFMPSSVA
 81 DVYDSTRKAP YSSVQGVRMF PNSNQHEETN AVSMSMPGFQ
121 SHHYAPGGRS FMNNNNNSQP LVGVPIMAPP ISILPPPGSI
161 VGTTDIRSSS KPIGSPAQLT IFYAGSVCVY DDISPEKAKA
201 IMLLAGNGSS MPQVFSPPQT HQQVVHHTRA SVDSSAMPPS
241 FMPTISYLSP EAGSSTNGLG ATKATRGLTS TYHNNQANGS
```

-continued
281 NINCPVPVSC STNVMAPTVA LPLARKASLA RFLEKRKERV

321 TSVSPYCLDK KSSTDCRRSM SECISSSLSS AT

A chromosomal DNA sequence for the *Arabidopsis thaliana* jasmonate-zim-domain protein 3 (JAZ3) protein with SEQ ID NO:50 is shown below as SEQ ID NO:51.

```
   1 GCGATTTGTT AATAAAACTA GAAATTGCGG TGAATTAACT
  41 TCATTCCACG TTTTTTCATT TTCTCCCTCA AAAGTCTCTG
  81 TTTTTTTTCC TTTTTCCGGC GAAGCTCTAT TTAGCTTGAT
 121 TCCGGCGTTT AACACGCGTT TTAATCGAAA CAGACATTTG
 161 AGATCGAATT AATTTTGTAG CGGGCTGTGT CTTTATTATA
 201 GATGGAGAGA GATTTTCTCG GGTTGGGTTC GAAAAATTCT
 241 CCGATCACTG TCAAGGAGGA AACCAGCGAA AGCTCTAGAG
 281 ATTCAGGTTA TTTATTACTC TTCTCAATTT TTCTGATTCT
 321 GATTGTTTTT AAATCGTAGA TTTGTTTGAT TGATTAGGAG
 361 TTATTAGGAC TACTTGTAGT ATGGAATTTG TTTTTGGATA
 401 GCTGATTTTA TGGCTTGCTC GGGAACTGGA ATTGTCAGTT
 441 TGTTGCTTGG AGCAGAACAT TGTCCTTTGC TTTTCTCGGG
 481 AGATGTAGAA TTTGGATTTG GAAAAACTAG TGTTCTTTTC
 521 CAAAGCCTTG TCTTAAACAT GCTTTCGGTC GGAGAAATTA
 561 ACGAGAACTA ATCTCAAGCT TCTAACATAA TTAAACTCGG
 601 TAAACTTTTT TTTACTAGAG TAAATTTTTT TGTTTTGTTT
 641 GAAGAGTCTT ATAATTGAGA AATACTTTAT TAGTTTATAC
 681 TAAAAAAAAA ACGAATACGT AAAATGTTGG AAAAGAGGGG
 721 ATGTATAGAG ACTGATACAA AAATGATAAA ATAGAGACGG
 761 TTGGTAGTAG GTAGAAAGAT TAAATATACT CAAAAGAGTG
 801 AGTTGGATTA GTTTATAAGA TGATTAACTT CTTGATTGTG
 841 TGAGTTGGAT TAGTTTATGA GATTATTAAA ATATTGATTG
 881 TGTATTTGTG TTGTGTGTTG ATTAAGCGGA ACTTGCGTTA
 921 GAATATTGTT CAAGGTACAA TGTGGAAATA ATAGTTTTCT
 961 CACCACGAGG AATATAATTA TTTCAACTTT GTTTTCTTAT
1001 CAGCCAAAAC GTGCCACACC ATAAAGTAG TGCATCAACA
1041 TGTGGTGTGG TGTGGTGGGG TTAAAGTTTG AATCTCTCTT
1081 TAATTTAAAC TATTAAAACA AACTTAAATT ATTGGAGTTT
1121 CGTACAATGA CTTTCAATCA AATGTTTTAG AATTAGACAC
1161 GGTTTTCGAA AGTGGTTTTC CCTCGTTGAA TTTGTCAACA
1201 GTATCAGATT CTACATTGTT GGTTACTAAT CTTTTCCTTG
1241 AAGTAGGTGT TGAATTAATC CTCTGTTGTT TATGTAAGGA
1281 GATCTCGAGA CATTTATGGT TAACAGTTAA CACTAGATGT
1321 TTGACTTTAA ACTGATTATC TTTTATTCTT TTTCTTTTGT
1361 AGCTCCCAAC AGAGGAATGA ACTGGTCTTT CTCAAACAAA
1401 GTATCAGCTT CTTCTTCTCA GTTTCTATCC TTCAGGCCAA
```

```
-continued
1441 CTCAAGAAGA TAGACATAGA AAGTCTGGAA ATTATCATCT
1481 TCCTCACTCT GGTTCCTTCA TGCCATCATC AGTAGCTGAT
1521 GTTTATGATT CAACCCGCAA AGCTCCTTAC AGTTCTGTAC
1561 AGGTATTTGT CATCAAAACC TATGTTAACC AAGACCCTTG
1601 TGTTTTTTTT ATCCTTCGCA AGATAGCTTT AAAAGTGAGC
1641 CCTGTTTTAT GAGCATATAG TAATTGGTTT TGAGTCTAGT
1681 TTAGCACAAG TTCATGGCAA TTAGTTTGTG GATCTAATCT
1721 TGGTTTAATA CTGATTCATT TTAAGTGTAA GCTAAGCTTC
1761 TCATTTTTGA TAAGTTAGTT CATACAATGC CTCACACCTA
1801 CTTTATGGCT TGTTACTCTC AGGGAGTGAG GATGTTCCCT
1841 AATTCCAATC AACACGAAGA AACTAACGCA GTTTCCATGT
1881 CGATGCCGGG TTTCCAGTCT CATCATTATG CACCAGGAGG
1921 AAGAAGCTTC ATGAACAATA ACAATAACTC ACAACCTTTG
1961 GTAGGAGTTC CTATCATGGC ACCTCCAATT TCAATCCTTC
2001 CTCCTCCAGG TTCCATTGTA GGGACTACTG ATATTAGGTA
2041 CCCACTAGTC ATCATATCAT ACAGAAACTC TTTCTACATT
2081 TTCATAGTTG ACTAAAGACT TATTTTTGTC AGATCTTCTT
2121 CCAAGCCAAT AGGTTCACCT GCGCAGTTGA CGATCTTTTA
2161 TGCCGGTTCA GTTTGTGTTT ACGATGACAT ATCTCCTGAA
2201 AAGGTATCTC AATCATTTTC TTCCATATAT GCATCTCTTT
2241 TACTCGTAAG GTATGGTACT CATTTGCTTT CTTTCATTTC
2281 TCAGGCAAAG GCGATAATGT TGCTAGCTGG AACGGTTCC
2321 TCTATGCCTC AAGTCTTTTC GCCGCCTCAA ACTCATCAAC
2361 AAGTGGTCCA TCATACTCGT GCCTCTGTCG ATTCTTCAGC
2401 TATGCCTCCT AGCTTCATGC CTACAATATC TTATCTTAGC
2441 CCTGAAGCTG GAAGTAGCAC AAAACGGACTC GGAGCCACAA
2481 AAGCGACAAG AGGCTTGACG TCAACATATC ACAACAACCA
2521 AGCTAATGGA TCCAATATTA ACTGCCCAGT ACCAGTTTCT
2561 TGTTCTACCA ATGTAATGGC TCCAACAGGT AAAAAACAAA
2601 GTCAGAGACC TGATACTACA TTCGCCATCT AACTTACTAG
2641 TATTTTCATG GATGTAACTT CATTCTCGTT CTGTTTCTTA
2681 TGCAGTGGCA TTACCTCTGG CTCGCAAAGC ATCCCTGGCT
2721 AGGTTTTTAG AGAAACGCAA AGAAAGGTAC GCAACACTTC
2761 TTTAGAATAC ACCATTCAAT AGTTTCTTGG GCTAACTCTC
2801 TTTCTCGCTG TGGGTTTCTC AGGGTCACGA GCGTATCCCC
2841 ATATTGCTTA GACAAGAAGT CATCGACAGA TTGTCGCAGA
2881 TCAATGTCTG AATGCATTAG TTCTTCTCTC AGCTCTGCAA
2921 CCTAATTTCA TCTACAGTAA GAAGGTTGCT TTAGACCACT
2961 CCACATCCAT ATTTGCATTT CAATGGCGGT CTTTTCAATG
3001 TCTCAGTTAA TTTTTCCTCA CTCGCCACAC TGAGTTTCTC
```

-continued

```
3041 CTTAGCTTTA TATATACGAT AGTGTATACT TTGTTTACAT
3081 GTTTTTTGGT GGAATGGAAC TTATGAGAGC ATATCAGATA
3121 TGTACTTGGG AAAATTAGTA GAAACTGTTT GTTTCTTTTT
3161 TTTTAACTCT GTTCTTTTGT ATATATCACT GAAGCTCGCA
3201 TATGTATAAT TCATGTAATG GAATTGCATC GCTTCTGTTT
3241 CCCTAAGTTA TTT
```

JAZ4 is also a repressor of jasmonate responses. One example of an *Arabidopsis thaliana* jasmonate-zim-domain protein 4 (JAZ4) protein sequence is shown below (SEQ ID NO:52).

```
  1 MERDFLGLGS KLSPITVKEE TNEDSAPSRG MMDWSFSSKV
 41 GSGPQFLSFG TSQQETRVNT VNDHLLSSAA MDQNQRTYFS
 81 SLQEDRVFPG SSQQDQTTIT VSMSEPNYIN SFINHQHLGG
121 SPIMAPPVSV FPAPTTIRSS SKPLPPQLTI FYAGSVLVYQ
161 DIAPEKAQAI MLLAGNGPHA KPVSQPKPQK LVHHSLPTTD
201 PPTMPPSFLP SISYIVSETR SSGSNGVTGL GPTKTKASLA
241 STRNNQTAAF SMAPTVGLPQ TRKASLARFL EKRKERVINV
281 SPYYVDNKSS IDCRTLMSEC VSCPPAHHLH
```

A chromosomal DNA sequence for the *Arabidopsis thaliana* jasmonate-zim-domain protein 4 (JAZ4) protein with SEQ ID NO:52 is shown below as SEQ ID NO:53.

```
   1 ATTAGAGGAA TCATAAATCG GCGGTGTGTG TAACTTCAAC
  41 TCACGTTTTT CATTTCTCTC CAAAGTCCTT CAATTGTTAC
  81 TAATTCTCTC TGATCTCTCA TTTCTTCTCT TCTCCGGTGA
 121 CATTTTTTTT CTCCCCCGCG AAAGCTAAAC CGTTTTTGTA
 161 TTCTCAACGA TTGATAAGCC TGATGGAGAG AGATTTTCTC
 201 GGGCTGGGAT CAAAGTTATC TCCGATAACT GTGAAGGAGG
 241 AAACTAACGA AGATTCAGGT AATTCATCTT CAACATCTTC
 281 CATTATGATC TGATGATTGT GTTTTTCATC TCACTTTTTT
 321 TTGTTTCTAT TTTTGTAATC TCTTTTTTTG TTTATTGTTC
 361 AAGTACATAT ATATTGTTTT TCTAGCTTGA TTGGGAGTCC
 401 TACTGTCTGG TTTTTTCTTG AACAAGAAAT TTTTTCTTCG
 441 TTTTCTCGGG AAGAGAAAAA ATAAATTAGG GTTTCTTTTT
 481 TCTTGATATA TATTTAAGAA ATTAGGTTTT AGTACTATAG
 521 ACAGAAATTT AGCTACTCGA ATTTGTTTGA CGTAGCCGAT
 561 GAAAAACAC GTTTTGGGAC TCGATAGTTA GAAAATTCAT
 601 ACGTTCACGA TCTACTTTTG AAGTTTTTTT CATTAAATAT
 641 TTTTTGCAAA CTACAAATGT ACAAGTATAC AACTATACAA
 681 GCAAACACCA AACTTGTTGA CGTTAGTAAT TTAACAAGTG
 721 TTAGTATTAT CTTTGAAAAA TAATATTCAG AGAACAAACT
 761 TGATTTTCTA GGTGACTAGG TGATGCATGT TTCTAAAGCT
 801 GTTGGTAATG TTGAGTGTTT TCAAAATAAT TTCGTTTTTT
 841 TCTTCAAACA GCCGACACCG ACAGAACAAA AATGCTATAT
 881 TTTTTTTGTT GCTTACAAAA TTGATCAATT GGTTTCAATA
 921 CAATAGTATC TTCTTTAGAA AAGATTGTTT TTTTCAAAGC
1001 CGGATTGAAT ATTGAGAATT AGAACATTGG CTGGTTATTC
1041 TTTTTGAAAA GTTTATGCCA TTTTTTAAGG TTTATTAAGC
1081 AACTTGAATT CTATCAGTAT TATTTAAAAA CGAAGACGTG
1121 AAATGTTGGG AAAAGAATGC GTTATATAGC GACCGGCTGA
1161 CGATTAGAGA TTTAACAACA AATGCAAGTT GAATTATATA
1201 AAAGCAAGAT TGATTGTGAC TTGATTAAGT TTTATTTCTA
1241 TCCAAGTAGA CTCATTGATT AAGTTAGGAT CATGTTGGGT
1281 ATTAAATTTA GATCAAGTTA CAATTGGAT GAATAATTTA
1321 CTTACCCACG AGGAATTTAA TAGTTAGTTC TTGTCTTTTT
1361 ATATTCCGAA ACGTGCCATT TCTTGAAAGT ATTTGTATGA
1401 TCACTATTTT CCCCAGTGTG TTTGGCTTTA TGCAGATTTG
1441 TTCATTGTTG ATGAATCTAA TGTTAAGAGT CGTCCACTTT
1481 AGCATAGCTA GATCTGAGTG TTTCCTAGTT TGATAAAATC
1521 TAAAGACATT TGCTCATGTT TCAGCCCCAA GTAGAGGTAT
1561 GATGGATTGG TCATTCTCAA GCAAAGTCGG TTCTGGTCCT
1601 CAGTTTCTTT CTTTTGGGAC ATCCCAACAA GAAACGCGTG
1641 TAAACACAGT CAATGATCAT TTGCTTTCTT CTGCTGCAAT
1681 GGATCAAAAC CAGAGAACTT ACTTCAGCTC ACTACAGGTT
1721 AGGCTATTTC TTGAAAAGAA AAAAAGTAGT GATAAAGTGT
1761 GATTTAGTGA CCTTGTAAGA AAGCTTGGCA ATTGGTTTAG
1801 TTTCTTCTGG TCTCAAAATT GATACAAAAT GATCTCAGGA
1841 AGACAGAGTG TTCCCAGGTT CCAGTCAGCA AGACCAAACA
1881 ACCATCACAG TCTCCATGTC CGAACCAAAC TACATCAACA
1921 GTTTCATAAA CCACCAACAT TTAGGAGGAT CTCCTATCAT
1961 GGCACCTCCA GTTTCAGTAT TTCCTGCTCC AACCACTATT
2001 AGGCATGCAC TGCATTCTAT CTTCTTCTGT TTAACATCAG
2041 ATACAGAACC TCTTTACTTC TATAGTTGAC TCGAGCTCCT
2081 TTATGTTCAT CTCCAGATCT TCTTCAAAAC CACTTCCCCC
2121 TCAGTTGACA ATCTTTTATG CCGGTTCAGT ATTAGTTTAC
2161 CAAGACATAG CTCCTGAAAA GGTAACCAAA TTTCCTTCAA
2221 TATGTGTTAC ATTACAGTCC AAGCTATCCA CTGACTAAGT
2241 ATTCAATCAA AGAAATAAGT TTCACGTATA GACATGCTGA
2281 AGTTATAGAA AGTTACTAAC CTGGTTTCAA CATACAGTAT
2321 GTTAATGATT CATAGATATG ATAAATCTTT GTCCTTACTT
2361 CTTCATTTAT TTTGTATTCA TAGGCCCAAG CTATCATGTT
2401 GCTAGCCGGA AATGGACCTC ATGCTAAACC GGTTTCACAA
2441 CCTAAACCTC AAAAACTGGT TCATCACTCT CTTCCAACCA
```

```
2481 CTGATCCTCC AACTATGCCT CCTAGTTTCC TGCCTTCCAT
2521 CTCTTACATT GTCTCTGAAA CCAGAAGTAG TGGATCCAAC
2561 GGGGTTACTG GACTTGGACC AACAAAAACA AAGGCGAGTT
2601 TAGCATCCAC GCGCAACAAC CAAACTGCTG CCTTCTCTAT
2641 GGCTCCAACA GGTTATAAAT GAAGTCTTAA CTCCTATTAA
2681 TGTTTTGTCA TCAAACTTCT ATCTTAGGTT TAGTTTGTTA
2721 TAACCAAAAA ATCTTGCTAT GATTTAATAC AGTGGGTTTA
2761 CCACAAACAC GCAAAGCATC CTTGGCTCGG TTCTTAGAGA
2801 AACGCAAAGA AAGGTACTGA GCTACAAGAT TATTCACTTA
2841 TTCACAATAT CAAAACACAG GTTTGCTGTA TATTGGCTTC
2881 GTTTTCTTGC AGGGTCATTA ACGTATCACC TTATTACGTA
2921 GACAACAAGT CATCAATAGA CTGTAGAACA CTGATGTCTG
2961 AATGTGTAAG CTGTCCTCCA GCTCATCATC TGCACTAAAA
3041 CCAATTTAGA CCCCTCATTG TTCTAAAGGC TTTTTCTTTT
3081 TTCTCTGGCT CTGTATCCTA TAGACTATAG TATAGTTGTT
3121 ATAGCTTTTG TTTATTCAGA TTTTAGTACA CTGGGCTTGT
3161 AAAAGCAAGT TATTTATATA TATCCTATAA ATTTAATTTG
3201 GATACTGTAT GTTTTGTCTT TACTCTTGCA TGTGTATAAA
3241 AAACATAAAA GTAAGACTAT TCAAGCT
```

JAZ9 is also a repressor of jasmonate responses. One example of an *Arabidopsis thaliana* jasmonate-zim-domain protein 9 (JAZ9) protein sequence is shown below (SEQ ID NO:54).

```
  1 MERDFLGLSD KQYLSNNVKH EVNDDAVEER GLSTKAAREW
 41 GKSKVFATSS EMPSSDFQEA KAFPGAYQWG SVSAANVFRR
 81 CQFGGAFQNA TPLLLGGSVP LPTHPSLVPR VASSGSSPQL
121 TIFYGGTISV FNDISPDKAQ AIMLCAGNGL KGETGDSKPV
161 REAERMYGKQ IHNTAATSSS SATHIDNFSR CRDTPVAATN
201 AMSMIESFNA APRNMIPSVP QARKASLARE LEKRKERLMS
241 AMPYKKMLLD LSTGESSGMN YSSTSPT
```

A chromosomal DNA sequence for the *Arabidopsis thaliana* jasmonate-zim-domain protein 9 (JAZ9) protein with SEQ ID NO:54 is shown below as SEQ ID NO:55.

```
   1 GCAAAGAGTT AAATAAGCCT CTCCAAAAGT GTGTCTGTAA
  41 CATTACCAAA ACGAAACCTT CCTTGTGGAT TCCCACTTCT
  81 TTCTTCTGTT TTCTTCTTCC TCTTCTTTAA ATTGGATGTT
 121 TTGGGCAAGA AACAGAGAGA AACACGTTAA TTTGAGAGTT
 161 TGTCATTGAA TATTTGGTTT GCAATGGAAA GAGATTTTCT
 201 GGGTTTGAGC GACAAGCAGT ATCTAAGTAA TAACGTTAAG
 241 CATGAGGTTA ACGATGATGC TGTCGAAGAA CGAGGTTTGT
 281 GTTCTTGTCT CGAGAATCTT TTATTTTAAT GTTTGAAGAA
 321 GAGATCAGTT TTCACTTTTA ACATAGCCGT ATAAAGTTGT
 361 TTATTTAAAT ATAATTTTTC AGATTCCAAA ACTTGAAAAA
 401 AAAAAGATTC CATTAAATCT TTTATAAAAA TGAGATTGGA
 441 TAGATTAGTC AAATTGACGA CCATAAAAAA TGATACTTAT
 481 AGGGTTAAGT ACGAAGGCAG CTAGAGAATG GGGGAAGTCA
 521 AAGGTTTTTG CTACTTCAAG TTTCATGCCT TCTTCAGATT
 561 TCCAGGTTGG TTCATCTTAA AATTTAACTT ACTCTGTATC
 601 AGTTTCAGAT GTTATGGCTA ATCTAATGGT TCTATAAGCT
 641 ACCGCATAAT CATGGTCGTC TTTTAGCATG TGCAAGAGGA
 681 GTACTCAATT ATGGTCTTGA TTAAAAAGAA GAATTTACTT
 721 TCAAATTATG TTAAACACAT CAATCACATA TTTATGAGAA
 761 AAGTTGTTTT CGTAAGAGAT AGCCACCGGA AAATGGTCGG
 801 ATAAATGGCC GAACTTTATC ATTTTTGTGT ATGTGGCCAA
 841 TCATTAACCA GGGAAAAAAA ATTGTTGGAT AAGTGCTAGT
 881 TAAGAGCTGG TAGGGTCGGT CGTCTGCCAG CCGCAAAGTT
 921 AGGGAAAAAA TAATTTAATA TTTTGTGGCG TTTGGTGTTT
 961 GGCGTTTGGA TCACGTTTAT TTCTTGGCAT TTTTCTAAAT
1001 TTAGAATGTA CAAAAAATTT AAAGACGTTG ACGATTAAAA
1041 TTTGAATTTA ACAAATTAGG AGGCTAAGGC GTTTCCGGGT
1081 GCATACCAGT GGGGATCAGT TTCTGCGGCC AATGTTTTCC
1121 GCAGATCCA ATTTGGTGGT GCGTTTCAAA ACGCGACGCC
1161 GCTTTTACTA GGCGGTTCAG TTCCTTTACC AACTCATCCT
1201 TCTCTTGTTC CACGGTAATT TCCATATTAT GATGCAAAAA
1241 CATTCAACAA TTTTTTTGCT CTTTTCATAT TTTGATTTGG
1281 TTATGTGGGT TTGTGGAAAC AGAGTGGCTT CCTCCGGATC
1321 ATCTCCTCAG CTCACAATCT TTTATGGCGG AACTATAAGC
1361 GTCTTTAATG ACATATCTCC CGATAAGGTA TATATAATCA
1401 AGATTCATAC AAATAACATT TACATAACAT TTACATGTTC
1441 TAAAACGGAC TATTCATGAT ATGTGAGTAG GCTCAAGCCA
1481 TCATGTTATG CGCCGGGAAC GGTTTGAAAG GTGAAACTGG
1521 AGATAGCAAA CCGGTTCGAG AAGCTGAAAG AATGTATGGA
1561 AAACAAATCC ATAACACTGC TGCTACCTCA TCAAGCTCTG
1601 CCACTCACAC TGATAATTTC TCAAGGTGTA GGGACACACC
1641 CGTTGCTGCG ACTAATGCAA TGAGCATGAT CGAATCATTC
1681 AATGCAGCTC CTCGTAACAT GATTCCTTCA GGTATGTGTG
1721 TCTAATATCA ACATCAAAAC AAAATATAAT CAAGATTTTT
1761 GCTTCCTCAA ATCATATGTC TAAACTCGAA AATTGCTTTT
1801 TTCCAGTCCC TCAAGCTCGG AAAGCATCCT TGGCTCGGTT
1841 CTTGGAGAAG CGCAAAGAGA GGTTTGATTT TGTATTTTTT
1881 TTCTTTATAG AAAATTTTGA GGTTTTTCAA TTGAATCTAA
```

```
1921 AAGAATTAT GTTTTGGTG CAGGCTTATG AGTGCAATGC

1961 CATACAAGAA GATGCTTCTT GATTTGTCGA CCGGAGAATC

2001 CAGTGGAATG AATTACTCTT CTACTTCTCC TACATAAAAC

2041 CTACACTTTT TTTTTTTTTT TTTACAATGG TAATTTGTAA

2081 TTGTAATCAT TAGATTATGA TTATATAGTT ACCATTTATA

2121 TTCTTACGAG CAGGAGAAGA CGTTAGGGCG TCTCTGTATT

2161 TGATCATTGT TTGTAATGCT TTGGTCTGTT TATTGTAGGA

2201 TTACATTATA ACTTTAAGAA CTAACAGATA TATGTTTGTC

2241 ATGGACTCAT GTCTGTCAAG AATTTAATAT CAAATAAAT

2281 TCACTATAAT TTTTTTT
```

JAZ10 is also a repressor of jasmonate responses. One example of an *Arabidopsis thaliana* jasmonate-zim-domain protein 10 (JAZ10) protein sequence is shown below (SEQ ID NO:56).

```
  1 MSKATIELDF LGLEKKQTNN APKPKFQKFL DRRRSFRDIQ

41 GAISKIDPEI IKSLLASTGN NSDSSAKSRS VPSTPREDQP

81 QIPISPVHAS LARSSTELVS GTVFMTIFYN GSVSVFQVSR

121 NKAGEIMKVA NEAASKKDES SMETDLSVIL PTTLRPKLFG

161 QNLEGDLPIA RRKSLQRFLE KRKERLVSTS PYYPTSA
```

A chromosomal DNA sequence for the *Arabidopsis thaliana* jasmonate-zim-domain protein 10 (JAZ10) protein with SEQ ID NO:56 is shown below as SEQ ID NO:57.

```
  1 AAAAACTCTC ACATGAGAAA TCAGAATCCG TTATTATTCC

41 TCCATTTATT CATCTCAAAA CCCATATCTC TCTGTCTTGA

81 TCTCTCTCTC ACTTTCTAAT AAGATCAAAG AAGATGTCGA

121 AAGCTACCAT AGAACTCGAT TTCCTCGGAC TTGAGAAGAA

161 AGAAACCAAC AACGCTCCTA AGCCTAAGTT CCAGAAATTT

201 CTCGATCGCC GTCGTAGTTT CCGAGGTTCG TTTGGTTTTT

241 AGTCGCTCTC TCTTTTTTTT TTCTTGCGAT AAATCGAATT

281 TATTCATATG GAACTCCTGC AGATATTCAA GGTGCGATTT

321 CGAAAATCGA TCCGGAGATT ATGAAATCGC TGTTAGCTTC

361 CACTGGAAAC AATTCCGATT CATCGGCTAA ATCTCGTTCG

401 GTTCCGTCTA CTCCGAGGGA AGATCAGCCT CAGATCCCGA

441 TTTCTCCGGT CCACGCGTCT CTCGCCAGGT ATTTTGTCT

481 TTCCGGTAAA GTTTTTTTTT TCTTTCTAAC TTTTTTGGCG

521 CTACCAGAAA AGACGAAAAA ATTTGAAATT CAAATTTTCA

561 AAACATTCAT TTTCCTCAGG TCTAGTACCG AACTCGTTTC

601 GGGAACTGTT CCTATGACGA TTTTCTACAA TGGAAGTGTT

641 TCAGTTTTCC AAGTGTCTCG TAACAAAGCT GGTGAAATTA

681 TGAAGGTCGC TAATGAAGCA GCATCTAAGA AAGACGAGTC

721 GTCGATGGAG ACAGATCTTT CGGTAATTCT TCCGACCACT

761 CTAAGACCAA AGCTCTTTGG CCAGAATCTA GAAGGAGGTT

801 AGTATAATAA AAATAAAAAT CACTTAGTGC TGGATTCTTC

841 TAGAATTTTA GTTACATATT ATTGCATGTA GAGATCTAAG

881 AAGAGTTTGT TGTTAGAGAG GAATTGGTTG CTAATTAGTT

921 TGGAATTAGA TATCAAAGAG TTAAAGACTA TAGTTTATGT

961 CTATACGTAT TAATATACGT TATTAATAAA AGTATAAACA

1001 TGTTGTTTAA TTTCTGATAA GAAACTGGTT TATGCGTGTG

1041 TATGCAGATC TTCCCATCGC AAGGAGAAAG TCACTGCAA

1081 GTTTTCTCGA GAAGCGGAAG GAGAGGTAAT GATTCTTCAA

1121 CAATCCAAGG ATTTTTACCC CGAAATAATT AAAGAAAGGT

1161 TTTTATTTTT CTCTCTCTCG ACCTTTTTTT TACTATAAGT

1201 TATTTAAGAT AGTAATTATG GGTCCTGCCT CTTTTACTCT

1241 CACATACAAC TTAAGATTCA ACTAGTTTTG TTCAAGAACG

1281 CACATGCTTA TACGTAGATA GATAATGGAG ATCAGTAGTA

1321 ATATCGGTAT ACGTAGGTTA CTATTGTAAT GGAACTTTTA

1361 AAAAGCGCGT TGACTTTGAG TCTTTGACTC TAGTTCTGTT

1401 TGCTACACCG ACAAGTTATA TTTTTCAAAA TGATGAGAAA

1441 ACGAGGAGAA ACACCGGAAA AAAATTTGAA CTTTTACTTT

1481 TATCAGACCA TACGGCCAAA GAAAGATCTG TATATTATAT

1521 AAGTTATCAC AAAACGCGGT TTCACATTTT CTTTTTCGTC

1561 TTGTTGTGTT TGCAGATTAG TATCAACATC TCCTTACTAT

1601 CCGACATCGG CCTAAACGAT CTCTTTTTAG ATTGGGACAT

1641 GGACCAAATT TGTCTTTTTC AATCGGAAGA CATCCATGTT

1681 CGTTTTTGGA TTTGGCTTAT TTCCAATCTT CTTTTGAAGC

1721 CTTCTTCGTC GTTGCTAAAT CGTATACTAT TCACGACAAA

1761 CGTTTTTAGG AGATTACGTT ACCTACTAAG ATTATATATA

1801 TTGGTTTGTT TTTAAAAATG TCTATTATCT TTATTGTCAT

1841 TGATAGCTTG ATTTAAGAAG CTCTCTCTTA TCCCGTGACC

1881 TTCTACTTTT GTTTTATTTT TTAGTATATG GTAAAGAAAA

1921 TTATAAC
```

Chromosomal sequences that encode repressors of jasmonic acid responses from many plant types and species can be modified to reduce or eliminate the expression and/or function of the encoded protein. For example, chromosomal sequences encoding jasmonic acid repressor genes from agriculturally important plants such as alfalfa (e.g., forage legume alfalfa), algae, avocado, barley, broccoli, Brussels sprouts, cabbage, canola, cassava cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of one or more encoded jasmonic acid regulatory proteins.

In some cases, more than one gene or chromosomal segment encoding a jasmonic acid regulatory protein can be modified to reduce or eliminate the expression and/or function of the encoded protein(s). In some cases, more than two genes or chromosomal segments encoding jasmonic acid regulatory proteins can be modified to reduce or eliminate the expression and/or function of the encoded proteins. In some cases, more than three genes or chromosomal segments encoding jasmonic acid regulatory proteins can be modified to reduce or eliminate the expression and/or function of the encoded proteins. In some cases, more than four genes or chromosomal segments encoding jasmonic acid regulatory proteins can be modified to reduce or eliminate the expression and/or function of the encoded proteins.

The following are examples of "JAZ-related" proteins and nucleic acids that can be modified to reduce or eliminate the expression and/or function thereof, and thereby generate plants with improved resistance to insects.

One example of a *Brassica rapa* protein called TIFY 10A-like (NCBI accession no. XP_009117562.1; GI:685367109) has significant sequence identity to the *Arabidopsis thaliana* JAZ1 protein with SEQ ID NO:48, as illustrated by the sequence comparison shown below. Domains of sequence homology are identified by asterisks below the sequence comparison.

```
73.0% identity in 211 residues overlap; Score: 634.0;
Gap frequency: 11.4%
Seq48    1 MSLFPCEASNMDSMVQDVKPTNLFPRQPSFSSSSSSLPKEDVLKMTQ---
           TTRSVKPESQ
Seq58   63 MSLFPCEASNMEPIGQDVKPKNLFPRQPSFSSSSSSLPKEDILKMTQATSSTRSVKPEPQ
           **********  ***** ******************* *****   ********

Seq48   58 TAPLTIFYAGQVIVFNDFSAEKAKEVINLASKGTANS------------------
           LAKN
Seq58  123 TAPLTIFYGGQVIVFNDFSAEKAKEVMDLASKGTANTFTGFTSNVNNNIQSVYTTNLANN
           ******** ****************  ********                       ***

Seq48   99 QTDIRSNIATIANQVPHPRKTTTQEPIQSSPTPLT-
           ELPIARRASLHRFLEKRKDRVTSK
Seq58  183 QTEMRSNIAPIPNQLPHLMKTTTQNPVQSSSTAMACELPIARRASLHRFLAKRKDRVTSK
           **  ***** *  **  ***** * *** *    **************
           *********

Seq48  158 APYQLCDPAKASSNPQTTGNM-SWLGLAAEI
Seq58  243 APYQLNDPAKASSKPQTGDNTTSWLGLAAEM
           ***** ******* ***  *  ********
```

This JAZ-related *Brassica rapa* protein, called TIFY 10A-like (NCBI accession no. XP_009117562.1; GI:685367109), has the following sequence (SEQ ID NO:58).

```
  1 MSSPMESSDF AATRRFSRKP SFSQTCSRLS QYLKENGSFG

41 DLSLGMACKP EVNGISRQPT TTMSLFPCEA SNMEPIGQDV

81 KPKNLFPRQP SFSSSSSSLP KEDILKMTQA TSSTRSVKPE

121 PQTAPLTIFY GGQVIVFNDF SAEKAKEVMD LASKGTANTF

161 TGFTSNVNNN IQSVYTTNLA NNQTEMRSNI APIPNQLPHL

201 MKTTTQNPVQ SSSTAMACEL PIARRASLHR FLAKRKDRVT

241 SKAPYQLNDP AKASSKPQTG DNTTSWLGLA AEM
```

A cDNA encoding the SEQ ID NO:58 protein is available as NCBI accession number XM_009119314.1 (GI: 685367108), and a chromosomal segment encoding the SEQ ID NO:58 protein is available as NCBI accession number AENI01008623.1 (GI:339949964).

One example of a *Brassica oleracea* protein, also referred to as protein TIFY 10A-like (NCBI accession no. XP_013583936.1; GI:922487335), has significant sequence identity to the *Arabidopsis thaliana* JAZ1 protein with SEQ ID NO:48, as illustrated by the sequence comparison shown below. Domains of sequence homology are identified by asterisks below the sequence comparison.

```
72.9% identity in 192 residues overlap; Score: 633.0; Gap frequency:
2.6%
Seq48    1 MSLFPCEASNMDSMV--QDVKPTNLFPRQPSFSSSSSSLPKEDVLKMTQTT-
           RSVKPESQ
Seq59   61 MSLFPCEASNVGSMAAAQDVKPKNLFPRQPSFSSSSSSIPKEDVPKMTQTTTRSLKPEPQ
           **********  **   ***** *************** *****  ***** ** ****
```

```
Seq48    58 TAPLTIFYAGQVIVFNDFSAEKAKEVINLASKGTANSLAKNQTDIRSNIATIANQVPHPR
Seq59   121 TAPLTIFYGGQVIVFNDFSAEKAKEVMNLANKGTANTFTGFTSTLNNNIAPTPNQVPHLM
            ******** ****************** *** *****          ***  *****

Seq48   118 KTTTQEPIQSSPTPLT-
            ELPIARRASLHRFLEKRKDRVTSKAPYQLCDPAKASSNPQTTG
Seq59   181 KAATQDPKQTSSAAMACELPIARRASLHRFLAKRKDRVTSKAPYQLNDPAKAYSKPQTGN
            *  ** * *          ************** ************ ***** * ***

Seq48   177 NM-SWLGLAAEI
Seq59   241 TTTSWLGLAADM
               *******
```

This JAZ-related *Brassica oleracea* protein referred to as protein TIFY 10A-like (NCBI accession no. XP_013583936.1; GI:922487335) has the following sequence (SEQ ID NO:59).

```
  1 MSSSMECSTT RRSSSGKPSF SLTCSRLSQY LKENGSFGDL

41 SLGMSCKPDT NGMSRKPTTT MSLFPCEASN VGSMAAAQDV

81 KPKNLFPRQP SFSSSSSSIP KEDVPKMTQT TTRSLKPEPQ

121 TAPLTIFYGG QVIVFNDFSA EKAKEVMNLA NKGTANTFTG

161 FTSTLNNNIA PTPNQVPHLM KAATQDPKQT SSAAMACELP

201 IARRASLHRF LAKRKDRVTS KAPYQLNDPA KAYSKPQTGN

241 TTTSWLGLAA DM
```

A cDNA encoding the SEQ ID NO:59 protein is available as NCBI accession number XM_013728482.1 (GI: 922487334), and a chromosomal segment encoding the SEQ ID NO:59 protein is available as NCBI accession number NC_027752.1 (GI:919506312).

An uncharacterized *Zea mays* protein referred to as LOC100276383 (NCBI accession no. NP_001308779.1 (GI: 1013071036) has significant sequence identity to the *Arabidopsis thaliana* JAZ1 protein with SEQ ID NO:48, as illustrated by the sequence comparison shown below. Domains of sequence homology are identified by asterisks below the sequence comparison.

This JAZ-related uncharacterized *Zea mays* protein referred to as LOC100276383 (NCBI accession no. NP_001308779.1 (GI: 1013071036) has the following sequence (SEQ ID NO:60).

```
  1 MAASARPGER ATSFAVACSL LSRFVRQNGV AAADLGLRIK

41 GEVEQQRTPA TTNSLPGAEG EEVERRKETM ELFPQSVGFS

81 IKDAAAPREE QGDKEKPKQL TIFYGGKVLV FDDFPADKAK

121 DLMQLASKGS PVVQNVALPQ PSAAAAVTTD KAVLDPVISL

161 AAAKKPARTN ASDMPIMRKA SLHRFLEKRK DRLNAKTPYQ

201 TAPSDAAPVK KEPESQPWLG LGPNAVDSSL NLS
```

A cDNA encoding the SEQ ID NO:60 protein is available as NCBI accession number NM_001321850.1 (GI: 1013071035), and a chromosomal segment encoding the SEQ ID NO:60 protein is on *Zea mays* chromosome 7 at NC_024465.1 (165496371 . . . 165497455), sequence available as NCBI accession number NC_024465.1 (GI: 662248746).

A *Glycine max* protein referred to as protein TIFY 10A-like (NCBI accession no. NP_001276307.1 (GI: 574584782)) has significant sequence identity to the *Arabidopsis thaliana* JAZ1 protein with SEQ ID NO:48, as illustrated by the sequence comparison shown below. Domains of sequence homology are identified by asterisks below the sequence comparison.

```
39.0% identity in 123 residues overlap; Score: 201.0; Gap frequency:
0.8%
Seq48    61 LTIFYAGQVIVFNDFSAEKAKEVINLASKGTANSLAKNQTDIRSNIATIANQVPHPRKTT
Seq60   100 LTIFYGGKVLVFDDFPADKAKDLMQLASKGSPVVQNVALPQPSAAAAVTTDKAVLDPVIS
            ***** * ** ** * ***    *****                  *

Seq48   121 TQEPIQSSPTPLTELPIARRASLHRFLEKRKDRVTSKAPYQLCDPAKASSNPQTTGNMSW
Seq60   160 LAAAKKPARTNASDMPIMRKASLHRFLEKRKDRLNAKTPYQTA-
            PSDAAPVKKEPESQPW
                    ** * *************  * ***     * **

Seq48   181 LGL
Seq60   219 LGL
            ***
```

45.5% identity in 145 residues overlap; Score: 271.0; Gap frequency: 4.8%
```
Seq48    42 VLKMTQTTRSVKPESQTAPLTIFYAGQVIVFNDFSAEKAKEVINLASKGTANSLAKNQTD
Seq61   101 IMVKSSAFKSMEKEPKAAQLTIFYAGQVVVFDDFPAEKLEEITSLAGKGISQS-----
                QN
            *    *   * ********* **  ** ***   *  ** **    *

Seq48   102 IRSNIATIANQVPHPRKTTTQEPIQSSPTPLTELPIARRASLHRFLEKRKDRVTSKAPYQ
Seq61   156 TSAYAHTHNQQVNHPSFVPNISPQAPSRPLVCDLPIARKASLHRFLSKRKDRIAAKAPYQ
            *****    * ** **       *   *    ***** ******* *****

Seq48   162 LCDPAKASSNPQTTGNMSWLGLAAE
Seq61   216 INNPNSASSKPAE--SMSWLGLGAQ
             *  *** *      ****** *
```

This JAZ-related *Glycine max* protein referred to as protein TIFY 10A-like (NCBI accession no. NP_001276307.1 (GI: 574584782) has the following sequence (SEQ ID NO:61).

```
  1 MSSSSEYLVF SSHHPANSPA EKSTFSQTCS LLSQYIKEKG

41 TFGDLTLGMT CTAETNGSPE TSCHSATTME LFPTIITQRN

61 PTTVDFLSPQ TAYPHHSEVP IMVKSSAFKS MEKEPKAAQL

121 TIFYAGQVVV FDDFPAEKLE EITSLAGKGI SQSQNTSAYA

161 HTHNQQVNHP SFVPNISPQA PSRPLVCDLP IARKASLHRF

201 LSKRKDRIAA KAPYQINNPN SASSKPAESM SWLGLGAQST
```

A cDNA encoding the SEQ ID NO:61 protein is available as NCBI accession number NM_001289378.1 (GI: 574584781), and a chromosomal segment encoding the SEQ ID NO:61 protein is on *Glycine max* chromosome 13 at NC_016100.2 (22541885 . . . 22544240), sequence available as NCBI accession number NC_016100.2 (GI:952545303).

An *Oryza sativa* protein referred to as protein TIFY 10b (Japonica Group; NCBI accession no. XP_015647536.1 (GI:1002286463) has significant sequence identity to the *Arabidopsis thaliana* JAZ1 protein with SEQ ID NO:48, as illustrated by the sequence comparison shown below. Domains of sequence homology are identified by asterisks below the sequence comparison.

38.5% identity in 156 residues overlap; Score: 213.0; Gap frequency: 4.5%
```
Seq48    34 SSSLPKEDVLKMTQTTRSVKPESQTAPLTIFYAGQVIVFNDFSAEKAKEVINLASKGTA-
Seq62    77 SAGFGQQDAITADSAADAREQEPEKRQLTIFYGGKVLVFNDFPADKAKGLMQLASKGSPV
              *       *            *    *****  *  ***** * ***   *****

Seq48    93 ---NSLAKNQTDIRSNI-ATIANQVPHPRKTTTQEPIQS-
               SPTPLTELPIARRASLHPFL
Seq62   137 APQNAAAPAPAAVTDNTKAPMAVPAPVSSLPTAQADAQKPARANASDMPIARKASLHRFL
               *  *     * *     *    *     *   *        ****
               *******

Seq48   148 EKRKDRVTSKAPYQLCDPAKASSNPQTTGNMSWLGL
Seq62   197 EKRKDRLNAKTPYQ-ASPSDATPVKKEPESQPWLGL
            ******  * ***  *               ****
```

This JAZ-related *Oryza sativa* protein referred to as protein TIFY 10b (Japonica Group; NCBI accession no. XP_015647536.1 (GI:1002286463) has the following sequence (SEQ ID NO:62).

```
  1 MAASARPVGV GGERATSFAM ACSLLSRYVR QNGALLAELG

41 LGIRGEGEAP RAAPATMSLL PGEAERKKET MELFPQSAGF
```
-continued
```
 81 GQQDAITADS AADAREQEPE KRQLTIFYGG KVLVFNDFPA

121 DKAKGLMQLA SKGSPVAPQN AAAPAPAAVT DNTKAPMAVP

161 APVSSLPTAQ ADAQKPARAN ASDMPIARKA SLHRFLEKRK

201 DRLNAKTPYQ ASPSDATPVK KEPESQPWLG LGPNAVVKPI

241 ERGQ
```

A cDNA encoding the SEQ ID NO:62 protein is available as NCBI accession number XM_015792050.1 (GI: 1002286462), and a chromosomal segment encoding the SEQ ID NO:62 protein is on *Oryza sativa* chromosome 7 at NC_029262.1 (25347990 . . . 25350243), sequence available as NCBI accession number NC_029262.1 (GI:996703426).

A *Zea mays* protein referred to as protein TIFY 6A-like (NCBI accession no. NP_001288506.1 (GI: 673921704) has significant sequence identity to the *Arabidopsis thaliana* JAZ3 protein with SEQ ID NO:50, as illustrated by the sequence comparison shown below. Domains of sequence homology are identified by asterisks below the sequence comparison.

```
36.6% identity in 161 residues overlap; Score: 165.0; Gap
frequency: 6.8%
Seq50  177 AQLTIFYAGSVCVYDDISPEKAKAIMLLAGNGSSMPQVFSPPQTHQQVVHHTRSVDSSA
Seq63  167 AQLTIFYAGSVNVFNNVSAEKAQELMFLASRGSSAPVACKPEAPPTLAPAKVTAPEVLLP
           *********** *    * ***  * **  *** *      *            *

Seq50  237 MPPSFMPTISYLSPEAGSSTNGLGATKATRGLTSTYH-NNQANGSNINCPVP--------
Seq63  227 AKQMLFQKPQHLSPPPSSVPGILQSAALPRSASSSSNLDSPAPKSSVPLAVPPVSQAPPA
               ***   *    *     *   *       * *           **

Seq50  288 --VSCSTNVMAPTVALPLARKASLARFLEKRKERVTSVSPY
Seq63  287 TLIATTTAAAIMPRAVPQARKASLARFLEKRKERVTTAAPY
              *      * * ****************** **
```

This JAZ-related *Zea mays* protein referred to as protein TIFY 6A-like (NCBI accession no. NP_001288506.1 (GI: 673921704) has the following sequence (SEQ ID NO:63).

```
  1 MERDFLAAIG KEQQHPRKEK AGGGAEESAY FGAAAVPAMD
 41 WSFASKPCAA PALMSFRSAA REEPSFPQFS ALDGTKNTAP
 81 RMLTHQRSFG PDSTQYAALH RAQNGARVVP VSSPFSQSNP
121 MFRVQSSPSL PNSTAFKQPP FAISNAVASS TVGSYGGTRD
161 AVRPRTAQLT IFYAGSVNVF NNVSAEKAQE LMFLASRGSS
201 APVACKPEAP PTLAPAKVTA PEVLLPAKQM LFQKPQHLSP
241 PPSSVPGILQ SAALPRSASS SSNLDSPAPK SSVPLAVPPV
281 SQAPPATLIA TTTAAAIMPR AVPQARKASL ARFLEKRKER
321 VTTAAPYPSA KSPLESSDTF GSGSASANAN DKSSCTDIAL
361 SSNHEESLCL GGQPRSIISF SEESPSTKLQ I
```

A cDNA encoding the SEQ ID NO:63 protein is available as NCBI accession number NM_001301577.1 (GI: 673921703), and a chromosomal segment encoding the SEQ ID NO:63 protein is on *Zea mays* chromosome 2 at NC_024460.1 (180086924 . . . 180089758, complement), sequence available as NCBI accession number NC_024460.1 (GI:662249846).

A *Glycine max* protein referred to as protein TIFY 6B-like isoform X1 (NCBI accession no. XP_003534135.1 (GI: 356531138) has significant sequence identity to the *Arabidopsis thaliana* JAZ3 protein with SEQ ID NO:50, as illustrated by the sequence comparison shown below. Domains of sequence homology are identified by asterisks below the sequence comparison.

```
38.9% identity in 378 residues overlap; Score: 417.0; Gap
frequency: 8.5%
Seq50    1 MERDFLGLGSKNSP-
             ITVKEETSESSRDSAPNRGMNWSFSNKVSASSSQFLSFRPTQEDR
Seq64    1 MEREFFGLSSKNGAWTTMKDDAVNKSRDQVRSSGMQWSFPNKVSALP-
             QFLSFKTNQEDK
           *** * ** ***        * *       ***     ** *** *****  ***** ***

Seq50   60 HRKSGNYHLPHSGSFMPSSVADVYDSTRKA--------------PYSSVQGVRMFPNS--
Seq64   60 PRKTILEPLASSG-
             YMAMSTQYAFDSNQKSFLGLTNRNLSISKHAAGNKQGMTVYPLQCC
              **      * **  *        **  *                         **   *

Seq50  104 -NQHEETNAVSMSMPGFQ-----
             SHHYAPGGRSFMNNNNNSQPLVGVPIMAPPISILPPP
Seq64  119 DAQSEEARIFSVSNQSNQVSPVLQSNLASTGLNMVNSVIKPQPF-
             GSKSSGTPLSILPSI
              * **    * *    *         *      *     ** *      * ****

Seq50  158 GSIVGTTDIRSSSKPIGSPAQLTIFYAGSVCVYDDISPEKAKAIMLLAGNGSSMPQVFSP
Seq64  178 GSIVGSTDLRNNSKSSTMPTQLTIFYAGSVCVYDDISPEKAKAIMLMAGNGYTPTEKMEL
           ***** ** **    *  *************************** ***** *    ****
```

```
Seq50  218 PQTHQQVVHHTRASVD----
           SSAMPPSFMPTISYLSPEAGSSTNGLGATKATRGLTSTYH
Seq64  238 PTVKLQPAISIPSKDDGFMISQSYPPSTFPTPLPLTSHVNSQPGGGSSSNKEISIIRQVG
             *      *      *   *  ***  **  *     *    *

Seq50  274 NNQANGSNINCPV--
           PVSCSTNVMAPTVALPLARKASLARFLEKRKERVTSVSPYCLDKK
Seq64  298 PSTAPTNHLESPIIGSIGSASKEKAQPVCLPQARKASLARFLEKRKGRMMRTSPYLYMSK
             *         *        *  * ** ************** *    ****

Seq50  332 SSTDCRRSMSECISSSLS
Seq64  358 KSPECSSSGSDSVSFSLN
            *   *  * *    * **
```

This JAZ-related *Glycine max* protein referred to as protein TIFY 6B-like isoform X1 (NCBI accession no. XP_003534135.1 (GI:356531138) has the following sequence (SEQ ID NO:64).

```
  1  MEREFFGLSS  KNGAWTTMKD  DAVNKSRDQV  RSSGMQWSFP

41  NKVSALPQFL  SFKTNQEDKP  RKTILEPLAS  SGYMAMSTQY

81  AFDSNQKSFL  GLTNRNLSIS  KHAAGNKQGM  TVYPLQCCDA

121  QSEEARIFSV  SNQSNQVSPV  LQSNLASTGL  NMVNSVIKPQ

161  PFGSKSSGTP  LSILPSIGSI  VGSTDLRNNS  KSSTMPTQLT

201  IFYAGSVCVY  DDISPEKAKA  IMLMAGNGYT  PTEKMELPTV

241  KLQPAISIPS  KDDGFMISQS  YPPSTFPTPL  PLTSHVNSQP

281  GGGSSSNKEI  SIIRQVGPST  APTNHLESPI  IGSIGSASKE

321  KAQPVCLPQA  RKASLARFLE  KRKGRMMRTS  PYLYMSKKSP

361  ECSSSGSDSV  SFSLNFSGSC  SLPATN
```

A cDNA encoding the SEQ ID NO:64 protein is available as NCBI accession number XM_003534087.3 (GI: 955341633), and a chromosomal segment encoding the SEQ ID NO:64 protein is on *Glycine max* chromosome 9 at NC_016096.2 (39883473 . . . 39889992), sequence available as NCBI accession number NC_016096.2 (GI:952545307).

An *Oryza sativa* protein referred to as protein TIFY 6b (NCBI accession no. XP_015612402.1 (GI: 1002297967) has significant sequence identity to the *Arabidopsis thaliana* JAZ3 protein with SEQ ID NO:50, as illustrated by the sequence comparison shown below. Domains of sequence homology are identified by asterisks below the sequence comparison.

This JAZ-related *Oryza sativa* protein, referred to as protein TIFY 6b (NCBI accession no. XP_015612402.1 (GI: 1002297967), has the following sequence (SEQ ID NO:65).

```
  1  MERDFLGAIG  KDEEQRRHAE  ERKESDYFGA  GGGAAAAAMD

41  WSFASRAALM  SFRSSSSAAA  AAAREETREL  AFPHFSALDG

81  AKMQQASHVL  ARQKSFGAES  HGIPQYALLA  AVHGAHRGQP

121  PHVLNGARVI  PASSPFNPNN  PMFRVQSSPN  LPNAVGAGGG

161  AFKQPPFAMG  NAVAGSTVGV  YGTRDMPKAK  AAQLTIFYAG

201  SVNVFNNVSP  EKAQELMFLA  SRGSLPSAPT  TVARMPEAHV

241  FPPAKVTVPE  VSPTKPMMLQ  KPQLVSSPVP  AISKPISVVS

281  QATSLPRSAS  SSNVDSNVTK  SSGPLVVPPT  SLPPPAQPET

321  LATTTAAAIM  PRAVPQARKA  SLARFLEKRK  ERVTTVAPYP

361  LAKSPLESSD  TMGSANDNKS  SCTDIALSSN  RDESLSLGQP

401  RTISFCEESP  STKLQI
```

A cDNA encoding the SEQ ID NO:65 protein is available as NCBI accession number XM_015756916.1 (GI: 1002297966), and a chromosomal segment encoding the SEQ ID NO:65 protein is on *Oryza saliva* chromosome 9 at NC_029264.1 (14056084 . . . 14060320, complement), sequence available as NCBI accession number NC_029264.1 (GI:996703424).

An uncharacterized *Zea mays* protein referred to as LOC100273108 (NCBI accession no. NP_001141029.1 (GI: 226500626) has significant sequence identity to the *Arabidopsis thaliana* JAZ4 protein with SEQ ID NO:52, as illustrated by the sequence comparison shown below. Domains of sequence homology are identified by asterisks below the sequence comparison.

```
37.3% identity in 177 residues overlap; Score: 142.0; Gap
frequency: 10.2%
Seq50  172 PIGSPAQLTIFYAGSVCVYDDISPEKAKAIMLLAGNGS---------SMPO--
           VFSPPQT
Seq65  187 PKAKAAQLTIFYAGSVNVFNNVSPEKAQELMFLASRGSLPSAPTTVARMPEAHVFPPAKV
              * ************* *   *****  *  **  **          **   ** *

Seq50  221 HQQVVHHTRASV-DSSAMPPSFMPTISY---
           LSPEAGSSTNGLGATKTRGLTSTYHNNQ
Seq65  247 TVPEVSPTKPMMLQKPQLVSSPVPAISKPISVVSQATSLPRSASSSNVDSNVTKSSGPLV
              *   *          *  *  * **     * *               *

Seq50  277 ANGSNINCPV-PVSCSTNVMAPTV--ALPLARKASLARFLEKRKERVTSVSPYCLDK
Seq65  307 VPPTSLPPPAQPETLATTTAAAIMPRAVPQARKASLARFLEKRKERVTTVAPYPLAK
              *    *    *      *  * *  ****************  *  * *
```

```
55.0% identity in 40 residues overlap;
Score: 106.0; Gap frequency: 0.0%
Seq52  138 RSSSKPLPPQLTIFYAGSVLVYQDIAPEKAQAIMLLAGNG
Seq66  172 RDVVRPKTAQLTIFYAGSVNVFDNVSAEKAQELMLLASRG
            *    *  **********  *   ****  ****   *

76.9% identity in 26 residues overlap;
Score: 102.0; Gap frequency: 0.0%
Seq52  258 LPQTRKASLARFLEKRKERVINVSPY
Seq66  321 VPQARKASLARFLEKRKERVTTAAPY
            ** ****************   **

48.0% identity in 25 residues overlap;
Score: 66.0; Gap frequency: 0.0%
Seq52   25 SAPSRGMMDWSFSSKVGSGPQFLSF
Seq66   47 AAAAAPAMDWSFASKPGAAPALMSF
             *  ***** **  *   *  **

38.5% identity in 26 residues overlap;
Score: 37.0; Gap frequency: 0.0%
Seq52    1 MERDFLGLGSKLSPITVKEETNEDSA
Seq66   14 MERDFLAAIGKEQQPHKEEAGAEES
          ******    *       ***
```

This JAZ-related uncharacterized *Zea mays* protein, referred to as LOC100273108 (NCBI accession no. NP_001141029.1 (GI:226500626), has the following sequence (SEQ ID NO:66).

```
241 ATQMLFQKPQ HVSPPSSAIS KPIPGILQAA SLPRSASSSN

281 LDSPFPKSSV PFPVSPVSQA PRAQPATIAA TTAAAIMPRA

321 VPQARKASLA RFLEKRKERV TTAAPYPSAK SPMESSDTFG

361 SGSANDKSSC TDIALSSNHE ESLCLGQPRN ISFIQESPST

401 KLQI
```

A cDNA encoding the SEQ ID NO:66 protein is available as NCBI accession number NM_001147557.1 (GI: 226500625), and a chromosomal segment encoding the SEQ ID NO:66 protein is on *Zea mays* chromosome 7 at NC_024465.1 (108871356 . . . 108874213, complement), sequence available as NCBI accession number NC_024465.1 (GI:662248746).

A *Glycine max* protein, referred to as protein TIFY 6B isoform X5 (NCBI accession number XP_006580448.1 (GI: 571456655), has significant sequence identity to the *Arabidopsis thaliana* JAZ4 protein with SEQ ID NO:52, as illustrated by the sequence comparison shown below. Domains of sequence homology are identified with asterisks below the sequence comparison.

```
37.0% identity in 322 residues overlap; Score: 273.0; Gap frequency:
8.7%
Seq52    1 MERDFLGLGSKLSPITVKEETNEDSAPSRG-----
           MMDWSFSSKVGSGPQFLSFGTSQQE
Seq67    1 MERDFMGLNLKEPLAVVKEEMNNDGCKNSGFKKGRIAQWPFSNKVSALPHLMSFKASQDD
           *****  **    * ****  *     *       *   *  **   *    **   **

Seq52   56 TRVNTVNDHLLSSAAMD-
           QNQRTYFSSLQEDRVFPGSSQQDQTTITVSMSEPNYINSFI-
Seq67   61 KTKNTVSDTLSSSGFMSILSQEAFDTSQKRSAGEPQMFSVPNQAISVSLGNPFLKNHFAA
             * * ** **    *         *    *         * **     *  *   *

Seq52  114 --NHQHLGGSPIMAP----
           PVSVFPAPTTIRSSSKPLPPQLTIFYAGSVLVYQDIAPEKA
Seq67  121 AGQKPLLGGIPVTTSHSVLPSAVAVAGMTESCNSVKPSAQLTIFYAGTVNIFDDISAEKA
             ***  *         *      *  *      *******  *   **
           ***

Seq52  168 QAIMLLAGNG-
           PHAKPVSQPKPQKLVHHSLPTTDPPTMPPSFLPSISYIVSETRSSGSNG
Seq67  181 QAIMLLAGNSLSAASNMAQPNVQVPISKLGAGAGVPVSQPANTSPGSGLSSPLSVSSHTG
           *********         **  *                   *       *    **

Seq52  227 V-TGLPTKTKASLASTRNN--QTAAFSMAP----------
           TVGLPQTRKASLARFLEKR
Seq67  241 VQSGSGLTSTDEFLAAKTTGVPNTPICNVEPPKVVSATTMLTSAVPQARKASLARFLEKR
           *      *    **       *        *         *  **  ************

Seq52  274 KERVINVSPYYVDNKSSIDCRT
Seq67  301 KERVMSAAPYNL-NKKSEECAT
           ****   **  *  **  *  *
```

This JAZ-related *Glycine max* protein, referred to as protein TIFY 6B isoform X5 (NCBI accession number XP_006580448.1 (GI:571456655), has the following sequence (SEQ ID NO:67).

```
  1 MAKSGASFPE SSWMERDFLA AIGKEQQHPH KEEAGAEESA

41 YTGGAGAAAA APAMDWSFAS KPGAAPALMS FRSASFPQFS

81 SFDGAKNPAP RILTHQRSFG PDSTHYAAAH RTQHALNGAR

121 VTPVSSPFNQ NSPMFRVQSS PSLPNGTAFK QPPFAINNNA

161 AASSTVGFYG TRDVVRPKTA QLTIFYAGSV NVFDNVSAEK

201 AQELMLLASR GSLPSSAPVA RKPEAPILAP AKVTAPEVLH
```

```
  1 MERDFMGLNL KEPLAVVKEE MNNDGCKNSG FKKGRIAQWP

41 FSNKVSALPH LMSFKASQDD KTKNTVSDTL SSSGFMSILS

61 QEAFDTSQKR SAGEPQMFSV PNQAISVSLG NPFLKNHFAA
```

```
121 AGQKPLLGGI PVTTSHSVLP SAVAVAGMTE SCNSVKPSAQ

161 LTIFYAGTVN IFDDISAEKA QAIMLLAGNS LSAASNMAQP

201 NVQVPISKLG AGAGVPVSQP ANTSPGSGLS SPLSVSSHTG

241 VQSGSGLTST DEFLAAKTTG VPNTPICNVE PPKVVSATTM

281 LTSAVPQARK ASLARFLEKR KERVMSAAPY NLNKKSEECA

321 TAEYAGVNFS ATNTVLAKQG
```

A cDNA encoding the SEQ ID NO:67 protein is available as NCBI accession number XM_006580385.2 (GI: 955322108), and a chromosomal segment encoding the SEQ ID NO:67 protein is on *Glycine max* chromosome 5 at NC_016092.2 (41222014 . . . 41225906), sequence available as NCBI accession number NC_016092.2 (GI:952545311).

An *Oryza sativa* protein, referred to as protein TIFY 6a isoform X2 (NCBI accession number XP_015651050.1 (GI: 1002293416), has significant sequence identity to the *Arabidopsis thaliana* JAZ4 protein with SEQ ID NO:52, as illustrated by the sequence comparison shown below. Domains of sequence homology are identified by asterisks below each sequence comparison.

```
80.8% identity in 26 residues overlap; Score: 106.0; Gap
frequency: 0.0%
Seq52   258 LPQTRKASLARFLEKRKERVINVSPY
Seq68   342 VPQARKASLARFLEKRKERVSSVAPY
            ** **************  *  **

44.7% identity in 47 residues overlap; Score: 87.0; Gap
frequency: 0.0%
Seq52   138 RSSSKPLPPQLTIFYAGSVLVYQDIAPEKAQAIMLLAGNGPHAKPVS
Seq68   193 RDLQNPKVTQMTIFYDGLVNVFDNIPVEKAQELMLLASRASIPSPPS
             *    *  ****  * *  *  ****   ****       *  *

41.7% identity in 24 residues overlap; Score: 39.0; Gap
frequency: 0.0%
Seq52     1 MERDFLGLGSKLSPITVKEETNED
Seq68     1 MERDFLGAIWRKEEPAGKPEEHSD
            *******            *  *

19.0% identity in 63 residues overlap; Score: 36.0; Gap
frequency: 0.0%
Seq52   123 IMAPPVSVFPAPTTIRSSSKPLPPQLTIFYAGSVLVYQDIAPEKAQAIMLLAGNGPHAKP
Seq68   227 LLASRASIPSPPSAARKSDSPISAAAKLTVPEALPARQIVVQKPEASVPLVSGVSNPITI
              *   *  * *  *                 *           *   *  *

Seq52   183 VSQ
Seq68   287 VSQ
            ***
```

This JAZ-related *Oryza sativa* protein, referred to as protein TIFY 6a isoform X2 (NCBI accession number XP_015651050.1 (GI: 1002293416), has the following sequence (SEQ ID NO:68).

```
  1 MERDFLGAIW RKEEAAGKPE EHSDYRGGGG GASAAMQWQF

41 PATKVGAASS AFMSFRSSAA AAREEDPKEA AVFDRFSLSG

81 FRPPPRPSPG DAFDGAAAMK QRQFGFNGRQ QYAAAAQHGH

121 REQGVDSYGV AAPHHFPSPS PSPRHPVPFG HANPMLRVHS

161 LPNVAGGSPY RNQSFSVGNS VAGSTVGVYG GPRDLQNPKV

201 TQMTIFYDGL VNVFDNIPVE KAQELMLLAS RASIPSPPSA

241 ARKSDSPISA AAKLTVPEAL PARQIVVQKP EASVPLVSGV

281 SNPITIVSQA VTLPKSFSSS NDSAGPKSGG LPLAVTPLSQ

321 ASPSQPIPVA TTNASAIMPR AVPQARKASL ARFLEKRKER

361 VSSVAPYPSS KSPLESSDTI GSPSTPSKSS CTDITPSTNN

401 CEDSLCLGQP RNISFSSQEP PSTKLQI
```

A cDNA encoding the SEQ ID NO:68 protein is available as NCBI accession number XM_015795564.1 (GI: 1002293415), and a chromosomal segment encoding the SEQ ID NO:68 protein is on *Oryza sativa* chromosome 8 at NC_029263.1 (20624989 . . . 20627964, complement), sequence available as NCBI accession number NC_029263.1 (GI:996703425).

A *Zea mays* protein referred to as putative tify domain/CCT motif transcription factor family protein (NCBI accession no. DAA40037.1 (GI:414589466)) has significant sequence identity to the *Arabidopsis thaliana* JAZ9 protein with SEQ ID NO:54, as illustrated by the sequence comparison shown below. Domains of sequence homology are identified by asterisks below each sequence comparison.

```
52.1% identity in 48 residues overlap; Score: 118.0; Gap frequency:
0.0%
Seq54   218 SVPQARKASLARFLEKRKERLMSAMPYKKMLLDLSTGESSGMNYSSTS
Seq69   263 AVPQARKASLARFLEKRKERVTTAAPYPSAKSPLESSDTFGSGSASAN
            ******************  * **      *    *      *

54.8% dentity in 31 residues overlap; Score: 96.0; Gap frequency:
0.0%
Seq54   119 QLTIFYGGTISVFNDISPDKAQAIMLCAGNG
Seq69   130 QLTIFYAGSVNVFNNVSAEKAQELMFLASRG
            ****** *  *** * *** *  *  *  *

34.6% identity in 26 residues overlap; Score: 34.0; Gap frequency:
0.0%
Seq54   110 RVASSGSSPQLTIFYGGTISVFNDIS
Seq69    85 RVQSSPSLPNSTAFKQPPFAISNAVA
            ** **  *  *  *      *
```

This JAZ-related uncharacterized *Zea mays* protein, referred to as putative tify domain/CCT motif transcription factor family protein (NCBI accession no. DAA40037.1 (GI: 414589466)), has the following sequence (SEQ ID NO:69).

```
  1 MDWSFASKPC AAPALMSFRS AAREEPSFPQ FSALDGTKNT
 41 APRMLTHQRS FGPDSTQYAA LHRAQNGARV VPVSSPFSQS
 81 NPMFRVQSSP SLPNSTAFKQ PPFAISNAVA SSTVGSYGGT
121 RDAVRPRTAQ LTIFYAGSVN VFNNVSAEKA QELMFLASRG
161 SSAPVACKPE APPTLAPAKV TAPEVLLPAK QMLFQKPQHL
201 SPPPSSVPGI LQSAALPRSA SSSSNLDSPA PKSSVPLAVP
241 PVSQAPPATL IATTTAAAIM PRAMPQARRA SLARFLEKRK
281 ERVTTAAPYP SAKSPLESSD TFGSGSASAN ANDKSSCTDI
321 ALSSNHEESL CLGGQPRSII SFSEESPSTK LQI
```

A chromosomal segment encoding the SEQ ID NO:69 protein is on *Zea mays* chromosome 2 at NC_024460.1 (180086924 . . . 180089758, complement), sequence available as NCBI accession number NC_024460.1 (GI: 662249846).

A *Glycine max* protein referred to as protein TIFY 6A isoform X6 (NCBI accession no XP_006580449.1 (GI: 571456657) has significant sequence identity to the *Arabidopsis thaliana* JAZ9 protein with SEQ ID NO:54, as illustrated by the sequence comparison shown below. Domains of sequence homology are identified by asterisks below each sequence comparison.

This JAZ-related *Glycine max* protein, referred to as protein TIFY 6A isoform X6 (NCBI accession no. XP_006580449.1 (GI:571456657)) has the following sequence (SEQ ID NO:70).

```
  1 MERDFMGLNL KEPLAVVKEE MNNDGCKNSG FKKGRIAQWP
 41 FSNKVSALPH LMSFKASQDD KTKNTVSDTL SSSGFMSILS
 81 QEAFDTSQKR SAGEPQMFSV PNQAISVSLG NPFLKNHFAA
121 AGQKPLLGGI PVTTSHSVLP SAVAVAGMTE SCVKPSAQLT
161 IFYAGTVNIF DDISAEKAQA IMLLAGNSLS AASNMAQPNV
201 QVPISKLGAG AGVPVSQPAN TSPGSGLSSP LSVSSHTGVQ
241 SGSGLTSTDE FLAAKTTGVP NTPICNVEPP KVVSATTMLT
281 SAVPQARKAS LARFLEKRKE RVMSAAPYNL NKKSEECATA
321 EYAGVNFSAT NTVLAKQG
```

A cDNA encoding the SEQ ID NO:70 protein is available as NCBI accession number XM_006580386.2 (GI: 955322109), and a chromosomal segment encoding the SEQ ID NO:70 protein is on *Glycine max* chromosome 5 at NC_016092.2 (41222014 . . . 41225906), sequence available as NCBI accession number NC_016092.2 (GI:952545311).

An unknown *Oryza sativa* protein with NCBI accession no. BAD28520.1 (GI:50251455) has significant sequence identity to the *Arabidopsis thaliana* JAZ9 protein with SEQ ID NO:54, as illustrated by the sequence comparison shown below. Domains of sequence homology are identified by asterisks below each sequence comparison.

```
39.8% identity in 176 residues overlap; Score: 167.0; Gap frequency:
15.3%
Seq54   117 SPQLTIFYGGTISVFNDISPDKAQAIMLCAGNGLKGETGDSKP----------------
Seq70   156 SAQLTIFYAGTVNIFDDISAEKAQAIMLLAGNSLSAASNMAQPNVQVPISKLGAGAGVPV
            * ****** **  * *** ******* ***  *                *

Seq54   160 VREAERMYGKQIHN-------
                TAATSSSSATHTDNFSRCRDTPVAATNAMSMIESFNAAP
Seq70   216 SQPANTSPGSGLSSPLSVSSHTGVQGSGLTSTDEFLAAKTTGVPNTPICNVEPPKVVSA
             *   *         *    *   * ** **   * *          * *

Seq54   213 RNMIPS-VPQARKASLARFLEKRKERLMSAMPYK--KMLLDLSTGESSGMNYSSTS
Seq70   276 TTMLTSAVPQARKASLARFLEKRKERVMSAAPYNLNKKSEECATAEYAGVNFSATN
            *   *  ******************  *** ***       *    * *   * *

40.0% identity in 40 residues overlap; Score: 66.0; Gap frequency:
2.5%
Seq54     1 MERDFLGLSDKQYLSNNVKHEVNDDAVEERGLSTKAAREW
Seq70     1 MERDFMGLNLKEPLAV-VKEEMNNDGCKNSGFKKGRIAQW
            ***** **  *   *  * *  **  *    *     *
```

```
40.9% identity in 66 residues overlap; Score: 116.0; Gap frequency:
1.5%
Seq54    84 GGAFQNATPLLLGGSVPLPTHPSLVPRVASSGSSPQLTIFYGGTISVFNDISPDKAQAIM
Seq71    51 GGAFKQP--
            PFAMGNAVAGSTVGVYGTRDMPKAKAAQLTIFYAGSVNVFNNVSPEKAQELM
            ****   *  *  *  *     *        ****** *   ***  ** ****

Seq54   144 LCAGNG
Seq71   110 FLASRG

*  *

56.1% identity in 41 residues overlap; Score: 110.0; Gap frequency:
0.0%
Seq54   218 SVPQARKASLARFLEKRKERLMSAMPYKKMLLDLSTGESSG
Seq71   225 AVPQARKASLARFLEKRKERVTTVAPYPLAKSPLESSDTMG
             ******************  **       *      *
```

This JAZ-related *Oryza sativa* protein with NCBI accession no. BAD28520.1 (GI:50251455) has the following sequence (SEQ ID NO:71).

```
  1 MQQASHVLAR QPPHVLNGAR VIPASSPFNP NNPMFRVQSS

41 PNLPNAVGAG GGAFKQPPFA MGNAVAGSTV GVYGTRDMPK

81 AKAAQLTIFY AGSVNVFNNV SPEKAQELMF LASRGSLPSA

121 PTTVARMPEA HVFPPAKVTV PEVSPTKPMM LQKPQLVSSP

161 VPAISKPISV VSQATSLPRS ASSSNVDSNV TKSSGPLVVP

201 PTSLPPPAQP ETLATTTAAA IMPRAVPQAR KASLARFLEK

241 RKERVTTVAP YPLAKSPLES SDTMGSANDN KSSCTDIALS

281 SNRDESLSLG QPRTISFCEE SPSTKLQI
```

A chromosomal segment encoding the SEQ ID NO:71 protein is on *Oryza sativa* chromosome 9 at NC_029264.1 (14056084 . . . 14060320, complement), sequence available as NCBI accession number NC_029264.1 (GI:996703424).

An uncharacterized *Zea mays* protein referred to as LOC100384222 (NCBI accession no. NP_001182812.1 (GI:308044557)) has significant sequence identity to the *Arabidopsis thaliana* JAZ10 protein with SEQ ID NO:56, as illustrated by the sequence comparison shown below. Domains of sequence homology are identified by asterisks below each sequence comparison.

This JAZ-related uncharacterized *Zea mays* protein referred to as LOC100384222 (NCBI accession no. NP_001182812.1 (GI:308044557)) has the following sequence (SEQ ID NO:72).

```
  1 MAGHAPARDK TTTGFAATCS LLSQFLKEKK GGLQGLGGLA

41 MAPAPAAGAG AFRPPTTMNL LSALDAAKAT VGEPEGHGQR

81 TGGNPREAAG EEAQQLTIFY GGKVVVFDRF PSAKVKDLLQ

121 IVSPPGADAV VDGAGAGAAV PTQNLPRPSH DSLSADLPIA

161 RRNSLHRFLE KRKDRITAKA PYQVNSSVGA EASKAEKPWL

201 GLGQEQEGSD GRQAGEEM
```

A cDNA encoding the SEQ ID NO:72 protein is available as NCBI accession number NM_001195883.1 (GI: 308044556), and a chromosomal segment encoding the SEQ ID NO:72 protein is on *Zea mays* chromosome 7 at NC_024465.1 (121257106 . . . 121259180, complement), sequence available as NCBI accession number NC_024465.1 (GI:662248746).

An uncharacterized *Glycine max* protein referred to as LOC100306524 (NCBI accession number NP_001236269.1 (GI:351723837) has significant sequence identity to the *Arabidopsis thaliana* JAZ10 protein with SEQ ID NO:56, as illustrated by the sequence comparison shown below. Domains of sequence homology are identified by asterisks below each sequence comparison.

```
36.2% identity in 94 residues overlap; Score: 126.0; Gap frequency:
3.2%
Seq56   105 MTIFYNGSVSVF-
            QVSRNKAGEIMKVANEAASKKDESSMETDLSVILPTTLRPKLFGOL
Seq72    96 LTIFYGGKVVVFDRFPSAKVKDLLQIVSPPGA--
            DAVVDGAGAGAAVPTQNLPRPSHDSL
            **** * **        *                  *           **  **

Seq56   164 EGDLPIARRKSLQRFLEKRKERLVSTSPYYPTSA
Seq72   154 SADLPIARRNSLHRFLEKRKDRITAKAPYQVNSS
              ******* ** ******* *   **  *
```

```
36.6% identity in 123 residues overlap; Score: 114.0; Gap frequency:
12.2%
Seq56    85 SPVHASLARSSTELVSGTVPMTIFYNGSVSVFQ-
            VSRNKAGEIMKVANEAASKKDESSME
Seq73    38 SPNKSVPASGLDAVIPSANQLTIFYNGSVCVYDGIPAEKVHEIMLIAAAAAKSTEMKKIG
            **  *            ******** *          *  ***  *  **

Seq56   144 TDLSVILPTTLRP---------------
            KLFGQNLEGDLPIARRKSLQRFLEKRKERLVST
Seq73    98 TQTTLISPAPSRPSSPHGITNNIGSSQKSSICRLQAEFPIARRHSLQRFLEKRRDRLGSK
            *   *  **                *     *   *****  ********  **  *

Seq56   190 SPY
Seq73   158 TPY
            **
```

This JAZ-related uncharacterized *Glycine max* protein referred to as LOC100306524 (NCBI accession number NP_001236269.1 (GI:351723837) has the following sequence (SEQ ID NO:73).

```
  1 MAAGVTVKSE VLESSPPEGV CSNTVENALV QTNLSDGSPN

41 KSVPASGLDA VIPSANQLTI FYNGSVCVYD GIPAEKVHEI

81 MLIAAAAKS  TEMKKIGTQT TLISPAPSRP SSPHGITNNI

121 GSSQKSSICR LQAEFPIARR HSLQRFLEKR RDRLGSKTPY

161 PSSPTTKVAD NIENNTCADN APELISLNRS EEEFQPTVSA

201 S
```

A cDNA encoding the SEQ ID NO:73 protein is available as NCBI accession number NM_001249340.2 (GI: 402766138), and a chromosomal segment encoding the SEQ ID NO:73 protein is on *Glycine max* chromosome 15 at NC_016102.2 (18552881 ... 18556339), sequence available as NCBI accession number NC_016102.2 (GI:952545301).

An *Oryza sativa* protein referred to as protein TIFY 9 with NCBI accession no. XP_015634258.1 (GI: 1002259863) has significant sequence identity to the *Arabidopsis thaliana* JAZ0 protein with SEQ ID NO:56, as illustrated by the sequence comparison shown below. Domains of sequence homology are identified by asterisks below each sequence comparison.

```
40.0% identity in 110 residues overlap; Score: 119.0; Gap frequency:
13.6%
Seq56    83 PISPVHASLARSSTELVSGTVPMTIFYNGSVSVFQVSRNKAGEIMKVANEAASKKDESSM
Seq74    65 PPPPSTAPVPEEMPGAAAAAAPMTLFYNGSVAVFDVSHDKAEAIMRMATEATKAKGLA--
            *  *             *** ****** ** **  **  ** ** *  **          *

Seq56   143 ETDLSVILPTTLRPKLFGQNLEGDLPIARRKSLQRFLEKRKERLVSTSPY
Seq74   123 ------------RGNAIVGNFAKE-PLTRTKSLQRFLSKRKERLTSLGPY
                        *    *   *      *  ******* ******  *  **

66.7% identity in 12 residues overlap; Score: 44.0; Gap frequency:
0.0%
Seq56     2 SKATIELDFLGL
Seq74     3 TRAPVELDFLGL
              *  *******
```

This JAZ-related *Oryza sativa* protein referred to as protein TIFY 9 with NCBI accession no. XP_015634258.1 (GI: 1002259863) has the following sequence (SEQ ID NO:74).

```
  1 MSTRAPVELD FLGLRAAAAD ADDRHAKSGG SSASSSSSIR

41 GMETSAIARI GPHLLRRVIA AAGPPPPPST APVPEEMPGA
```

-continued
```
 81 AAAAAPMTLF YNGSVAVFDV SHDKAEAIMR MATEATKAKG

121 LARGNAIVGN FAKEPLTRTK SLQRFLSKRK ERLTSLGPYQ

161 VGGPAAVGAT TSTTTKSFLA KEEEHTAS
```

A cDNA encoding the SEQ ID NO:74 protein is available as NCBI accession number XM_015778772.1 (GI: 1002259862), and a chromosomal segment encoding the SEQ ID NO:74 protein is on *Oryza sativa* chromosome 4 at NC_029259.1 (19492605 ... 19497181), sequence available as NCBI accession number NC_029259.1 (GI:996703429).

Chromosomal sites encoding any of the conserved amino acids and conserved domains illustrated by the sequence comparisons shown above can be deleted or mutated to reduce the activity of the proteins described herein.

For example, a wild type plant can express JAZ polypeptides or JAZ-related polypeptides with at least 70%, or at least 75%, or at least 80%, or at least 85%, or at least 90%, or at least 95%, or at least 97%, or at least 98%, or at least 99% sequence identity to any of SEQ ID NOs:48, 50, 52, 54, 56, 58-73, or 74.

However, the mutant jazQ plant cells, plants, and/or seeds with increased jasmonic acid responses and improved insect resistance can express mutant JAZ and/or JAZ-related polypeptides that have reduced activity. Such JAZ and/or JAZ-related polypeptides that have reduced JAZ activity can have less than 99%, or less than 98/o %, or less than 95%, or less than 90%, or less than 85%, or less than 75%, or less than 60%, or less than 50%, or less than 40%, or less than 30%, or less than 20% sequence identity to any of SEQ ID NOs:48, 50, 52, 54, 56, 58-73, or 74.

The mutant JAZ and/or JAZ-related polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved JAZ and/or JAZ-related domain or the entire endogenous JAZ and/or JAZ-related gene or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be employed are shown in Tables 1 and 2.

Transformation of Plant Cells

Mutations can be introduced into any of the MYC, MYC-related. JAZ JAZ-related, PHYB or PHYB-related plant genomes by introducing targeting vectors, T-DNA, transposons, nucleic acids encoding TALENS, CRISPR, or ZFN nucleases, and combinations thereof into a recipient plant cell to create a transformed cell. In addition plant cells can be transformed to include a PIF4 transgene, for example, by transformation of the plant cells with a PIF4 expression cassette or expression vector.

The frequency of occurrence of cells taking up exogenous (foreign) DNA can sometimes be low. However, certain cells from virtually any dicot or monocot species can be stably transformed, and these cells can be regenerated into transgenic plants, through the application of the techniques disclosed herein. The plant cells, plants, and seeds can therefore be monocotyledons or dicotyledons.

The cell(s) that undergo transformation may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods available to those of skill in the art. Examples include: Transformation by direct DNA transfer into plant cells by electroporation (U.S. Pat. Nos. 5,384,253 and 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988), Gordon Kamm et al., The Plant Cell. 2:603 618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf disk protocol (Horsch et al., Science 227:1229 1231 (1985). Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472,869). For example, embryogenic cell lines derived from immature *Zea mays* embryos can be transformed by accelerated particle treatment as described by Gordon Kamm et al. (The Plant Cell. 2:603 618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation can be carried out with "naked" DNA where the expression cassette may be simply carried, for example, on any *E. coli* derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation. i.e., contains totipotent cells. Type I or Type II embryonic maize callus and immature embryos are exemplary *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the targeting vector and/or other nucleic acids for an effective period of time. This may range from a less than one second pulse of electricity for electroporation to a 2-3 day co cultivation in the presence of plasmid bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic cells were bombarded with intact cells of the bacteria *E. coli* or *Agrobacterium tumefaciens* containing plasmids with either the β-glucouronidase or bar gene engineered for expression in maize. Bacteria were inactivated by ethanol dehydration prior to bombardment. A low level of transient expression of the β-glucouronidase gene was observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here in one may obtain up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments, the plant is not *Arabidopsis thaliana*.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera.

All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L, can be selected with sub-lethal levels of bialaphos. Slowly growing tissue was subsequently screened for expression of the luciferase gene and transformants can be identified.

Regeneration and Seed Production

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to have the mutations. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the mutations into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced myc, JAZ or phyB mutations or PIF4 expression cassette, the plant is self-pollinated at least once in order to produce a homozygous backcross converted inbred containing the mutations. Progeny of these plants are true breeding.

Alternatively, seed from transformed mutant plant lines regenerated from transformed tissue cultures is grown in the field and self-pollinated to generate true breeding plants.

Seed from the fertile transgenic plants can then be evaluated for the presence of the desired MYC, JAZ, or PhyB mutation, the desired PIF4 expression cassette, and/or the expression of the desired mutant protein. Transgenic plant and/or seed tissue can be analyzed using standard methods such as SDS polyacrylamide gel electrophoresis, liquid chromatography (e.g., HPLC) or other means of detecting a mutation.

Once a transgenic plant with a mutant sequence and having improved growth and insect resistance is identified, seeds from such plants can be used to develop true breeding plants. The true breeding plants are used to develop a line of plants with an increase insect resistance relative to wild type, and acceptable growth characteristics while still maintaining other desirable functional agronomic traits. Adding the mutation to other plants can be accomplished by back-crossing with this trait and with plants that do not exhibit this trait and studying the pattern of inheritance in segregating generations. Those plants expressing the target trait (insect resistance, good growth) in a dominant fashion are preferably selected. Back-crossing is carried out by crossing the original fertile transgenic plants with a plant from an inbred line exhibiting desirable functional agronomic characteristics while not necessarily expressing the trait of an increased insect resistance and good plant growth. The resulting progeny are then crossed back to the parent that expresses the increased insect resistance and good plant growth. The progeny from this cross will also segregate so that some of the progeny carry the trait and some do not. This back-crossing is repeated until an inbred line with the desirable functional agronomic traits, and with expression of the trait involving an increase in insect resistance and good plant growth. Such insect resistance and good plant growth can be expressed in a dominant fashion.

The new transgenic plants can also be evaluated for a battery of functional agronomic characteristics such as growth, lodging, kernel hardness, yield, resistance to disease and insect pests, drought resistance, and/or herbicide resistance.

Plants that may be improved by these methods include but are not limited to agricultural plants of all types, oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues

To confirm the presence of MYC, JAZ, and/or PHYB mutations and/or a PIF4 expression cassette in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced MYC, JAZ or PhyB mutations or of RNA expressed from an introduced PIF4 expression cassette. For example, PCR also be used to reverse transcribe RNA into DNA, using enzymes such as reverse transcriptase, and then this DNA can be amplified through the use of conventional PCR techniques.

For example, if no amplification of PHYB mRNAs is observed, then a deletion mutation has successfully been introduced.

Information about mutations can also be obtained by primer extension or single nucleotide polymorphism (SNP) analysis.

Further information about the nature of the RNA product may be obtained by Northern blotting. This technique will demonstrate the presence of an RNA species and give information about the integrity of that RNA. The presence of some mutations can be detected by Northern blotting. The presence or absence of an RNA species (e.g., PIF4 RNA) can also be determined using dot or slot blot Northern hybridizations. These techniques are modifications of Northern blotting and also demonstrate the presence or absence of an RNA species.

While Southern blotting and PCR may be used to detect the presence of MYC, JAZ and/or PHYB mutations or the presence of a PIF4 expression cassette, they do not provide information as to whether the preselected DNA segment is being expressed. Expression may be evaluated by specifically identifying the protein products of the introduced PIF4 expression cassette or the introduced mutations, by detecting that no PHYB proteins are expressed, or evaluating the phenotypic changes brought about by such mutation.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products, or the absence thereof, that have been separated by electrophoretic techniques. Additional techniques may be employed to absolutely confirm the identity of a mutation such as evaluation by screening for reduced transcription (or no transcription) of MYC, JAZ, and/or PHYB mRNAs, by screening for PIF4 expression, or by amino acid sequencing following purification. The Examples of this application also provide assay procedures for detecting and quantifying insect resistance and plant growth. Other procedures may be additionally used.

The expression of a gene product can also be determined by evaluating the phenotypic results of its expression. These assays also may take many forms including but not limited to analyzing changes in the insect resistance, growth characteristics, or other physiological properties of the plant. Expression of selected DNA segments encoding different amino acids or having different sequences and may be detected by amino acid analysis or sequencing.

The following Examples describe some of the experiments performed in the development of the invention.

Example 1: Materials and Methods

This Example describes some of the material and methods employed in the development of the invention.

Plant Material and Growth Conditions.

*Arabidopsis thaliana* Columbia ecotype (Col-0) was used as a wild-type (WT) parent for all experiments. Soil-grown plants were maintained at 20° C. (±1° C.) with 16 h light at a light intensity of 120 µE m$^{-2}$ s$^{-1}$ and 8 h dark unless otherwise noted. For the first 10 days after seed sowing, trays containing potted plants were covered with a transparent plastic dome to increase humidity. For experiments involving growth of seedlings on agar plates, seeds were surface sterilized for 15 min in a solution containing 50% (v/v) bleach and 0.1% (v/v) Triton X-100, washed 10 times with sterile water and then stratified in dark at 4° C. for 2 days. Seeds were then sown on 0.7% (w/v) agar media containing half-strength Murashige and Skoog (MS; Caisson Labs) salts supplemented with 0.8% (w/v) sucrose.

Transfer DNA (T-DNA) insertion mutants used for construction of jazQ were obtained from the *Arabidopsis* Biological Research Center (ABRC; The Ohio State University) and named as follows: jaz1-SM (jaz1, JIC-SM.22668), jaz3-GK (jaz3, GK-097F09) jaz4-1 (faz4, SALK_141628) jaz9-GK (jaz9, GK-265H05) and jaz10-1 (jaz10, SAIL_92_D08). See FIG. 1G.

The jaz3-GK and jaz9-GK lines were backcrossed to Col-0 to remove unlinked T-DNA insertions. The jaz10-1 was backcrossed to Col-0 to remove a qrt1-2 mutation present in the SAIL lines (McElver et al., *Genetics* 159, 1751-1763 (2001)). The jaz4-1 and jaz10-1 mutants are described by Jiang et al. (*Plant Cell* 26, 230-245 (2014)), and Sehr et al. (*Plant J* 63, 811-822 (2010)). The jazQ phyB sextuple mutant was obtained from a genetic cross between mutant jazQ and the mutant phyB reference allele phyB-9 (Reed et al., *Plant Cell* 5, 147-157 (1993)). The higher-order pifq (pif7-1/pif3-3 pif4-2/pif5-3) and dellaQ (gai-t6/rgat2/rgl1-1/rgl2-1 rgl3-1) mutants are discussed by Feng et al. (*Nature* 451, 475-479 (2008)) and Leivar et al., (*Curr Biol* 18, 1815-1823 (2008)).

PCR Analysis.

PCR-based genotyping of jazQ and lower-order mutants relied on primer sets flanking T-DNA insertion sites, together with a third primer recognizing the border of the inserted T-DNA. The forward, reverse, and border primers used were the following:

JAZ1 (At1g19180):

5'-ACCGAGACACATTCCCGATT-3', (SEQ ID NO: 75)

5'-CATCAGGCTTGCATGCCATT-3', (SEQ ID NO: 76)
and

5'-ACGAATAAGAGCGTCCATTTTAGAG-3'; (SEQ ID NO: 77)

JAZ3 (At3g17860):

5'-ACGGTTCCTCTATGCCTCAAGTC-3', (SEQ ID NO: 129)

5'-GTGGAGTGGTCTAAAGCAACCTTC-3', (SEQ ID NO: 78)
and

5'-ATAACGCTGCGGACATCTACATT-3'; (SEQ ID NO: 79)

JAZ4 (At1g48500):

5'-TCAGGAAGACAGAGTGTTCCC-3', (SEQ ID NO: 80)

5'-TGCGTTTCTCTAAGAACCGAG-3', (SEQ ID NO: 81)
and

5'-TTGGGTGATGGTTCACGTAG-3'; (SEQ ID NO: 83)

JAZ9 (At1g70700):

5'-TACCGCATAATCATGGTCGTC-3', (SEQ ID NO: 84)

5'-TCATGCTCATTGCATTAGTCG-3', (SEQ ID NO: 85)
and

5'-CTTTGAAGACGTGGTTGGAACG-3'; (SEQ ID NO: 86)

JAZ10 (At5g13220):

5'-ATTTCTCGATCGCCGTCGTAGT-3', (SEQ ID NO: 87)

5'-GCCAAAGAGCTTTGGTCTTAGAGTG-3', (SEQ ID NO: 88)
and

5'-GTCTAAGCGTCAATTTGTTTACACC-3'. (SEQ ID NO: 89)

Reverse transcription-PCR (RT-PCR) was used to confirm the presence or absence of JAZ transcripts in wild type (WT) and mutant jazQ plants. For this purpose, RNA was extracted from eight-day-old seedlings grown on MS plates containing 20 µM MeJA. Frozen tissue was homogenized with a mortar and pestle and RNA was extracted using an RNeasy kit (Qiagen) with on-column DNase (Qiagen) treatment. cDNA was reverse transcribed from one µg total RNA with a High Capacity cDNA Reverse Transcription kit (Applied Biosystems, ABI). RT-PCR was performed using primer sets designed to amplify the five JAZ genes and the internal control ACTIN1 (At2g37620). The forward and reverse primer sets used were as follows:

JAZ1:

5'-ATGTCGAGTTCTATGGAATGTTCTG-3', (SEQ ID NO: 90)
and

5'-TCATATTTCAGCTGCTAAACCGAGCC-3'; (SEQ ID NO: 91)

JAZ3:

5'-ATGGAGAGAGATTTTCTCGGG-3', (SEQ ID NO: 92)
and

5'-TTAGGTTGCAGAGCTGAGAGAAG-3'; (SEQ ID NO: 93)

JAZ4:

5'-ATGGAGAGAGATTTTCTCGG-3', (SEQ ID NO: 94)
and

5'-CAGATGATGAGCTGGAGGAC-3; (SEQ ID NO: 95)

JAZ9:

5'-ATGGAAAGAGATTTTCTGGGTTTG-3', (SEQ ID NO: 96)
and

5'-TTATGTAGGAGAAGTAGAAGAGTAATTCA-3'; (SEQ ID NO: 97)

JAZ10:

5'-ATGTCGAAAGCTACCATAGAAC-3', (SEQ ID NO: 98)
and

5'-GATAGTAAGGAGATGTTGATACTAATCTCT-3'; (SEQ ID NO: 99)
and

ACTIN1:

5'-ATGGCTGATGGTGAAGACATTCAA-3', (SEQ ID NO: 100)
and

5'-TCAGAAGCACTTCCTGTGAACAAT-3'. (SEQ ID NO: 101)

RT-PCR reactions were performed with the following conditions: 94° C. for 5 min, followed by 30 cycles of denaturation (45 sec at 94° C.), annealing (30 sec at 52° C.), and elongation (1.5 min at 72° C.). Final elongation step was performed at 72° C. for 10 min and completed reactions were maintained at 12° C. Forty elongation cycles were used to detect the JAZ4 transcripts, which accumulate at low levels in WT plants (Chung et al., *Plant Physiol* 146, 952-964 (2008)).

Root Growth Assays.

The effect of exogenous JA on seedling root growth inhibition has been described by Shyu et al. (*Plant Cell* 24, 536-550 (2012)). Seedlings were grown on square Petri plates (Fisher) containing MS medium supplemented with the indicated concentration of methyl-jasmonic acid (MeJA; Sigma-Aldrich). Plates were incubated vertically in a growth chamber maintained at 21° C. under continuous light for 8 days. Primary root length was measured using the ImageJ software (see website at imagej.nih.gov/ij/). WT and mutant lines were grown on the same plate to control for plate-to-plate variation.

Quantification of Secondary Metabolites.

Anthocyanins were quantified as described by Kang et al. (*Plant Physiol* 164 (2014)), with minor modifications. Petioles were excised from 4-week-old plants and extracted in 1 ml methanol (MeOH) containing 1% (v/v) HCl. Samples were incubated overnight at 4° C. with constant agitation. Anthocyanin pigments in the resulting extract were measured spectrophotometrically and calculated as $A_{530}-0.25 (A_{657})$ g$^{-1}$ fresh weight. Glucosinolates were quantified as described by Barth & Jander (*Plant J* 46, 549-562 (2006)) with minor modifications. Eight-day-old seedlings grown on solid MS medium were collected into two-mL tubes (approximately 50 seedlings per tube) and immediately frozen in liquid nitrogen. WT and mutant lines were grown on the same plate to avoid plate-to-plate variation. Frozen tissue was lyophilized, ground to a fine powder and extracted with 1 ml 80% MeOH containing an internal standard (25 nmol sinigrin, Sigma-Aldrich). Samples were briefly vortexed, incubated at 75° C. for 15 min, and then centrifuged at 23° C. at 10,000×g for 10 min. Resulting supernatants were applied to Sephadex A-25 columns (Amersham). Glucosinolates were released from the columns as desulfoglucosinolates with a solution containing 30 μL of aryl sulfatase (3.0 mg ml$^{-1}$; Sigma) and 70 μL water (HPLC-grade). Following an overnight incubation in the dark at 23° C., samples were eluted from the columns with 200 μL 80% MeOH and 200 μL water. Samples were then lyophilized to complete dryness and re-dissolved in 100 μL water.

Desulfoglucosinoaltes were detected by HPLC and quantified as described by Barth & Jander (*Plant J* 46, 549-562 (2006)). Compound abbreviations in FIG. 1C correspond to the following: 3MSP, 3-methylsulfinylpropylglucosinolate; 4MSB, 4-methylsulfinylbutylglucosinolate; 5MSP, 5-methylsulfinylpentylyglucosinolate; 4OHI3M, 4-hydroxyindol-3-ylmethylglucosinolate; 7MSH, 7-methylsulfinylheptylglucosinolate; 4MTB, 4-methylthiobutylglucosinolate; 8MSO, 8-methylsulfinyloctylglucosinolate; I3M, indol-3-ylmethylglucosinolate; 4MI3M, 4-methoxyindol-3-ylmethylglucosinolate; 1MI3M, 1-methoxyindol-3-ylmethylglucosinolate; 7MTH, 7-methylthioheptylglucosinolate; and 8MTO, 8-methylthiooctylglucosinolate.

Insect Feeding Assays.

Insect feeding assays were performed with soil-grown plants maintained in a growth chamber at 19° C. and a photoperiod of 8 h light (120 μE m$^{-2}$ s$^{-1}$) and 16 h dark. Neonate *Trichoplusia ni* larvae (Benzon Research) were transferred to the center of fully expanded rosette leaves of 6-week-old plants, as previously described by Herde et al. (*Methods Mol Biol* 1011, 51-61 (2013)). Four larvae were reared on each of 12 plants per genotype. Plants were then covered with a transparent dome and returned to the chamber for 10 d, after which larval weights were measured.

Growth and Flowering Time Measurements.

Three-to-four week-old soil-grown plants were used for all measurements (10 plants per measurement), unless indicated otherwise. Petiole length of the third true leaf was measured with a caliper after leaf excision. Bolting time was measured in a separate set of plants by counting the number of true leaves on the main stem and the number of days from sowing until bolting (i.e., floral buds visible in the center of the rosette). The same set of plants was subsequently used to assess the length of time to opening of the first flower. Rosette diameter and leaf area were determined by photographing rosettes from the top with a Nikon D80 camera. The resulting images were used to calculate Feret diameter using ImageJ analysis. Total leaf area was determined with GIMP software (see website at gimp.org). Leaf dry weight was determined by weighing excised rosettes (without roots) after freeze drying for two days in a lyophilizer.

jazQ Suppressor Screen and Identification of sjq11.

Approximately 50,000 jazQ mutant seeds were further mutagenized by immersion in a solution of 0.1% or 0.2% (v/v) ethyl methanesulfonate (EMS, Sigma-Aldrich) for 16 hours at room temperature, with constant agitation. Seeds ($M_1$ generation) were thoroughly washed with water, stratified in the dark at 4° C. for two days and then immediately sown on soil. $M_2$ seed was collected from 16 pools of self-pollinated $M_1$ plants (approximately 1,000 $M_1$ plants/pool). Soil-grown $M_2$ plants (~2000 plants/pool) were visually screened for individuals having a larger rosette size than jazQ mutant seedlings. Putative sjq (suppressors of the jazQ) mutants were rescreened in the M3 generation to confirm heritability of phenotypes. Insight into the causal mutation in sjq11 came from the observation that sjq11 seedlings grown on MS medium in continuous white light for 3 days have elongated hypocotyls. Subsequent hypocotyl growth assays in monochromatic red light (Warnasooriya & Montgomery, *Plant Physiol* 149, 424-433 (2009)) confirmed a defect in red light signaling. Briefly, sjq11 (M3 generation) and control seeds were plated on MS medium lacking sucrose and stratified at 4° C. in the dark for two days. Mutant and control lines were grown on the same plate to control for plate-to-plate variation. A 3 hours a pulse of white light was then administered to improve synchronous seed germination. Plates were then returned to darkness for one day at 21° C. and then transferred to a monochromatic LED chamber outfitted to emit red light (670±20 nm; 25 μE μE m$^{-2}$ s$^{-1}$). As a control, a set of plates containing each genotype was maintained in darkness. Following three days of growth, seedling hypocotyls were measured by ImageJ software analysis of scanned images. Allelism tests performed with Fi seedlings (obtained from the cross between sjq11 and phyB-9) revealed a lack of genetic complementation. Sequencing of the PHYB gene (AT2G18790) in sjq11 revealed a C→T transition that introduces a stop codon in a region of the gene that encodes the chromophore-binding domain of PHYB (see FIG. 2G).

Gene Expression Profiling.

Global gene expression profiling in 8-day-old whole seedlings (Col-0 WT, mutant jazQ, mutant phyB-9, mutant jazQ phyB-9) was assessed by mRNA sequencing (RNA-seq) performed on the Ilumina HiSeq 2000 platform. Seedlings were grown in continuous light on solid MS medium supplemented with sucrose. For each replicate sample, approximately 200 seedlings were harvested for RNA extraction. WT and mutant seedlings were grown on the same plate to minimize plate-to-plate variation.

Three independent RNA samples (biological replicates) were sequenced per genotype. Total RNA was isolated as described above and RNA integrity was assessed with a 2100 Bioanalyzer (Agilent Technologies). All samples utilized had an integrity score of at least 7.0. Single-end (50 bp) sequencing was performed at the Michigan State University Research Technologies Service Facility (see website at rtsf.natsci.msu.edu). Barcoded sequencing libraries were constructed using the Illumina RNAseq kit according to the manufacturer's instructions and were multiplexed in six libraries per lane. The average number of sequencing reads was 18.4±4.3 million per sample. Raw sequencing reads were assessed with Illumina quality control tools filters and FASTX toolkit (see website at hannonlab.cshl.edu/fastx_toolkit/). Reads were mapped to gene models in TAIR10 with the program RSEM (version 1.2.11) set for default parameters (Li & Dewey, *BMC Bioinformatics* 12, 323, (2011)). Data was expressed as transcripts per million (TPM), and the average TPM±standard error for *Arabidopsis* genes.

DESeq (version 1.18.0; see Anders & Huber, *Genome Biol* 11, R106 (2010)) was used to normalize expected counts from RSEM and to assess differential gene expression by comparing normalized counts in WT to those in a particular mutant. Gene ontology (GO) analysis of enriched functional categories was performed using BiNGO (version 2.44, Maere et al., *Bioinformatics* 21, 3448-3449 (2005)). The hypergeometric test with Benjamini & Hochberg's FDR correction was used to calculate over-represented and under-represented GO categories among differentially expressed genes, using a P value<0.05.

For wounding experiments, three-week old soil-grown seedlings were wounded twice across the midvein of four leaves (leaves 3-6, counted from first rosette leaf). After 1 h, the wounded leaves of two plants were pooled and immediately frozen in liquid nitrogen. Equivalent leaves of two unwounded plants were pooled and collected as controls. The experiment was independently replicated twice, with each experiment consisting of 3-4 biological replicates. Frozen tissue was homogenized with a TissueLyser II (Qiagen) and RNA was extracted using an RNeasy kit (Qiagen) with on-column DNase (Qiagen) treatment, as per the manufacturer's instructions. RNA quality was assessed by $A_{260}/A_{280}$ ratios using a ND-1000 UV Nanodrop spectrophotometer (Thermo Scientific). cDNA was reverse transcribed using a High-Capacity cDNA Reverse Transcription kit (Applied Biosystems, ABI), as per the manufacturer's instructions, and cDNA was diluted to 0.5 ng/µL with nuclease-free water, qRT-PCR was performed as described by Attaran et al. (*Plant Physiol* 165, 1302-1314 (2014)), with minor modifications. Briefly, reactions were performed on an ABI 7500 Fast qPCR instrument, and consisted of 5 µL of 2× Power SYBR Green (ABI) master mix, 2 uL diluted cDNA template (1 ng total), 1 µL 5 uM forward and reverse primers, and nuclease-free water for 10 µL total reaction volume. The forward and reverse primers used were the following:

```
PP2A:
                                (SEQ ID NO: 102)
5'-AAGCAGCGTAATCGGTAGG-3'
and
                                (SEQ ID NO: 103)
5'-GCACAGCAATCGGGTATAAAG-3';

AOS:
                                (SEQ ID NO: 104)
5'-GGAGAACTCACGATGGGAGCGATT-3'
and
                                (SEQ ID NO: 105)
5'-GCGTCGTGGCTTTCGATAACCAGA-3';

LOX3:
                                (SEQ ID NO: 106)
5'-GCTGGCGGTTCGACATG-3'
and
                                (SEQ ID NO: 107)
5'-GCCATTCCTCTGCGAATTAGA-3';

MYC2:
                                (SEQ ID NO: 108)
5'-AGAAACTCCAAATCAAGAACCAGCTC-3'
and
                                (SEQ ID NO: 109)
5'-CCGGTTTAATCGAAGAACACGAAGAC-3'.
```

Reactions were run with the following conditions: 95° C. for 10 min, then 40 cycles of 15 s at 95° C. for denaturation and 60 s at 60° C. for annealing and polymerization. A dissociation curve was performed at the end of each reaction to confirm primer specificity using default parameters (15 s at 95° C., 60 s at 60° C.-95° C. in 1° C. increments, and 15 s at 95° C.). Target gene expression was normalized to the expression of PP2a, which is stable under JA-inducing conditions. The normalization incorporated primer efficiencies determined for each primer pair using LinRegPCR v2012.0[46] from the log-linear phase of each amplification plot.

Overexpression of PIF4 in the Mutant jazQ Background.

The 35S::PIF4-TAP overexpression construct (see Lee & Thomashow, *Proc Natl Acad Sci USA* 109, 15054-15059 (2012)). Transformation of mutant jazQ plants with *Agrobacterium tumefaciens* (strain C58C1) was performed using the flower dip method (Clough & Bent, *Plant J* 16, 735-743 (1998)). Multiple independent transformed lines (T1 generation) were selected on MS plates containing gentamycin and transferred to soil for subsequent analysis. Homozygous lines were selected by testing the T3 progeny for gentamycin resistance.

Photosynthesis Measurements.

Gas exchange measurements were obtained as described by Attaran et al. (*Plant Physiol* 165, 1302-1314 (2014)), and Li et al. (*Photosynth Res* 112, 49-61 (2012)). Plants were grown in plastic containers ("Conetainers", Steuwe and Sons, Tangent, Oreg., USA) on an 8 h light (19° C.)/16 h dark (16° C.) photoperiod and 120 µmol m$^{-2}$ s$^{-1}$ photosynthetic photon flux density (PPFD). Single mature rosette leaves (attached) from 8- to 10-week-old plants were used to obtain $CO_2$ response curves on a LI-6400XT system (LI-COR Biosciences, Lincoln, Nebr., USA) outfitted with a standard leaf chamber (chamber area=6 cm$^2$). Leaves were supplied with an artificial air mixture consisting of 20% $O_2$, 80% $N_2$, and 400 ppm $CO_2$ at intensity of light 500 µmol m$^{-2}$ s$^{-1}$. Leaf temperature was maintained at ~20° C. (block temperature set to 18° C.). Leaves were acclimated under this condition for at least 30 min before the start of each experiment. Assimilation rates were normalized to projected leaf area as measured by image analysis with the GIMP software. Area-based and whole plant-based photosynthesis and respiration was determined at four time points of the *Arabidopsis* growth cycle as described by Weraduwage et al. (*Front Plant Sci* 6, 167 (2015)), in plants grown under short-day conditions.

In situ chlorophyll a fluorescence measurements were performed in a Percival AR41L2 (Geneva Scientific, see website at geneva-scientific.com) refitted as a Dynamic Environment Photosynthesis imager (DEPI), as described by Attaran et al. (*Plant Physiol* 165, 1302-1314 (2014)), Dutta et al. (*Plant J* 84, 428-442 (2015)), and Kramer et al. (WO 2013181433 A2 (2013)). Images were processed using visual phenomics software (Tessmer et al., *BMC Syst Biol* 7, (Suppl 6) S17 (2013)). The quantum yield of PSII ($\Phi$II) was calculated as $(F'_M - F_S)/F'_M$, where $F_S$ is the steady-state fluorescence and $F'_M$ is the fluorescence maximum at steady state (Baker, *Annu Rev Plant Biol* 59, 89-113 (2008)).

Leaf Thickness Measurements.

Leaf cross sections obtained from the 5$^{th}$ leaf of 22-day old rosette leaves were examined under an Olympus FluoView FV 1000, Confocal Laser Scanning Microscope (Olympus, N.J., USA) in the Center for Advanced Microscopy, Michigan State University. Leaf thickness was measured as the distance between the abaxial and adaxial surfaces of the leaf as described by Weraduwage et al. (*Front Plant Sci* 6, 167 (2015)).

Measurement of Total Chlorophyll and Rubisco Concentration in Leaves.

Extraction and quantification of chlorophyll was carried out using a protocol modified from Lichtenthaler & Wellbum (*Biochem Soc Trans* 11, 591-592 (1983)). Total chlorophyll was extracted from 54-d old *Arabidopsis* rosette leaves with 96% ethanol. Absorbance of the extracted chlorophyll was measured spectrophotometrically at 665 nm and 649 nm and the total chlorophyll was calculated using the following equation:

$$Chl_a + Chl_b = (13.95 A_{665} - 6.88 A_{649}) + (24.96 A_{649} - 7.32 A_{665}).$$

Total protein was extracted from 54-d old *Arabidopsis* rosette leaves using a Plant Total Protein Extraction Kit (Sigma-Aldrich, MO, USA). A modified Lowry Assay was performed to measure the total protein concentration in the extract and the purity and quality of the extracted protein were determined by denaturing polyacrylamide gel electrophoresis. Equal amounts of total protein were loaded onto an automated capillary-based size western blotting system (ProteinSimple Wes System, San Jose Calif., USA). All procedures were performed with manufacturer's reagents according to their user manual. Protein separation and immunodetection were performed automatically on the individual capillaries using the default settings.

Antibodies raised against the large subunit of Rubisco (rabbit antibodies, AS03 037; Agrisera, Sweden; dilution used 1:650) were used to detect Rubisco in each protein sample. For quantification, all subsequent data generated was analyzed with the 'Compass Software' provided by manufacturer (ProteinSimple, San Jose Calif.). Peak heights of the fluorescence signals were used to calculate relative differences of Rubisco concentration between samples. Rubisco concentration per unit leaf area was calculated based on the total protein concentration and measurements of leaf area per unit mass.

Example 2: Mutants with Enhanced Jasmonate (JA)-Regulated Defense Against Insects A genetic screen was performed to identify mutants of *Arabidopsis* that display enhanced jasmonate (JA)-regulated defense against insect herbivory without an associated reduction in leaf growth. This screen leveraged a signaling model predicting that removal of JAZ repressor proteins would constitutively activate defense and inhibit growth (FIG. 1A). A mutant plant line (jaz quintuple or jazQ) was developed with T-DNA insertion mutations in five (JAZ1/3/4/9/10) of the 13 *Arabidopsis* JAZ genes (FIG. 1G). These JAZs were selected on the basis of their phylogenetic relationship, their demonstrated role in inhibiting MYC transcription factors, and their capacity to interact with DELLA proteins that antagonistically link JA signaling to gibberellic acid (GA)-mediated growth responses (FIG. 1A).

Figure 1B:
Figure 1C:
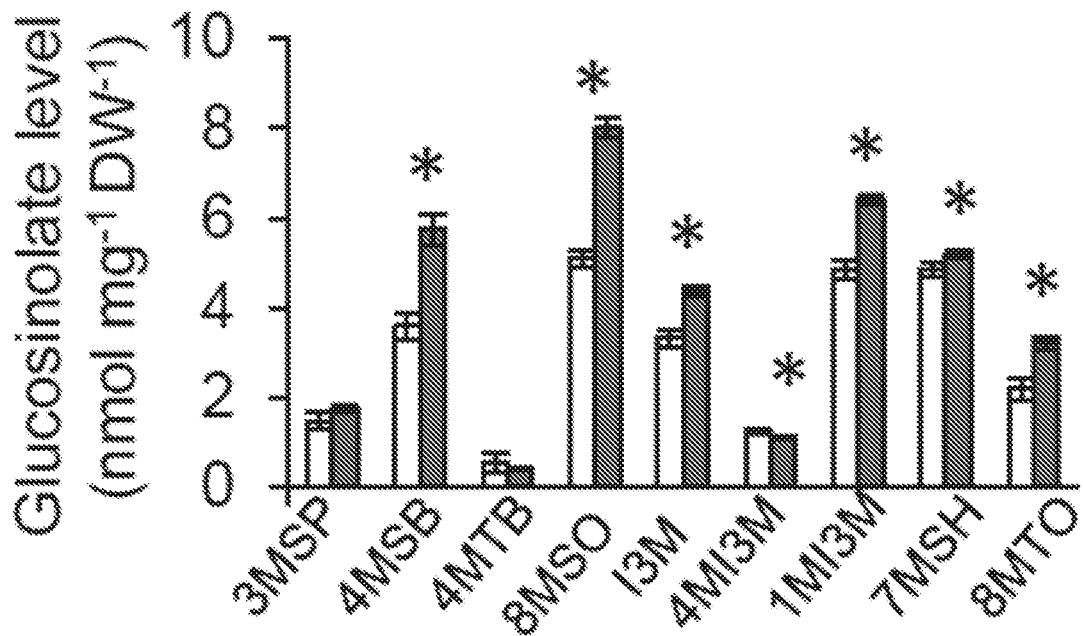
Figure 1D:
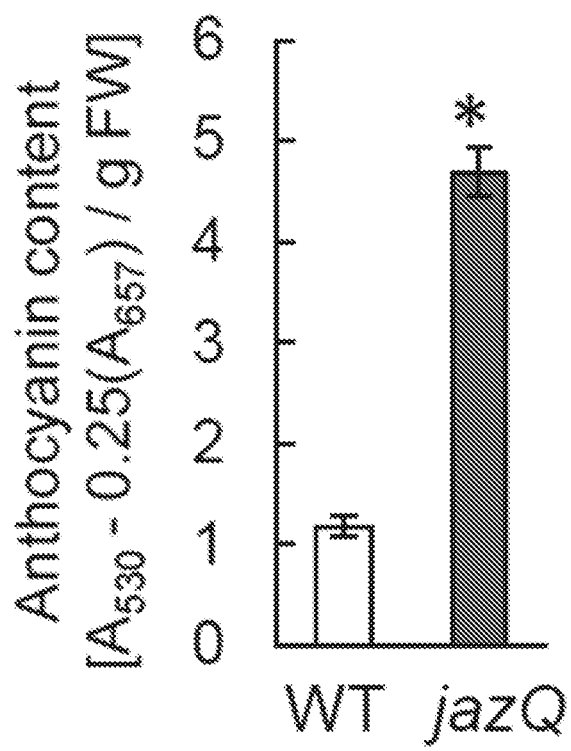
Figure 1E:
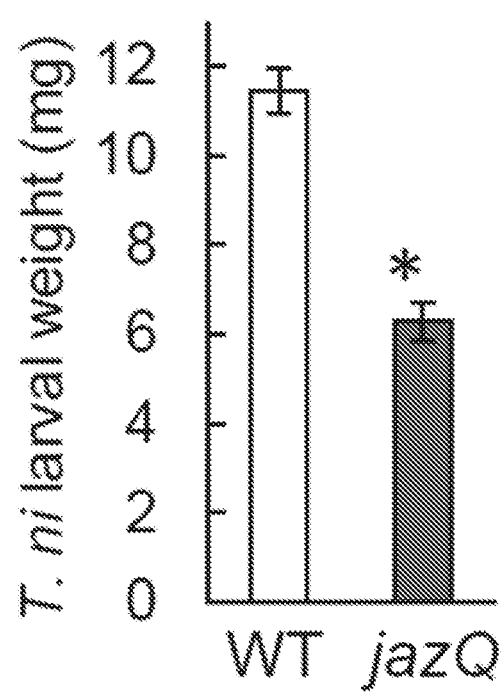
Figure 1F:
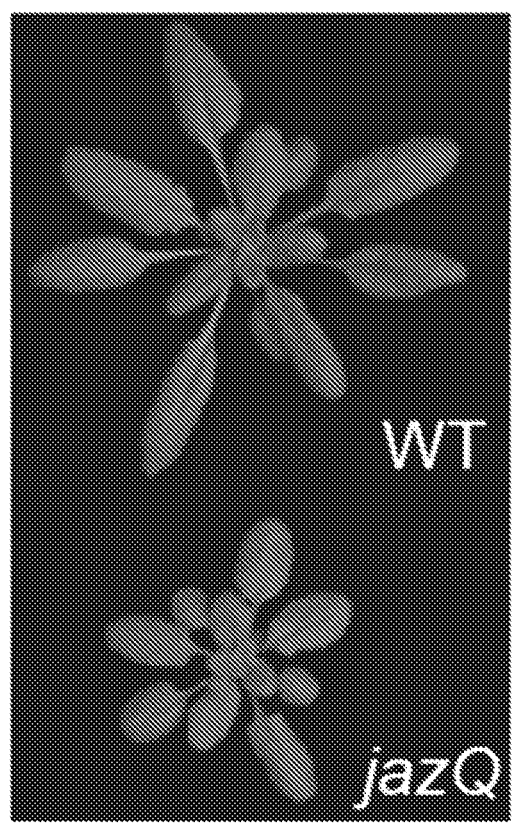
Figure 1G:
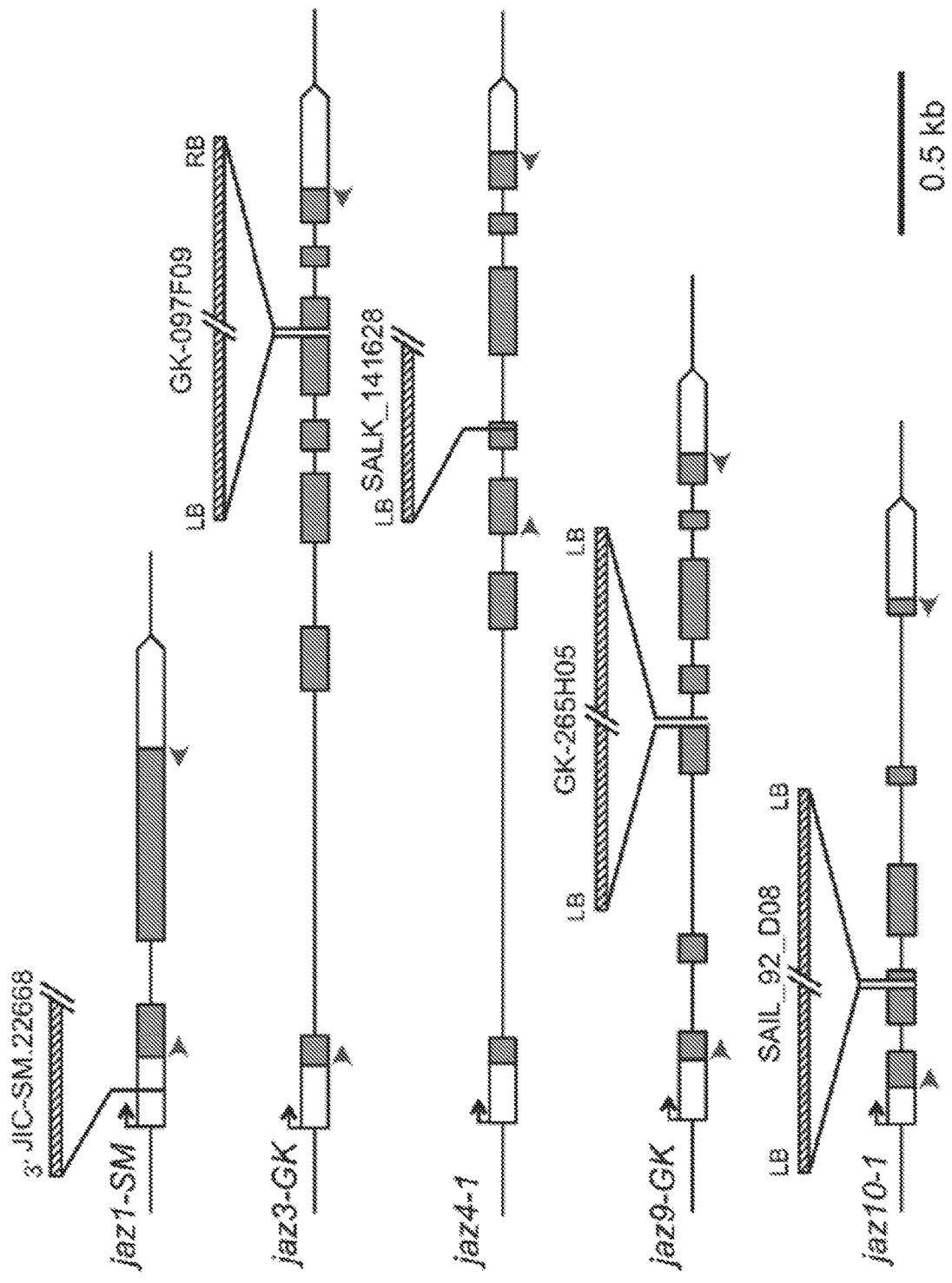
Figure 1I:
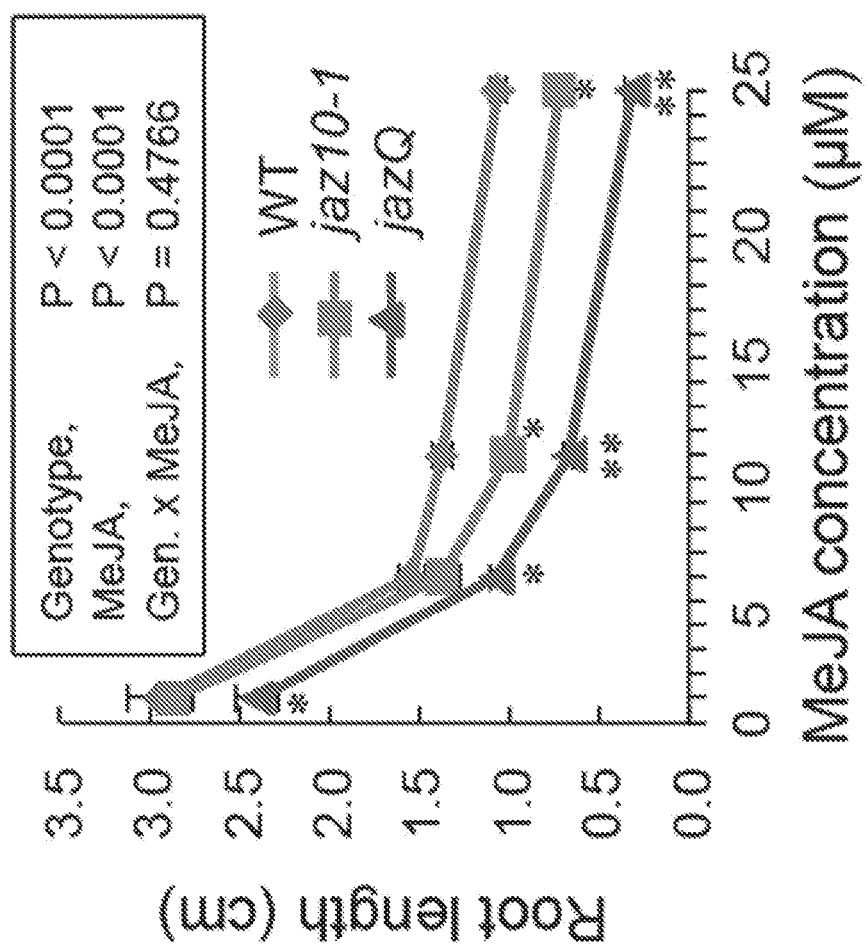
Figure 1H:
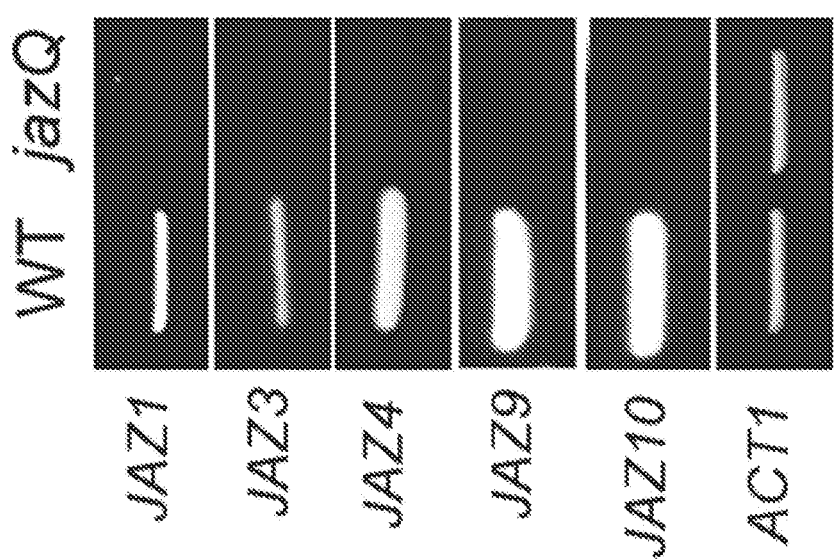

Root growth assays showed that mutant jazQ seedlings have both an increased sensitivity to exogenous JA and a constitutive short-root phenotype (FIGS. 1B and 1I). The short root phenotype is consistent with recent genetic analysis of JA signaling in roots (Gasperini et al., *PLoS Genet* 11, e1005300 (2015)). Glucosinolates and anthocyanins, whose biosynthesis in *Arabidopsis* is positively regulated by jasmonic acid, accumulated to higher levels in jazQ mutant seedlings than in wild type (WT) seedlings (FIG. 1C-1D). Soil-grown jazQ mutant plants had remarkably heightened resistance to attack by the generalist herbivore *Trichoplusia ni* (FIG. 1E). In contrast to these elevated defense traits, leaf area, petiole length, and rosette dry weight were all reduced in jazQ mutants relative to WT (FIG. 1F). The jazQ mutations also delayed the time to bolting but did not affect the number of leaves at the time of bolting. These results demonstrate that jazQ mutant plants exhibit constitutive growth-defense antagonism (i.e., reduced growth with enhanced defense) and thus provide a unique genetic model with which to interrogate how JA-triggered immunity inhibits growth.

Figure 2A:
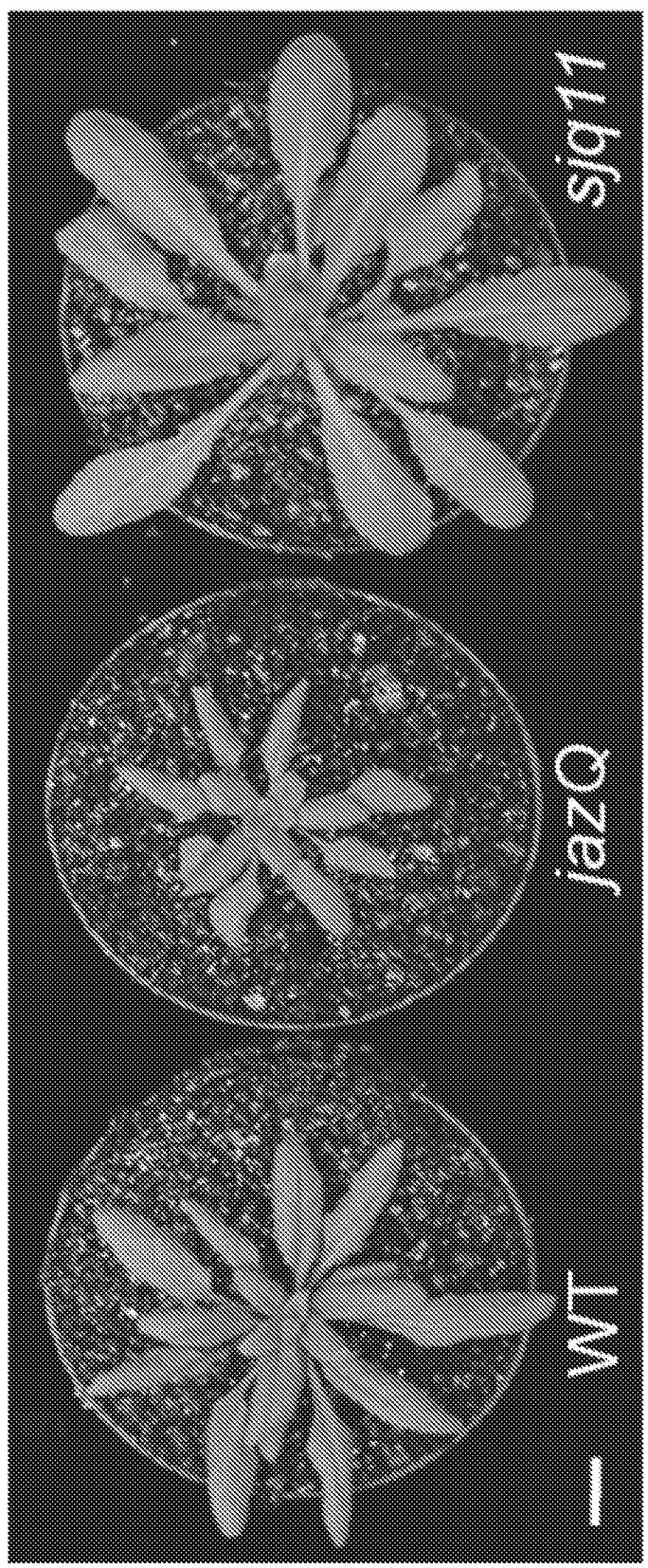
FIG. 2A-2H illustrate that mutant jazQ phyB plants simultaneously grow well and defend against insect infestation.
Figure 2B:
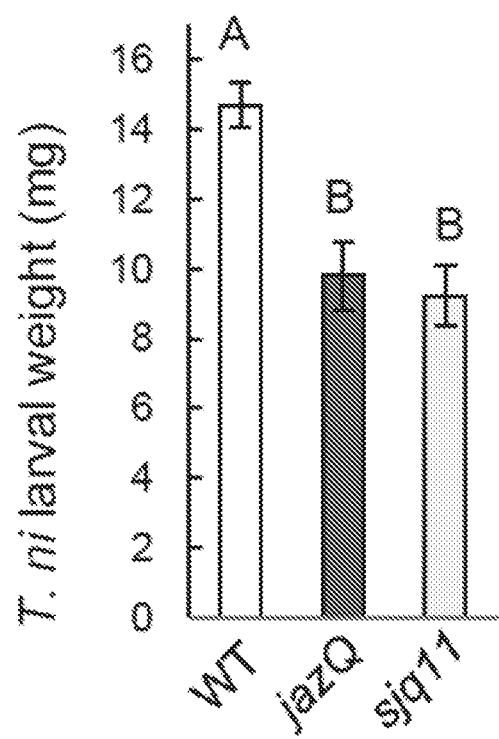
Figure 2C:
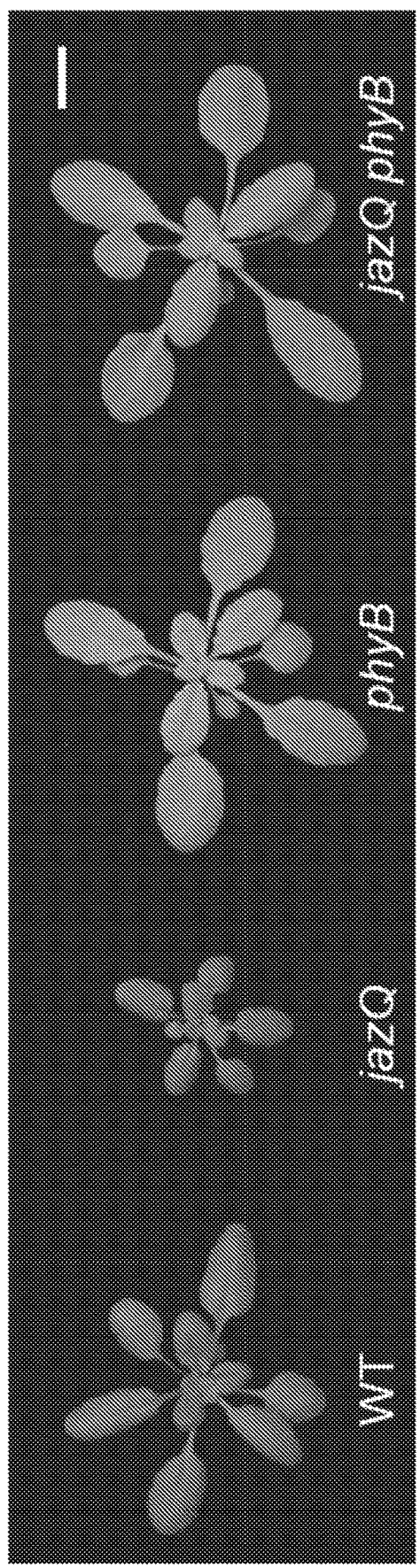

Example 3: Screen for Mutants with Enhanced Jasmonate (JA)-Regulated Defense Against Insects without Reduced Leaf Growth An ethyl methanesulfonate (EMS)-mutagenized population of jazQ was visually screened for mutants with increased rosette size and persistence of elevated leafanthocyanin content. Among several suppressor of jazQ (sjq) mutants identified, one line (sjq11) showed a particularly striking leaf growth pattern that was heritable in the M$_3$ generation (FIG. 2A). Importantly, bioassays performed with *T. ni* larvae showed that sjq11 plants also maintained heightened defenses (FIG. 2B). Characterization of sjq11 plants revealed phenotypes similar to those described for phytochrome B (phyB) photoreceptor mutants, including early flowering time, as well as elongated hypocotyls and petioles under continuous white light. Genetic allelism tests and DNA sequencing confirmed that sjq11 harbors a null mutation in the PHYB gene (FIG. 2G). To eliminate the possibility that additional EMS mutations contribute to the sjq11 phenotype, further studies were performed with a jazQ phyB sextuple mutant obtained by crossing the reference phyB-9 null allele into the jazQ mutant background.

Example 4: Analysis of Growth and Defense Traits in jazQ phyB Plants

Analysis of growth and defense traits in jazQ phyB mutant plants showed that the jazQ and phyB "single" mutant phenotypes were largely additive and often tissue specific. Mutant jazQ phyB seedlings, for example, retained the JA-hypersensitive root growth inhibition and red-light insensitive hypocotyl elongation phenotypes of jazQ and phyB, respectively. Adult jazQ phyB mutant plants grown in soil resembled phyB in having elongated petioles, flat rosette leaves, and early flowering time (FIG. 2). The phyB mutation is thus epistatic to jazQ for these traits. The rosette diameter, projected leaf area, and dry mass of jazQ phyB rosette leaves exceeded that of the jazQ and phyB parents, indicating that the combination of jazQ and phyB has transgressive effects on leaf growth (FIG. 2D).

Figure 2F:
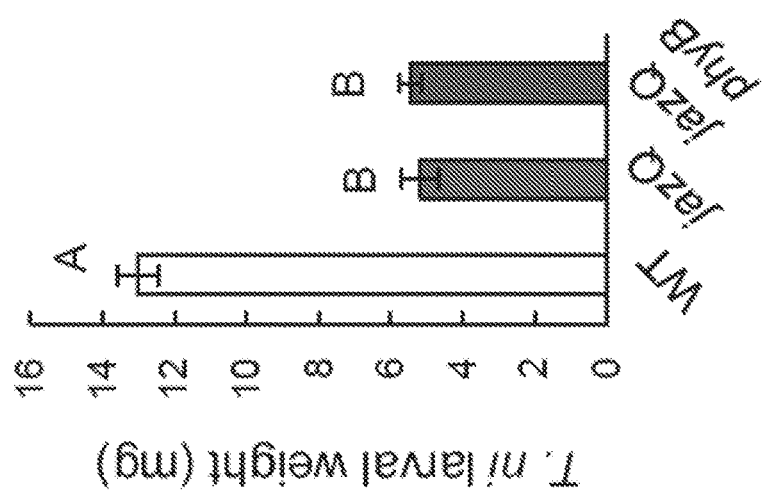
Figure 2E:
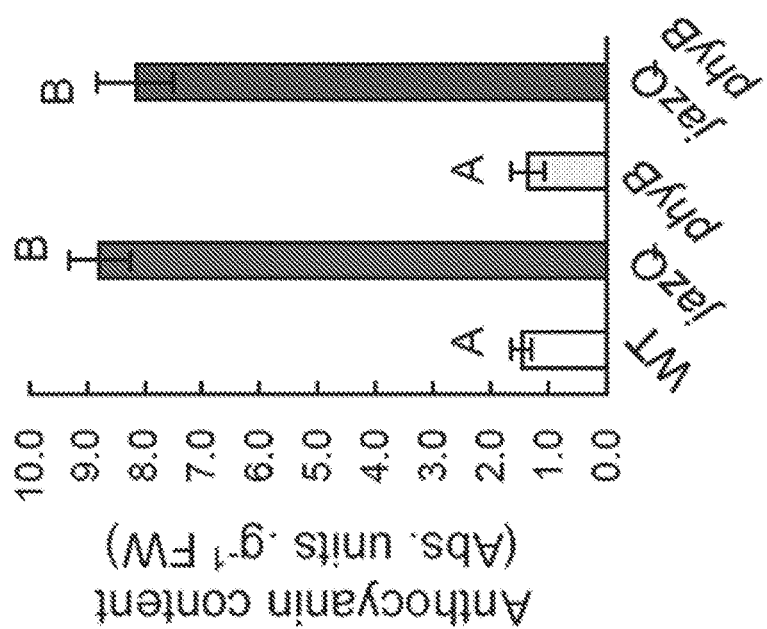
Figure 2D:
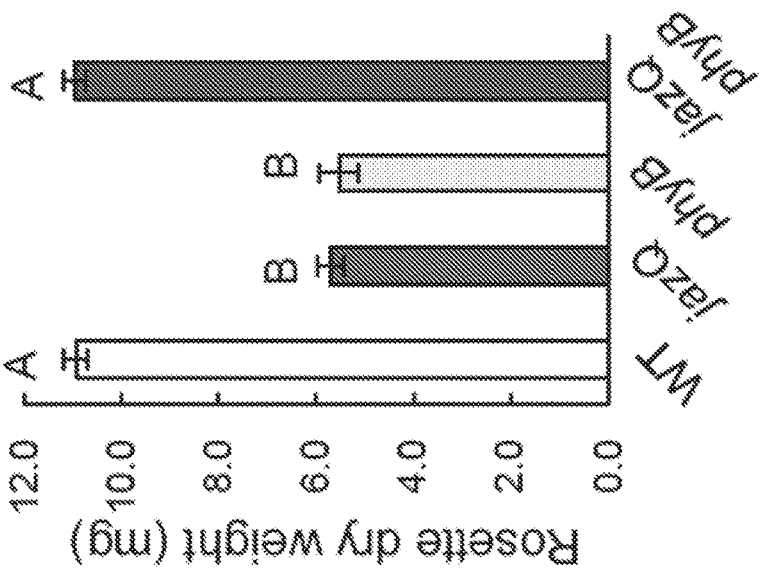
Figure 2G:
Figure 2H:
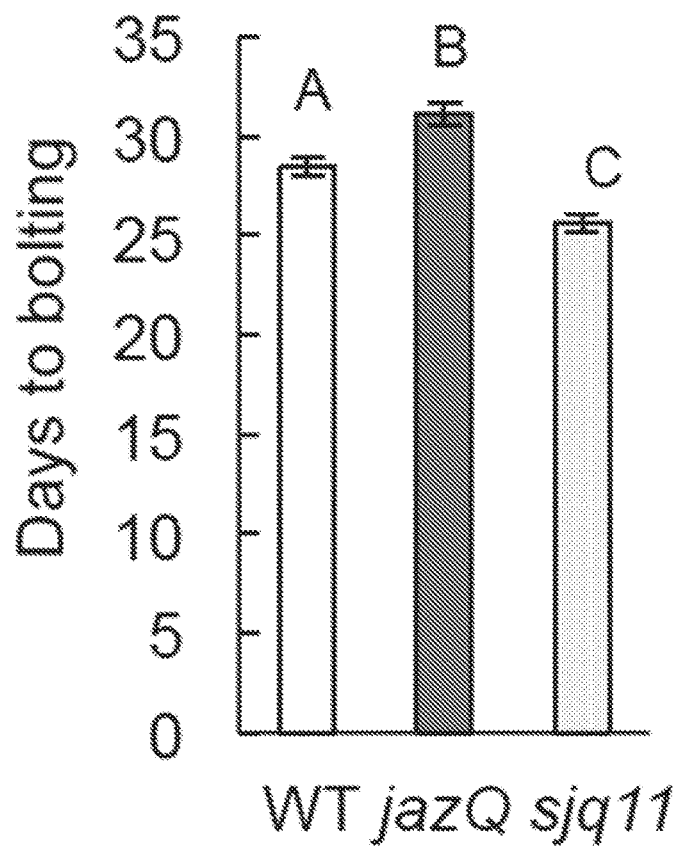

Despite its robust vegetative growth, jazQ phyB mutant plants maintained the heightened anti-insect defense and anthocyanin content of jazQ (FIG. 2E-2F). The effect of combining jazQ and phyB mutations on resistance to *T. ni* feeding was particularly striking because phyB mutations alone cause high susceptibility to this herbivore. The jazQ phenotype is therefore epistatic to phyB with respect to leaf defense traits. These data demonstrate that phyB mutations fully suppresses the slow growth of mutant jazQ rosette leaves without compromising heightened resistance to *T. ni* feeding.

The JA and PHYB signaling pathways interact to mediate growth-defense balance during the shade avoidance response. Within this signaling network, GA stimulates cell extension growth by promoting the degradation of DELLA proteins that repress PIF transcription factors (FIG. 1A; see also de Lucas et al. *Nature* 451, 480-484 (2008)). Reciprocal antagonism between the JA and GA pathways involves JAZ-DELLA interactions that prevent these repressors from inhibiting their cognate transcription factors (Hou et al., *Dev Cell* 19, 884-894 (2010); Yang et al., *Proc Natl Acad Sci USA* 109, 1192-1200 (2012)). JA-GA crosstalk is integrated with the shade avoidance response through PHYB-mediated perception of changes in the ratio of red to far red (R:FR) light. Low R:FR ratios indicative of leaf shading reduce PHYB activity to relieve repression on PIFs, thereby promoting rapid growth through the concerted action of auxin and brassinosteroids (FIG. 1A). Concurrent with this growth response to plant competitors, inactivation of PHYB by low R:FR (or phyB mutation) also leads to depletion of DELLA proteins, increased JAZ stability, accelerated turnover of MYCs, and suppression of JA-triggered immune responses.

Example 5: Expression Patterns of Wild Type, jazQ, phyB, and jazQ phyB Seedlings This Example describes transcript profiles obtained by mRNA sequencing of WT, mutant jazQ, mutant phyB, and mutant jazQ phyB seedling tissues to ascertain how the combination of phyB and jazQ mutations affects gene expression.

Figure 3:
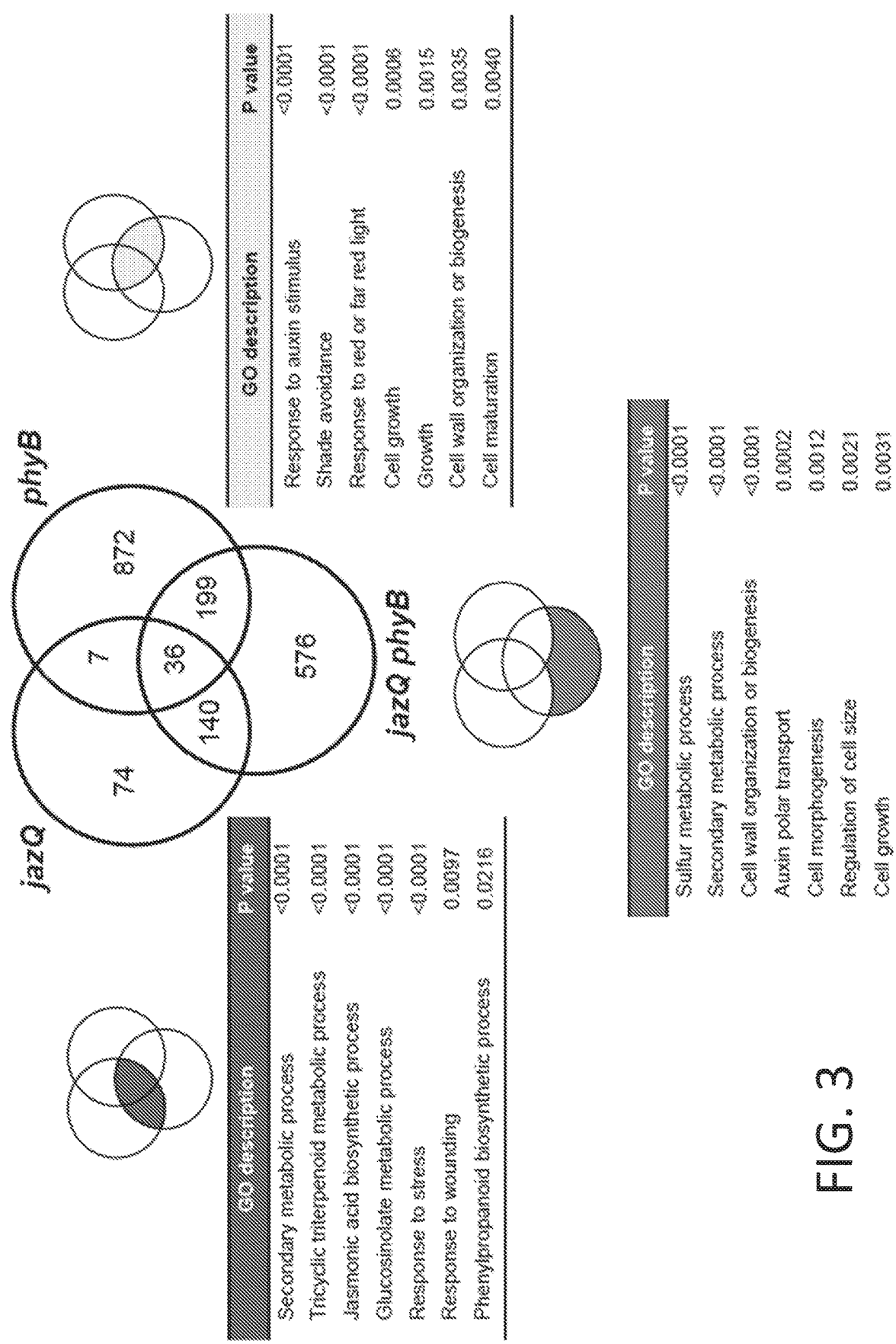
FIG. 3 illustrates that the combination of jazQ and phyB mutations promotes expression of growth-related and defense-related genes. WT, mutant jazQ, mutant phyB and mutant jazQ/phyB seedlings were grown for 8 days in continuous white light prior to RNA extraction and analysis of gene expression by mRNA sequencing. The Venn diagram shows the number of genes upregulated in comparisons between WT and each of the three mutants. GO analysis of functional categories was performed with gene sets that are shared between mutant jazQ and mutant jazQ phyB (blue intersect), shared between mutant phyB and mutant jazQ phyB (yellow intersect), or unique to mutant jazQ phyB (green shade).

"Secondary metabolism" and "response to stress" and were among the biological processes most significantly overrepresented in ontologies of 257 genes expressed to higher levels in jazQ than in WT (FIG. 3). This gene set included glucosinolate biosynthesis genes that are direct targets of MYC2, as well as genes involved in the synthesis of triterpenoids, jasmonates, and various defense proteins.

Consistent with their enhanced defense stature, jazQ phyB plants maintained increased expression of the majority (68%) of genes that are upregulated in jazQ (FIG. 3). By comparison, analysis of growth-related genes revealed that the set of 235 genes upregulated in both phyB and jazQ phyB genetic backgrounds is enriched for functional classes involved in responses to auxin, shade avoidance, cell wall organization, and light stimulus (FIG. 3). Several genes within this group have been shown to be direct targets for PIF transcription factor binding (Oh et al., Nat Cell Biol 14, 802-809 (2012); Hornitschek et al., Plant J 71, 699-711 (2012); and Zhang et al., PLoS Genet 9, e1003244 (2013)). These data indicate that the combination of jazQ and phyB mutations promotes simultaneous expression of defense and growth-related genes that are controlled, at least in part, by the MYC and PIF transcriptional modules, respectively.

Among the 576 transcripts whose abundance was significantly increased in jazQ phyB mutants but not jazQ or phyB mutants, there was a strong over-representation of GO terms related to secondary metabolism, cell wall organization, growth, and auxin transport (FIG. 3). These data indicate that the combination of jazQ and phyB mutations leads to increased expression of certain growth and defense responses in jazQ phyB mutant plants. Quantitative PCR analysis showed that wound-induced expression of select JA-response genes was significantly higher in jazQ phyB mutant leaves than WT leaves, which may also contribute to the heightened defense of jazQ phyB mutant plants relative to WT. The synergistic effects of jazQ and phyB mutations on gene expression may thus result from functional interaction between MYCs and PIFs at the level of protein-protein interaction or altered binding to common cis-regulatory elements in target genes.

Example 6: Photosynthetic Efficiency

This Example describes investigations of whether jazQ and phyB mutations interact to modulate leaf photosynthetic efficiency.

PIF activity can repress chloroplast development and photosynthetic competency, and the inventors have observed that "photosynthesis" was a characteristic most significantly overrepresented among genes that are repressed in both phtB mutant and jazQ phyB mutant seedlings. Non-invasive, whole-plant chlorophyll fluorescence imaging (Attaran et al., Plant Physiol 165, 1302-1314 (2014)) was used to determine how genetic perturbations within the PHYB-GA-JA signaling network affect photosystem II efficiency ($\Phi_{II}$) under various light regimes, including those designed to simulate natural environments (see FIG. 4A).

Figure 4A:
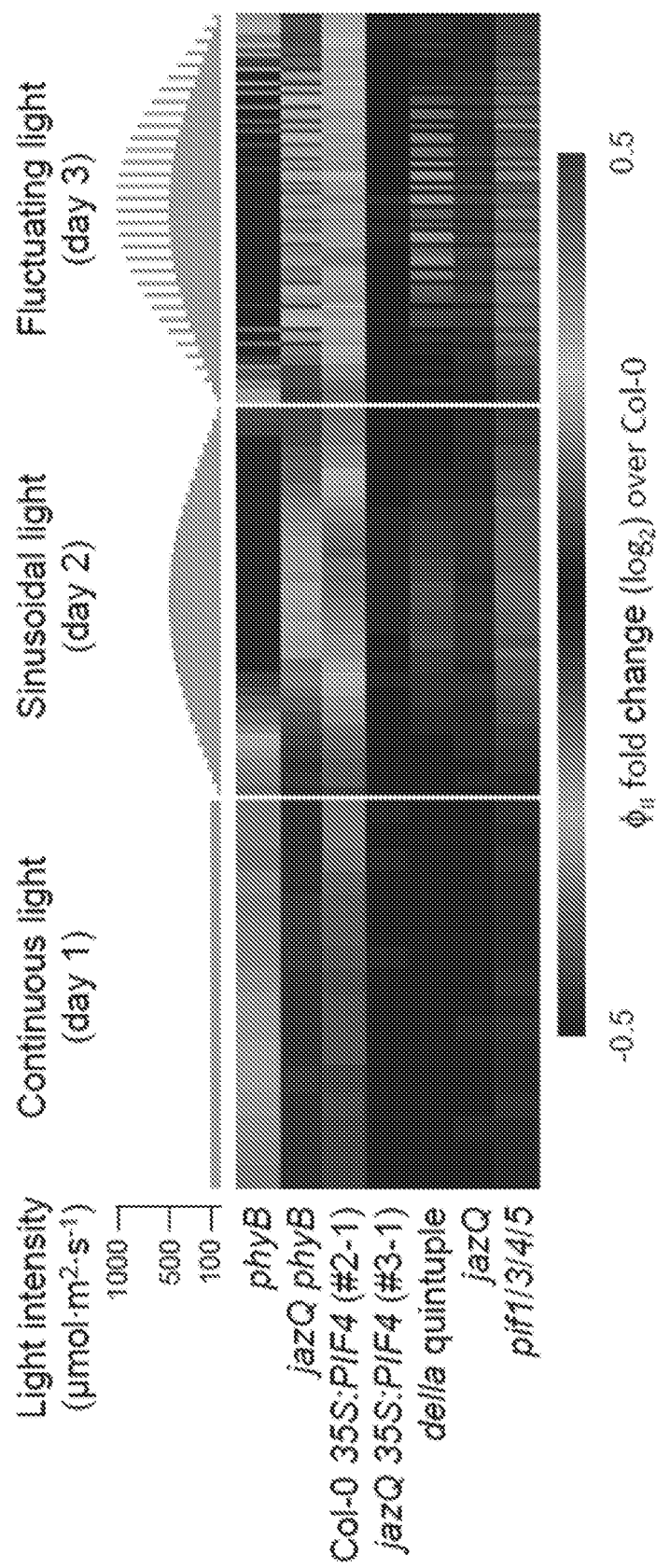
FIGS. 4A-4E illustrate that jazQ and phyB mutations interact to modulate photosynthesis and leaf architecture.

Mutant phyB plants had reduced $\Phi_{II}$ under continuous low light intensity and this effect was exacerbated under the sinusoidal and fluctuating light regimes. A similar decrease in $\Phi_{II}$ was observed in Col-0 transgenic plants (35S:PIF4) that overexpressed PIF4. Interestingly, the negative effect of phyB mutations and 35S:PIF4 on $\Phi_{II}$ was rescued by jazQ mutations, which alone had little (or very weak positive) effect on $\Phi_{II}$ (FIG. 4A). Consistent with the role of PIFs in repressing photosynthesis, a pif1/3/4/5 quadruple mutant (pifq) showed increased $\Phi_{II}$ under fluctuating light conditions, whereas loss of DELLAs in the della quintuple mutant (dellaQ) reduced $\Phi_{II}$. That $\Phi_{II}$ was lower in phyB leaves than in dellaQ leaves suggests that phyB has a predominate role in repressing PIF activity in leaves under these growth conditions.

To obtain additional insight into physiological processes that underlie growth-defense vigor of jazQ phyB mutant plants, the relationship between photosynthesis and leaf growth was investigated to obtain an estimate of leaf construction costs. Gas exchange experiments showed that phyB mutant eaves have significantly lower photosynthetic rate per unit leaf area whereas photosynthetic capacity of jazQ mutant plants relating to leaf area or dry weight basis was comparable to WT (FIG. 4B), consistent with our chlorophyll fluorescence measurements. Mutant phyB leaves also contained less area-based chlorophyll and Rubisco (D-ribulose-1,5-bisphosphate carboxylase/oxygenase) than WT.

Figure 4C:
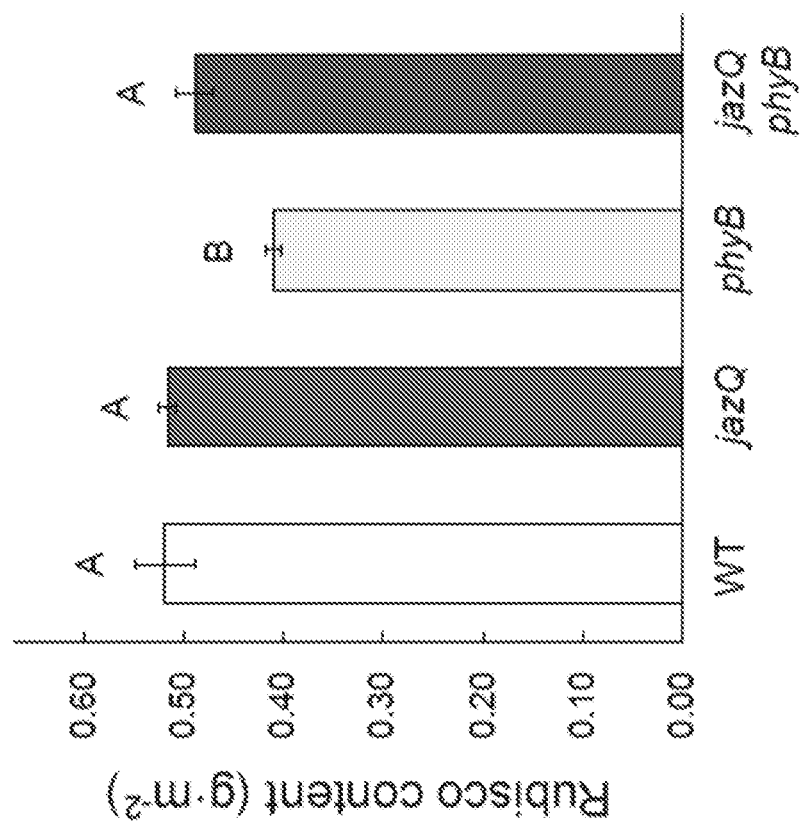
Figure 4B:
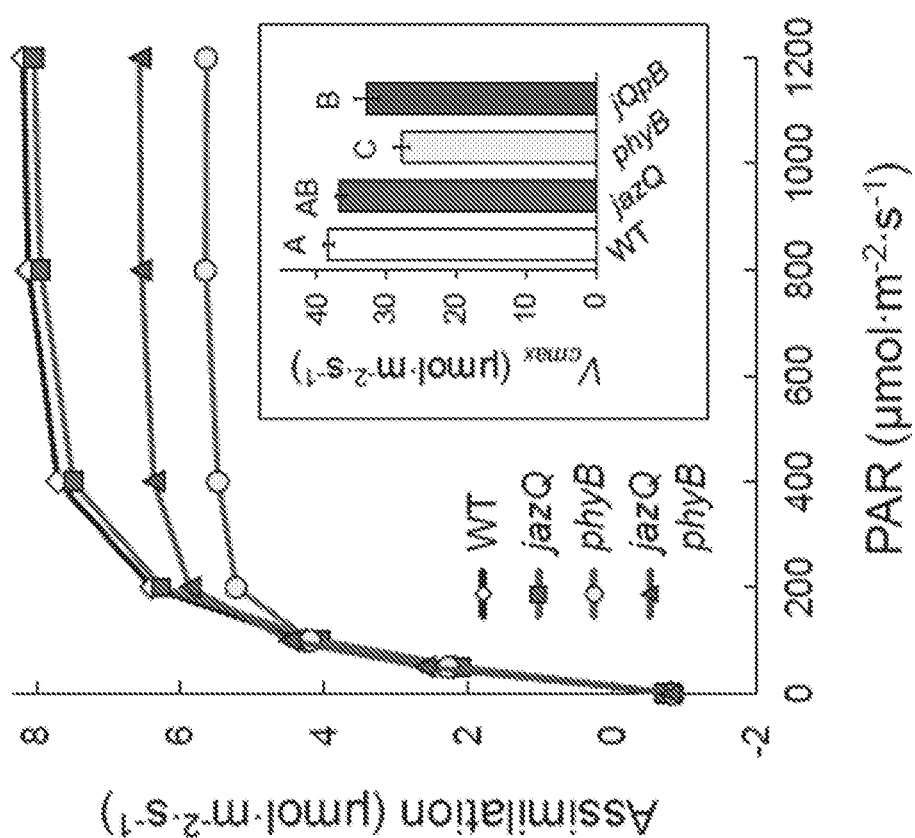
Figure 4E:
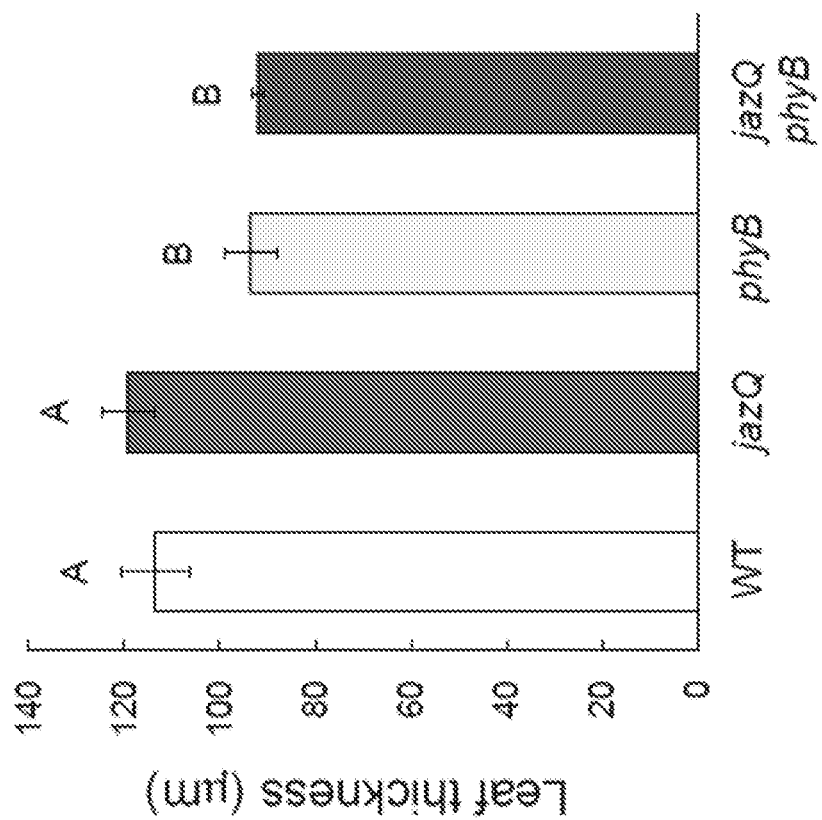
Figure 4D:
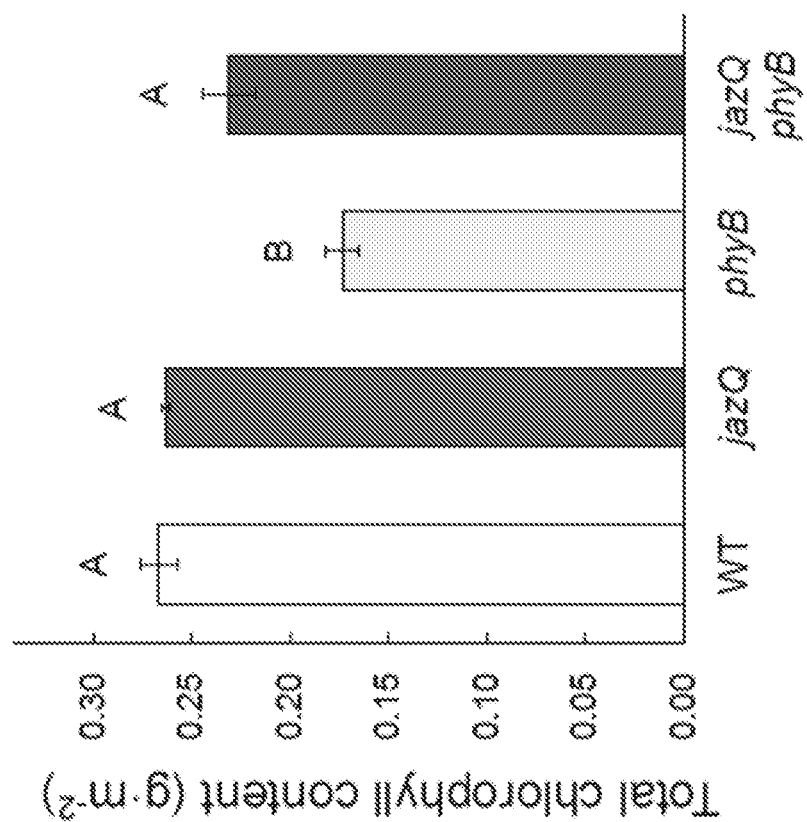
Figure 5D:
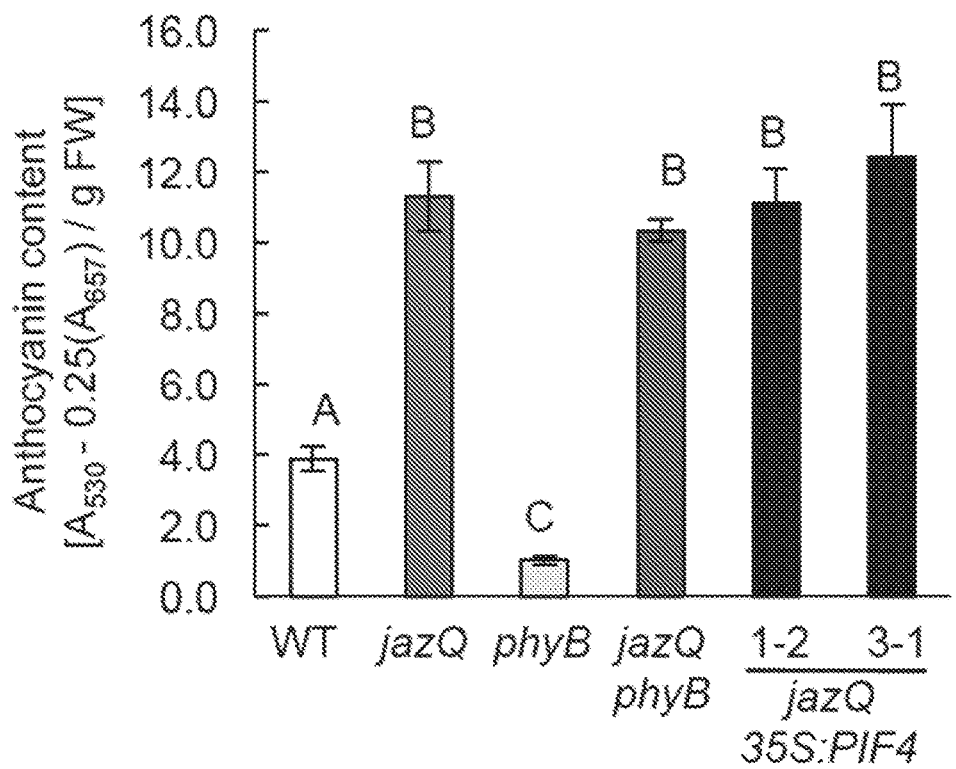
Figure 5E:
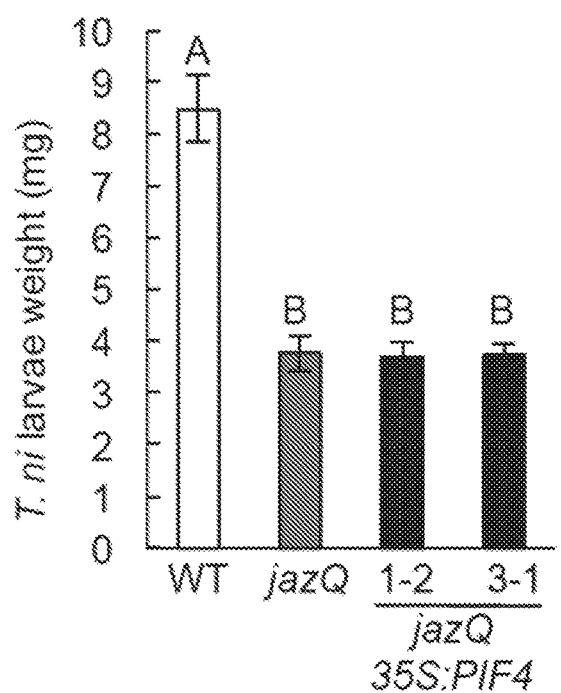

Modeling of photosynthetic parameters showed that the reduced photosynthetic capacity of mutant phyB at high light results in part from a limitation in Rubisco activity. Mutations in jazQ partially rescued the low photosynthetic capacity of phyB leaves, as well as the low area-based Rubisco and chlorophyll content of phyB mutations (FIG. 4C-4D). In addition, mutant phyB leaves were thinner than WT and mutant jazQ leaves; this trait was retained in jazQ phyB mutant plants (FIG. 4D).

Because of the greater projected leaf area available to intercept light (due to longer petioles and flatter, thinner leaves), the whole plant photosynthetic rate in jazQ phyB mutant plants was similar to WT. Thus, costs associated with jazQ phyB mutations one leaf structure may be lowered through increased partitioning of carbon to leaf area at the expense of leaf thickness. These data suggest that changes in leaf architecture rather than increased efficiency of the photosynthetic apparatus may contribute to the growth-defense vigor of jazQ phyB mutant plants relative to WT plants.

In summary, an unbiased genetic approach was employed to show that JA-mediated growth-defense antagonism can be effectively eliminated through genetic removal of JAZ and phyB repressors that respectively restrain the MYC and PIF transcription modules in WT plants. In highlighting a general role for transcriptional repressors in tuning photoassimilate use efficiency in mature plants, the results described herein provide new insight into how JA and light signaling pathways are integrated to control the balance between growth and immune responses. Note also that the expression of genes involved in abiotic stress response is repressed in jazQ phyB mutant plants.

The ability of jazQ phyB mutant leaves to grow and at the same time defend against insects and other threats indicates that JA signaling does not simply divert photoassimilates or other metabolic resources to defense processes at the expense of growth. The data described herein support a conclusion that the linkage between JA-triggered immunity and growth inhibition is more accurately viewed as a phenotypic consequence of interconnected transcriptional networks that evolved to optimize fitness in the face of episodic, unpredictable encounters with plant consumers and competitors.

Genetic removal of transcriptional repressors that coordinate growth and immune responses provides an approach to combine desirable traits in new ways, and increase the productivity of densely planted crops with less dependence on pesticides.

Example 7: Overexpression of PIF4 in the jazQ Background Leads to Partial Rescue of Growth without Compromising Defense The phyB-Jasmonic acid crosstalk led the inventors to test the hypothesis that the combination of jazQ and phyB mutations causes concomitant de-repression of the MYC and PIF transcriptional programs to drive growth and defense simultaneously (FIG. 1A). The inventors then tested what effect overexpression of PIF4 would have in the jazQ mutant background.

As shown in FIG. 5A-5E, overexpression of PIF4 partially rescued the small rosette size and short petiole length of jazQ mutations without affecting anthocyanin accumulation and resistance to $T.\ ni$ feeding. This finding indicates that increased PIF4-mediated growth does not attenuate the defense status of jazQ mutation on leaf structures. These findings also indicate that other PIFs may contribute to the growth vigor of jazQ phyB mutant plants.

Example 8: MYC3$^{L152A}$ and MYC3$^{E148A/M155A}$ Mutants

Figure 7A:
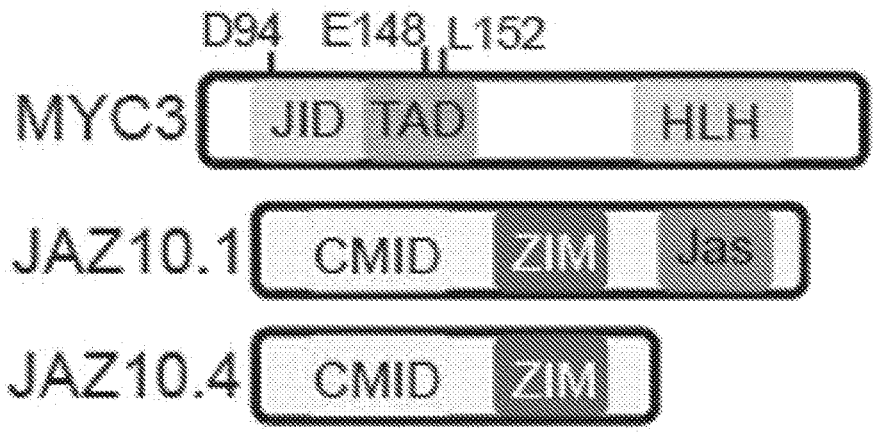
FIG. 7A-7E illustrate structure-based design of dominant MYC transcription factors.
Figure 7B:
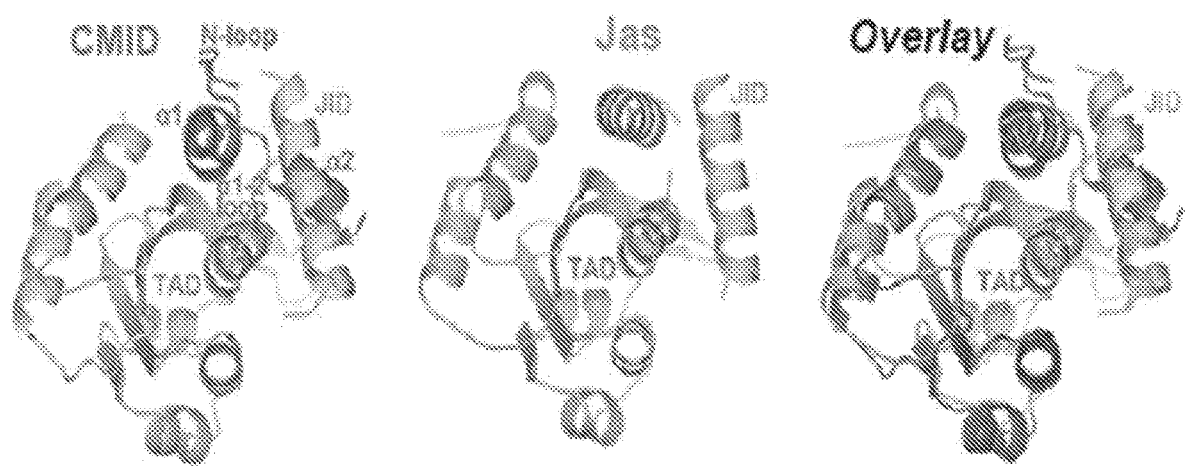

JAZ proteins contain two distinct structural motifs that bind to the JAZ-interacting domain (JID) of MYC (FIG. 7A-7B). All JAZ proteins contain a C-terminal Jas motif that, in the absence of jasmonic acid, forms an extended α-helix that binds JID (Zhang et al. 2015; Katsir et al. 2008; Melotto et al. 2008). A subset of JAZ proteins (e.g., JAZ10 and JAZ1) contain a cryptic MYC-interaction domain (CMID) near the N-terminus that also binds the JID (Moreno et al. 2013; Chung and Howe 2009; Goossens et al. 2015). Comparison of the x-ray crystal structures of the MYC3-JAZ10$^{CMID}$ and MYC3-JAZ10$^{Jas}$ complexes showed that whereas the Jas motif binds MYC as a single continuous α-helix, the CMID adopts a bipartite structure in which one helix occupies the Jas-binding groove of MYC and a second helix makes contact with the backside of this groove (FIG. 7B). This clamp-like action of the CMID engages MYCs with higher affinity than the Jas helix and also effectively masks the MED25 binding site of MYC (Zhang et al. 2017). Sequence alignments indicate that CMID-containing JAZs are present in diverse plant species but none have been characterized to date.

The inventors have used structural information for rational design of dominant MYC transcription factors (MYC$^D$ TFs) that are insensitive to binding by both the Jas and CMID of JAZ. The inventors hypothesize that such dominant mutant MYC proteins can strongly activate defense gene expression in the absence of JA elicitation. Three AtMYC$^D$ variants have been reported in the literature: MYC3$^{D94N}$ (atr2L) allele)(Smolen et al. 2002), the corresponding MYC2 mutant (MYC2$^{D105N}$)(Goossens et al. 2015), and MYC2$^{E165K}$ (myc2-322B) (Gasperini et al. 2015). These MYC variants exhibit weak constitutive JA responses as a consequence of losing interaction with the Jas motif of JAZ.

The inventors hypothesize that design of MYC$^D$ TFs that are insensitive to both Jas and CMID binding will result in much stronger activation of JA-dependent defenses, and that the combination of these myc$^D$ alleles with phyB will drive robust growth and defense simultaneously.

The structural information from the MYC3-CMID complex was used to generate site-directed mutants of MYC3 that have reduced interaction with the JAZ10.4 splice variant, which contains a CMID but not a Jas motif (Chung and Howe 2009). Several promising mutants were made.

Binding studies were performed to evaluate the mutant MYC proteins. AtMYC2 and its paralogs (MYC3, MYC4, and MYC5) within subclade IIIe of the bHLH superfamily bind to G-box motifs to promote the expression of a large portion of JA-responsive genes in cells containing elevated JA levels (Fernández-Calvo et al. 2011; Schweizer et al. 2013; Major et al. 2017). Low levels of JA stabilize JAZs to permit JAZ binding to the JAZ-interacting domain (JID) of MYCs. JAZ binding to the JID represses MYC activity by two distinct mechanisms.

First, JAZs use their EAR and ZIM motifs to recruit the TOPLESS (TPL) co-repressor and associated chromatin-modifying enzymes (Shyu et al. 2012; Pauwels et al. 2010). Second, JAZ binding to the JID competitively inhibits MYC interaction with the MED25 subunit of the Mediator of RNA polymerase II transcription complex, which promotes transcription by bridging DNA-bound transcription factors to RNA polymerase II (Zhang et al. 2015). Although the JID and adjacent transactivation domain (TAD) of MYC were initially mapped as discrete regions (Kazan & Manners 2013), recent structural analysis of JAZ9-MYC3 complexes revealed that the JID and TAD functionally overlap to form a continuous groove that binds both JAZ and the MED25 in a competitive manner (Zhang et al. 2015).

The interactions of mutants (MYC3$^{L152A}$ and MYC3$^{E148A/M155A}$) with JAZ10.4 and MED25 was evaluated using yeast two-hybrid analyses to visualize MED25 and JAZ10.4 (bait) interactions with wild-type MYC3 and MYC3 point mutants (prey).

Figure 7C:
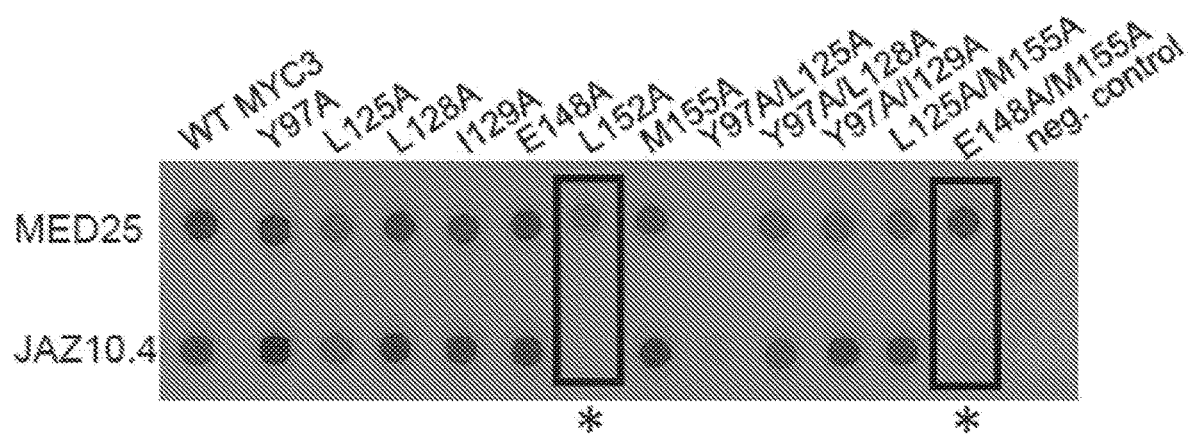

The MYC3$^{L152A}$ and MYC3$^{E148A/M155A}$ mutant protein exhibited strongly reduced JAZ10.4 interaction but still interacted with MED25 (FIG. 7C).

Functional analysis of these and other MYC$^D$ transcription factors in planta was performed by overexpressing the transcription factors in *Arabidopsis* with subsequent testing of the resulting transgenic lines for increased resistance to 5-methyl tryptophan (5-MT), a toxic analog of the amino acid tryptophan.

Figure 7D:
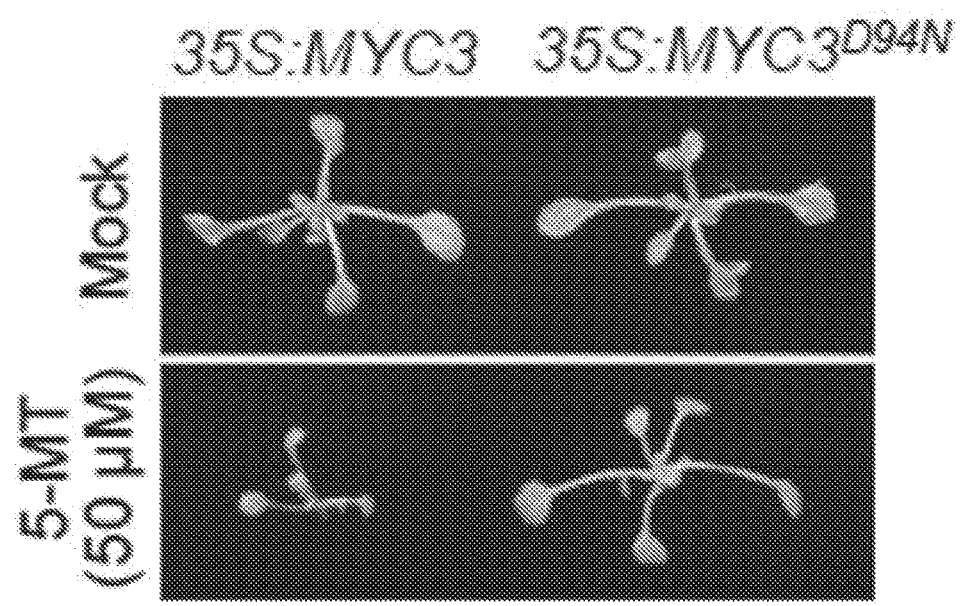

For example, a dominant allele (atr2D allele) encoding MYC3$^{D94N}$ was identified in a genetic screen for 5-MT-resistant plants (Smolen et al. 2002). Preliminary results show that overexpression from the 35S promoter of MYC3$^{D94N}$ but not wild-type MYC3 confers 5-MT resistance (FIG. 7D).

Similarly, overexpression in *Arabidopsis* of a tomato (*Solanum lycopersicum*) MYC2 protein with SEQ ID NO:19 that was modified to have a D132N mutation confers resistance of the genetically modified Arabidopsis plants to 5-MT (data not shown).

Example 9: Expression of Dominant Mutant Myc2 Reduces Primary Root Inhibition This Example illustrates that overexpression of a dominant MYC2 mutant transcription factor (with D105N+E165K mutations) in *Arabidopsis* reduces primary root inhibition in response to treatment with 5-methyltryptophan.

Methods

Primary root length in the presence of 15 µM 5-MT was evaluated for 14-day-old seedlings of non-transgenic (NT) phyB-9 mutant plants or phyB-9 mutant plants that overexpressed either wild-type (WT) MYC2 or a MYC2$^{D105N/E165K}$ mutant allele that harbors two point mutations (D105N and E165K) that prevent JAZ binding. Primary root length was determined as the root length of a given genotype grown in the presence of 15 µM 5-MT normalized to the root length of the same genotype grown in the absence of 5-MT.

Results

Figure 7E:
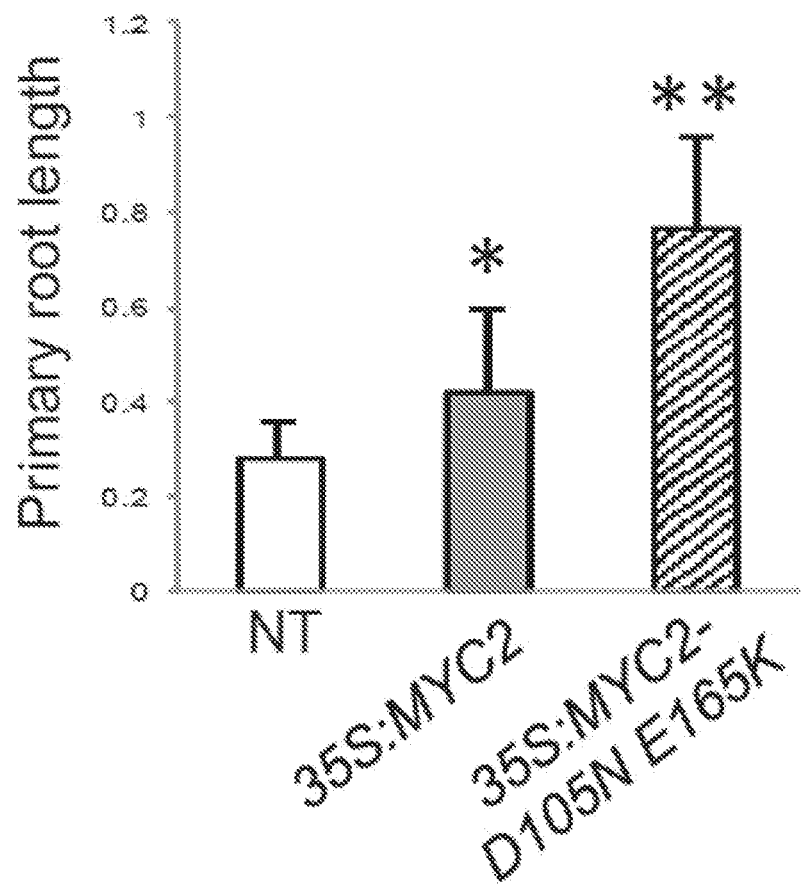

FIG. 7E graphically illustrates that the primary root length of 14-day-old seedlings of non-transgenic (NT)phyB-9 mutant plants (left bar) was less than observed for the phyB-9 mutant plants that overexpress either wild-type (WT) MYC2 (middle bar) or a MYC2 derivative (MYC2$^{D105N/E165K}$; right bar) harboring two point mutations (D105N and E165K) that prevent JAZ binding. Asterisks indicate significant differences in relative root length (*P=0.0017, **P=2E-08) in comparisons to phyB. Error bars represent SEM, n>20. Hence, expression of such dominant MYC transcription factors conferred resistance to 15 µM 5-MT and fostered growth of the plant as indicated by the significantly increased length of the plants' primary root.

These findings provide proof-of-concept that 5-MT resistance can be used to quantify MYC$^D$ activity in planta for rationale design of dominant MYC TFs.

In summary, the inventors have developed a structure-guided pipeline (that incorporates site-directed mutagenesis, yeast two-hybrid analysis of JAZ repressor and MED25 co-activator interaction, and functional analysis of 5-MT resistance in *Arabidopsis*) to design and characterize MYC$^D$ TFs, from any plant species. Plants engineered to express dominant MYC transcription factors in a phyB mutant background can exhibit enhanced growth and defense at the same time.

REFERENCES

1. Stamp, N. Out of the quagmire of plant defense hypotheses. *Q Rev Biol* 78, 23-55 (2003).
2. Zust. T., Rasmann, S. & Agrawal, A. A. Growth-defense tradeoffs for two major anti-herbivore traits of the common milkweed *Asclepias syriaca*. *Oikos* 124, 1404-1415 (2015).
3. Herms, D. A. & Mattson, W. J. The dilemma of plants—To grow or defend. *Q Rev Biol* 67, 283-335 (1992).
4. Huot, B., Yao, J., Montgomery, B. L. & He, S. Y. Growth-defense tradeoffs in plants; a balancing act to optimize fitness. *Mol Plant* 7, 1267-1287 (2014).
5. Moreno, J. E., Tao, Y., Chory, J. & Ballare, C. L. Ecological modulation of plant defense via phytochrome control of jasmonate sensitivity. *Proc Natl Acad Sci USA* 106, 4935-4940 (2009).
6. Havko, N. E. et al. Control of carbon assimilation and partitioning by jasmonate: An accounting of growth-defense balance. *Plants* 5, 7 (2016).
7. Kliebenstein, D. J. False idolatry of the mythical growth versus immunity tradeoff in molecular systems plant pathology. *Physiol Mol Plant Pathol*, in press, doi: 10.1016/j.pmpp.2016.02.004 (2016).
8. Hu, P. et al. JAV1 controls jasmonate-regulated plant defense. *Mol Cell* 50, 504-515 (2013).
9. Leone, M., Keller, M. M., Cerrudo, I. & Ballare, C. L. To grow or defend? Low red:far-red ratios reduce jasmonate sensitivity in *Arabidopsis* seedlings by promoting DELLA degradation and increasing JAZ10 stability. *New Phytol* 204, 355-367 (2014).
10. Thireault, C. et al. Repression of jasmonate signaling by a non-TIFY JAZ protein in *Arabidopsis*. *Plant J* 82, 669-679 (2015).
11. Thines, B. et al. JAZ repressor proteins are targets of the SCF$^{COI1}$ complex during jasmonate signalling. *Nature* 448, 661-665 (2007).
12. Chini. A. et al. The JAZ family of repressors is the missing link in jasmonate signalling. *Nature* 448, 666-671 (2007).
13. Yan, Y. et al. A downstream mediator in the growth repression limb of the jasmonate pathway. *Plant Cell* 19, 2470-2483 (2007).
14. Hou, X., Lee, L. Y., Xia, K., Yan. Y. & Yu, H. DELLAs modulate jasmonate signaling via competitive binding to JAZs. *Dev Cell* 19, 884-894 (2010).
15. Yang, D. L. et al. Plant hormone jasmonate prioritizes defense over growth by interfering with gibberellin signaling cascade. *Proc Natl Acad Sci USA* 109, 1192-1200 (2012).
16. Fernandez-Calvo, P. et al. The *Arabidopsis* bHLH Transcription Factors MYC3 and MYC4 are targets of JAZ repressors and act additively with MYC2 in the activation of jasmonate responses. *Plant Cell* 23, 701-715 (2011).
17. Schweizer, F. et al. *Arabidopsis* basic helix-loop-helix transcription factors MYC2, MYC3, and MYC4 regulate glucosinolate biosynthesis, insect performance, and feeding behavior. *Plant Cell* 25, 3117-3132 (2013).
18. Gasperini, D. et al. Multilayered organization of jasmonate signalling in the regulation of root growth. *PLoS Genet* 11, e1005300 (2015).
19. Qi. T. et al. The Jasmonate-ZIM-domain proteins interact with the WD-Repeat/bHLH/MYB complexes to regulate jasmonate-mediated anthocyanin accumulation and trichome initiation in *Arabidopsis thaliana*. *Plant Cell* 23, 1795-1814 (2011).
20. de Lucas, M. et al. A molecular framework for light and gibberellin control of cell elongation. *Nature* 451, 480-484 (2008).
21. Casal, J. J. Photoreceptor signaling networks in plant responses to shade. *Annu Rev Plant Biol* 64, 403-427 (2013).
22. Ballare, C. L. Light regulation of plant defense. *Annu Rev Plant Biol* 65, 335-363 (2014).
23. Oh, E., Zhu, J. Y. & Wang, Z. Y. Interaction between BZR1 and PIF4 integrates brassinosteroid and environmental responses. *Nat Cell Biol* 14, 802-809 (2012).
24. Chico, J. M. et al. Repression of jasmonate-dependent defenses by shade involves differential regulation of protein stability of MYC transcription factors and their JAZ repressors in *Arabidopsis*. *Plant Cell* 26, 1967-1980 (2014).

25 Hornitschek, P. et al. Phytochrome interacting factors 4 and 5 control seedling growth in changing light conditions by directly controlling auxin signaling. *Plant J* 171, 699-711 (2012).

26 Zhang, Y. et al. A quartet of PIF bHLH factors provides a transcriptionally centered signaling hub that regulates seedling morphogenesis through differential expression-patterning of shared target genes in *Arabidopsis*. *PLoS Genet* 9, e1003244 (2013).

27 Leivar, P. & Monte, E. PIFs: systems integrators in plant development. *Plant Cell* 26, 56-78 (2014).

28 Attaran, E. et al. Temporal dynamics of growth and photosynthesis suppression in response to jasmonate signaling. *Plant Physiol* 165, 1302-1314 (2014).

29 Boccalandro, H. E. et al. Phytochrome B enhances photosynthesis at the expense of water-use efficiency in *Arabidopsis*. *Plant Physiol* 150, 1083-1092 (2009).

30 Weraduwage, S. M. et al. The relationship between leaf area growth and biomass accumulation in *Arabidopsis thaliana*. *Front Plant Sci* 6, 167 (2015).

31 McElver, J. et al. Insertional mutagenesis of genes required for seed development in *Arabidopsis thaliana*. *Genetics* 159, 1751-1763 (2001).

32 Jiang, Y., Liang, G., Yang, S. & Yu, D. *Arabidopsis* WRKY57 functions as a node of convergence for jasmonic acid- and auxin-mediated signaling in jasmonic acid-induced leaf senescence. *Plant Cell* 26, 230-245 (2014).

33 Sehr, E. M. et al. Analysis of secondary growth in the *Arabidopsis* shoot reveals a positive role of jasmonate signalling in cambium formation. *Plant J* 63, 811-822 (2010).

34 Reed, J. W., Nagpal, P., Poole, D. S., Furuya. M. & Chory, J. Mutations in the gene for the red/far-red light receptor phytochrome B alter cell elongation and physiological responses throughout *Arabidopsis* development. *Plant Cell* 5, 147-157 (1993).

35 Feng, S. H. et al. Coordinated regulation of *Arabidopsis thaliana* development by light and gibberellins. *Nature* 451, 475-479 (2008).

36 Leivar, P. et al. Multiple phytochrome-interacting bHLH transcription factors repress premature seedling photomorphogenesis in darkness. *Curr Biol* 18, 1815-1823 (2008).

37 Chung, H. S. et al. Regulation and function of *Arabidopsis* JASMONATE ZIM-domain genes in response to wounding and herbivory *Plant Physiol* 146, 952-964 (2008).

38 Shyu, C. et al. JAZ8 lacks a canonical degron and has an EAR motif that mediates transcriptional repression of jasmonate responses in *Arabidopsis*. *Plant Cell* 24, 536-550 (2012).

39 Kang, J. H. et al. The flavonoid biosynthetic enzyme chalcone isomerase modulates terpenoid production in glandular trichomes of tomato. *Plant Physiol* 164 (2014).

40 Barth, C. & Jander, G. *Arabidopsis* myrosinases TGG1 and TGG2 have redundant function in glucosinolate breakdown and insect defense. *Plant J* 46, 549-562 (2006).

41 Herde, M., Koo, A. J. & Howe, G. A. Elicitation of jasmonate-mediated defense responses by mechanical wounding and insect herbivory. *Methods Mol Biol* 1011.51-61 (2013).

42 Wamasooriya, S. N. & Montgomery, B. L. Detection of spatial-specific phytochrome responses using targeted expression of biliverdin reductase in *Arabidopsis*. *Plant Physiol* 149, 424-433 (2009).

43 Li, B. & Dewey. C. N. RSEM: accurate transcript quantification from RNA-Seq data with or without a reference genome. *BMC Bioinformatics* 12, 323, (2011).

44 Anders, S. & Huber, W. Differential expression analysis for sequence count data. *Genome Biol* 11, R106 (2010).

45 Maere, S., Heymans, K. & Kuiper, M. BiNGO: a Cytoscape plugin to assess overrepresentation of Gene Ontology categories in biological networks. *Bioinformatics* 21, 3448-3449 (2005).

46 Ruijter. J. M. et al. Amplification efficiency: linking baseline and bias in the analysis of quantitative PCR data. *Nucleic Acids Res* 37, e45 (2009).

47 Lee, C. M. & Thomashow, M. F. Photoperiodic regulation of the C-repeat binding factor (CBF) cold acclimation pathway and freezing tolerance in *Arabidopsis thaliana*. *Proc Natl Acad Sci USA* 109, 15054-15059 (2012).

48 Clough, S. J. & Bent, A. F. Floral Dip: A simplified method for *Agrobacterium*-mediated transformation of *Arabidopsis thaliana*. *Plant J* 16, 735-743 (1998).

49 Li, Z. R., Gao, J. P., Benning, C. & Sharkey, T. D. Characterization of photosynthesis in *Arabidopsis* ER-to-plastid lipid trafficking mutants. *Photosynth Res* 112, 49-61 (2012).

50 Dutta, S. et al. Non-invasive, whole-plant imaging of chloroplast movement and chlorophyll fluorescence reveals photosynthetic phenotypes independent of chloroplast photorelocation defects in chloroplast division mutants. *Plant J* 84, 428-442 (2015).

51 Kramer, D., Cruz, J., Hall, C., Kovac, W. K. & Zegarac. R. Plant phenometrics systems and methods and devices related thereto. United States Patent WO 2013181433 A2 (2013).

52 Tessmer, O. L., Jiao, Y., Cruz, J. A., Kramer, D. M. & Chen, J. Functional approach to high-throughput plant growth analysis. *BMC Syst Biol* 7, (Suppl 6) S17 (2013).

53 Baker, N. R. Chlorophyll fluorescence: a probe of photosynthesis in vivo. *Annu Rev Plant Biol* 59, 89-113 (2008).

54 Lichtenthaler, H. K. & Wellbum. A. R. Determinations of total carotenoids and chlorophylls a and b of leaf extracts in different solvents. *Biochem Soc Trans* 11, 591-592 (1983).

55 Sonderby, I. E., Geu-Flores, F. & Halkier. B. A. Biosynthesis of glucosinolates-gene discovery and beyond. *Trends Plant Sci* 15, 283-290 (2010).

56. Zhang et al., Structural basis of JAZ repression of MYC transcription factors in jasmonate signalling, *Nature* 525: 269-273 (2015).

57. Katsir et al., COI1 is a critical component of a receptor for jasmonate and the bacterial virulence factor coronatine, *Proc. Natl. Acad. Sci. U.S.A.* 105(19): 7100-7105 (2008).

58. Melotto et al., A critical role of two positively charged amino acids in the Jas motif of *Arabidopsis* JAZ proteins in mediating coronatine- and jasmonoyl isoleucine-dependent interactions with the COI1 F-box protein, *The Plant journal: for cell and molecular biology* 55(6): 979-988 (2008).

59. Smolen et al., Dominant alleles of the basic helix-loop-helix transcription factor ATR2 activate stress-responsive genes in *Arabidopsis, Genetics* 161(3): 1235-1246 (2002).

60. Moreno et al., Negative feedback control of jasmonate signaling by an alternative splice variant of JAZ10, *Plant physiology* 162(2): 1006-1017 (2013).

61. Chung & Howe, A critical role for the TIFY motif in repression of jasmonate signaling by a stabilized splice variant of the JASMONATE ZIM-domain protein JAZ10 in *Arabidopsis*, The Plant Cell 21(1): 131-145 (2009).
62. Goossens et al., Change of a conserved amino acid in the MYC2 and MYC3 transcription factors leads to release of JAZ repression and increased activity, The New Phytologist 206(4): 1229-1237 (2015).
63. Zhang et al., Structural insights into alternative splicing-mediated desensitization of jasmonate signaling. *Proc. Natl. Acad. Sci. U.S.A.* 114(7): 1720-1725 (2017).
64. Major et al., Regulation of growth-defense balance by the JASMONATE ZIM-DOMAIN (JAZ)-MYC transcriptional module, The New Phytologist (2017).
65. Pauwels et al., NINJA connects the co-repressor TOPLESS to jasmonate signalling, Nature 464(7289): 788-791 (2010).
66. Kazan & Manners, MYC2: the master in action, Molecular Plant 6(3): 686-703 (2013).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A plant, plant cell, or plant seed comprising at least one mutant MYC protein with at least one mutation within or outside of a JAZ-interacting domain (JID) of the MYC protein, and a phyB loss-of-function mutation.
2. The plant, plant cell, or plant seed of statement 1, wherein the mutation within or outside of the JAZ-interacting domain (JID) reduces binding of the MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof.
3. The plant, plant cell, or plant seed of statement 1 or 2, wherein the mutation within or outside of the JAZ-interacting domain (JID) reduces binding of the MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein. JAZ10 protein. JAZ11 protein. JAZ12 protein, JAZ13 protein, or a combination thereof by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the MYC mutation(s)).
4. The plant, plant cell, or plant seed of statement 1, 2, or 3, wherein the JAZ-interacting domain (JID) has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.
5. The plant, plant cell, or plant seed of statement 1-3 or 4, wherein the mutant MYC protein has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 1, 13, 15, 17, 19, 21, 23, 25, or 27.
6. The plant, plant cell, or plant seed of statement 1-4 or 5, wherein the mutant MYC protein has at least 40%, or at least 50%, or at least 60%, or at least 70%, or at least 80%, or at least 90%, or at least 95%, or at least 97%, or at least 99% sequence identity to any of SEQ ID NOs: 1, 3, 5, 7, 9, 11, 13, 15, 17, 19, 21, 23, 25, or 27.
7. The plant, plant cell, or plant seed of statement 1-5 or 6, wherein the mutant MYC protein is expressed from a dominant MYC genomic allele, from an expression cassette encoding the mutant MYC protein, or from an expression cassette encoding a dominant mutant MYC protein.
8. The plant, plant cell, or plant seed of statement 1-6 or 7, comprising a heterologous MYC transgene or MYC expression cassette that encodes the mutant MYC protein.
9. The plant, plant cell, or plant seed of statement 1-7 or 8, comprising a heterologous MYC transgene comprising a promoter operably linked to a nucleic acid segment encoding the mutant MYC protein.
10. The plant, plant cell, or plant seed of statement 1-8 or 9, comprising a heterologous MYC transgene comprising a promoter operably linked to a cDNA encoding the mutant MYC protein.
11. The plant, plant cell, or plant seed of statement 1-9 or 10, wherein the plant, plant cell, or plant seed (or plant grown from the plant seed) has reduced PHYB activity compared to a wild type plant without the phyB loss-of-function mutation.
12. The plant, plant cell, or plant seed of statement 1-10 or 11, wherein the plant, plant cell, or plant seed expresses a PHYB protein with less than 99%, or less than 98%, or less than 95%, or less than 90%, or less than 85%, or less than 75% or less than 60%, or less than 50%, or less than 40%, or less than 30%, or less than 20% sequence identity to any of SEQ ID NOs:30, 32, 33, 34, 35, 36, or 37.
13. The plant, plant cell, or plant seed of statement 1-11 or 12, wherein the plant, plant cell, or plant seed comprises a deletion in a chromosomal PhyB or PhyB-related chromosomal site, a substitution within a chromosomal PhyB or PhyB-related chromosomal site, or an insertion into a chromosomal PhyB or PhyB-related chromosomal site.
14. The plant, plant cell, or plant seed of statement 1-12 or 13, wherein the plant, plant cell, or plant seed comprises a deletion, substitution, or insertion of a chromosomal PhyB or PhyB-related chromosomal site so that a truncated PHYB polypeptide, a mutant PHYB polypeptide, or no PHYB polypeptide is expressed.
15. The plant, plant cell, or plant seed of statement 1-13 or 14, comprising at least one loss-of-function mutation(s) in at least four or five genes encoding transcriptional repressors of jasmonic acid (JAZ) responses.
16. The plant, plant cell, or plant seed of statement 1-14 or 15, comprising at least one loss-of-function mutation(s) in at least four or five genes encoding transcriptional repressors of jasmonic acid (JAZ) responses that comprise one or more deletions, substitutions, or insertions into at least four or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

17. The plant, plant cell, or plant seed of statement 1-15 or 16, wherein the plant or a plant grown from the seed has less leaf damage from insect feeding than a wild type plant of the same species (but without phyB, phyB-related, or MYC gene mutations) grown under the same environmental conditions.

18. The plant, plant cell, or plant seed of statement 1-16 or 17, wherein the plant or a plant grown from the seed has 5% less, or 10% less, or 20% less, or 30% less, or 40% less, or 50% less, or 60% less, or 70% less, or 80% less, or 90% less, or 100% less leaf damage from insect feeding than a wild type plant of the same species (but without PHYB, PHYB-related, or MYC gene mutations) grown under the same environmental conditions.

19. The plant, plant cell, or plant seed of statement 1-17 or 18, further comprising a heterologous PIF4 transgene or PIF4 expression cassette.

20. The plant, plant cell, or plant seed of statement 1-18 or 19, further comprising a heterologous PIF4 transgene comprising a promoter operably linked to a nucleic acid segment encoding a PIF4 polypeptide.

21. The plant, plant cell, or plant seed of statement 1-19 or 20, further comprising a heterologous PIF4 transgene encoding a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42, or 44.

22. The plant, plant cell, or plant seed of statement 1-20 or 21, further comprising a heterologous PIF4 transgene comprising a promoter operably linked to a cDNA encoding a PIF4 polypeptide.

23. The plant, plant cell, or plant seed of statement 1-21 or 22, further comprising a heterologous PIF4 transgene comprising a promoter operably linked to a cDNA encoding a PIF4 polypeptide, where the promoter functions (e.g., promotes transcription) during plant development or growth.

24. The plant, plant cell, or plant seed of statement 1-22 or 23, wherein the plant or a plant grown from the seed exhibits resistance to environmental stress compared to a wild type plant of the same species under the same environmental conditions.

25. The plant, plant cell, or plant seed of statement 1-23 or 24, wherein the plant or a plant grown from the seed has at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same environmental conditions.

26. The plant, plant cell, or plant seed of statement 1-24 or 25, wherein rosette weight of the plant or a plant grown from the seed is about 80% to about 120%, or about 90% to about 110% of the rosette dry weight of wild type plants grown for the same time and under the same conditions.

27. The plant, plant cell, or plant seed of statement 1-25 or 26, which is a food crop species (e.g., sugar beets, beets, tomatoes, lettuce, spinach, carrots, peppers, peas, broccoli, beans, asparagus), a legume species (e.g., peas, beans, lentils, peanuts), a fiber-containing plant species, a tree species, flax, a grain species (e.g., maize, wheat, barley, oats, rice, sorghum, millet, and rye), a grass species (e.g., switchgrass, prairie grass, wheat grass, sudangrass, sorghum, straw-producing plants), a woody plant species (e.g., a poplar species, pine species, or eucalyptus species), a softwood, a hardwood, an oil and/or starch producing plant species (e.g., canola, potatoes, lupins, sunflower and cottonseed), a forage plant species (e.g., alfalfa, clover, or fescue).

28. A method comprising cultivating the plant or plant seed of statement 1-26 or 27.

29. The method of statement 28, wherein the plant or plant grown from the plant seed has less insect damage than a plant or plant grown from a seed without the mutation(s) but cultivated under similar growing conditions.

30. The method of statements 28 or 29, wherein the plant or plant grown from the plant seed has less insect larval and/or adult insect feeding than a plant or plant grown from a seed without the mutation(s) but cultivated under similar growing conditions.

31. The method of statement 28, 29, or 30, further comprising harvesting the plant or harvesting seeds, grain, fruit, vegetables, or biomass of the plant.

32. A method comprising (a) introducing into one or more plant cell at least one chromosomal loss-of-function mutation in a PHYB or PHYB-related gene and introducing at least one mutation into an endogenous MYC gene; and (b) generating a plant from the one or more plant cell(s).

33. The method of statement 32, wherein the mutation in the MYC gene is within or outside of a MYC JAZ-interacting domain (JID) encoded by the MYC gene.

34. The method of statement 32 or 33, wherein the mutation in the MYC gene is a dominant mutation.

35. The method of statement 32, 33, or 34, wherein the mutation in the MYC gene reduces binding of an encoded MYC protein to a JAZ protein selected from a JAZ1 protein. JAZ2 protein, JAZ3 protein, JAZ4 protein, JAZ5 protein, JAZ6 protein, JAZ7 protein, JAZ8 protein, JAZ9 protein. JAZ10 protein, JAZ11 protein, JAZ12 protein, JAZ13 protein, or a combination thereof.

36. The method of statement 32-34 or 35, wherein the mutation in the MYC gene reduces binding of an encoded MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein. JAZ10 protein. JAZ11 protein, JAZ12 protein, JAZ13 protein, or a combination thereof by at least 20%, or at least 30%, or at least 40%, or at least 50%, or at least 60%, or at least 70%, or at least 80%, or at least 90%, or at least 95%, or at least 97%, or at least 99% compared to a wild type plant of the same species (that does not have the MYC mutation(s)).

37. The method of statement 32-35 or 36, wherein the MYC gene encodes a JAZ-interacting domain (JID) that has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.

38. The method of statement 32-36 or 37, wherein the MYC gene encodes a MYC protein less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 11, 13, 15, 17, 19, 21, 23, 25, or 27.

39. The method of statement 32-37 or 38, wherein the MYC protein has at least 40%, or at least 50%, or at least 60%, or at least 70%, or at least 80%, or at least 90%, or at least 95%, or at least 97%, or at least 99% sequence identity to any of SEQ ID NOs: 1, 3, 5, 7, 9, 11, 13, 15, 17, 19, 21, 23, 25, or 27.

40. The method of statement 32-38 or 39, wherein the plant has reduced PHYB activity compared to a wild type plant without the PhyB loss-of-function mutation.

41. The method of statement 32-39 or 40, wherein the plant expresses a PHYB protein with less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37.

42. The method of statement 32-40 or 41, wherein the plant comprises a deletion of a chromosomal PhyB or PhyB-related chromosomal site, a substitution within a chromosomal PhyB or PhyB-related chromosomal site, or an insertion into a chromosomal PhyB or PhyB-related chromosomal site.

43. The method of statement 32-41 or 42, wherein the plant comprises a deletion, substitution, or insertion of a chromosomal PhyB or PhyB-related chromosomal site so that a truncated PHYB polypeptide, a mutant PHYB polypeptide, or no PHYB polypeptide is expressed.

44. The method of statement 32-42 or 43, wherein the plant cell comprises at least one loss-of-function mutation(s) in at least four or five genes encoding transcriptional repressors of jasmonic acid (JAZ) responses.

45. The method of statement 32-43 or 44, further comprising introducing into one or more plant cell at least one chromosomal loss-of-function mutation in at least four or five genes encoding transcriptional repressors of jasmonic acid (JAZ) responses.

46. The method of statement 32-44 or 45, wherein the plant comprises one or more deletions, substitutions, or insertions into at least four or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

47. The method of statement 32-45 or 46, wherein the plant exhibits resistance to environmental stress compared to a wild type plant of the same species under the same environmental conditions.

48. The method of statement 32-46 or 47, further comprising obtaining seeds from the plant.

49. The method of statement 32-47 or 48, further comprising harvesting the plant or harvesting grain, fruit, vegetables, or biomass of the plant.

50. A method comprising (a) introducing into one or more plant cell at least one transgene or expression cassette encoding a mutant MYC nucleic acid segment that encodes a mutant MYC protein; and (b) generating a plant from the one or more plant cell(s).

51. The method of statement 50, wherein the mutant MYC nucleic acid segment has at least one mutation within or outside of an encoded MYC JAZ-interacting domain (JID).

52. The method of statement 50 or 51, wherein the mutant MYC nucleic acid has a dominant mutation.

53. The method of statement 50, 51 or 52, wherein the mutant MYC protein has reduced binding to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof.

54. The method of statement 50-52 or 53, wherein the mutant MYC protein has binding to a JAZ protein selected from a JAZ1 protein, JAZ2 protein, JAZ3 protein, JAZ4 protein, JAZ5 protein, JAZ6 protein. JAZ7 protein, JAZ8 protein, JAZ9 protein, JAZ10 protein, JAZ11 protein, JAZ12 protein, JAZ13 protein, or a combination thereof that is reduced by at least 20%, or at least 30%, or at least 40%, or at least 50%, or at least 60%, or at least 70%, or at least 80%, or at least 90%, or at least 95%, or at least 97%, or at least 99% compared to a wild type plant of the same species (that does not have the MYC mutation(s)).

55. The method of statement 50-53 or 54, wherein the mutant MYC protein has a JAZ-interacting domain (JID) that has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.

56. The method of statement 50-54 or 55, wherein the mutant MYC protein has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 11, 13, 15, 17, 19, 21, 23, 25, or 27.

57. The method of statement 50-55 or 56, wherein the mutant MYC protein has at least 40%, or at least 50%, or at least 60%, or at least 70%, or at least 80%, or at least 90%, or at least 95%, or at least 97%, or at least 99% sequence identity to any of SEQ ID NOs:1, 3, 5, 7, 9, 11, 13, 15, 17, 19, 21, 23, 25, or 27.

58. The method of statement 50-56 or 57, wherein the plant has reduced PHYB activity compared to a wild type plant without the PhyB loss-of-function mutation.

59. The method of statement 50-57 or 58, wherein the plant expresses a PHYB protein with less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37.

60. The method of statement 50-58 or 59, wherein the plant comprises a deletion of a chromosomal PhyB or PhyB-related chromosomal site, a substitution within a chromosomal PhyB or PhyB-related chromosomal site, or an insertion into a chromosomal PhyB or PhyB-related chromosomal site.

61. The method of statement 50-59 or 60, wherein the plant comprises a deletion, substitution, or insertion of a chromosomal PhyB or PhyB-related chromosomal site so that a truncated PHYB polypeptide, a mutant PHYB polypeptide, or no PHYB polypeptide is expressed.

62. The method of statement 50-60 or 61, wherein the plant cell comprises at least one loss-of-function mutation(s) in at least four or five genes encoding transcriptional repressors of jasmonic acid (JAZ) responses.

63. The method of statement 50-61 or 62, further comprising introducing into one or more plant cell at least one chromosomal loss-of-function mutation in one to five genes encoding transcriptional repressors of jasmonic acid (JAZ) responses.

64. The method of statement 50-62 or 63, wherein the plant comprises one or more deletions, substitutions, or insertions into one or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

65. The method of statement 50-63 or 64, wherein the plant exhibits resistance to environmental stress compared to a wild type plant of the same species under the same environmental conditions.

66. The method of statement 50-64 or 65, further comprising obtaining seeds from the plant.

67. The method of statement 50-65 or 67, further comprising harvesting the plant or harvesting grain, fruit, vegetables, or biomass of the plant.

68. A plant, plant cell, or plant seed comprising at least one chromosomal loss-of-function mutation in a PHYB or PHYB-related gene and a loss-of-function mutation in at least one gene encoding a transcriptional repressor of jasmonic acid responses.

69. The plant, plant cell, or plant seed of statement 68, comprising at least one chromosomal loss-of-function mutation in a PHYB or PHYB-related gene and a loss-of-function mutation in at least two or at least three genes encoding transcriptional repressors of jasmonic acid responses.

70. The plant, plant cell, or plant seed of statement 68 or 69, comprising at least one loss-of-function mutation(s) in at least four or five genes encoding transcriptional repressors of jasmonic acid responses.

71. The plant, plant cell, or plant seed of statement 68, 69 or 70, wherein the loss-of-function mutation(s) comprise one or more deletions, substitutions, or insertions into at least four or five genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

72. The plant, plant cell, or plant seed of statement 68-70 or 71, wherein the loss-of-function mutation(s) comprise one or more insertions into at least four or five genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

73. The plant, plant cell, or plant seed of statement 68-71 or 72, wherein the loss-of-function mutation(s) comprise one or more deletions in genomic nucleic acids encoding transcriptional repressors of jasmonic acid response (JAZ) proteins with at least at least 700% or at least 750% or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

74. The plant, plant cell, or plant seed of statement 68-72 or 74, wherein the loss-of-function mutation(s) comprise one or more nucleotide substitutions in genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of SEQ ID NO:48, 50, 52, 54, 56, 58-73, or 74.

75. The plant, plant cell, or plant seed of statement 68-73 or 74, wherein the loss-of-function mutation(s)s reduce transcription of genomic nucleic acids encoding transcriptional repressors of jasmonic acid response (JAZ) proteins by at least 70%, or at least 75%, or at least 80%, or at least 85%, or at least 90%, or at least 95%, or at least 97%, or at least 98%, or at least 99% compared to a wild type plant of the same species (without the loss-of-function mutations) grown under the same conditions.

76. The plant, plant cell, or plant seed of statement 68-74 or 75, wherein the chromosomal loss-of-function mutation(s) comprise one or more deletions, substitutions, or insertions into one or more genomic nucleic acid that encodes a PHYB protein or a PHYB-related protein with at least at least 70%, or at least 75%, or at least 80%, or at least 85%, or at least 90%, or at least 95%, or at least 97%, or at least 98%, or at least 99% sequence identity to any of SEQ ID NOs: 30, 32, 33, 34, 35, 36, or 37.

77. The plant, plant cell, or plant seed of statement 68-75 or 76, wherein the loss-of-function mutations reduce transcription and/or translation of at least three genes encoding transcriptional repressors of jasmonic acid responses by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have mutations in genes encoding transcriptional repressors of jasmonic acid response).

78. The plant, plant cell, or plant seed of statement 68-76 or 77, wherein the loss-of-function mutations reduce transcription and/or translation of the phyB gene, or of the phyB-related gene by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have phyB, phyB-related, or transcriptional repressors of jasmonic acid response gene mutations).

79. The plant, plant cell, or plant seed of statement 68-77 or 78, wherein the plant or a plant grown from the seed has less leaf damage from insect feeding than a wild type plant of the same species (but without phyB, phyB-related, or transcriptional repressors of jasmonic acid response gene mutations) grown under the same conditions.

80. The plant, plant cell, or plant seed of statement 68-78 or 79, wherein the plant or a plant grown from the seed has 5% less, or 10% less, or 20% less, or 30% less, or 40% less, or 50% less, or 60% less, or 70% less, or 80% less, or 90% less, or 100% less leaf damage from insect feeding than a wild type plant of the same species (but without PHYB, PHYB-related, or transcriptional repressors of jasmonic acid response gene mutations) grown under the same conditions.

81. The plant, plant cell, or plant seed of statement 68-79 or 80, wherein the plant or a plant grown from the seed has at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same conditions.

82. The plant, plant cell, or plant seed of statement 68-80 or 81, wherein rosette weight of the plant or a plant grown from the seed is about 80% to about 120%, or about 90% to about 110% of the rosette dry weight of wild type plants grown for the same time and under the same conditions.

83. The plant, plant cell, or plant seed of statement 68-81 or 82, further comprising a heterologous PIF4 transgene or PIF4 expression cassette.

84. The plant, plant cell, or plant seed of statement 68-82 or 83, further comprising a heterologous PIF4 transgene comprising a promoter operably linked to a nucleic acid segment encoding a PIF4 polypeptide.

85. The plant, plant cell, or plant seed of statement 68-83 or 84, further comprising a heterologous PIF4 transgene encoding a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42 or 44.

86. The plant, plant cell, or plant seed of statement 68-84 or 85, further comprising a heterologous PIF4 transgene comprising a promoter operably linked to a cDNA encoding a PIF4 polypeptide.

87. The plant, plant cell, or plant seed of statement 68-85 or 86, further comprising a heterologous PIF4 transgene comprising a promoter operably linked to a cDNA encoding a PIF4 polypeptide, where the promoter functions (e.g., promotes transcription) during plant development or growth.

88. A method comprising cultivating the plant or plant seed of statement 50-86 or 87.

89. The method of statement 88, wherein less insecticide is needed or less insecticide is applied to a plant or plant grown from the seed than would be applied to a plant or plant grown from a seed without the mutation(s) but cultivated under similar growing conditions.

90. The method of statement 88 or 89, wherein the plant or plant grown from the plant seed has less insect damage than a plant or plant grown from a seed without the mutation(s) but cultivated under similar growing conditions.

91. The method of statement 88, 89, or 90, wherein the plant or plant grown from the plant seed has less insect larval and/or adult insect feeding than a plant or plant grown from a seed without the mutation(s) but cultivated under similar growing conditions.

92. A method comprising (a) introducing at least one chromosomal loss-of-function mutation in a PHYB or PHYB-related gene and introducing at least one loss-of-function mutation in at least one gene encoding a transcriptional repressor of jasmonic acid responses into one or more plant cells; and (b) generating a plant from the one or more plant cells.

93. A method comprising (a) introducing at least one chromosomal loss-of-function mutation in a PHYB or PHYB-related gene and introducing at least one loss-of-function mutation in at least three genes encoding transcriptional repressors of jasmonic acid responses into one or more plant cells; and (b) generating a plant from the one or more plant cells.

94. The method of statement 92 or 93, further comprising introducing a heterologous PIF4 transgene comprising a promoter operably linked to a cDNA encoding a PIF4 polypeptide into the one or more plant cells.

95. The method of statement 92, 93 or 94, further comprising introducing at least one mutation in at least one JAZ interacting domain (JID) of a MYC protein encoded by a MYC gene into the one or more plant cells.

96. The method of statement 92-94 or 95, further comprising obtaining seeds from the plant.

97. The method of statement 28-67, 88-95 or 96, wherein the plant has a primary root that 1.5-fold longer, of 2-fold longer, or 2.3-fold longer, or 2.5-fold longer, or 2.7-fold longer, or 3-fold longer than the average primary root length of wild type plants grown for the same time and under the same conditions.

98. The method of statement 97, wherein the conditions are environmental stress conditions.

99. The method of statement 97 or 98, wherein the conditions comprise growth in the presence of 5-methyl-tryptophan.

100. The plant, plant cell, or plant seed of statement 1-26, 68-86, or 87, wherein the plant has a primary root that 1.5-fold longer, of 2-fold longer, or 2.3-fold longer, or 2.5-fold longer, or 2.7-fold longer, or 3-fold longer than the average primary root length of wild type plants grown for the same time and under the same conditions.

101. The plant, plant cell, or plant seed of statement 100, wherein the conditions are environmental stress conditions.

102. The plant, plant cell, or plant seed of statement 100 or 101, wherein the conditions comprise growth in the presence of 5-methyl-tryptophan.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a." "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A genetically modified and non-naturally occurring mutant plant cell, a mutant plant, or a mutant plant seed obtained thereof, comprising:
   (a) a PhyB loss-of-function mutation comprising at least one mutation to an amino acid in the amino acid sequence as set forth in SEQ ID NO: 30; and
   (b) a modified MYC nucleic acid encoding a mutant MYC protein comprising at least one mutation within a JAZ-interacting domain (JID) region of the mutant MYC protein that reduces or eliminates interaction of the mutant MYC protein with JAZ proteins, wherein the JAZ interacting domain (JID) has less than 100% and more than 95% amino acid sequence identity to the amino acid sequence as set forth in SEQ ID NO:2, and wherein said mutant MYC protein has less than 100% amino acid sequence identity and at least 95% amino acid sequence identity to the amino acid sequence as set forth in SEQ ID NO: 1,
   and wherein the genetically modified and non-naturally occurring mutant plant cell, said mutant plant, or said mutant plant seed obtained thereof is transgenic mutant, and wherein expression or lack of expression of said PhyB loss-of-function mutant protein, and expression of said MYC mutant protein recues wild-type plant biomass and concurrently provides JA (jasmonic acid)-controlled defense in said genetically modified and non-naturally occurring mutant plant cell, said mutant plant, or said mutant plant seed obtained thereof as compared to a control plant of the same species that is grown under identical conditions.

2. The genetically modified and non-naturally occurring mutant plant cell, said mutant plant, or said mutant plant seed obtained thereof, of claim 1, wherein the PhyB loss-of-function mutation comprises a deletion, substitution, or insertion of a chromosomal PhyB site so that a truncated PHYB polypeptide, a mutant PHYB polypeptide, or no PHYB polypeptide is expressed.

3. The genetically modified and non-naturally occurring mutant plant cell, said mutant plant, or said mutant plant seed obtained thereof, of claim 1, wherein the mutant MYC protein has at least one mutation in the amino acid sequence as set forth in SEQ ID NO: 1, and within the JAZ-interacting domain (JID) protein region as set forth in SEQ ID NO: 2.

4. The genetically modified and non-naturally occurring mutant plant cell, said mutant plant, or said mutant plant seed obtained thereof, of claim 1, wherein the mutant MYC protein has reduced binding to a JAZ1 protein, and wherein the binding is reduced by at least 20% as compared to a corresponding wild type MYC protein that does not have the MYC mutation.

5. The genetically modified and non-naturally occurring mutant plant cell, said mutant plant, or said mutant plant seed obtained thereof, of claim 1, comprising one or more mutations in one or five wild-type genomic JAZ nucleic acids that encode JAZ proteins with at least 95% amino acid sequence identity to the amino acid sequence amino acid sequence as set forth in SEQ ID NO: 48.

6. The genetically modified and non-naturally occurring mutant plant cell, said mutant plant, or said mutant plant seed obtained thereof, of claim 1, comprising a loss-of-function chromosomal mutation in an endogenous jaz1 gene.

* * * * *

SEQUENCE LISTING

<160> NUMBER OF SEQ ID NOS: 129

<210> SEQ ID NO 1
<211> LENGTH: 623
<212> TYPE: PRT
<213> ORGANISM: Arabidopsis thaliana

<400> SEQUENCE: 1

```
Met Thr Asp Tyr Arg Leu Gln Pro Thr Met Asn Leu Trp Thr Thr Asp
1               5                   10                  15

Asp Asn Ala Ser Met Met Glu Ala Phe Met Ser Ser Ser Asp Ile Ser
            20                  25                  30

Thr Leu Trp Pro Pro Ala Ser Thr Thr Thr Thr Ala Thr Thr Glu
        35                  40                  45

Thr Thr Pro Thr Pro Ala Met Glu Ile Pro Ala Gln Ala Gly Phe Asn
    50                  55                  60

Gln Glu Thr Leu Gln Gln Arg Leu Gln Ala Leu Ile Glu Gly Thr His
65                  70                  75                  80

Glu Gly Trp Thr Tyr Ala Ile Phe Trp Gln Pro Ser Tyr Asp Phe Ser
                85                  90                  95

Gly Ala Ser Val Leu Gly Trp Gly Asp Gly Tyr Tyr Lys Gly Glu Glu
            100                 105                 110

Asp Lys Ala Asn Pro Arg Arg Arg Ser Ser Ser Pro Pro Phe Ser Thr
        115                 120                 125

Pro Ala Asp Gln Glu Tyr Arg Lys Lys Val Leu Arg Glu Leu Asn Ser
    130                 135                 140

Leu Ile Ser Gly Gly Val Ala Pro Ser Asp Asp Ala Val Asp Glu Glu
145                 150                 155                 160

Val Thr Asp Thr Glu Trp Phe Phe Leu Val Ser Met Thr Gln Ser Phe
                165                 170                 175

Ala Cys Gly Ala Gly Leu Ala Gly Lys Ala Phe Ala Thr Gly Asn Ala
            180                 185                 190

Val Trp Val Ser Gly Ser Asp Gln Leu Ser Gly Ser Gly Cys Glu Arg
        195                 200                 205
```

```
Ala Lys Gln Gly Gly Val Phe Gly Met His Thr Ile Ala Cys Ile Pro
    210                 215                 220

Ser Ala Asn Gly Val Val Glu Val Gly Ser Thr Glu Pro Ile Arg Gln
225                 230                 235                 240

Ser Ser Asp Leu Ile Asn Lys Val Arg Ile Leu Phe Asn Phe Asp Gly
                245                 250                 255

Gly Ala Gly Asp Leu Ser Gly Leu Asn Trp Asn Leu Asp Pro Asp Gln
                260                 265                 270

Gly Glu Asn Asp Pro Ser Met Trp Ile Asn Asp Pro Ile Gly Thr Pro
            275                 280                 285

Gly Ser Asn Glu Pro Gly Asn Gly Ala Pro Ser Ser Ser Ser Gln Leu
        290                 295                 300

Phe Ser Lys Ser Ile Gln Phe Glu Asn Gly Ser Ser Ser Thr Ile Thr
305                 310                 315                 320

Glu Asn Pro Asn Leu Asp Pro Thr Pro Ser Pro Val His Ser Gln Thr
                325                 330                 335

Gln Asn Pro Lys Phe Asn Asn Thr Phe Ser Arg Glu Leu Asn Phe Ser
                340                 345                 350

Thr Ser Ser Ser Thr Leu Val Lys Pro Arg Ser Gly Glu Ile Leu Asn
            355                 360                 365

Phe Gly Asp Glu Gly Lys Arg Ser Ser Gly Asn Pro Asp Pro Ser Ser
        370                 375                 380

Tyr Ser Gly Gln Thr Gln Phe Glu Asn Lys Arg Lys Arg Ser Met Val
385                 390                 395                 400

Leu Asn Glu Asp Lys Val Leu Ser Phe Gly Asp Lys Thr Ala Gly Glu
                405                 410                 415

Ser Asp His Ser Asp Leu Glu Ala Ser Val Val Lys Glu Val Ala Val
            420                 425                 430

Glu Lys Arg Pro Lys Lys Arg Gly Arg Lys Pro Ala Asn Gly Arg Glu
        435                 440                 445

Glu Pro Leu Asn His Val Glu Ala Glu Arg Gln Arg Arg Glu Lys Leu
        450                 455                 460

Asn Gln Arg Phe Tyr Ala Leu Arg Ala Val Val Pro Asn Val Ser Lys
465                 470                 475                 480

Met Asp Lys Ala Ser Leu Leu Gly Asp Ala Ile Ala Tyr Ile Asn Glu
                485                 490                 495

Leu Lys Ser Lys Val Val Lys Thr Glu Ser Glu Lys Leu Gln Ile Lys
            500                 505                 510

Asn Gln Leu Glu Glu Val Lys Leu Glu Leu Ala Gly Arg Lys Ala Ser
        515                 520                 525

Ala Ser Gly Gly Asp Met Ser Ser Ser Cys Ser Ser Ile Lys Pro Val
530                 535                 540

Gly Met Glu Ile Glu Val Lys Ile Ile Gly Trp Asp Ala Met Ile Arg
545                 550                 555                 560

Val Glu Ser Ser Lys Arg Asn His Pro Ala Ala Arg Leu Met Ser Ala
                565                 570                 575

Leu Met Asp Leu Glu Leu Glu Val Asn His Ala Ser Met Ser Val Val
            580                 585                 590

Asn Asp Leu Met Ile Gln Gln Ala Thr Val Lys Met Gly Phe Arg Ile
        595                 600                 605

Tyr Thr Gln Glu Gln Leu Arg Ala Ser Leu Ile Ser Lys Ile Gly
    610                 615                 620
```

<210> SEQ ID NO 2
<211> LENGTH: 61
<212> TYPE: PRT
<213> ORGANISM: Arabidopsis thaliana

<400> SEQUENCE: 2

Tyr Asp Phe Ser Gly Ala Ser Val Leu Gly Trp Gly Asp Gly Tyr Tyr
1               5                   10                  15

Lys Gly Glu Glu Asp Lys Ala Asn Pro Arg Arg Ser Ser Ser Pro
            20                  25                  30

Pro Phe Ser Thr Pro Ala Asp Gln Glu Tyr Arg Lys Lys Val Leu Arg
        35                  40                  45

Glu Leu Asn Ser Leu Ile Ser Gly Gly Val Ala Pro Ser
50                  55                  60

<210> SEQ ID NO 3
<211> LENGTH: 592
<212> TYPE: PRT
<213> ORGANISM: Arabidopsis thaliana

<400> SEQUENCE: 3

Met Asn Gly Thr Thr Ser Ser Ile Asn Phe Leu Thr Ser Asp Asp Asp
1               5                   10                  15

Ala Ser Ala Ala Ala Met Glu Ala Phe Ile Gly Thr Asn His His Ser
            20                  25                  30

Ser Leu Phe Pro Pro Pro Gln Gln Pro Gln Pro Gln Phe Asn
        35                  40                  45

Glu Asp Thr Leu Gln Gln Arg Leu Gln Ala Leu Ile Glu Ser Ala Gly
50                  55                  60

Glu Asn Trp Thr Tyr Ala Ile Phe Trp Gln Ile Ser His Asp Phe Asp
65                  70                  75                  80

Ser Ser Thr Gly Asp Asn Thr Val Ile Leu Gly Trp Gly Asp Gly Tyr
                85                  90                  95

Tyr Lys Gly Glu Glu Asp Lys Glu Lys Lys Asn Asn Thr Asn Thr
            100                 105                 110

Ala Glu Gln Glu His Arg Lys Arg Val Ile Arg Glu Leu Asn Ser Leu
        115                 120                 125

Ile Ser Gly Gly Ile Gly Val Ser Asp Glu Ser Asn Asp Glu Glu Val
130                 135                 140

Thr Asp Thr Glu Trp Phe Phe Leu Val Ser Met Thr Gln Ser Phe Val
145                 150                 155                 160

Asn Gly Val Gly Leu Pro Gly Glu Ser Phe Leu Asn Ser Arg Val Ile
                165                 170                 175

Trp Leu Ser Gly Ser Gly Ala Leu Thr Gly Ser Gly Cys Glu Arg Ala
            180                 185                 190

Gly Gln Gly Gln Ile Tyr Gly Leu Lys Thr Met Val Cys Ile Ala Thr
        195                 200                 205

Gln Asn Gly Val Val Glu Leu Gly Ser Ser Glu Val Ile Ser Gln Ser
210                 215                 220

Ser Asp Leu Met His Lys Val Asn Asn Leu Phe Asn Phe Asn Asn Gly
225                 230                 235                 240

Gly Gly Asn Asn Gly Val Glu Ala Ser Ser Trp Gly Phe Asn Leu Asn
                245                 250                 255

Pro Asp Gln Gly Glu Asn Asp Pro Ala Leu Trp Ile Ser Glu Pro Thr
            260                 265                 270

```
Asn Thr Gly Ile Glu Ser Pro Ala Arg Val Asn Asn Gly Asn Asn Ser
            275                 280                 285

Asn Ser Asn Ser Lys Ser Asp Ser His Gln Ile Ser Lys Leu Glu Lys
        290                 295                 300

Asn Asp Ile Ser Ser Val Glu Asn Gln Asn Arg Gln Ser Ser Cys Leu
305                 310                 315                 320

Val Glu Lys Asp Leu Thr Phe Gln Gly Gly Leu Leu Lys Ser Asn Glu
                325                 330                 335

Thr Leu Ser Phe Cys Gly Asn Glu Ser Ser Lys Lys Arg Thr Ser Val
            340                 345                 350

Ser Lys Gly Ser Asn Asn Asp Glu Gly Met Leu Ser Phe Ser Thr Val
        355                 360                 365

Val Arg Ser Ala Ala Asn Asp Ser Asp His Ser Asp Leu Glu Ala Ser
    370                 375                 380

Val Val Lys Glu Ala Ile Val Val Glu Pro Pro Glu Lys Lys Pro Arg
385                 390                 395                 400

Lys Arg Gly Arg Lys Pro Ala Asn Gly Arg Glu Glu Pro Leu Asn His
                405                 410                 415

Val Glu Ala Glu Arg Gln Arg Arg Glu Lys Leu Asn Gln Arg Phe Tyr
            420                 425                 430

Ser Leu Arg Ala Val Val Pro Asn Val Ser Lys Met Asp Lys Ala Ser
        435                 440                 445

Leu Leu Gly Asp Ala Ile Ser Tyr Ile Asn Glu Leu Lys Ser Lys Leu
    450                 455                 460

Gln Gln Ala Glu Ser Asp Lys Glu Glu Ile Gln Lys Lys Leu Asp Gly
465                 470                 475                 480

Met Ser Lys Glu Gly Asn Asn Gly Lys Gly Cys Gly Ser Arg Ala Lys
                485                 490                 495

Glu Arg Lys Ser Ser Asn Gln Asp Ser Thr Ala Ser Ser Ile Glu Met
            500                 505                 510

Glu Ile Asp Val Lys Ile Ile Gly Trp Asp Val Met Ile Arg Val Gln
        515                 520                 525

Cys Gly Lys Lys Asp His Pro Gly Ala Arg Phe Met Glu Ala Leu Lys
530                 535                 540

Glu Leu Asp Leu Glu Val Asn His Ala Ser Leu Ser Val Val Asn Asp
545                 550                 555                 560

Leu Met Ile Gln Gln Ala Thr Val Lys Met Gly Ser Gln Phe Phe Asn
                565                 570                 575

His Asp Gln Leu Lys Val Ala Leu Met Thr Lys Val Gly Glu Asn Tyr
            580                 585                 590

<210> SEQ ID NO 4
<211> LENGTH: 55
<212> TYPE: PRT
<213> ORGANISM: Arabidopsis thaliana

<400> SEQUENCE: 4

Ser Thr Gly Asp Asn Thr Val Ile Leu Gly Trp Gly Asp Gly Tyr Tyr
1               5                   10                  15

Lys Gly Glu Glu Asp Lys Glu Lys Lys Asn Asn Thr Asn Thr Ala
            20                  25                  30

Glu Gln Glu His Arg Lys Arg Val Ile Arg Glu Leu Asn Ser Leu Ile
        35                  40                  45

Ser Gly Gly Ile Gly Val Ser
    50                  55
```

<210> SEQ ID NO 5
<211> LENGTH: 589
<212> TYPE: PRT
<213> ORGANISM: Arabidopsis thaliana

<400> SEQUENCE: 5

```
Met Ser Pro Thr Asn Val Gln Val Thr Asp Tyr His Leu Asn Gln Ser
1               5                   10                  15

Lys Thr Asp Thr Thr Asn Leu Trp Ser Thr Asp Asp Ala Ser Val
            20                  25                  30

Met Glu Ala Phe Ile Gly Gly Gly Ser Asp His Ser Ser Leu Phe Pro
        35                  40                  45

Pro Leu Pro Pro Pro Leu Pro Gln Val Asn Glu Asp Asn Leu Gln
    50                  55                  60

Gln Arg Leu Gln Ala Leu Ile Glu Gly Ala Asn Glu Asn Trp Thr Tyr
65                  70                  75                  80

Ala Val Phe Trp Gln Ser Ser His Gly Phe Ala Gly Glu Asp Asn Asn
                85                  90                  95

Asn Asn Asn Thr Val Leu Leu Gly Trp Gly Asp Gly Tyr Tyr Lys Gly
            100                 105                 110

Glu Glu Glu Lys Ser Arg Lys Lys Lys Ser Asn Pro Ala Ser Ala Ala
        115                 120                 125

Glu Gln Glu His Arg Lys Arg Val Ile Arg Glu Leu Asn Ser Leu Ile
    130                 135                 140

Ser Gly Gly Val Gly Gly Gly Asp Glu Ala Gly Asp Glu Glu Val Thr
145                 150                 155                 160

Asp Thr Glu Trp Phe Phe Leu Val Ser Met Thr Gln Ser Phe Val Lys
                165                 170                 175

Gly Thr Gly Leu Pro Gly Gln Ala Phe Ser Asn Ser Asp Thr Ile Trp
            180                 185                 190

Leu Ser Gly Ser Asn Ala Leu Ala Gly Ser Ser Cys Glu Arg Ala Arg
        195                 200                 205

Gln Gly Gln Ile Tyr Gly Leu Gln Thr Met Val Cys Val Ala Thr Glu
    210                 215                 220

Asn Gly Val Val Glu Leu Gly Ser Ser Glu Ile Ile His Gln Ser Ser
225                 230                 235                 240

Asp Leu Val Asp Lys Val Asp Thr Phe Phe Asn Phe Asn Asn Gly Gly
                245                 250                 255

Gly Glu Phe Gly Ser Trp Ala Phe Asn Leu Asn Pro Asp Gln Gly Glu
            260                 265                 270

Asn Asp Pro Gly Leu Trp Ile Ser Glu Pro Asn Gly Val Asp Ser Gly
        275                 280                 285

Leu Val Ala Ala Pro Val Met Asn Asn Gly Asn Asp Ser Thr Ser
    290                 295                 300

Asn Ser Asp Ser Gln Pro Ile Ser Lys Leu Cys Asn Gly Ser Ser Val
305                 310                 315                 320

Glu Asn Pro Asn Pro Lys Val Leu Lys Ser Cys Glu Met Val Asn Phe
                325                 330                 335

Lys Asn Gly Ile Glu Asn Gly Gln Glu Asp Ser Ser Asn Lys Lys
            340                 345                 350

Arg Ser Pro Val Ser Asn Asn Glu Glu Gly Met Leu Ser Phe Thr Ser
        355                 360                 365

Val Leu Pro Cys Asp Ser Asn His Ser Asp Leu Glu Ala Ser Val Ala
```

```
                370              375              380
Lys Glu Ala Glu Ser Asn Arg Val Val Glu Pro Glu Lys Lys Pro
385                  390              395              400

Arg Lys Arg Gly Arg Lys Pro Ala Asn Gly Arg Glu Glu Pro Leu Asn
            405              410              415

His Val Glu Ala Glu Arg Gln Arg Glu Lys Leu Asn Gln Arg Phe
                420              425              430

Tyr Ser Leu Arg Ala Val Val Pro Asn Val Ser Lys Met Asp Lys Ala
            435              440              445

Ser Leu Leu Gly Asp Ala Ile Ser Tyr Ile Ser Glu Leu Lys Ser Lys
        450              455              460

Leu Gln Lys Ala Glu Ser Asp Lys Glu Leu Gln Lys Gln Ile Asp
465              470              475              480

Val Met Asn Lys Glu Ala Gly Asn Ala Lys Ser Val Lys Asp Arg
                485              490              495

Lys Cys Leu Asn Gln Glu Ser Ser Val Leu Ile Glu Met Glu Val Asp
            500              505              510

Val Lys Ile Ile Gly Trp Asp Ala Met Ile Arg Ile Gln Cys Ser Lys
        515              520              525

Arg Asn His Pro Gly Ala Lys Phe Met Glu Ala Leu Lys Glu Leu Asp
530              535              540

Leu Glu Val Asn His Ala Ser Leu Ser Val Val Asn Asp Leu Met Ile
545              550              555              560

Gln Gln Ala Thr Val Lys Met Gly Asn Gln Phe Phe Thr Gln Asp Gln
                565              570              575

Leu Lys Val Ala Leu Thr Glu Lys Val Gly Glu Cys Pro
            580              585

<210> SEQ ID NO 6
<211> LENGTH: 57
<212> TYPE: PRT
<213> ORGANISM: Arabidopsis thaliana

<400> SEQUENCE: 6

Asn Asn Asn Asn Asn Thr Val Leu Leu Gly Trp Gly Asp Gly Tyr Tyr
1               5                   10                  15

Lys Gly Glu Glu Glu Lys Ser Arg Lys Lys Ser Asn Pro Ala Ser
            20                  25                  30

Ala Ala Glu Gln Glu His Arg Lys Arg Val Ile Arg Glu Leu Asn Ser
                35              40              45

Leu Ile Ser Gly Gly Val Gly Gly Gly
            50                  55

<210> SEQ ID NO 7
<211> LENGTH: 751
<212> TYPE: PRT
<213> ORGANISM: Oryza sativa

<400> SEQUENCE: 7

Met Trp Val Leu Leu Ser Pro Leu Leu Thr Thr Lys Asn Pro Phe His
1               5                   10                  15

Pro Ile Pro Ile Pro Thr Phe Pro Leu Leu Phe Ser Ser Ser Leu
            20                  25                  30

Val Gly Val Leu Phe Gln Ile Lys Ser Asn Leu Glu Glu Glu Glu Ile
            35                  40                  45

Glu Ile Lys Ser Met Asn Leu Trp Thr Asp Asp Asn Ala Ser Met Met
```

```
                50                  55                  60
Glu Ala Phe Met Ala Ser Ala Asp Leu Pro Ala Phe Pro Trp Gly Ala
65                  70                  75                  80

Ala Ser Thr Pro Pro Pro Pro Pro Pro His His His His Gln
                85                  90                  95

Gln Gln Gln Gln Gln Val Leu Pro Pro Ala Ala Pro Ala Ala
                100                 105                 110

Ala Ala Phe Asn Gln Asp Thr Leu Gln Gln Arg Leu Gln Ser Ile Ile
                115                 120                 125

Glu Gly Ser Arg Glu Thr Trp Thr Tyr Ala Ile Phe Trp Gln Ser Ser
130                 135                 140

Ile Asp Val Ser Thr Gly Ala Ser Leu Leu Gly Trp Gly Asp Gly Tyr
145                 150                 155                 160

Tyr Lys Gly Cys Asp Asp Lys Arg Lys Gln Arg Ser Ser Thr Pro
                165                 170                 175

Ala Ala Ala Ala Glu Gln Glu His Arg Lys Arg Val Leu Arg Glu Leu
                180                 185                 190

Asn Ser Leu Ile Ala Gly Ala Gly Ala Ala Pro Asp Glu Ala Val Glu
                195                 200                 205

Glu Glu Val Thr Asp Thr Glu Trp Phe Phe Leu Val Ser Met Thr Gln
210                 215                 220

Ser Phe Pro Asn Gly Leu Gly Leu Pro Gly Gln Ala Leu Phe Ala Ala
225                 230                 235                 240

Gln Pro Thr Trp Ile Ala Thr Gly Leu Ser Ser Ala Pro Cys Asp Arg
                245                 250                 255

Ala Arg Gln Ala Tyr Thr Phe Gly Leu Arg Thr Met Val Cys Leu Pro
                260                 265                 270

Leu Ala Thr Gly Val Leu Glu Leu Gly Ser Thr Asp Val Ile Phe Gln
                275                 280                 285

Thr Gly Asp Ser Ile Pro Arg Ile Arg Ala Leu Phe Asn Leu Ser Ala
                290                 295                 300

Ala Ala Ala Ser Ser Trp Pro Pro His Pro Asp Ala Ala Ser Ala Asp
305                 310                 315                 320

Pro Ser Val Leu Trp Leu Ala Asp Ala Pro Met Asp Met Lys Asp
                325                 330                 335

Ser Ile Ser Ala Ala Asp Ile Ser Val Ser Lys Pro Pro Pro Pro
                340                 345                 350

Pro His Gln Ile Gln His Phe Glu Asn Gly Ser Thr Ser Thr Leu Thr
                355                 360                 365

Glu Asn Pro Ser Pro Ser Val His Ala Pro Thr Pro Ser Gln Pro Ala
370                 375                 380

Ala Pro Pro Gln Arg Gln Gln Gln Gln Gln Ser Ser Gln Ala Gln
385                 390                 395                 400

Gln Gly Pro Phe Arg Arg Glu Leu Asn Phe Ser Asp Phe Ala Ser Asn
                405                 410                 415

Gly Gly Ala Ala Ala Pro Pro Phe Phe Lys Pro Glu Thr Gly Glu Ile
                420                 425                 430

Leu Asn Phe Gly Asn Asp Ser Ser Ser Gly Arg Arg Asn Pro Ser Pro
                435                 440                 445

Ala Pro Pro Ala Ala Thr Ala Ser Leu Thr Thr Ala Pro Gly Ser Leu
                450                 455                 460

Phe Ser Gln His Thr Pro Thr Leu Thr Ala Ala Ala Asn Asp Ala Lys
465                 470                 475                 480
```

-continued

Ser Asn Asn Gln Lys Arg Ser Met Glu Ala Thr Ser Arg Ala Ser Asn
                485                 490                 495

Thr Asn Asn His Pro Ala Ala Thr Ala Asn Glu Gly Met Leu Ser Phe
            500                 505                 510

Ser Ser Ala Pro Thr Thr Arg Pro Ser Thr Gly Thr Gly Ala Pro Ala
        515                 520                 525

Lys Ser Glu Ser Asp His Ser Asp Leu Glu Ala Ser Val Arg Glu Val
    530                 535                 540

Glu Ser Ser Arg Val Val Ala Pro Pro Glu Ala Glu Lys Arg Pro
545                 550                 555                 560

Arg Lys Arg Gly Arg Lys Pro Ala Asn Gly Arg Glu Glu Pro Leu Asn
                565                 570                 575

His Val Glu Ala Glu Arg Gln Arg Arg Glu Lys Leu Asn Gln Arg Phe
            580                 585                 590

Tyr Ala Leu Arg Ala Val Val Pro Asn Val Ser Lys Met Asp Lys Ala
        595                 600                 605

Ser Leu Leu Gly Asp Ala Ile Ser Tyr Ile Asn Glu Leu Arg Gly Lys
    610                 615                 620

Leu Thr Ala Leu Glu Thr Asp Lys Glu Thr Leu Gln Ser Gln Met Glu
625                 630                 635                 640

Ser Leu Lys Lys Glu Arg Asp Ala Arg Pro Pro Ala Pro Ser Gly Gly
                645                 650                 655

Gly Gly Asp Gly Gly Ala Arg Cys His Ala Val Glu Ile Glu Ala Lys
            660                 665                 670

Ile Leu Gly Leu Glu Ala Met Ile Arg Val Gln Cys His Lys Arg Asn
        675                 680                 685

His Pro Ala Ala Arg Leu Met Thr Ala Leu Arg Glu Leu Asp Leu Asp
    690                 695                 700

Val Tyr His Ala Ser Val Ser Val Val Lys Asp Leu Met Ile Gln Gln
705                 710                 715                 720

Val Ala Val Lys Met Ala Ser Arg Val Tyr Ser Gln Asp Gln Leu Asn
                725                 730                 735

Ala Ala Leu Tyr Thr Arg Ile Ala Glu Pro Gly Thr Ala Ala Arg
            740                 745                 750

<210> SEQ ID NO 8
<211> LENGTH: 52
<212> TYPE: PRT
<213> ORGANISM: Oryza sativa

<400> SEQUENCE: 8

Ser Thr Gly Ala Ser Leu Leu Gly Trp Gly Asp Gly Tyr Tyr Lys Gly
1               5                   10                  15

Cys Asp Asp Asp Lys Arg Lys Gln Arg Ser Ser Thr Pro Ala Ala Ala
                20                  25                  30

Ala Glu Gln Glu His Arg Lys Arg Val Leu Arg Glu Leu Asn Ser Leu
            35                  40                  45

Ile Ala Gly Ala
    50

<210> SEQ ID NO 9
<211> LENGTH: 705
<212> TYPE: PRT
<213> ORGANISM: Zea mays

<400> SEQUENCE: 9

```
Met Asn Leu Trp Thr Asp Asp Asn Ala Ser Met Met Glu Ala Phe Met
1               5                   10                  15
Ala Ser Ala Asp Leu Pro Thr Phe Pro Trp Gly Ala Pro Ala Gly Gly
            20                  25                  30
Gly Asn Ser Ser Ala Ala Ala Ser Pro Pro Pro Gln Met Pro
        35                  40                  45
Ala Ala Thr Ala Pro Gly Phe Asn Gln Asp Thr Leu Gln Gln Arg Leu
50                  55                  60
Gln Ala Met Ile Glu Gly Ser Arg Glu Thr Trp Thr Tyr Ala Ile Phe
65                  70                  75                  80
Trp Gln Ser Ser Leu Asp Ser Ala Thr Gly Ala Ser Leu Leu Gly Trp
                85                  90                  95
Gly Asp Gly Tyr Tyr Lys Gly Cys Asp Glu Asp Lys Arg Lys Gln Lys
                100                 105                 110
Pro Leu Thr Pro Ser Ala Gln Ala Glu Gln Glu His Arg Lys Arg Val
            115                 120                 125
Leu Arg Glu Leu Asn Ser Leu Ile Ser Gly Ala Ala Ala Ala Pro Asp
130                 135                 140
Glu Ala Val Glu Glu Val Thr Asp Thr Glu Trp Phe Phe Leu Val
145                 150                 155                 160
Ser Met Thr Gln Ser Phe Leu Asn Gly Ser Gly Leu Pro Gly Gln Ala
                165                 170                 175
Leu Phe Ala Gly Gln Pro Thr Trp Ile Ala Ser Gly Leu Ser Ser Ala
                180                 185                 190
Pro Cys Glu Arg Ala Arg Gln Ala Tyr Asn Phe Gly Leu Arg Thr Met
                195                 200                 205
Val Cys Phe Pro Val Gly Thr Gly Val Leu Glu Leu Gly Ser Thr Asp
210                 215                 220
Val Val Phe Lys Thr Ala Glu Ser Met Ala Lys Ile Arg Ser Leu Phe
225                 230                 235                 240
Gly Gly Gly Ala Gly Gly Gly Ser Trp Pro Pro Val Gln Pro Gln Ala
                245                 250                 255
Pro Ser Ser Gln Gln Pro Ala Ala Gly Ala Asp His Ala Glu Thr Asp
                260                 265                 270
Pro Ser Met Leu Trp Leu Ala Asp Ala Pro Val Met Asp Ile Lys Asp
                275                 280                 285
Ser Leu Ser His Pro Ser Ala Glu Ile Ser Val Ser Lys Pro Pro
                290                 295                 300
His Pro Pro Gln Ile His Phe Glu Asn Gly Ser Thr Ser Thr Leu Thr
305                 310                 315                 320
Glu Asn Pro Ser Pro Ser Val His Ala Pro Pro Pro Pro Ala Pro
                325                 330                 335
Ala Ala Pro Gln Gln Arg Gln His Gln His Gln Asn Gln Ala His Gln
                340                 345                 350
Gly Pro Phe Arg Arg Glu Leu Asn Phe Ser Asp Phe Ala Ser Thr Pro
                355                 360                 365
Ser Leu Ala Ala Thr Pro Pro Phe Phe Lys Pro Glu Ser Gly Glu Ile
            370                 375                 380
Leu Ser Phe Gly Ala Asp Ser Asn Ala Arg Arg Asn Pro Ser Pro Val
385                 390                 395                 400
Pro Pro Ala Ala Thr Ala Ser Leu Thr Thr Ala Pro Gly Ser Leu Phe
                405                 410                 415
```

Ser Gln His Thr Ala Thr Met Thr Ala Ala Ala Asn Asp Ala Lys
        420             425                 430

Asn Asn Asn Lys Arg Ser Met Glu Ala Thr Ser Arg Ala Ser Asn Thr
            435                 440                 445

Asn His His Pro Ala Ala Thr Ala Asn Glu Gly Met Leu Ser Phe Ser
        450                 455                 460

Ser Ala Pro Thr Thr Arg Pro Ser Thr Gly Thr Gly Ala Pro Ala Lys
465                 470                 475                 480

Ser Glu Ser Asp His Ser Asp Leu Asp Ala Ser Val Arg Glu Val Glu
                485                 490                 495

Ser Ser Arg Val Val Ala Pro Pro Glu Ala Glu Lys Arg Pro Arg
            500                 505                 510

Lys Arg Gly Arg Lys Pro Ala Asn Gly Arg Glu Glu Pro Leu Asn His
            515                 520                 525

Val Glu Ala Glu Arg Gln Arg Arg Glu Lys Leu Asn Gln Arg Phe Tyr
            530                 535                 540

Ala Leu Arg Ala Val Val Pro Asn Val Ser Lys Met Asp Lys Ala Ser
545                 550                 555                 560

Leu Leu Gly Asp Ala Ile Ser Tyr Ile Asn Glu Leu Arg Gly Lys Leu
                565                 570                 575

Thr Ser Leu Glu Thr Asp Lys Glu Thr Leu Gln Thr Gln Val Glu Ala
            580                 585                 590

Leu Lys Lys Glu Arg Asp Ala Arg Pro Pro Ser His Ser Ala Gly Leu
            595                 600                 605

Gly Gly His Asp Gly Gly Pro Arg Cys His Ala Val Glu Ile Asp Ala
        610                 615                 620

Lys Ile Leu Gly Leu Glu Ala Met Ile Arg Val Gln Cys His Lys Arg
625                 630                 635                 640

Asn His Pro Ser Ala Arg Leu Met Thr Ala Leu Arg Glu Leu Asp Leu
                645                 650                 655

Asp Val Tyr His Ala Ser Val Ser Val Val Lys Asp Leu Met Ile Gln
                660                 665                 670

Gln Val Ala Val Lys Met Ala Ser Arg Val Tyr Thr Gln Asp Gln Leu
            675                 680                 685

Ser Ala Ala Leu Tyr Ser Arg Leu Ala Glu Pro Gly Ser Ala Met Gly
        690                 695                 700
Arg
705

<210> SEQ ID NO 10
<211> LENGTH: 52
<212> TYPE: PRT
<213> ORGANISM: Zea mays

<400> SEQUENCE: 10

Ala Thr Gly Ala Ser Leu Leu Gly Trp Gly Asp Gly Tyr Tyr Lys Gly
1               5                   10                  15

Cys Asp Glu Asp Lys Arg Lys Gln Lys Pro Leu Thr Pro Ser Ala Gln
            20                  25                  30

Ala Glu Gln Glu His Arg Lys Arg Val Leu Arg Glu Leu Asn Ser Leu
        35                  40                  45

Ile Ser Gly Ala
    50

<210> SEQ ID NO 11

```
<211> LENGTH: 703
<212> TYPE: PRT
<213> ORGANISM: Zea mays

<400> SEQUENCE: 11

Met Asn Leu Trp Thr Asp Asp Asn Ala Ser Met Met Glu Ala Phe Met
1               5                   10                  15

Ala Ser Ala Asp Leu Pro Ala Tyr Pro Trp Gly Ala Pro Ala Gly Gly
            20                  25                  30

Gly Asn Pro Pro Pro Gln Met Pro Pro Ala Met Ala Met Ala Pro
        35                  40                  45

Gly Phe Asn Gln Asp Thr Leu Gln Gln Arg Leu Gln Ala Met Ile Glu
50                  55                  60

Gly Ser Arg Glu Thr Trp Thr Tyr Ala Ile Phe Trp Gln Ser Ser Leu
65                  70                  75                  80

Asp Ala Ala Thr Gly Ala Ser Leu Leu Gly Trp Gly Asp Gly Tyr Tyr
                85                  90                  95

Lys Gly Cys Asp Asp Lys Arg Arg His Arg Pro Pro Leu Thr Pro
            100                 105                 110

Ala Ala Gln Ala Glu Gln Glu His Arg Lys Arg Val Leu Arg Glu Leu
        115                 120                 125

Asn Ser Leu Ile Ser Gly Gly Ala Ser Ala Ala Pro Ala Pro Ala Pro
130                 135                 140

Asp Glu Ala Val Glu Glu Val Thr Asp Thr Glu Trp Phe Phe Leu
145                 150                 155                 160

Val Ser Met Thr Gln Ser Phe Leu Asn Gly Ser Gly Leu Pro Gly Gln
                165                 170                 175

Ala Leu Phe Ala Gly His His Thr Trp Ile Ala Ala Gly Leu Ser Ser
            180                 185                 190

Ala Pro Cys Asp Arg Ala Arg Gln Ala Tyr Asn Phe Gly Leu Arg Thr
        195                 200                 205

Met Val Cys Phe Pro Val Gly Thr Gly Val Leu Glu Leu Gly Ser Thr
210                 215                 220

Asp Val Val Phe Gln Thr Ala Glu Thr Met Ala Lys Ile Arg Ser Leu
225                 230                 235                 240

Phe Gly Gly Gly Pro Gly Gly Ser Trp Pro Pro Val Gln Pro Gln
                245                 250                 255

Ala Ala Pro Gln Gln His Ala Ala Glu Ala Asp Gln Ala Ala Glu
            260                 265                 270

Thr Asp Pro Ser Val Leu Trp Leu Ala Asp Ala Pro Val Val Asp Ile
        275                 280                 285

Lys Asp Ser Tyr Ser His Pro Ser Ala Ala Glu Ile Ser Val Ser Lys
290                 295                 300

Pro Pro Pro Pro Pro Pro Pro Gln Ile His Phe Glu Asn Gly Ser
305                 310                 315                 320

Thr Ser Thr Leu Thr Glu Asn Pro Ser Pro Ser Val His Ala Pro Pro
                325                 330                 335

Ala Pro Pro Ala Pro Pro Gln Arg Gln Gln Asn Gln Gly Pro Phe
            340                 345                 350

Arg Arg Glu Leu Asn Phe Ser Asp Phe Ala Ser Asn Pro Ser Leu Ala
        355                 360                 365

Ala Ala Pro Pro Phe Phe Lys Pro Glu Ser Gly Glu Ile Leu Ser Phe
370                 375                 380

Gly Val Asp Ser Asn Ala Gln Arg Asn Pro Ser Pro Ala Pro Pro Ala
```

```
            385                 390                 395                 400
        Ser Leu Thr Thr Ala Pro Gly Ser Leu Phe Ser Gln Ser Gln His Thr
                        405                 410                 415

Ala Thr Ala Ala Ala Asn Asp Ala Lys Asn Asn Asn Asn Asn Asn Lys
                    420                 425                 430

Arg Ser Met Glu Ala Thr Ser Leu Ala Ser Asn Thr Asn His His Pro
                435                 440                 445

Ala Ala Ala Ala Asn Glu Gly Met Leu Ser Phe Ser Ser Ala Pro Thr
            450                 455                 460

Ala Arg Pro Ser Ala Gly Thr Gly Ala Pro Ala Lys Ser Glu Ser Asp
        465                 470                 475                 480

His Ser Asp Leu Asp Ala Ser Val Arg Glu Val Glu Ser Ser Arg Val
                        485                 490                 495

Val Ala Pro Pro Pro Glu Ala Glu Lys Arg Pro Arg Lys Arg Gly Arg
                    500                 505                 510

Lys Pro Ala Asn Gly Arg Glu Glu Pro Leu Asn His Val Glu Ala Glu
                515                 520                 525

Arg Gln Arg Arg Glu Lys Leu Asn Gln Arg Phe Tyr Ala Leu Arg Ala
            530                 535                 540

Val Val Pro Asn Val Ser Lys Met Asp Lys Ala Ser Leu Leu Gly Asp
        545                 550                 555                 560

Ala Ile Ser Tyr Ile Asn Glu Leu Arg Gly Lys Leu Thr Ser Leu Glu
                        565                 570                 575

Ser Asp Arg Glu Thr Leu Gln Ala Gln Val Glu Ala Leu Lys Lys Glu
                    580                 585                 590

Arg Asp Ala Arg Pro His Pro His Pro Ala Ala Gly Leu Gly Gly His
                595                 600                 605

Asp Ala Gly Gly Pro Arg Cys His Ala Val Glu Ile Asp Ala Lys Ile
            610                 615                 620

Leu Gly Leu Glu Ala Met Ile Arg Val Gln Cys His Lys Arg Asn His
        625                 630                 635                 640

Pro Ser Ala Arg Leu Met Thr Ala Leu Arg Glu Leu Asp Leu Asp Val
                        645                 650                 655

Tyr His Ala Ser Val Ser Val Val Lys Asp Leu Met Ile Gln Gln Val
                    660                 665                 670

Ala Val Lys Met Ala Ser Arg Met Tyr Ser Gln Asp Gln Leu Ser Ala
                675                 680                 685

Ala Leu Tyr Ser Arg Leu Ala Glu Pro Gly Ser Val Met Gly Arg
            690                 695                 700

<210> SEQ ID NO 12
<211> LENGTH: 53
<212> TYPE: PRT
<213> ORGANISM: Zea mays

<400> SEQUENCE: 12

Ala Thr Gly Ala Ser Leu Leu Gly Trp Gly Asp Gly Tyr Tyr Lys Gly
        1               5                   10                  15

Cys Asp Asp Asp Lys Arg Arg His Arg Pro Pro Leu Thr Pro Ala Ala
                        20                  25                  30

Gln Ala Glu Gln Glu His Arg Lys Arg Val Leu Arg Glu Leu Asn Ser
                    35                  40                  45

Leu Ile Ser Gly Gly
            50
```

<210> SEQ ID NO 13
<211> LENGTH: 706
<212> TYPE: PRT
<213> ORGANISM: Brachypodium distachyon

<400> SEQUENCE: 13

```
Met Asn Leu Trp Thr Asp Asp Asn Ala Ser Met Met Glu Ala Phe Met
1               5                   10                  15

Ala Ser Ala Ala Asp Leu Pro Thr Phe Pro Trp Gly Ala Ala Ala
            20                  25                  30

Thr Pro Pro Pro Ala Ala Val Met Pro Gln Gln Pro Ala Phe Asn
        35                  40                  45

Gln Asp Thr Leu Gln Gln Arg Leu Gln Ala Ile Ile Glu Gly Ser Arg
    50                  55                  60

Glu Thr Trp Thr Tyr Ala Ile Phe Trp Gln Ser Ser Thr Asp Ala Gly
65                  70                  75                  80

Ala Gly Ala Ser Leu Leu Gly Trp Gly Asp Gly Tyr Tyr Lys Gly Cys
                85                  90                  95

Asp Asp Ala Asp Lys Arg Ala Arg Gln Gln Pro Thr Pro Ala Ser Ala
            100                 105                 110

Ala Glu Gln Glu His Arg Lys Arg Val Leu Arg Glu Leu Asn Ser Leu
        115                 120                 125

Ile Ala Gly Gly Ala Ala Pro Asp Glu Ala Val Glu Glu
    130                 135                 140

Val Thr Asp Thr Glu Trp Phe Phe Leu Val Ser Met Thr Gln Ser Phe
145                 150                 155                 160

Pro Asn Gly Met Gly Leu Pro Gly Gln Ala Leu Tyr Thr Arg Gln Pro
                165                 170                 175

Thr Trp Ile Ala Ser Gly Leu Ala Ser Ala Pro Cys Glu Arg Ala Arg
            180                 185                 190

Gln Ala Tyr Thr Phe Gly Leu Arg Thr Met Val Cys Ile Pro Val Gly
        195                 200                 205

Thr Gly Val Leu Glu Leu Gly Ala Thr Glu Val Ile Phe Gln Thr Ala
    210                 215                 220

Asp Ser Leu Gly Arg Ile Arg Ser Leu Phe Asn Leu Asn Gly Gly Gly
225                 230                 235                 240

Gly Gly Gly Gly Ala Gly Ser Ser Trp Pro Pro Val Ala Pro His Gln
                245                 250                 255

Gln His Gly Gly Asp Gln Ala Glu Thr Asp Pro Ser Val Leu Trp Leu
            260                 265                 270

Thr Asp Ala Pro Val Gly Asp Met Lys Glu Ser Pro Ser Val Glu Ile
        275                 280                 285

Ser Val Ser Lys Pro Pro Pro Pro Gln Ile His His Phe Glu Asn
    290                 295                 300

Gly Ser Thr Ser Thr Leu Thr Glu Asn Ala Gly Pro Ser Leu His Ala
305                 310                 315                 320

His Gln Gln Pro Ala Thr Leu Ala Pro Ala Ala Pro Arg Gln Asn
                325                 330                 335

Gln His Pro His Gln Leu Gln Leu Gln His Gln Ser Gln Gln Gln
            340                 345                 350

Gln Gln Gln Gln Gln Gly Pro Phe Arg Arg Glu Leu Asn Phe Ser Asp
        355                 360                 365

Phe Ala Thr Asn Ala Ser Val Thr Val Thr Pro Pro Phe Phe Lys Pro
    370                 375                 380
```

Glu Ser Gly Glu Ile Leu Asn Phe Gly Ala Asp Ser Thr Arg Arg
385                 390                 395                 400

Asn Pro Ser Pro Ala Pro Ala Ala Ala Ser Leu Thr Thr Ala
        405                 410                 415

Pro Gly Ser Leu Phe Ser Gln His Thr Ala Thr Val Thr Ala Pro Thr
            420                 425                 430

Asn Glu Ala Lys Asn Asn Pro Lys Arg Ser Met Glu Ala Thr Ser Arg
            435                 440                 445

Ala Ser Asn Thr Asn His His Pro Ser Ala Thr Ala Asn Glu Gly Met
            450                 455                 460

Leu Ser Phe Ser Ser Ala Pro Thr Thr Arg Pro Ser Thr Gly Thr Gly
465                 470                 475                 480

Ala Pro Ala Lys Ser Glu Ser Asp His Ser Asp Leu Glu Ala Ser Val
                485                 490                 495

Arg Glu Val Glu Ser Ser Arg Val Val Pro Pro Glu Glu Lys Arg
                500                 505                 510

Pro Arg Lys Arg Gly Arg Lys Pro Ala Asn Gly Arg Glu Glu Pro Leu
            515                 520                 525

Asn His Val Glu Ala Glu Arg Gln Arg Arg Glu Lys Leu Asn Gln Arg
            530                 535                 540

Phe Tyr Ala Leu Arg Ala Val Val Pro Asn Val Ser Lys Met Asp Lys
545                 550                 555                 560

Ala Ser Leu Leu Gly Asp Ala Ile Ser Tyr Ile Asn Glu Leu Arg Gly
                565                 570                 575

Lys Met Thr Ala Leu Glu Ser Asp Lys Asp Thr Leu His Ser Gln Ile
            580                 585                 590

Glu Ala Leu Lys Lys Glu Arg Asp Ala Arg Pro Val Ala Pro Leu Ser
            595                 600                 605

Gly Val His Asp Ser Gly Pro Arg Cys His Ala Val Glu Ile Glu Ala
            610                 615                 620

Lys Ile Leu Gly Leu Glu Ala Met Ile Arg Val Gln Cys His Lys Arg
625                 630                 635                 640

Asn His Pro Ala Ala Lys Leu Met Thr Ala Leu Arg Glu Leu Asp Leu
                645                 650                 655

Asp Val Tyr His Ala Ser Val Ser Val Val Lys Asp Ile Met Ile Gln
                660                 665                 670

Gln Val Ala Val Lys Met Pro Asn Arg Val Tyr Ser Gln Asp Gln Leu
            675                 680                 685

Asn Ala Ala Leu Tyr Ser Arg Leu Ala Glu Pro Gly Ala Pro Val Pro
            690                 695                 700

Ile Arg
705

<210> SEQ ID NO 14
<211> LENGTH: 52
<212> TYPE: PRT
<213> ORGANISM: Brachypodium distachyon

<400> SEQUENCE: 14

Ala Gly Ala Ser Leu Leu Gly Trp Gly Asp Gly Tyr Tyr Lys Gly Cys
1               5                   10                  15

Asp Asp Ala Asp Lys Arg Ala Arg Gln Gln Pro Thr Pro Ala Ser Ala
            20                  25                  30

Ala Glu Gln Glu His Arg Lys Arg Val Leu Arg Glu Leu Asn Ser Leu 35                  40                  45

Ile Ala Gly Gly
    50

<210> SEQ ID NO 15
<211> LENGTH: 707
<212> TYPE: PRT
<213> ORGANISM: Sorghum bicolor

<400> SEQUENCE: 15

Met Asn Leu Trp Thr Asp Asp Asn Ala Ser Met Met Glu Ala Phe Met
1               5                   10                  15

Ala Ser Ala Asp Leu Pro Thr Phe Pro Trp Gly Ala Thr Ala Gly Gly
            20                  25                  30

Gly Asn Ser Ser Ala Ala Ala Thr Pro Pro Pro Pro Gln Met
        35                  40                  45

Pro Ala Ala Ala Met Ala Pro Gly Phe Asn Gln Asp Thr Leu Gln Gln
    50                  55                  60

Arg Leu Gln Ala Met Ile Glu Gly Ser Ser Glu Thr Trp Thr Tyr Ala
65                  70                  75                  80

Ile Phe Trp Gln Ser Ser Leu Asp Ala Ala Thr Gly Ala Ser Leu Leu
                85                  90                  95

Gly Trp Gly Asp Gly Tyr Tyr Lys Gly Cys Asp Asp Asp Lys Arg Lys
            100                 105                 110

Gln Arg Pro Leu Thr Pro Ala Ala Gln Ala Glu Gln Glu His Arg Lys
        115                 120                 125

Arg Val Leu Arg Glu Leu Asn Ser Leu Ile Ser Gly Ala Ala Ala Ala
    130                 135                 140

Pro Asp Glu Ala Val Glu Glu Val Thr Asp Thr Glu Trp Phe Phe
145                 150                 155                 160

Leu Val Ser Met Thr Gln Ser Phe Leu Asn Gly Ser Gly Leu Pro Gly
                165                 170                 175

Gln Ala Leu Phe Ala Gly Gln Pro Thr Trp Ile Ala Ser Gly Leu Ser
            180                 185                 190

Ser Ala Pro Cys Glu Arg Ala Arg Gln Ala Tyr Asn Phe Gly Leu Arg
        195                 200                 205

Thr Met Val Cys Phe Pro Val Gly Thr Gly Val Leu Glu Leu Gly Ser
    210                 215                 220

Thr Asp Val Val Phe Gln Thr Ala Glu Ser Met Ala Lys Ile Arg Ser
225                 230                 235                 240

Leu Phe Gly Gly Gly Ala Gly Gly Gly Ser Trp Pro Pro Gln Ala
                245                 250                 255

Pro Ser His Gln Gln Pro Ala Ala Gly Pro Asp Gln Ala Glu Thr Asp
            260                 265                 270

Leu Trp Leu Ala Asp Ala Pro Val Met Asp Ile Lys Asp Ser Met Ser
        275                 280                 285

His Pro Ser Ala Glu Ile Ser Val Ser Lys Pro Pro Pro Pro Pro
    290                 295                 300

Pro Pro Gln Ile His Phe Glu Asn Ala Ser Thr Ser Thr Leu Thr Glu
305                 310                 315                 320

Asn Pro Ser Pro Ser Val His Ala Ala Pro Gln Pro Ala Pro Ala
                325                 330                 335

Ala Ala Pro Gln Arg Gln His Gln His Gln Asn Gln Ala His Gln Gly
            340                 345                 350

-continued

Pro Phe Arg Arg Glu Leu Asn Phe Ser Asp Phe Ala Ser Thr Asn Pro
            355                 360                 365

Ser Ser Leu Ala Ala Thr Pro Pro Phe Phe Lys Pro Glu Ser Gly Glu
    370                 375                 380

Ile Leu Ser Phe Gly Ala Asp Ser Asn Ala Arg Arg Asn Pro Ser Pro
385                 390                 395                 400

Ala Pro Pro Ala Ala Thr Ala Ser Leu Thr Thr Ala Pro Gly Ser Leu
                405                 410                 415

Phe Ser Gln His Thr Ala Thr Met Thr Gln Ala Ala Ala Asn Asp
            420                 425                 430

Ala Lys Asn Asn Asn Lys Arg Ser Met Glu Ala Thr Ser Arg Ala Ser
        435                 440                 445

Asn Thr Asn His His Pro Ala Ala Thr Ala Asn Glu Gly Met Leu Ser
450                 455                 460

Phe Ser Ser Ala Pro Thr Thr Arg Pro Ser Thr Gly Thr Gly Ala Pro
465                 470                 475                 480

Ala Lys Ser Glu Ser Asp His Ser Asp Leu Asp Ala Ser Val Arg Glu
                485                 490                 495

Val Glu Ser Ser Arg Val Val Ala Pro Pro Glu Ala Glu Lys Arg
            500                 505                 510

Pro Arg Lys Arg Gly Arg Lys Pro Ala Asn Gly Arg Glu Glu Pro Leu
        515                 520                 525

Asn His Val Glu Ala Glu Arg Gln Arg Arg Glu Lys Leu Asn Gln Arg
    530                 535                 540

Phe Tyr Ala Leu Arg Ala Val Val Pro Asn Val Ser Lys Met Asp Lys
545                 550                 555                 560

Ala Ser Leu Leu Gly Asp Ala Ile Ser Tyr Ile Asn Glu Leu Arg Gly
                565                 570                 575

Lys Leu Thr Ser Leu Glu Ser Asp Lys Asp Thr Leu Gln Ala Gln Ile
            580                 585                 590

Glu Ala Leu Lys Lys Glu Arg Asp Ala Arg Pro Pro Ala His Ala Ala
        595                 600                 605

Gly Leu Gly Gly His Asp Gly Gly Pro Arg Cys His Ala Val Glu Ile
    610                 615                 620

Asp Ala Lys Ile Leu Gly Leu Glu Ala Met Ile Arg Val Gln Cys His
625                 630                 635                 640

Lys Arg Asn His Pro Ser Ala Arg Leu Met Thr Ala Leu Arg Glu Leu
                645                 650                 655

Asp Leu Asp Val Tyr His Ala Ser Val Ser Val Val Lys Asp Leu Met
            660                 665                 670

Ile Gln Gln Val Ala Val Lys Met Ala Ser Arg Ile Tyr Ser Gln Asp
        675                 680                 685

Gln Leu Asn Ala Ala Leu Tyr Ser Arg Leu Ala Glu Pro Gly Ser Ala
    690                 695                 700

Met Gly Arg
705

<210> SEQ ID NO 16
<211> LENGTH: 51
<212> TYPE: PRT
<213> ORGANISM: Sorghum bicolor

<400> SEQUENCE: 16

Ala Thr Gly Ala Ser Leu Leu Gly Trp Gly Asp Gly Tyr Tyr Lys Gly
1               5                   10                  15

Cys Asp Asp Asp Lys Arg Lys Gln Arg Pro Leu Thr Pro Ala Ala Gln
            20                  25                  30

Ala Glu Gln Glu His Arg Lys Arg Val Leu Arg Glu Leu Asn Ser Leu
        35                  40                  45

Ile Ser Gly
    50

<210> SEQ ID NO 17
<211> LENGTH: 462
<212> TYPE: PRT
<213> ORGANISM: Camelina sativa
<220> FEATURE:
<221> NAME/KEY: VARIANT
<222> LOCATION: (1)...(462)
<223> OTHER INFORMATION: Xaa = Any Amino Acid

<400> SEQUENCE: 17

Met Thr Asp Tyr Arg Leu Gln Pro Thr Met Asn Leu Trp Thr Thr Asp
1               5                   10                  15

Asp Asn Ala Ser Met Met Glu Ala Phe Ile Ser Ser Asp Ile Ser
            20                  25                  30

Thr Leu Trp Pro Met Ala Thr Thr Thr Thr Thr Thr Thr Ala Thr
        35                  40                  45

Thr Ser Ala Pro Ala Thr Ala Met Asp Ile Pro Ala Pro Ala Gly Phe
    50                  55                  60

Asn Gln Glu Thr Leu Gln Gln Arg Leu Gln Ala Leu Ile Glu Gly Thr
65                  70                  75                  80

Asn Glu Gly Trp Thr Tyr Ala Ile Phe Trp Gln Pro Ser Tyr Asp Phe
                85                  90                  95

Ser Gly Ala Ser Val Leu Gly Trp Gly Asp Gly Tyr Tyr Lys Gly Glu
            100                 105                 110

Glu Asp Lys Ala Lys Pro Arg Gln Arg Ser Ser Pro Pro Phe Ser
        115                 120                 125

Thr Pro Ala Asp Gln Glu Tyr Arg Lys Lys Val Leu Arg Glu Leu Asn
    130                 135                 140

Ser Leu Ile Ser Gly Gly Val Ala Pro Ser Asp Asp Ala Val Asp Glu
145                 150                 155                 160

Glu Val Thr Asp Thr Glu Trp Phe Phe Leu Val Ser Met Thr Gln Ser
                165                 170                 175

Phe Ala Cys Gly Ala Gly Leu Ala Gly Arg Ala Phe Ser Thr Gly Asn
            180                 185                 190

Ala Val Trp Val Ser Gly Ser Asp Gln Leu Ser Gly Ser Gly Cys Glu
        195                 200                 205

Arg Ala Lys Gln Gly Gly Val Phe Gly Met Gln Thr Ile Ala Cys Ile
    210                 215                 220

Pro Ser Ala Asn Gly Val Val Glu Val Gly Ser Thr Glu Gln Ile Arg
225                 230                 235                 240

Gln Ser Ser Asp Leu Ile Asn Lys Val Arg Val Leu Phe Asn Leu Asp
                245                 250                 255

Gly Gly Ala Gly Asp Leu Ser Gly Leu Asp Trp Asn Leu Asp Pro Asp
            260                 265                 270

Gln Gly Glu Asn Asp Pro Ser Met Trp Ile Asn Asp Pro Ile Gly Ala
        275                 280                 285

Pro Gly Ser Asn Glu Pro Gly Asn Gly Ala Pro Ser Ser Ser Ser Gln
    290                 295                 300

```
Leu Phe Ser Lys Ser Ile Gln Phe Glu Asn Gly Ser Ser Thr Ile
305                 310                 315                 320

Thr Glu Asn Pro Asn Pro Asp Pro Thr Pro Ser Pro Val His Ser Gln
            325                 330                 335

Thr Gln Asn Pro Lys Phe Ser Asn Asn Phe Ser Arg Glu Leu Asn Phe
            340                 345                 350

Ser Thr Ser Ser Ser Thr Leu Val Lys Pro Arg Ser Gly Glu Ile Leu
            355                 360                 365

Ser Phe Gly Asp Asp Gly Lys Arg Gly Ser Gly Asn Pro Asp Pro Ser
370                 375                 380

Ser Tyr Ser Gly Gln Thr Gln Phe Glu Asn Lys Arg Lys Lys Ser Pro
385                 390                 395                 400

Asn Glu Asp Lys Val Leu Ser Phe Gly Asp Lys Thr Thr Gly Glu Ser
            405                 410                 415

Asp His Ser Asp Leu Glu Ala Ser Val Val Lys Glu Val Ala Val Glu
            420                 425                 430

Lys Arg Pro Lys Lys Arg Gly Arg Lys Pro Ala Asn Gly Arg Glu Glu
            435                 440                 445

Pro Leu Asn Xaa Met Ile Tyr Val Ile His Ser Pro Asn Pro
450                 455                 460

<210> SEQ ID NO 18
<211> LENGTH: 80
<212> TYPE: PRT
<213> ORGANISM: Camelina sativa

<400> SEQUENCE: 18

Gln Arg Leu Gln Ala Leu Ile Glu Gly Thr Asn Glu Gly Trp Thr Tyr
1               5                   10                  15

Ala Ile Phe Trp Gln Pro Ser Tyr Asp Phe Ser Gly Ala Ser Val Leu
            20                  25                  30

Gly Trp Gly Asp Gly Tyr Tyr Lys Gly Glu Glu Asp Lys Ala Lys Pro
        35                  40                  45

Arg Gln Arg Ser Ser Ser Pro Pro Phe Ser Thr Pro Ala Asp Gln Glu
    50                  55                  60

Tyr Arg Lys Lys Val Leu Arg Glu Leu Asn Ser Leu Ile Ser Gly Gly
65                  70                  75                  80

<210> SEQ ID NO 19
<211> LENGTH: 689
<212> TYPE: PRT
<213> ORGANISM: Solanum lycopersicum

<400> SEQUENCE: 19

Met Thr Glu Tyr Ser Leu Pro Thr Met Asn Leu Trp Asn Asn Ser Thr
1               5                   10                  15

Ser Asp Asp Asn Val Ser Met Met Glu Ala Phe Met Ser Ser Asp Leu
            20                  25                  30

Ser Phe Trp Ala Thr Asn Asn Ser Thr Ser Ala Ala Val Val Gly Val
        35                  40                  45

Asn Ser Asn Leu Pro His Ala Ser Ser Asn Thr Pro Ser Val Phe Ala
    50                  55                  60

Pro Ser Ser Ser Thr Ser Ala Ser Thr Leu Ser Ala Ala Ala Thr Val
65                  70                  75                  80

Asp Ala Ser Lys Ser Met Pro Phe Phe Asn Gln Glu Thr Leu Gln Gln
            85                  90                  95
```

```
Arg Leu Gln Ala Leu Ile Asp Gly Ala Arg Glu Thr Trp Thr Tyr Ala
                100                 105                 110
Ile Phe Trp Gln Ser Ser Val Val Asp Phe Ser Ser Pro Ser Val Leu
        115                 120                 125
Gly Trp Gly Asp Gly Tyr Tyr Lys Gly Glu Glu Asp Lys Ala Lys Arg
    130                 135                 140
Lys Leu Ser Val Ser Ser Pro Ala Tyr Ile Ala Glu Gln Glu His Arg
145                 150                 155                 160
Lys Lys Val Leu Arg Glu Leu Asn Ser Leu Ile Ser Gly Ala Pro Pro
                165                 170                 175
Gly Thr Asp Asp Ala Val Asp Glu Glu Val Thr Asp Thr Glu Trp Phe
        180                 185                 190
Phe Leu Ile Ser Met Thr Gln Ser Phe Val Asn Gly Ser Gly Leu Pro
    195                 200                 205
Gly Gln Ala Leu Tyr Ser Ser Pro Ile Trp Val Ala Gly Thr Glu
                210                 215                 220
Lys Leu Ala Ala Ser His Cys Glu Arg Val Arg Gln Ala Gln Gly Phe
225                 230                 235                 240
Gly Leu Gln Thr Ile Val Cys Ile Pro Ser Ala Asn Gly Val Val Glu
                245                 250                 255
Leu Gly Ser Thr Glu Leu Ile Val Gln Ser Ser Asp Leu Met Asn Lys
        260                 265                 270
Val Arg Val Leu Phe Asn Phe Ser Asn Asp Leu Gly Ser Gly Ser Trp
    275                 280                 285
Ala Val Gln Pro Glu Ser Asp Pro Ser Ala Leu Trp Leu Thr Asp Pro
290                 295                 300
Ser Ser Ser Gly Met Glu Val Arg Glu Ser Leu Asn Thr Val Gln Thr
305                 310                 315                 320
Asn Ser Val Pro Ser Ser Asn Ser Asn Lys Gln Ile Ala Tyr Gly Asn
                325                 330                 335
Glu Asn Asn His Pro Ser Gly Asn Gly Gln Ser Cys Tyr Asn Gln Gln
        340                 345                 350
Gln Gln Lys Asn Pro Pro Gln Gln Gln Thr Gln Gly Phe Phe Thr Arg
    355                 360                 365
Glu Leu Asn Phe Ser Glu Phe Gly Phe Asp Gly Ser Ser Asn Arg Asn
370                 375                 380
Gly Asn Ser Ser Val Ser Cys Lys Pro Glu Ser Gly Glu Ile Leu Asn
385                 390                 395                 400
Phe Gly Asp Ser Thr Lys Lys Ser Ala Ser Ser Ala Asn Val Asn Leu
                405                 410                 415
Phe Thr Gly Gln Ser Gln Phe Gly Ala Gly Glu Glu Asn Asn Asn Lys
        420                 425                 430
Asn Lys Lys Arg Ser Ala Thr Ser Arg Gly Ser Asn Glu Glu Gly Met
    435                 440                 445
Leu Ser Phe Val Ser Gly Thr Val Leu Pro Ser Ser Gly Met Lys Ser
450                 455                 460
Gly Gly Gly Gly Gly Glu Asp Ser Glu His Ser Asp Leu Glu Ala Ser
465                 470                 475                 480
Val Val Lys Glu Ala Asp Ser Ser Arg Val Val Glu Pro Glu Lys Arg
                485                 490                 495
Pro Arg Lys Arg Gly Arg Lys Pro Ala Asn Gly Arg Glu Glu Pro Leu
        500                 505                 510
Asn His Val Glu Ala Glu Arg Gln Arg Arg Glu Lys Leu Asn Gln Arg
```

```
              515                 520                 525
Phe Tyr Ala Leu Arg Ala Val Val Pro Asn Val Ser Lys Met Asp Lys
    530                 535                 540

Ala Ser Leu Leu Gly Asp Ala Ile Ser Tyr Ile Asn Glu Leu Lys Ser
545                 550                 555                 560

Lys Leu Gln Asn Thr Glu Ser Asp Lys Glu Asp Leu Lys Ser Gln Ile
                565                 570                 575

Glu Asp Leu Lys Lys Glu Ser Arg Arg Pro Gly Pro Pro Pro Pro Pro
            580                 585                 590

Asn Gln Asp Leu Lys Met Ser Ser His Thr Gly Gly Lys Ile Val Asp
        595                 600                 605

Val Asp Ile Asp Val Lys Ile Ile Gly Trp Asp Ala Met Ile Arg Ile
    610                 615                 620

Gln Cys Asn Lys Lys Asn His Pro Ala Ala Arg Leu Met Ala Ala Leu
625                 630                 635                 640

Met Glu Leu Asp Leu Asp Val His His Ala Ser Val Ser Val Val Asn
                645                 650                 655

Asp Leu Met Ile Gln Gln Ala Thr Val Lys Met Gly Ser Arg His Tyr
            660                 665                 670

Thr Glu Glu Gln Leu Arg Val Ala Leu Thr Ser Lys Ile Ala Glu Thr
        675                 680                 685

His

<210> SEQ ID NO 20
<211> LENGTH: 53
<212> TYPE: PRT
<213> ORGANISM: Solanum lycopersicumv

<400> SEQUENCE: 20

Phe Ser Ser Pro Ser Val Leu Gly Trp Gly Asp Gly Tyr Tyr Lys Gly
1               5                   10                  15

Glu Glu Asp Lys Ala Lys Arg Lys Leu Ser Val Ser Ser Pro Ala Tyr
            20                  25                  30

Ile Ala Glu Gln Glu His Arg Lys Lys Val Leu Arg Glu Leu Asn Ser
        35                  40                  45

Leu Ile Ser Gly Ala
    50

<210> SEQ ID NO 21
<211> LENGTH: 464
<212> TYPE: PRT
<213> ORGANISM: Solanum lycopersicum

<400> SEQUENCE: 21

Met Thr Asp Tyr Arg Leu Trp Ser Asn Thr Asn Thr Asn Thr Cys
1               5                   10                  15

Asp Asp Thr Met Met Met Asp Ser Phe Leu Ser Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95
```

Gly Asp Gly Tyr Tyr Lys Gly Glu Glu Asp Lys Asn Lys Arg Arg Gly
            100                 105                 110

Ser Ser Ser Ser Ala Ala Asn Phe Val Ala Glu Gln Glu His Arg Lys
            115                 120                 125

Lys Val Leu Arg Glu Leu Asn Ser Leu Ile Ser Gly Val Gln Ala Ser
            130                 135                 140

Ala Gly Asn Gly Thr Asp Asp Ala Val Asp Glu Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Pro Ile Trp Val Thr
            180                 185                 190

Gly Thr Glu Lys Leu Ala Ala Ser Gln Cys Glu Arg Ala Arg Gln Ala
            195                 200                 205

Gln Gly Phe Gly Leu Gln Thr Ile Val Cys Ile Pro Ser Pro Glu Ser
210                 215                 220

Arg Glu Ile Leu Asn Phe Gly Asp Ser Ser Lys Arg Phe Ser Gly Gln
225                 230                 235                 240

Ser Gln Leu Gly Pro Gly Pro Gly Leu Met Glu Glu Asn Lys Asn Lys
            245                 250                 255

Asn Lys Asn Lys Lys Arg Ser Leu Gly Ser Arg Gly Asn Asn Glu Glu
            260                 265                 270

Gly Met Leu Ser Phe Val Ser Gly Val Ile Leu Pro Thr Ser Thr Met
            275                 280                 285

Gly Lys Ser Gly Asp Ser Asp His Ser Asp Leu Glu Ala Ser Val Val
            290                 295                 300

Lys Glu Ala Val Val Glu Pro Glu Lys Lys Pro Arg Lys Arg Gly Arg
305                 310                 315                 320

Lys Pro Ala Asn Gly Arg Glu Glu Pro Leu Asn His Val Glu Ala Glu
                325                 330                 335

Arg Gln Arg Arg Glu Lys Leu Asn Gln Arg Phe Tyr Glu Leu Arg Ser
            340                 345                 350

Gln Ile Glu Cys Leu Arg Lys Glu Leu Thr Asn Lys Gly Ser Ser Asn
            355                 360                 365

Tyr Ser Ala Ser Pro Pro Leu Asn Gln Asp Val Lys Ile Val Asp Met
370                 375                 380

Asp Ile Asp Val Lys Val Ile Gly Trp Asp Ala Met Ile Arg Ile Gln
385                 390                 395                 400

Cys Ser Lys Lys Asn His Pro Ala Ala Arg Leu Met Ala Ala Leu Lys
                405                 410                 415

Asp Leu Asp Leu Asp Val His His Ala Ser Val Ser Val Val Asn Asp
            420                 425                 430

Leu Met Ile Gln Gln Ala Thr Val Lys Met Gly Ser Arg Leu Tyr Ala
            435                 440                 445

Gln Glu Gln Leu Arg Ile Ala Leu Thr Ser Lys Ile Ala Glu Ser Arg
            450                 455                 460

<210> SEQ ID NO 22
<211> LENGTH: 54
<212> TYPE: PRT
<213> ORGANISM: Solanum lycopersicum

<400> SEQUENCE: 22

Phe Ala Ser Gln Thr Val Leu Gly Trp Gly Asp Gly Tyr Tyr Lys Gly

```
1               5                   10                  15
Glu Glu Asp Lys Asn Lys Arg Arg Gly Ser Ser Ser Ser Ala Ala Asn
                20                  25                  30

Phe Val Ala Glu Gln Glu His Arg Lys Lys Val Leu Arg Glu Leu Asn
                35                  40                  45

Ser Leu Ile Ser Gly Val
        50

<210> SEQ ID NO 23
<211> LENGTH: 692
<212> TYPE: PRT
<213> ORGANISM: Solanum tuberosum

<400> SEQUENCE: 23

Met Thr Glu Tyr Ser Leu Pro Thr Met Asn Leu Trp Asn Asn Ser Thr
1               5                   10                  15

Ser Asp Asp Asn Val Ser Met Met Glu Ala Phe Met Ser Ser Asp Leu
                20                  25                  30

Ser Phe Trp Ala Thr Thr Asn Ser Thr Thr Asn Ser Ala Ser Ala
        35                  40                  45

Ala Val Val Gly Val Asn Ser Asn Leu Leu His Thr Asn Asn Asn Asn
    50                  55                  60

Pro Ser Val Phe Pro Leu Ser Ser Ser Thr Ser Val Ser Ala Ala Ala
65                  70                  75                  80

Ala Val Asp Ala Thr Lys Ser Met Pro Phe Phe Asn Gln Glu Thr Leu
                85                  90                  95

Gln Gln Arg Leu Gln Ala Leu Ile Asp Gly Ala Arg Glu Thr Trp Thr
                100                 105                 110

Tyr Ala Ile Phe Trp Gln Ser Ser Val Val Asp Phe Ser Ser Pro Ser
            115                 120                 125

Val Leu Gly Trp Gly Asp Gly Tyr Tyr Lys Gly Glu Glu Asp Lys Ala
        130                 135                 140

Lys Arg Lys Leu Ala Val Ser Ser Pro Ala Tyr Ile Ala Glu Gln Glu
145                 150                 155                 160

His Arg Lys Lys Val Leu Arg Glu Leu Asn Ser Leu Ile Ser Gly Ala
                165                 170                 175

Pro Ala Gly Thr Asp Asp Ala Val Asp Glu Glu Val Thr Asp Thr Glu
            180                 185                 190

Trp Phe Phe Leu Ile Ser Met Thr Gln Ser Phe Val Asn Gly Ser Gly
        195                 200                 205

Leu Pro Gly Gln Ala Leu Tyr Ser Ser Ser Pro Ile Trp Val Ala Gly
    210                 215                 220

Thr Glu Lys Leu Ala Ala Ser His Cys Glu Arg Val Arg Gln Ala Gln
225                 230                 235                 240

Gly Phe Gly Leu Gln Thr Ile Val Cys Ile Pro Ser Ala Asn Gly Val
                245                 250                 255

Val Glu Leu Gly Ser Thr Glu Leu Ile Val Glu Ser Ser Asp Leu Met
            260                 265                 270

Asn Lys Val Arg Val Leu Phe Asn Phe Ser Asn Asp Leu Gly Ser Gly
        275                 280                 285

Ser Trp Ala Val Gln Pro Glu Ser Asp Pro Ser Ala Leu Trp Leu Thr
    290                 295                 300

Glu Pro Ser Ser Ser Gly Met Glu Val Arg Glu Ser Leu Asn Thr Val
305                 310                 315                 320
```

```
Gln Thr Asn Ser Val Pro Ser Ser Asn Ser Asn Lys Gln Ile Ala Tyr
                325                 330                 335

Ala Asn Glu Asn His Gln Ser Gly Asn Gly Gln Ser Cys Tyr Asn
            340                 345                 350

Leu Gln Gln Gln Gln Asn Asn Pro Pro Gln Gln Gln Thr Gln Gly Phe
                355                 360                 365

Phe Thr Arg Glu Leu Asn Phe Ser Glu Phe Gly Phe Asp Gly Ser Ser
            370                 375                 380

Asn Arg Asn Gly Asn Ala Ser Leu Ser Cys Lys Pro Glu Ser Gly Glu
385                 390                 395                 400

Ile Leu Asn Phe Gly Asp Ser Thr Lys Lys Ser Ala Ser Ser Ala Asn
                405                 410                 415

Val Asn Leu Phe Thr Gly Gln Ser Gln Phe Gly Ala Val Glu Glu Asn
                420                 425                 430

Asn Asn Asn Lys Asn Lys Lys Arg Ser Ala Thr Ser Arg Gly Ser Asn
                435                 440                 445

Glu Glu Gly Met Leu Ser Phe Val Ser Gly Thr Val Leu Pro Ser Ser
    450                 455                 460

Gly Met Lys Ser Gly Gly Gly Gly Glu Asp Ser Glu His Ser Asp
465                 470                 475                 480

Leu Glu Ala Ser Val Val Lys Glu Ala Asp Ser Ser Arg Val Val Glu
                485                 490                 495

Pro Glu Lys Arg Pro Arg Lys Arg Gly Arg Lys Pro Ala Asn Gly Arg
                500                 505                 510

Glu Glu Pro Leu Asn His Val Glu Ala Glu Arg Gln Arg Arg Glu Lys
                515                 520                 525

Leu Asn Gln Arg Phe Tyr Ala Leu Arg Ala Val Val Pro Asn Val Ser
    530                 535                 540

Lys Met Asp Lys Ala Ser Leu Leu Gly Asp Ala Ile Ser Tyr Ile Asn
545                 550                 555                 560

Glu Leu Lys Ser Lys Leu Gln Asn Thr Glu Ser Asp Lys Glu Asp Leu
                565                 570                 575

Lys Ser Gln Ile Glu Asp Leu Lys Lys Glu Ser Arg Arg Pro Gly Pro
                580                 585                 590

Pro Pro Pro Asn Gln Asp Leu Lys Ile Gly Gly Lys Ile Val Asp Val
            595                 600                 605

Asp Ile Asp Val Lys Ile Ile Gly Trp Asp Ala Met Ile Gly Ile Gln
            610                 615                 620

Cys Asn Lys Lys Asn His Pro Ala Ala Arg Leu Met Ala Ala Leu Met
625                 630                 635                 640

Glu Leu Asp Leu Asp Val His His Ala Ser Val Ser Val Val Asn Asp
                645                 650                 655

Leu Met Ile Gln Gln Ala Thr Val Lys Met Gly Ser Arg His Tyr Thr
                660                 665                 670

Glu Glu Gln Leu Arg Val Ala Leu Lys Ser Lys Ile Ala Glu Thr Pro
                675                 680                 685

Leu Glu Ser Arg
    690

<210> SEQ ID NO 24
<211> LENGTH: 53
<212> TYPE: PRT
<213> ORGANISM: Solanum tuberosum

<400> SEQUENCE: 24
```

```
Phe Ser Ser Pro Ser Val Leu Gly Trp Gly Asp Gly Tyr Tyr Lys Gly
1               5                   10                  15

Glu Glu Asp Lys Ala Lys Arg Lys Leu Ala Val Ser Ser Pro Ala Tyr
            20                  25                  30

Ile Ala Glu Gln Glu His Arg Lys Lys Val Leu Arg Glu Leu Asn Ser
            35                  40                  45

Leu Ile Ser Gly Ala
        50
```

<210> SEQ ID NO 25
<211> LENGTH: 646
<212> TYPE: PRT
<213> ORGANISM: Solanum tuberosum

<400> SEQUENCE: 25

```
Met Thr Asp Tyr Arg Leu Trp Ser Asn Ser Asn Thr Asn Thr Asn Ser
1               5                   10                  15

Asp Asp Asn Met Met Asp Ala Phe Leu Ser Ser Asp Pro Ser Ser
            20                  25                  30

Phe Trp Pro Asn Arg Thr Ser Ile Ser Pro Thr Pro Val Asn Gly Gly
            35                  40                  45

Val Gly Glu Thr Met Pro Phe Phe Asn Gln Glu Ser Leu Gln Gln Arg
    50                  55                  60

Leu Gln Ala Leu Ile Asp Gly Ala Arg Glu Ser Trp Ala Tyr Ala Ile
65                  70                  75                  80

Phe Trp Gln Ser Ser Ser Thr Ser Asp Phe Ala Thr Pro Ser Val Leu
                85                  90                  95

Gly Trp Gly Asp Gly Tyr Tyr Lys Gly Glu Glu Asn Lys Asn Lys Arg
            100                 105                 110

Arg Ala Ser Ser Ser Ser Thr Asn Phe Val Ala Glu Gln Glu His Arg
            115                 120                 125

Lys Lys Val Leu Arg Glu Leu Asn Ser Leu Ile Ser Gly Val Gln Ala
        130                 135                 140

Thr Gly Ala Gly Ser Gly Gly Asp Asp Ala Val Asp Glu Glu Val Thr
145                 150                 155                 160

Asp Thr Glu Trp Phe Phe Leu Ile Ser Met Thr Gln Ser Phe Ala Asn
                165                 170                 175

Gly Asn Gly Leu Pro Gly Leu Ala Met Tyr Ser Ser Pro Ile Trp
            180                 185                 190

Val Thr Gly Thr Glu Lys Leu Ala Gly Ser Gln Cys Glu Arg Ala Arg
            195                 200                 205

Gln Ala Gln Gly Phe Gly Leu Gln Thr Ile Val Cys Ile Pro Ser Ala
        210                 215                 220

Asn Gly Val Val Glu Leu Gly Ser Thr Glu Leu Ile Phe Glu Ser Ser
225                 230                 235                 240

Asp Leu Met Asn Lys Val Lys Tyr Leu Phe Asn Phe Asn Ile Asp Met
                245                 250                 255

Gly Ser Val Thr Gly Ser Gly Ser Gly Ser Cys Ala Val His Pro Glu
            260                 265                 270

Pro Asp Pro Ser Ala Leu Trp Leu Thr Asp Pro Ser Ser Ser Val Val
            275                 280                 285

Glu Ala Lys Asp Ser Leu Ile Asn Ser Ser Ser Arg Asp Val Gln Leu
        290                 295                 300

Val Phe Gly Asn Glu Asn Ser Glu Asn Gly Thr Gln Asn Gln Gln His
```

```
                305                 310                 315                 320
Ser Gln Gln Thr Gln Gly Phe Phe Thr Lys Glu Leu Asn Phe Ser Gly
                    325                 330                 335

Tyr Gly Phe Asp Gly Ser Ser Thr Arg Asn Lys Asn Gly Asn Ser Ser
                340                 345                 350

Ile Ser Cys Lys Pro Glu Thr Arg Glu Ile Leu Asn Phe Gly Asp Ser
            355                 360                 365

Ser Lys Lys Ser Gly Ser Leu Phe Ser Gly Ser Gln Phe Gly Pro
370                 375                 380

Gly Thr Gly Leu Gly Leu Met Glu Glu Asn Lys Asn Asn Asn Lys Lys
385                 390                 395                 400

Arg Ser Leu Ala Ser Arg Gly Asn Asn Glu Lys Gly Met Leu Ser Phe
                405                 410                 415

Val Ser Gly Val Ile Leu Pro Thr Ser Thr Met Gly Lys Ser Gly Gly
                420                 425                 430

Gly Gly Asn Phe Asp His Ser Asp Leu Glu Ala Ser Val Val Lys Glu
                435                 440                 445

Ala Ile Val Glu Pro Glu Arg Lys Pro Arg Lys Arg Gly Arg Lys Pro
            450                 455                 460

Ala Asn Gly Arg Glu Glu Pro Leu Asn His Val Glu Ala Glu Arg Gln
465                 470                 475                 480

Arg Arg Glu Lys Leu Asn Gln Arg Phe Tyr Ala Leu Arg Ala Val Val
                485                 490                 495

Pro Asn Val Ser Lys Met Asp Lys Ala Ser Leu Leu Gly Asp Ala Ile
                500                 505                 510

Ala Tyr Ile Asn Glu Leu Lys Ser Lys Val Gln Asn Ser Asp Leu Asp
            515                 520                 525

Lys Glu Glu Leu Arg Ser Gln Ile Glu Ser Leu Arg Lys Glu Leu Ala
530                 535                 540

Asn Lys Gly Ser Ser Asn Tyr Ser Ser Ser Pro Pro Ser Asn Gln Asp
545                 550                 555                 560

Leu Lys Ile Val Asp Met Asp Ile Asp Val Lys Val Ile Gly Trp Asp
                565                 570                 575

Ala Met Ile Arg Ile Gln Cys Ser Lys Lys Asn His Pro Ala Ala Arg
                580                 585                 590

Leu Met Ala Ala Leu Lys Asp Leu Asp Leu Asp Val His His Ala Ser
                595                 600                 605

Val Ser Val Val Asn Asp Leu Met Ile Gln Gln Ala Thr Val Lys Met
            610                 615                 620

Gly Ser Arg Leu Tyr Ala Gln Glu Gln Leu Thr Ile Ala Leu Thr Ser
625                 630                 635                 640

Lys Phe Ala Glu Ser Arg
                645

<210> SEQ ID NO 26
<211> LENGTH: 53
<212> TYPE: PRT
<213> ORGANISM: Solanum tuberosum

<400> SEQUENCE: 26

Phe Ala Thr Pro Ser Val Leu Gly Trp Gly Asp Gly Tyr Tyr Lys Gly
1               5                   10                  15

Glu Glu Asn Lys Asn Lys Arg Arg Ala Ser Ser Ser Thr Asn Phe
            20                  25                  30
```

```
Val Ala Glu Gln Glu His Arg Lys Lys Val Leu Arg Glu Leu Asn Ser
         35                  40                  45

Leu Ile Ser Gly Val
         50

<210> SEQ ID NO 27
<211> LENGTH: 699
<212> TYPE: PRT
<213> ORGANISM: Catharanthus roseus

<400> SEQUENCE: 27

Met Thr Asp Tyr Arg Leu Gln Pro Lys Met Asn Leu Trp Gly Thr Thr
1               5                   10                  15

Thr Asn Thr Ala Ala Ser Pro Ile Ile Thr Ser Asp Asp Asn Ser Ser
            20                  25                  30

Met Met Glu Ala Phe Met Thr Ser Ser Asp Pro Ile Ser Leu Trp Pro
         35                  40                  45

Pro Ser Met Ser Val Asn His His Pro Pro Thr Pro Thr Ser Ser
     50                  55                  60

Ala Val Thr Thr Ala Val Asp Ser Ala Lys Ser Met Pro Ala Gln Pro
65                  70                  75                  80

Ala Phe Phe Asn Gln Glu Asn Leu Gln Gln Arg Leu Gln Thr Leu Ile
                85                  90                  95

Asp Gly Ala Arg Glu Ser Trp Thr Tyr Ala Ile Phe Trp Gln Ser Ser
            100                 105                 110

Val Val Glu Phe Ala Gly Pro Ser Val Leu Gly Trp Gly Asp Gly Tyr
         115                 120                 125

Tyr Lys Gly Glu Glu Asp Lys Gly Lys Arg Lys Asn Ser Ser Ser Ala
130                 135                 140

Ser Ser Phe Ala Glu Gln Glu His Arg Lys Lys Val Leu Arg Glu Leu
145                 150                 155                 160

Asn Ser Leu Ile Ala Gly Pro Gln Gly Thr Ala Asp Asp Ala Val Asp
                165                 170                 175

Glu Glu Val Thr Asp Thr Glu Trp Phe Phe Leu Ile Ser Met Thr Gln
            180                 185                 190

Ser Phe Val Ser Gly Ser Gly Leu Pro Gly Gln Ala Leu Tyr Asn Ser
         195                 200                 205

Asn Pro Val Trp Val Thr Gly Ala Gly Arg Leu Ala Val Ser His Cys
     210                 215                 220

Asp Arg Ala Arg Gln Ala Gln Ser Phe Gly Leu Gln Thr Leu Val Cys
225                 230                 235                 240

Ile Pro Ser Ala Asn Gly Val Val Glu Leu Gly Ser Thr Glu Leu Ile
                245                 250                 255

Phe Gln Ser Ser Asp Leu Met Asn Lys Val Arg Ile Leu Phe Asn Phe
            260                 265                 270

Asn Asn Ile Asp Leu Gly Ser Ser Gly Pro Trp Pro Glu Asn Asp
         275                 280                 285

Pro Ser Ser Leu Trp Leu Thr Asp Pro Ser Pro Ser Gly Val Gly Val
     290                 295                 300

Lys Glu Gly Val Asn Thr Asn Asn Thr Ser Val Gln Gly Asn Ser
305                 310                 315                 320

Ile Pro Ser Gly Asn Lys Gln Gln Leu Val Phe Gly Asn Asn Asp Asn
                325                 330                 335

His Pro Thr Thr Ser Thr Leu Thr Asp His Pro Gly Ala Gly Ala Val
            340                 345                 350
```

```
Asn Ser Tyr Asn Asn Ser Ser Gln Asn Ala Gln Gln Pro Gln Gly Ser
        355                 360                 365

Phe Phe Thr Arg Glu Leu Asn Phe Ser Glu Tyr Gly Phe Glu Arg Ser
        370                 375                 380

Ser Val Lys Asn Gly Asn Cys Lys Pro Glu Ser Gly Glu Ile Leu Asn
385                 390                 395                 400

Phe Gly Gly Glu Ser Val Thr Lys Lys Asn Ser Val Ser Gly Asn Gly
                405                 410                 415

Asn Leu Phe Ser Val Gln Ser Gln Phe Gly Ala Gly Glu Glu Asn Lys
            420                 425                 430

Asn Lys Lys Arg Pro Ser Pro Val Ser Arg Gly Ser Asn Asp Glu Gly
        435                 440                 445

Met Leu Ser Phe Thr Ser Gly Val Val Leu Pro Ser Thr Gly Val Val
        450                 455                 460

Lys Ser Ser Gly Gly Gly Gly Gly Asp Ser Asp His Ser Asp Leu
465                 470                 475                 480

Glu Ala Ser Val Val Lys Glu Ala Glu Ser Ser Arg Val Val Asp Pro
                485                 490                 495

Glu Lys Arg Pro Arg Lys Arg Gly Arg Lys Pro Ala Asn Gly Arg Glu
            500                 505                 510

Glu Pro Leu Asn His Val Glu Ala Glu Arg Gln Arg Glu Lys Leu
        515                 520                 525

Asn Gln Arg Phe Tyr Ala Leu Arg Ala Val Val Pro Asn Val Ser Lys
        530                 535                 540

Met Asp Lys Ala Ser Leu Leu Gly Asp Ala Ile Ser Tyr Ile Asn Glu
545                 550                 555                 560

Leu Lys Ala Lys Leu Gln Thr Thr Glu Thr Asp Lys Asp Glu Leu Lys
                565                 570                 575

Asn Gln Leu Asp Ser Leu Lys Lys Glu Leu Ala Ser Lys Glu Ser Arg
            580                 585                 590

Leu Leu Ser Ser Pro Asp Gln Asp Leu Lys Ser Ser Asn Lys Gln Ser
        595                 600                 605

Val Gly Asn Leu Asp Met Asp Ile Asp Val Lys Ile Ile Gly Arg Glu
        610                 615                 620

Ala Met Ile Arg Val Gln Ser Ser Lys Asn Asn His Pro Ala Ala Arg
625                 630                 635                 640

Val Met Gly Ala Leu Lys Asp Leu Asp Leu Glu Leu His Ala Ser
                645                 650                 655

Val Ser Val Val Asn Asp Leu Met Ile Gln Gln Asn Thr Val Arg Met
            660                 665                 670

Gly Ser Arg Phe Tyr Thr Gln Glu Gln Leu Arg Ile Ala Leu Thr Ser
        675                 680                 685

Arg Ile Ala Gly Asn Ser Met Arg Leu Leu Val
    690                 695

<210> SEQ ID NO 28
<211> LENGTH: 51
<212> TYPE: PRT
<213> ORGANISM: Catharanthus roseus

<400> SEQUENCE: 28

Phe Ala Gly Pro Ser Val Leu Gly Trp Gly Asp Gly Tyr Tyr Lys Gly
1               5                   10                  15

Glu Glu Asp Lys Gly Lys Arg Lys Asn Ser Ser Ser Ala Ser Ser Phe
```

```
                20                  25                  30
Ala Glu Gln Glu His Arg Lys Lys Val Leu Arg Glu Leu Asn Ser Leu
            35                  40                  45

Ile Ala Gly
    50

<210> SEQ ID NO 29

<400> SEQUENCE: 29

000

<210> SEQ ID NO 30
<211> LENGTH: 1172
<212> TYPE: PRT
<213> ORGANISM: Arabidopsis thaliana

<400> SEQUENCE: 30

Met Val Ser Gly Val Gly Gly Ser Gly Gly Gly Arg Gly Gly Gly Arg
1               5                   10                  15

Gly Gly Glu Glu Glu Pro Ser Ser His Thr Pro Asn Asn Arg Arg
            20                  25                  30

Gly Gly Glu Gln Ala Gln Ser Ser Gly Thr Lys Ser Leu Arg Pro Arg
            35                  40                  45

Ser Asn Thr Glu Ser Met Ser Lys Ala Ile Gln Gln Tyr Thr Val Asp
    50                  55                  60

Ala Arg Leu His Ala Val Phe Glu Gln Ser Gly Glu Ser Gly Lys Ser
65                  70                  75                  80

Phe Asp Tyr Ser Gln Ser Leu Lys Thr Thr Thr Tyr Gly Ser Ser Val
                85                  90                  95

Pro Glu Gln Gln Ile Thr Ala Tyr Leu Ser Arg Ile Gln Arg Gly Gly
            100                 105                 110

Tyr Ile Gln Pro Phe Gly Cys Met Ile Ala Val Asp Glu Ser Ser Phe
        115                 120                 125

Arg Ile Ile Gly Tyr Ser Glu Asn Ala Arg Glu Met Leu Gly Ile Met
    130                 135                 140

Pro Gln Ser Val Pro Thr Leu Glu Lys Pro Glu Ile Leu Ala Met Gly
145                 150                 155                 160

Thr Asp Val Arg Ser Leu Phe Thr Ser Ser Ser Ile Leu Leu Glu
                165                 170                 175

Arg Ala Phe Val Ala Arg Glu Ile Thr Leu Leu Asn Pro Val Trp Ile
            180                 185                 190

His Ser Lys Asn Thr Gly Lys Pro Phe Tyr Ala Ile Leu His Arg Ile
        195                 200                 205

Asp Val Gly Val Val Ile Asp Leu Glu Pro Ala Arg Thr Glu Asp Pro
    210                 215                 220

Ala Leu Ser Ile Ala Gly Ala Val Gln Ser Gln Lys Leu Ala Val Arg
225                 230                 235                 240

Ala Ile Ser Gln Leu Gln Ala Leu Pro Gly Gly Asp Ile Lys Leu Leu
                245                 250                 255

Cys Asp Thr Val Val Glu Ser Val Arg Asp Leu Thr Gly Tyr Asp Arg
            260                 265                 270

Val Met Val Tyr Lys Phe His Glu Asp Glu His Gly Glu Val Val Ala
        275                 280                 285

Glu Ser Lys Arg Asp Asp Leu Glu Pro Tyr Ile Gly Leu His Tyr Pro
    290                 295                 300
```

-continued

```
Ala Thr Asp Ile Pro Gln Ala Ser Arg Phe Leu Phe Lys Gln Asn Arg
305                 310                 315                 320

Val Arg Met Ile Val Asp Cys Asn Ala Thr Pro Val Leu Val Val Gln
            325                 330                 335

Asp Asp Arg Leu Thr Gln Ser Met Cys Leu Val Gly Ser Thr Leu Arg
        340                 345                 350

Ala Pro His Gly Cys His Ser Gln Tyr Met Ala Asn Met Gly Ser Ile
    355                 360                 365

Ala Ser Leu Ala Met Ala Val Ile Ile Asn Gly Asn Glu Asp Asp Gly
370                 375                 380

Ser Asn Val Ala Ser Gly Arg Ser Ser Met Arg Leu Trp Gly Leu Val
385                 390                 395                 400

Val Cys His His Thr Ser Ser Arg Cys Ile Pro Phe Pro Leu Arg Tyr
            405                 410                 415

Ala Cys Glu Phe Leu Met Gln Ala Phe Gly Leu Gln Leu Asn Met Glu
        420                 425                 430

Leu Gln Leu Ala Leu Gln Met Ser Glu Lys Arg Val Leu Arg Thr Gln
    435                 440                 445

Thr Leu Leu Cys Asp Met Leu Leu Arg Asp Ser Pro Ala Gly Ile Val
450                 455                 460

Thr Gln Ser Pro Ser Ile Met Asp Leu Val Lys Cys Asp Gly Ala Ala
465                 470                 475                 480

Phe Leu Tyr His Gly Lys Tyr Pro Leu Gly Val Ala Pro Ser Glu
            485                 490                 495

Val Gln Ile Lys Asp Val Val Glu Trp Leu Leu Ala Asn His Ala Asp
        500                 505                 510

Ser Thr Gly Leu Ser Thr Asp Ser Leu Gly Asp Ala Gly Tyr Pro Gly
    515                 520                 525

Ala Ala Ala Leu Gly Asp Ala Val Cys Gly Met Ala Val Ala Tyr Ile
530                 535                 540

Thr Lys Arg Asp Phe Leu Phe Trp Phe Arg Ser His Thr Ala Lys Glu
545                 550                 555                 560

Ile Lys Trp Gly Gly Ala Lys His His Pro Glu Asp Lys Asp Asp Gly
            565                 570                 575

Gln Arg Met His Pro Arg Ser Ser Phe Gln Ala Phe Leu Glu Val Val
        580                 585                 590

Lys Ser Arg Ser Gln Pro Trp Glu Thr Ala Glu Met Asp Ala Ile His
    595                 600                 605

Ser Leu Gln Leu Ile Leu Arg Asp Ser Phe Lys Glu Ser Glu Ala Ala
610                 615                 620

Met Asn Ser Lys Val Val Asp Gly Val Val Gln Pro Cys Arg Asp Met
625                 630                 635                 640

Ala Gly Glu Gln Gly Ile Asp Glu Leu Gly Ala Val Ala Arg Glu Met
            645                 650                 655

Val Arg Leu Ile Glu Thr Ala Thr Val Pro Ile Phe Ala Val Asp Ala
        660                 665                 670

Gly Gly Cys Ile Asn Gly Trp Asn Ala Lys Ile Ala Glu Leu Thr Gly
    675                 680                 685

Leu Ser Val Glu Glu Ala Met Gly Lys Ser Leu Val Ser Asp Leu Ile
690                 695                 700

Tyr Lys Glu Asn Glu Ala Thr Val Asn Lys Leu Leu Ser Arg Ala Leu
705                 710                 715                 720
```

-continued

```
Arg Gly Asp Glu Glu Lys Asn Val Glu Val Lys Leu Lys Thr Phe Ser
            725                 730                 735
Pro Glu Leu Gln Gly Lys Ala Val Phe Val Val Asn Ala Cys Ser
            740                 745                 750
Ser Lys Asp Tyr Leu Asn Asn Ile Val Gly Val Cys Phe Val Gly Gln
            755                 760                 765
Asp Val Thr Ser Gln Lys Ile Val Met Asp Lys Phe Ile Asn Ile Gln
            770                 775                 780
Gly Asp Tyr Lys Ala Ile Val His Ser Pro Asn Pro Leu Ile Pro Pro
785                 790                 795                 800
Ile Phe Ala Ala Asp Glu Asn Thr Cys Cys Leu Glu Trp Asn Met Ala
                    805                 810                 815
Met Glu Lys Leu Thr Gly Trp Ser Arg Ser Glu Val Ile Gly Lys Met
            820                 825                 830
Ile Val Gly Glu Val Phe Gly Ser Cys Cys Met Leu Lys Gly Pro Asp
            835                 840                 845
Ala Leu Thr Lys Phe Met Ile Val Leu His Asn Ala Ile Gly Gly Gln
            850                 855                 860
Asp Thr Asp Lys Phe Pro Phe Pro Phe Phe Asp Arg Asn Gly Lys Phe
865                 870                 875                 880
Val Gln Ala Leu Leu Thr Ala Asn Lys Arg Val Ser Leu Glu Gly Lys
                    885                 890                 895
Val Ile Gly Ala Phe Cys Phe Leu Gln Ile Pro Ser Pro Glu Leu Gln
            900                 905                 910
Gln Ala Leu Ala Val Gln Arg Arg Gln Asp Thr Glu Cys Phe Thr Lys
            915                 920                 925
Ala Lys Glu Leu Ala Tyr Ile Cys Gln Val Ile Lys Asn Pro Leu Ser
            930                 935                 940
Gly Met Arg Phe Ala Asn Ser Leu Leu Glu Ala Thr Asp Leu Asn Glu
945                 950                 955                 960
Asp Gln Lys Gln Leu Leu Glu Thr Ser Val Ser Cys Glu Lys Gln Ile
                    965                 970                 975
Ser Arg Ile Val Gly Asp Met Asp Leu Glu Ser Ile Glu Asp Gly Ser
            980                 985                 990
Phe Val Leu Lys Arg Glu Glu Phe Phe Leu Gly Ser Val Ile Asn Ala
            995                 1000                1005
Ile Val Ser Gln Ala Met Phe Leu Leu Arg Asp Arg Gly Leu Gln Leu
            1010                1015                1020
Ile Arg Asp Ile Pro Glu Glu Ile Lys Ser Ile Glu Val Phe Gly Asp
1025                1030                1035                1040
Gln Ile Arg Ile Gln Gln Leu Leu Ala Glu Phe Leu Leu Ser Ile Ile
                    1045                1050                1055
Arg Tyr Ala Pro Ser Gln Glu Trp Val Glu Ile His Leu Ser Gln Leu
            1060                1065                1070
Ser Lys Gln Met Ala Asp Gly Phe Ala Ala Ile Arg Thr Glu Phe Arg
            1075                1080                1085
Met Ala Cys Pro Gly Glu Gly Leu Pro Pro Glu Leu Val Arg Asp Met
            1090                1095                1100
Phe His Ser Ser Arg Trp Thr Ser Pro Glu Gly Leu Gly Leu Ser Val
1105                1110                1115                1120
Cys Arg Lys Ile Leu Lys Leu Met Asn Gly Glu Val Gln Tyr Ile Arg
                    1125                1130                1135
Glu Ser Glu Arg Ser Tyr Phe Leu Ile Ile Leu Glu Leu Pro Val Pro
```

1140            1145            1150
Arg Lys Arg Pro Leu Ser Thr Ala Ser Gly Ser Gly Asp Met Met Leu
        1155            1160            1165

Met Met Pro Tyr
    1170

<210> SEQ ID NO 31
<211> LENGTH: 4550
<212> TYPE: DNA
<213> ORGANISM: Arabidopsis thaliana

<400> SEQUENCE: 31

```
cttcaattta ttttattggt ttctccactt atctccgatc tcaattctcc ccattttctt       60
cttcctcaag ttcaaaattc ttgagaattt agctctacca gaattcgtct ccgataacta      120
gtggatgatg attcacccta aatccttcct tgtctcaagg taattctgag aaatttctca      180
aattcaaaat caaacggcat ggtttccgga gtcgggggta gtggcggtgg ccgtggcggt      240
ggccgtggcg gagaagaaga accgtcgtca agtcacactc ctaataaccg aagaggagga      300
gaacaagctc aatcgtcggg aacgaaatct ctcagaccaa gaagcaacac tgaatcaatg      360
agcaaagcaa ttcaacagta caccgtcgac gcaagactcc acgccgtttt cgaacaatcc      420
ggcgaatcag ggaaatcatt cgactactca caatcactca aaacgacgac gtacggttcc      480
tctgtacctg agcaacagat cacagcttat ctctctcgaa tccagcgagg tggttacatt      540
cagcctttcg gatgtatgat cgccgtcgat gaatccagtt tccggatcat cggttacagt      600
gaaaacgcca gagaaatgtt agggattatg cctcaatctg ttcctactct tgagaaacct      660
gagattctag ctatgggaac tgatgtgaga tctttgttca cttcttcgag ctcgattcta      720
ctcgagcgtg ctttcgttgc tcgagagatt accttgttaa atccggtttg gatccattcc      780
aagaatactg gtaaaccgtt ttacgccatt cttcatagga ttgatgttgg tgttgttatt      840
gatttagagc cagctagaac tgaagatcct gcgctttcta ttgctggtgc tgttcaatcg      900
cagaaactcg cggttcgtgc gatttctcag ttacaggctc ttcctggtgg agatattaag      960
cttttgtgtg acactgtcgt ggaaagtgtg agggacttga ctggttatga tcgtgttatg     1020
gtttataagt tcatgaaga tgagcatgga gaagttgtag ctgagagtaa acgagatgat     1080
ttagagcctt atattggact gcattatcct gctactgata ttcctcaagc gtcaaggttc     1140
ttgtttaagc agaaccgtgt ccgaatgata gtagattgca atgccacacc tgttcttgtg     1200
gtccaggacg ataggctaac tcagtctatg tgcttggttg ttctactct tagggctcct     1260
catggttgtc actctcagta tatggctaac atgggatcta ttgcgtcttt agcaatggcg     1320
gttataatca atggaaatga agatgatggg agcaatgtag ctagtggaag aagctcgatg     1380
aggctttggg gtttggttgt tgccatcac acttcttctc gctgcatacc gtttccgcta     1440
aggtatgctt gtgagttttt gatgcaggct ttcggtttac agttaaacat ggaattgcag     1500
ttagctttgc aaatgtcaga gaaacgcgtt ttgagaacgc agacactgtt atgtgatatg     1560
cttctgcgtg actcgcctgc tggaattgtt acacagagtc ccagtatcat ggacttagtg     1620
aaatgtgacg gtgcagcatt tctttaccac gggaagtatt acccgttggg tgttgctcct     1680
agtgaagttc agataaaaga tgttgtggag tggttgcttg cgaatcatgc ggattcaacc     1740
ggattaagca ctgatagttt aggcgatgcg gggtatcccg tgcagctgc gttaggggat     1800
gctgtgtgcg gtatggcagt tgcatatatc acaaaaagag acttttcttt ttggtttcga     1860
tctcacactg cgaaagaaat caaatgggga ggcgctaagc atcatccgga ggataaagat     1920
```

```
gatgggcaac gaatgcatcc tcgttcgtcc tttcaggctt ttcttgaagt tgttaagagc    1980
cggagtcagc catgggaaac tgcggaaatg gatgcgattc actcgctcca gcttattctg    2040
agagactctt ttaaagaatc tgaggcggct atgaactcta aagttgtgga tggtgtggtt    2100
cagccatgta gggatatggc gggggaacag gggattgatg agttaggtgc agttgcaaga    2160
gagatggtta ggctcattga gactgcaact gttcctatat tcgctgtgga tgccggaggc    2220
tgcatcaatg gatggaacgc taagattgca gagttgacag gtctctcagt tgaagaagct    2280
atggggaagt ctctggtttc tgatttaata tacaaagaga atgaagcaac tgtcaataag    2340 cttcttttctc gtgctttgag aggtatattc agttcttcag ctatgttgta tctgcggtgt    2400
atataccaat tcgcgggtat ttgattattt tgttgcattt ggcaatgcag gggacgagga    2460
aaagaatgtg gaggttaagc tgaaaacttt cagccccgaa ctacaaggga aagcagtttt    2520
tgtggttgtg aatgcttgtt ccagcaagga ctacttgaac aacattgtcg gcgtttgttt    2580
tgttggacaa gacgttacta gtcagaaaat cgtaatggat aagttcatca acatacaagg    2640
agattacaag gctattgtac atagcccaaa ccctctaatc ccgccaattt ttgctgctga    2700
cgagaacacg tgctgcctgg aatgaacat ggcgatggaa aagcttacgg gttggtctcg    2760
cagtgaagtg attgggaaaa tgattgtcgg ggaagtgttt gggagctgtt gcatgctaaa    2820
gggtcctgat gctttaacca agttcatgat tgtattgcat aatgcgattg gtggccaaga    2880
tacggataag ttccctttcc cattctttga ccgcaatggg aagtttgttc aggctctatt    2940
gactgcaaac aagcgggtta gcctcgaggg aaaggttatt ggggctttct gtttcttgca    3000
aatcccgagc cctgagctgc agcaagcttt agcagtccaa cggaggcagg acacagagtg    3060
tttcacgaag gcaaaagagt tggcttatat ttgtcaggtg ataaagaatc ctttgagcgg    3120
tatgcgtttc gcaaactcat tgttggaggc cacagacttg aacgaggacc agaagcagtt    3180
acttgaaaca agtgtttctt gcgagaaaca gatctcaagg atcgtcgggg acatggatct    3240
tgaaagcatt gaagacgggt gagtatagtt agaatttatc tagaagctag ttttgcttac    3300
ttcacaaaat gtgaccaaat cccaaatttt gttttttttca ttgatcagtt catttgtgct    3360
aaagagggaa gagtttttcc ttggaagtgt cataaacgcg attgtaagtc aagcgatgtt    3420
cttattaagg gacagaggtc ttcagctgat ccgtgacatt cccgaagaga tcaaatcaat    3480
agaggttttt ggagaccaga taaggattca acagctcctg gctgagtttc tgctgagtat    3540
aatccggtat gcaccatctc aagagtgggt ggagatccat ttaagccaac tttcaaagca    3600
aatggctgat ggattcgccg ccatccgcac agaattcagg tacatttcat tgttcccgct    3660
gttgtctcca catatccata accaaaatta tgcaatccgg tttttttggt tccttatttt    3720
gtacataaag aaaatgaatt tggtttggtt aattacgaat tgatttagg cgtttaaaga    3780 atttgaggtt ttaaccaatt cactatttgt tttggttatt gtttagttgg aacctagatt    3840
agtttgattt ttgtattcgg tttagtcgac ttgggaactt ttagacacat ccataggcct    3900
agaattagca gtcaaggaat gtaatgtttt caaattgatg aaaaccagct caaaagtgta    3960
aaacttgggt ttcatgtgtt ggtgtctttg ttatgtcttt attcgttgtt tgcagaatgg    4020
cgtgtccagg tgaaggtctg cctccagagc tagtccgaga catgttccat agcagcaggt    4080
ggacaagccc tgaaggttta ggtctaagcg tatgtcgaaa gattttaaag ctaatgaacg    4140
gtgaggttca atacatccga gaatcagaac ggtcctattt cctcatcatt ctggaactcc    4200
ctgtacctcg aaagcgacca ttgtcaactg ctagtggaag tggtgacatg atgctgatga    4260
```

-continued

```
tgccatatta gtcacacttc agttggtatg agagtttgta tcattgtatg agtgtttgtg    4320
tgtctaacga cgtcggagga ggatagaaag ttttttttt gtttccggtg agattagtag     4380
agaagaggga gattatttgc gttcagctca gctcgccgga aaaaaaacgt aacagtagtt    4440
gtagagaatt tcaagacttt tgtttgtgct gtgtaaattg acaactccga gagaaacaaa    4500
acaatgagat aagaagagag catattaatc gatgaccaat ccttttaatt              4550
```

<210> SEQ ID NO 32
<211> LENGTH: 1161
<212> TYPE: PRT
<213> ORGANISM: Zea mays

<400> SEQUENCE: 32

```
Met Ala Ser Gly Ser Arg Ala Thr Pro Thr Arg Ser Pro Ser Ala
1               5                   10                  15

Arg Pro Glu Ala Pro Arg His Ala His His His His Ser Gln Ser
                20                  25                  30

Ser Gly Gly Ser Thr Ser Arg Ala Gly Gly Ala Ala Ala Thr Glu
            35                  40                  45

Ser Val Ser Lys Ala Val Ala Gln Tyr Thr Leu Asp Ala Arg Leu His
50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Glu Gln Gln Ile Ala
                85                  90                  95

Ala Tyr Leu Ser Arg Ile Gln Arg Gly Gly His Ile Gln Pro Phe Gly
                100                 105                 110

Cys Thr Leu Ala Val Ala Asp Asp Ser Ser Phe Arg Leu Leu Ala Phe
            115                 120                 125

Ser Glu Asn Ser Pro Asp Leu Leu Asp Leu Ser Pro His His Ser Val
130                 135                 140

Pro Ser Leu Asp Ser Ser Ala Pro Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
                180                 185                 190

Arg Val Ser Ser Lys Pro Phe Tyr Ala Ile Leu His Arg Ile Asp Val
            195                 200                 205

Gly Val Val Ile Asp Leu Glu Pro Ala Arg Thr Glu Asp Pro Ala Leu
    210                 215                 220

Ser Ile Ala Gly Ala Val Gln Ser Gln Lys Leu Ala Val Arg Ala Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
```

-continued

```
                325                 330                 335
Gly Leu Ser Gln Pro Leu Cys Leu Val Gly Ser Thr Leu Arg Ala Pro
            340                 345                 350
His Gly Cys His Ala Gln Tyr Met Ala Asn Met Gly Ser Ile Ala Ser
            355                 360                 365
Leu Val Met Ala Val Ile Ile Ser Ser Gly Gly Asp Asp Glu Gln Thr
            370                 375                 380
Gly Arg Gly Gly Ile Ser Ser Ala Met Lys Leu Trp Gly Leu Val Val
385                 390                 395                 400
Cys His His Thr Ser Pro Arg Cys Ile Pro Phe Pro Leu Arg Tyr Ala
            405                 410                 415
Cys Glu Phe Leu Met Gln Ala Phe Gly Leu Gln Leu Asn Met Glu Leu
            420                 425                 430
Gln Leu Ala His Gln Leu Ser Glu Lys His Ile Leu Arg Thr Gln Thr
            435                 440                 445
Leu Leu Cys Asp Met Leu Leu Arg Asp Ser Pro Thr Gly Ile Val Thr
            450                 455                 460
Gln Ser Pro Ser Ile Met Asp Leu Val Lys Cys Asp Gly Ala Ala Leu
465                 470                 475                 480
Tyr Tyr His Gly Lys Tyr Tyr Pro Leu Gly Val Thr Pro Thr Glu Ser
            485                 490                 495
Gln Ile Lys Asp Ile Ile Glu Trp Leu Thr Val Phe His Gly Asp Ser
            500                 505                 510
Thr Gly Leu Ser Thr Asp Ser Leu Ala Asp Ala Gly Tyr Leu Gly Ala
            515                 520                 525
Ala Ala Leu Gly Glu Ala Val Cys Gly Met Ala Val Ala Tyr Ile Thr
            530                 535                 540
Pro Ser Asp Tyr Leu Phe Trp Phe Arg Ser His Thr Ala Lys Glu Ile
545                 550                 555                 560
Lys Trp Gly Gly Ala Lys His His Pro Glu Asp Lys Asp Asp Gly Gln
            565                 570                 575
Arg Met His Pro Arg Ser Ser Phe Lys Ala Phe Leu Glu Val Val Lys
            580                 585                 590
Ser Arg Ser Leu Pro Trp Glu Asn Ala Glu Met Asp Ala Ile His Ser
            595                 600                 605
Leu Gln Leu Ile Leu Arg Asp Ser Phe Arg Asp Ala Ala Glu Gly Thr
            610                 615                 620
Asn Asn Ser Lys Ala Ile Val Asn Gly Gln Val Gln Leu Arg Glu Leu
625                 630                 635                 640
Glu Leu Arg Gly Ile Asn Glu Leu Ser Ser Val Ala Arg Glu Met Val
            645                 650                 655
Arg Leu Ile Glu Thr Ala Thr Val Pro Ile Phe Ala Val Asp Thr Asp
            660                 665                 670
Gly Cys Ile Asn Gly Trp Asn Ala Lys Ile Ala Glu Leu Thr Gly Leu
            675                 680                 685
Ser Val Glu Glu Ala Met Gly Lys Ser Leu Val Asn Asp Leu Ile Phe
            690                 695                 700
Lys Glu Ser Glu Ala Thr Val Glu Lys Leu Leu Ser Arg Ala Leu Arg
705                 710                 715                 720
Gly Glu Glu Asp Lys Asn Val Glu Ile Lys Leu Lys Thr Phe Gly Ser
            725                 730                 735
Glu Gln Ser Lys Gly Pro Ile Phe Val Val Asn Ala Cys Ser Ser
            740                 745                 750
```

-continued

```
Arg Asp Tyr Thr Gln Asn Ile Val Gly Val Cys Phe Val Gly Gln Asp
            755                 760                 765

Val Thr Gly Gln Lys Val Val Met Asp Lys Phe Val Asn Ile Gln Gly
    770                 775                 780

Asp Tyr Lys Ala Ile Val His Asn Pro Asn Pro Leu Ile Pro Pro Ile
785                 790                 795                 800

Phe Ala Ser Asp Glu Asn Thr Ser Cys Ser Glu Trp Asn Thr Ala Met
                805                 810                 815

Glu Lys Leu Thr Gly Trp Ser Arg Gly Val Val Gly Lys Phe Leu
                820                 825                 830

Ile Gly Glu Val Phe Gly Asn Cys Cys Arg Leu Lys Gly Pro Asp Ala
                835                 840                 845

Leu Thr Lys Phe Met Val Ile Ile His Asn Ala Ile Gly Gly Gln Asp
                850                 855                 860

Tyr Glu Lys Phe Pro Phe Ser Phe Phe Asp Lys Asn Gly Lys Tyr Val
865                 870                 875                 880

Gln Ala Leu Leu Thr Ala Asn Thr Arg Ser Lys Met Asp Gly Lys Ser
                885                 890                 895

Ile Gly Ala Phe Cys Phe Leu Gln Ile Ala Ser Thr Glu Ile Gln Gln
                900                 905                 910

Ala Phe Glu Ile Gln Arg Gln Gln Glu Lys Lys Cys Tyr Ala Arg Met
                915                 920                 925

Lys Glu Leu Ala Tyr Ile Cys Gln Glu Ile Lys Asn Pro Leu Ser Gly
                930                 935                 940

Ile Arg Phe Thr Asn Ser Leu Leu Gln Met Thr Asp Leu Asn Asp Asp
945                 950                 955                 960

Gln Arg Gln Phe Leu Glu Thr Ser Ser Ala Cys Glu Lys Gln Met Ser
                965                 970                 975

Lys Ile Val Lys Asp Ala Ser Leu Gln Ser Ile Glu Asp Gly Ser Leu
                980                 985                 990

Val Leu Glu Gln Ser Glu Phe Ser Leu Gly Asp Val Met Asn Ala Val
                995                 1000                1005

Val Ser Gln Ala Met Leu Leu Leu Arg Glu Arg Asp Leu Gln Leu Ile
    1010                1015                1020

Arg Asp Ile Pro Asp Glu Ile Lys Asp Ala Ser Ala Tyr Gly Asp Gln
1025                1030                1035                1040

Cys Arg Ile Gln Gln Val Leu Ala Asp Phe Leu Leu Ser Met Val Arg
                1045                1050                1055

Ser Ala Pro Ser Glu Asn Gly Trp Val Glu Ile Gln Val Arg Pro Asn
                1060                1065                1070

Val Lys Gln Asn Ser Asp Gly Thr Asn Thr Glu Leu Phe Ile Phe Arg
                1075                1080                1085

Phe Ala Cys Pro Gly Glu Gly Leu Pro Ala Asp Val Val Gln Asp Met
                1090                1095                1100

Phe Ser Asn Ser Gln Trp Ser Thr Gln Glu Gly Val Gly Leu Ser Thr
1105                1110                1115                1120

Cys Arg Lys Ile Leu Lys Leu Met Gly Gly Glu Val Gln Tyr Ile Arg
                1125                1130                1135

Glu Ser Glu Arg Ser Phe Phe Leu Ile Val Leu Glu Gln Pro Gln Pro
                1140                1145                1150

Arg Pro Ala Ala Gly Arg Glu Ile Val
                1155                1160
```

<210> SEQ ID NO 33
<211> LENGTH: 1161
<212> TYPE: PRT
<213> ORGANISM: Zea mays

<400> SEQUENCE: 33

```
Met Ala Ser Gly Ser Arg Ala Thr Pro Thr Arg Ser Pro Ser Ser Ala
1               5                   10                  15

Arg Pro Glu Ala Pro Arg His Ala His His His His Ser Gln Ser
            20                  25                  30

Ser Gly Gly Ser Thr Ser Arg Ala Gly Gly Gly Ala Ala Thr Glu
        35                  40                  45

Ser Val Ser Lys Ala Val Ala Gln Tyr Thr Leu Asp Ala Arg Leu His
    50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Ser Glu Gln Gln Ile Ala
                85                  90                  95

Ala Tyr Leu Ser Arg Ile Gln Arg Gly Gly His Ile Gln Pro Phe Gly
            100                 105                 110

Cys Thr Leu Ala Val Ala Asp Asp Ser Ser Phe Arg Leu Leu Ala Phe
        115                 120                 125

Ser Glu Asn Ser Pro Asp Leu Leu Asp Leu Ser Pro His His Ser Val
    130                 135                 140

Pro Ser Leu Asp Ser Ser Ala Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
            180                 185                 190

Arg Val Ser Ser Lys Pro Phe Tyr Ala Ile Leu His Arg Ile Asp Val
        195                 200                 205

Gly Val Val Ile Asp Leu Glu Pro Ala Arg Thr Glu Asp Pro Ala Leu
    210                 215                 220

Ser Ile Ala Gly Ala Val Gln Ser Gln Lys Leu Ala Val Arg Ala Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
            260                 265                 270

Val Tyr Arg Phe His Glu Asp Glu His Gly Glu Val Val Ala Glu Ser
        275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
            340                 345                 350

His Gly Cys His Ala Gln Tyr Met Ala Asn Met Gly Ser Ile Ala Ser
        355                 360                 365

Leu Val Met Ala Val Ile Ile Ser Ser Gly Gly Asp Asp Glu Gln Thr
    370                 375                 380
```

```
Gly Arg Gly Gly Ile Ser Ser Ala Met Lys Leu Trp Gly Leu Val Val
385                 390                 395                 400

Cys His His Thr Ser Pro Arg Cys Ile Pro Phe Pro Leu Arg Tyr Ala
                405                 410                 415

Cys Glu Phe Leu Met Gln Ala Phe Gly Leu Gln Leu Asn Met Glu Leu
            420                 425                 430

Gln Leu Ala His Gln Leu Ser Glu Lys His Ile Leu Arg Thr Gln Thr
        435                 440                 445

Leu Leu Cys Asp Met Leu Leu Arg Asp Ser Pro Thr Gly Ile Val Thr
450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
            500                 505                 510

Thr Gly Leu Ser Thr Asp Ser Leu Ala Asp Ala Gly Tyr Leu Gly Ala
        515                 520                 525

Ala Ala Leu Gly Glu Ala Val Cys Gly Met Ala Val Ala Tyr Ile Thr
530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
            580                 585                 590

Ser Arg Ser Leu Pro Trp Glu Asn Ala Glu Met Asp Ala Ile His Ser
        595                 600                 605

Leu Gln Leu Ile Leu Arg Asp Ser Phe Arg Asp Ala Ala Glu Gly Thr
610                 615                 620

Asn Asn Ser Lys Ala Ile Val Asn Gly Gln Val Gln Leu Arg Glu Leu
625                 630                 635                 640

Glu Leu Arg Gly Ile Asn Glu Leu Ser Ser Val Ala Arg Glu Met Val
                645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
        675                 680                 685

Ser Val Glu Glu Ala Met Gly Lys Ser Leu Val Asn Asp Leu Ile Phe
690                 695                 700

Lys Glu Ser Glu Ala Thr Val Glu Lys Leu Leu Ser Arg Ala Leu Arg
705                 710                 715                 720

Gly Glu Glu Asp Lys Asn Val Glu Ile Lys Leu Lys Thr Phe Gly Ser
                725                 730                 735

Glu Gln Tyr Lys Gly Pro Ile Phe Val Val Asn Ala Cys Ser Ser
            740                 745                 750

Arg Asp Tyr Thr Gln Asn Ile Val Gly Val Cys Phe Val Gly Gln Asp
        755                 760                 765

Val Thr Gly Gln Lys Val Val Met Asp Lys Phe Val Asn Ile Gln Gly
        770                 775                 780

Asp Tyr Lys Ala Ile Val His Asn Pro Asn Pro Leu Ile Pro Pro Ile
785                 790                 795                 800
```

```
Phe Ala Ser Asp Glu Asn Thr Ser Cys Ser Glu Trp Asn Thr Ala Met
                805                 810                 815

Glu Lys Leu Thr Gly Trp Ser Arg Gly Glu Val Val Gly Lys Phe Leu
            820                 825                 830

Ile Gly Glu Val Phe Gly Asn Cys Cys Arg Leu Lys Gly Pro Asp Ala
        835                 840                 845

Leu Thr Lys Phe Met Val Ile Ile His Asn Ala Ile Gly Gly Gln Asp
    850                 855                 860

Tyr Glu Lys Phe Pro Phe Ser Phe Phe Asp Lys Asn Gly Lys Tyr Val
865                 870                 875                 880

Gln Ala Leu Leu Thr Ala Asn Thr Arg Ser Lys Met Asp Gly Lys Ser
                885                 890                 895

Ile Gly Ala Phe Cys Phe Leu Gln Ile Ala Ser Thr Glu Ile Gln Gln
            900                 905                 910

Ala Phe Glu Ile Gln Arg Gln Gln Glu Lys Lys Cys Tyr Ala Arg Met
        915                 920                 925

Lys Glu Leu Ala Tyr Ile Cys Gln Glu Ile Lys Asn Pro Leu Ser Gly
    930                 935                 940

Ile Arg Phe Thr Asn Ser Leu Leu Gln Met Thr Asp Leu Asn Asp Asp
945                 950                 955                 960

Gln Arg Gln Phe Leu Glu Thr Ser Ser Ala Cys Glu Lys Gln Met Ser
                965                 970                 975

Lys Ile Val Lys Asp Ala Ser Leu Gln Ser Ile Glu Asp Gly Ser Leu
            980                 985                 990

Val Leu Glu Gln Ser Gly Phe Ser Leu Gly Asp Val Met Asn Ala Val
        995                 1000                1005

Val Ser Gln Ala Met Leu Leu Leu Arg Glu Arg Asp Leu Gln Leu Ile
    1010                1015                1020

Arg Asp Ile Pro Asp Glu Ile Lys Asp Ala Ser Ala Tyr Gly Asp Gln
1025                1030                1035                1040

Cys Arg Ile Gln Gln Val Leu Ala Asp Phe Leu Leu Ser Met Val Arg
                1045                1050                1055

Ser Ala Pro Ser Glu Asn Gly Trp Val Glu Ile Gln Val Arg Pro Asn
            1060                1065                1070

Val Lys Gln Asn Ser Asp Gly Thr Asn Thr Glu Leu Phe Ile Phe Arg
    1075                1080                1085

Phe Ala Cys Pro Gly Glu Gly Leu Pro Ala Asp Val Val Gln Asp Met
    1090                1095                1100

Phe Ser Asn Ser Gln Trp Ser Thr Gln Glu Gly Val Gly Leu Ser Thr
1105                1110                1115                1120

Cys Arg Lys Ile Leu Lys Leu Met Gly Gly Glu Val Gln Tyr Ile Arg
                1125                1130                1135

Glu Ser Glu Arg Ser Phe Phe Leu Ile Val Leu Glu Gln Pro Gln Pro
            1140                1145                1150

Arg Pro Ala Ala Gly Arg Glu Ile Val
        1155                1160

<210> SEQ ID NO 34
<211> LENGTH: 1166
<212> TYPE: PRT
<213> ORGANISM: Zea mays

<400> SEQUENCE: 34

Met Ala Ser Asp Ser Arg Pro Pro Lys Arg Ser Pro Ser Ala Arg Arg
1               5                   10                  15
```

-continued

```
Val Ala Pro Arg His Ala His His His Ser Gln Ser Gly Gly
             20                  25              30

Ser Thr Ser Arg Ala Gly Ala Gly Gly Gly Gly Ala Ala Ala
             35                  40              45

Thr Glu Ser Val Ser Lys Ala Val Ala Gln Tyr Asn Leu Asp Ala Arg
 50                  55                  60

Leu His Ala Val Phe Glu Gln Ser Gly Ala Ser Gly Arg Ser Phe Asp
 65                  70                  75                  80

Tyr Ser Gln Ser Leu Arg Ala Pro Pro Thr Pro Ser Ser Glu Gln Gln
                     85                  90                  95

Ile Ala Ala Tyr Leu Ser Arg Ile Gln Arg Gly Gly His Ile Gln Pro
                 100                 105                 110

Leu Gly Cys Thr Leu Ala Val Ala Asp Asp Ser Ser Phe Arg Leu Leu
             115                 120                 125

Ala Phe Ser Glu Asn Ala Ala Asp Leu Leu Asp Leu Ser Pro His His
 130                 135                 140

Ser Val Pro Ser Leu Asp Ser Val Ala Leu Pro Pro Val Ser Leu Gly
145                 150                 155                 160

Ala Asp Ala Arg Leu Tyr Phe Ser Pro Ser Ser Ala Val Leu Leu Glu
                 165                 170                 175

Arg Ala Phe Ala Ala Arg Glu Ile Ser Leu Leu Asn Pro Leu Trp Ile
             180                 185                 190

His Ser Arg Ala Ser Ser Lys Pro Phe Tyr Ala Ile Leu His Arg Ile
         195                 200                 205

Asp Val Gly Val Val Ile Asp Leu Glu Pro Ala Arg Thr Glu Asp Pro
     210                 215                 220

Ala Leu Ser Ile Ala Gly Ala Val Gln Ser Gln Lys Leu Ala Val Arg
225                 230                 235                 240

Ala Ile Ser Arg Leu Gln Ala Leu Pro Gly Gly Asp Val Lys Leu Leu
                 245                 250                 255

Cys Asp Thr Val Val Glu His Val Arg Glu Leu Thr Gly Tyr Asp Arg
             260                 265                 270

Val Met Val Tyr Lys Phe His Glu Asp Glu His Gly Glu Val Val Ala
         275                 280                 285

Glu Ser Arg Arg Asp Asn Leu Glu Pro Tyr Leu Gly Leu His Tyr Pro
 290                 295                 300

Ala Thr Asp Ile Pro Gln Ala Ser Arg Phe Leu Phe Gln Gln Asn Arg
305                 310                 315                 320

Val Arg Met Ile Ala Asp Cys His Ala Ile Pro Val Arg Val Ile Gln
                 325                 330                 335

Asp Pro Gly Leu Ser Gln Gln Leu Cys Leu Val Gly Ser Thr Leu Arg
             340                 345                 350

Ala Pro His Gly Cys His Ala Gln Tyr Met Ala Asn Met Gly Ser Ile
         355                 360                 365

Ala Ser Leu Val Met Ala Val Ile Ile Ser Ser Gly Asp Asp Glu
 370                 375                 380

Arg Thr Gly Arg Gly Ala Ile Ser Ser Ser Met Lys Leu Trp Gly Leu
385                 390                 395                 400

Val Val Cys His His Thr Ser Pro Arg Cys Ile Pro Phe Pro Leu Arg
                 405                 410                 415

Tyr Ala Cys Glu Phe Leu Met Gln Ala Phe Gly Leu Gln Leu Asn Met
             420                 425                 430
```

-continued

Glu Leu Gln Leu Ala His Gln Leu Ser Glu Lys His Ile Leu Arg Thr
            435                 440                 445

Gln Thr Leu Leu Cys Asp Met Leu Leu Arg Asp Ser Pro Ala Gly Ile
450                 455                 460

Ile Thr Gln Ser Pro Ser Val Met Asp Leu Val Lys Cys Asp Gly Ala
465                 470                 475                 480

Ala Leu Tyr Tyr Arg Gly Lys Tyr Tyr Pro Leu Gly Val Thr Pro Thr
                485                 490                 495

Glu Ser Gln Ile Lys Asp Ile Ile Glu Trp Leu Thr Val Cys His Gly
            500                 505                 510

Asp Ser Thr Gly Leu Ser Thr Asp Ser Leu Ala Asp Ala Gly Tyr Leu
        515                 520                 525

Gly Ala Val Ala Leu Gly Asp Ala Val Cys Gly Met Ala Val Ala Tyr
530                 535                 540

Ile Thr Pro Ser Asp Tyr Leu Phe Trp Phe Arg Ser His Thr Ala Lys
545                 550                 555                 560

Glu Ile Lys Trp Gly Gly Ala Lys His His Pro Glu Asp Lys Asp Asp
                565                 570                 575

Gly Gln Arg Met His Pro Arg Ser Ser Phe Lys Ala Phe Leu Glu Val
            580                 585                 590

Val Lys Ser Arg Ser Leu Ser Trp Glu Asn Ala Glu Met Asp Ala Ile
        595                 600                 605

His Ser Leu Gln Leu Ile Leu Arg Asp Ser Phe Arg Asp Ala Ala Glu
    610                 615                 620

Gly Thr Ser Asn Ser Lys Ala Ile Val Asn Gly Gln Arg Gln Leu Gly
625                 630                 635                 640

Glu Leu Glu Leu Arg Gly Ile Asn Glu Leu Ser Ser Val Ala Arg Glu
                645                 650                 655

Met Val Arg Leu Ile Glu Thr Ala Thr Val Pro Ile Phe Ala Val Asp
            660                 665                 670

Thr Asp Gly Cys Ile Asn Gly Trp Asn Ala Lys Ile Ala Glu Leu Thr
        675                 680                 685

Gly Leu Ser Val Glu Glu Ala Met Gly Lys Ser Leu Val Asn Asp Leu
690                 695                 700

Ile Phe Lys Glu Cys Asp Asp Ile Val Glu Lys Leu Leu Ser Arg Ala
705                 710                 715                 720

Leu Arg Gly Glu Glu Asp Lys Asn Val Glu Ile Lys Leu Lys Thr Phe
                725                 730                 735

Gly Ser Glu Gln Ser Lys Gly Ala Ile Phe Val Ile Val Asn Ala Cys
            740                 745                 750

Ser Ser Arg Asp Tyr Thr Gln Asn Ile Val Gly Val Cys Phe Val Gly
        755                 760                 765

Gln Asp Val Thr Gly Gln Lys Val Val Met Asp Lys Phe Ile Asn Ile
770                 775                 780

Gln Gly Asp Tyr Lys Ala Ile Val His Asn Pro Asn Pro Leu Leu Pro
785                 790                 795                 800

Pro Ile Phe Ala Ser Asp Glu Asn Thr Ser Cys Ser Glu Trp Asn Thr
                805                 810                 815

Ala Met Glu Lys Leu Thr Gly Trp Ser Arg Glu Val Val Gly Lys
            820                 825                 830

Phe Leu Ile Gly Glu Val Phe Gly Asn Cys Cys Arg Leu Lys Gly Pro
        835                 840                 845

Asp Ala Leu Thr Lys Phe Met Val Val Ile His Asn Ala Ile Glu Gly

His Asp Ser Glu Lys Phe Pro Phe Ser Phe Phe Asp Lys Asn Gly Lys
        850                 855                 860
865                 870                 875                 880

Tyr Val Gln Ala Leu Leu Thr Ala Asn Thr Arg Ser Lys Met Asp Gly
                    885                 890                 895

Lys Ser Ile Gly Ala Phe Cys Phe Leu Gln Ile Ala Ser Ala Glu Ile
                900                 905                 910

Gln Gln Ala Phe Glu Ile Gln Arg Gln Gln Glu Lys Lys Cys Tyr Ala
                915                 920                 925

Arg Met Lys Glu Leu Ala Tyr Ile Cys Gln Glu Ile Lys Asn Pro Leu
        930                 935                 940

Ser Gly Ile Arg Phe Thr Asn Ser Leu Leu Gln Met Thr Asp Leu Asn
945                 950                 955                 960

Asp Asp Gln Arg Gln Phe Leu Glu Thr Ser Ala Cys Glu Lys Gln
                965                 970                 975

Met Ser Lys Ile Val Lys Asp Ala Ser Leu Lys Ser Ile Glu Asp Gly
                980                 985                 990

Ser Leu Val Leu Glu Lys Ser Glu Phe Ser Leu Gly Asp Val Met Asn
        995                 1000                1005

Ala Val Val Ser Gln Thr Met Ser Leu Leu Arg Glu Arg Asp Leu Gln
    1010                1015                1020

Leu Ile Arg Asp Ile Pro Asp Glu Ile Lys Asp Ala Ser Ala Tyr Gly
1025                1030                1035                1040

Asp Gln Phe Arg Ile Gln Gln Val Leu Ala Asp Phe Leu Leu Ser Met
                1045                1050                1055

Ala Gln Ser Ala Pro Ser Glu Asn Gly Trp Val Glu Ile Gln Val Arg
            1060                1065                1070

Pro Asn Val Lys Gln Asn Tyr Asp Gly Thr Asp Thr Glu Leu Phe Ile
            1075                1080                1085

Phe Arg Phe Ala Cys Pro Gly Glu Gly Leu Pro Ala Asp Ile Val Gln
        1090                1095                1100

Asp Met Phe Ser Asn Ser Gln Trp Ser Thr Gln Glu Gly Val Gly Leu
1105                1110                1115                1120

Ser Thr Cys Arg Lys Ile Leu Lys Leu Met Gly Gly Glu Val Gln Tyr
                1125                1130                1135

Ile Arg Glu Ser Glu Arg Ser Phe Phe Leu Ile Val Leu Glu Leu Pro
            1140                1145                1150

Gln Pro Arg Leu Ala Ala Gly Arg Glu Asn Gln Leu Ile Cys
            1155                1160                1165

<210> SEQ ID NO 35
<211> LENGTH: 1137
<212> TYPE: PRT
<213> ORGANISM: Glycine max

<400> SEQUENCE: 35

Met Ala Ser Ala Ser Gly Ala Ala Asn Ser Val Pro Pro Gln
1               5                   10                  15

Ile His Thr Ser Arg Thr Lys Leu Ser His His Ser Ser Asn Asn Asn
            20                  25                  30

Asn Asn Ile Asp Ser Met Ser Lys Ala Ile Ala Gln Tyr Thr Glu Asp
        35                  40                  45

Ala Arg Leu His Ala Val Phe Glu Gln Ser Gly Glu Ser Gly Arg Ser
    50                  55                  60

```
Phe Asn Tyr Ser Glu Ser Ile Arg Ile Ala Ser Glu Ser Val Pro Glu
 65                  70                  75                  80

Gln Gln Ile Thr Ala Tyr Leu Val Lys Ile Gln Arg Gly Gly Phe Ile
                 85                  90                  95

Gln Pro Phe Gly Ser Met Ile Ala Val Asp Glu Pro Ser Phe Arg Ile
            100                 105                 110

Leu Gly Tyr Ser Asp Asn Ala Arg Asp Met Leu Gly Ile Thr Pro Gln
        115                 120                 125

Ser Val Pro Ser Leu Asp Asp Lys Asn Asp Ala Ala Phe Ala Leu Gly
    130                 135                 140

Thr Asp Val Arg Ala Leu Phe Thr His Ser Ser Ala Leu Leu Leu Glu
145                 150                 155                 160

Lys Ala Phe Ser Ala Arg Glu Ile Ser Leu Met Asn Pro Ile Trp Ile
                165                 170                 175

His Ser Arg Thr Ser Gly Lys Pro Phe Tyr Gly Ile Leu His Arg Ile
            180                 185                 190

Asp Val Gly Ile Val Asp Leu Glu Pro Ala Arg Thr Glu Asp Pro
        195                 200                 205

Ala Leu Ser Ile Ala Gly Ala Val Gln Ser Gln Lys Leu Ala Val Arg
    210                 215                 220

Ala Ile Ser Gln Leu Gln Ser Leu Pro Gly Gly Asp Val Lys Leu Leu
225                 230                 235                 240

Cys Asp Thr Val Val Glu Ser Val Arg Glu Leu Thr Gly Tyr Asp Arg
                245                 250                 255

Val Met Val Tyr Lys Phe His Glu Asp Glu His Gly Glu Val Val Ser
            260                 265                 270

Glu Ser Lys Arg Pro Asp Leu Glu Pro Tyr Ile Gly Leu His Tyr Pro
        275                 280                 285

Ala Thr Asp Ile Pro Gln Ala Ser Arg Phe Leu Phe Lys Gln Asn Arg
    290                 295                 300

Val Arg Met Ile Val Asp Cys His Ala Ser Ala Val Arg Val Val Gln
305                 310                 315                 320

Asp Glu Ala Leu Val Gln Pro Leu Cys Leu Val Gly Ser Thr Leu Arg
                325                 330                 335

Ala Pro His Gly Cys His Ala Gln Tyr Met Ala Asn Met Gly Ser Ile
            340                 345                 350

Ala Ser Leu Val Met Ala Val Ile Ile Asn Gly Asn Asp Glu Glu Gly
        355                 360                 365

Val Gly Gly Arg Ser Ser Met Arg Leu Trp Gly Leu Val Val Cys His
    370                 375                 380

His Thr Ser Ala Arg Cys Ile Pro Phe Pro Leu Arg Tyr Ala Cys Glu
385                 390                 395                 400

Phe Leu Met Gln Ala Phe Gly Leu Gln Leu Asn Met Glu Leu Gln Leu
                405                 410                 415

Ala Ala Gln Ser Leu Glu Lys Arg Val Leu Arg Thr Gln Thr Leu Leu
            420                 425                 430

Cys Asp Met Leu Leu Arg Asp Ser Pro Thr Gly Ile Val Thr Gln Ser
        435                 440                 445

Pro Ser Ile Met Asp Leu Val Lys Cys Asp Gly Ala Ala Leu Tyr Phe
    450                 455                 460

Gln Gly Asn Tyr Tyr Pro Leu Gly Val Thr Pro Thr Glu Ala Gln Ile
465                 470                 475                 480

Arg Asp Ile Ile Glu Trp Leu Leu Ala Phe His Gly Asp Ser Thr Gly
```

-continued

```
                485                 490                 495
Leu Ser Thr Asp Ser Leu Gly Asp Ala Gly Tyr Pro Gly Ala Ala Ser
                500                 505                 510
Leu Gly Asp Ala Val Cys Gly Met Ala Val Ala Tyr Ile Thr Glu Lys
                515                 520                 525
Asp Phe Leu Phe Trp Phe Arg Ser His Thr Ala Lys Glu Ile Lys Trp
                530                 535                 540
Gly Gly Ala Lys His His Pro Glu Asp Lys Asp Asp Gly Gln Arg Met
545                 550                 555                 560
His Pro Arg Ser Ser Phe Lys Ala Phe Leu Glu Val Val Lys Ser Arg
                565                 570                 575
Ser Leu Pro Trp Glu Asn Ala Glu Met Asp Ala Ile His Ser Leu Gln
                580                 585                 590
Leu Ile Leu Arg Asp Ser Phe Lys Asp Ala Glu His Arg Asn Ser Lys
                595                 600                 605
Ala Val Val Asp Pro His Val Ser Glu Gln Glu Leu Gln Gly Val Asp
                610                 615                 620
Glu Leu Ser Ser Val Ala Arg Glu Met Val Arg Leu Ile Glu Thr Ala
625                 630                 635                 640
Thr Ala Pro Ile Phe Ala Val Asp Val Asp Gly His Val Asn Gly Trp
                645                 650                 655
Asn Ala Lys Val Ser Glu Leu Thr Gly Leu Pro Val Glu Glu Ala Met
                660                 665                 670
Gly Lys Ser Leu Val His Asp Leu Val Phe Lys Glu Ser Glu Glu Thr
                675                 680                 685
Met Asn Lys Leu Leu Ser Arg Ala Leu Lys Gly Glu Glu Asp Lys Asn
                690                 695                 700
Val Glu Ile Lys Met Arg Thr Phe Gly Pro His Gln Asn Lys Ala
705                 710                 715                 720
Val Phe Leu Val Val Asn Ala Cys Ser Ser Lys Asp Phe Thr Asn Asn
                725                 730                 735
Val Val Gly Val Cys Phe Val Gly Gln Asp Val Thr Gly Gln Lys Ile
                740                 745                 750
Val Met Asp Lys Phe Ile Asn Ile Gln Gly Asp Tyr Lys Ala Ile Val
                755                 760                 765
His Ser Pro Asn Pro Leu Ile Pro Pro Ile Phe Ala Ser Asp Asp Asn
                770                 775                 780
Thr Cys Cys Leu Glu Trp Asn Thr Ala Met Glu Lys Leu Thr Gly Trp
785                 790                 795                 800
Gly Arg Val Asp Val Ile Gly Lys Met Leu Val Gly Glu Val Phe Gly
                805                 810                 815
Ser Cys Cys Gln Leu Lys Gly Ser Asp Ser Ile Thr Lys Phe Met Ile
                820                 825                 830
Val Leu His Asn Ala Leu Gly Gly Gln Asp Thr Asp Lys Phe Pro Phe
                835                 840                 845
Ser Phe Leu Asp Arg His Gly Lys Tyr Val Gln Thr Phe Leu Thr Ala
                850                 855                 860
Asn Lys Arg Val Asn Met Glu Gly Gln Ile Ile Gly Ala Phe Cys Phe
865                 870                 875                 880
Leu Gln Ile Met Ser Pro Glu Leu Gln Gln Ala Leu Lys Ala Gln Arg
                885                 890                 895
Gln Gln Glu Lys Asn Ser Phe Gly Arg Met Lys Glu Leu Ala Tyr Ile
                900                 905                 910
```

```
Cys Gln Gly Val Lys Asn Pro Leu Ser Gly Ile Arg Phe Thr Asn Ser
            915                 920                 925

Leu Leu Glu Ala Thr Ser Leu Thr Asn Glu Gln Lys Gln Phe Leu Glu
        930                 935                 940

Thr Ser Val Ala Cys Glu Lys Gln Met Leu Lys Ile Ile Arg Asp Val
945                 950                 955                 960

Asp Leu Glu Ser Ile Glu Asp Gly Ser Leu Glu Leu Glu Lys Gly Glu
                965                 970                 975

Phe Leu Leu Gly Asn Val Ile Asn Ala Val Val Ser Gln Val Met Leu
            980                 985                 990

Leu Leu Arg Glu Arg Asn Leu Gln Leu Ile Arg Asp Ile Pro Glu Glu
        995                 1000                1005

Ile Lys Thr Leu Ala Val Tyr Gly Asp Gln Leu Arg Ile Gln Gln Val
    1010                1015                1020

Leu Ser Asp Phe Leu Leu Asn Ile Val Arg Tyr Ala Pro Ser Pro Asp
1025                1030                1035                1040

Gly Trp Val Glu Ile His Val Arg Pro Arg Ile Lys Gln Ile Ser Asp
                1045                1050                1055

Gly Leu Thr Leu Leu His Ala Glu Phe Arg Met Val Cys Pro Gly Glu
            1060                1065                1070

Gly Leu Pro Pro Glu Leu Ile Gln Asp Met Phe Asn Asn Ser Arg Trp
        1075                1080                1085

Gly Thr Gln Glu Gly Leu Gly Leu Ser Met Ser Arg Lys Ile Leu Lys
    1090                1095                1100

Leu Met Asn Gly Glu Val Gln Tyr Ile Arg Glu Ala Glu Arg Cys Tyr
1105                1110                1115                1120

Phe Tyr Val Leu Leu Glu Leu Pro Val Thr Arg Arg Ser Ser Lys Lys
                1125                1130                1135

Cys

<210> SEQ ID NO 36
<211> LENGTH: 1100
<212> TYPE: PRT
<213> ORGANISM: Glycine max

<400> SEQUENCE: 36

Met Ser Lys Ala Ile Ala Gln Tyr Thr Glu Asp Ala Arg Leu His Ala
1               5                   10                  15

Val Phe Glu Gln Ser Gly Glu Ser Gly Arg Ser Phe Asn Tyr Ser Glu
            20                  25                  30

Ser Ile Arg Ile Ala Ser Glu Ser Val Pro Glu Gln Gln Ile Thr Ala
        35                  40                  45

Tyr Leu Val Lys Ile Gln Arg Gly Gly Phe Ile Gln Pro Phe Gly Ser
    50                  55                  60

Met Ile Ala Val Asp Glu Pro Ser Phe Arg Ile Leu Gly Tyr Ser Asp
65                  70                  75                  80

Asn Ala Arg Asp Met Leu Gly Ile Thr Pro Gln Ser Val Pro Ser Leu
                85                  90                  95

Asp Asp Lys Asn Asp Ala Ala Phe Ala Leu Gly Thr Asp Val Arg Ala
            100                 105                 110

Leu Phe Thr His Ser Ser Ala Leu Leu Leu Glu Lys Ala Phe Ser Ala
        115                 120                 125

Arg Glu Ile Ser Leu Met Asn Pro Ile Trp Ile His Ser Arg Thr Ser
    130                 135                 140
```

```
Gly Lys Pro Phe Tyr Gly Ile Leu His Arg Ile Asp Val Gly Ile Val
145                 150                 155                 160

Ile Asp Leu Glu Pro Ala Arg Thr Glu Asp Pro Ala Leu Ser Ile Ala
                165                 170                 175

Gly Ala Val Gln Ser Gln Lys Leu Ala Val Arg Ala Ile Ser Gln Leu
            180                 185                 190

Gln Ser Leu Pro Gly Gly Asp Val Lys Leu Leu Cys Asp Thr Val Val
        195                 200                 205

Glu Ser Val Arg Glu Leu Thr Gly Tyr Asp Arg Val Met Val Tyr Lys
    210                 215                 220

Phe His Glu Asp Glu His Gly Glu Val Val Ser Glu Ser Lys Arg Pro
225                 230                 235                 240

Asp Leu Glu Pro Tyr Ile Gly Leu His Tyr Pro Ala Thr Asp Ile Pro
                245                 250                 255

Gln Ala Ser Arg Phe Leu Phe Lys Gln Asn Arg Val Arg Met Ile Val
            260                 265                 270

Asp Cys His Ala Ser Ala Val Arg Val Val Gln Asp Glu Ala Leu Val
        275                 280                 285

Gln Pro Leu Cys Leu Val Gly Ser Thr Leu Arg Ala Pro His Gly Cys
    290                 295                 300

His Ala Gln Tyr Met Ala Asn Met Gly Ser Ile Ala Ser Leu Val Met
305                 310                 315                 320

Ala Val Ile Ile Asn Gly Asn Asp Glu Glu Gly Val Gly Gly Arg Ser
                325                 330                 335

Ser Met Arg Leu Trp Gly Leu Val Val Cys His His Thr Ser Ala Arg
            340                 345                 350

Cys Ile Pro Phe Pro Leu Arg Tyr Ala Cys Glu Phe Leu Met Gln Ala
        355                 360                 365

Phe Gly Leu Gln Leu Asn Met Glu Leu Gln Leu Ala Ala Gln Ser Leu
    370                 375                 380

Glu Lys Arg Val Leu Arg Thr Gln Thr Leu Leu Cys Asp Met Leu Leu
385                 390                 395                 400

Arg Asp Ser Pro Thr Gly Ile Val Thr Gln Ser Pro Ser Ile Met Asp
                405                 410                 415

Leu Val Lys Cys Asp Gly Ala Ala Leu Tyr Phe Gln Gly Asn Tyr Tyr
            420                 425                 430

Pro Leu Gly Val Thr Pro Thr Glu Ala Gln Ile Arg Asp Ile Ile Glu
        435                 440                 445

Trp Leu Leu Ala Phe His Gly Asp Ser Thr Gly Leu Ser Thr Asp Ser
    450                 455                 460

Leu Gly Asp Ala Gly Tyr Pro Gly Ala Ala Ser Leu Gly Asp Ala Val
465                 470                 475                 480

Cys Gly Met Ala Val Ala Tyr Ile Thr Glu Lys Asp Phe Leu Phe Trp
                485                 490                 495

Phe Arg Ser His Thr Ala Lys Glu Ile Lys Trp Gly Gly Ala Lys His
            500                 505                 510

His Pro Glu Asp Lys Asp Asp Gly Gln Arg Met His Pro Arg Ser Ser
        515                 520                 525

Phe Lys Ala Phe Leu Glu Val Val Lys Ser Arg Ser Leu Pro Trp Glu
    530                 535                 540

Asn Ala Glu Met Asp Ala Ile His Ser Leu Gln Leu Ile Leu Arg Asp
545                 550                 555                 560
```

```
Ser Phe Lys Asp Ala Glu His Arg Asn Ser Lys Ala Val Val Asp Pro
            565                 570                 575

His Val Ser Glu Gln Glu Leu Gln Gly Val Asp Glu Leu Ser Ser Val
        580                 585                 590

Ala Arg Glu Met Val Arg Leu Ile Glu Thr Ala Thr Ala Pro Ile Phe
    595                 600                 605

Ala Val Asp Val Asp Gly His Val Asn Gly Trp Asn Ala Lys Val Ser
610                 615                 620

Glu Leu Thr Gly Leu Pro Val Glu Glu Ala Met Gly Lys Ser Leu Val
625                 630                 635                 640

His Asp Leu Val Phe Lys Glu Ser Glu Thr Met Asn Lys Leu Leu
            645                 650                 655

Ser Arg Ala Leu Lys Gly Glu Glu Asp Lys Asn Val Glu Ile Lys Met
        660                 665                 670

Arg Thr Phe Gly Pro Glu His Gln Asn Lys Ala Val Phe Leu Val Val
    675                 680                 685

Asn Ala Cys Ser Ser Lys Asp Phe Thr Asn Asn Val Val Gly Val Cys
690                 695                 700

Phe Val Gly Gln Asp Val Thr Gly Gln Lys Ile Val Met Asp Lys Phe
705                 710                 715                 720

Ile Asn Ile Gln Gly Asp Tyr Lys Ala Ile Val His Ser Pro Asn Pro
            725                 730                 735

Leu Ile Pro Pro Ile Phe Ala Ser Asp Asn Thr Cys Cys Leu Glu
        740                 745                 750

Trp Asn Thr Ala Met Glu Lys Leu Thr Gly Trp Gly Arg Val Asp Val
    755                 760                 765

Ile Gly Lys Met Leu Val Gly Glu Val Phe Gly Ser Cys Cys Gln Leu
770                 775                 780

Lys Gly Ser Asp Ser Ile Thr Lys Phe Met Ile Val Leu His Asn Ala
785                 790                 795                 800

Leu Gly Gly Gln Asp Thr Asp Lys Phe Pro Phe Ser Phe Leu Asp Arg
            805                 810                 815

His Gly Lys Tyr Val Gln Thr Phe Leu Thr Ala Asn Lys Arg Val Asn
        820                 825                 830

Met Glu Gly Gln Ile Ile Gly Ala Phe Cys Phe Leu Gln Ile Met Ser
    835                 840                 845

Pro Glu Leu Gln Gln Ala Leu Lys Ala Gln Arg Gln Gln Glu Lys Asn
850                 855                 860

Ser Phe Gly Arg Met Lys Glu Leu Ala Tyr Ile Cys Gln Gly Val Lys
865                 870                 875                 880

Asn Pro Leu Ser Gly Ile Arg Phe Thr Asn Ser Leu Leu Glu Ala Thr
            885                 890                 895

Ser Leu Thr Asn Glu Gln Lys Gln Phe Leu Glu Thr Ser Val Ala Cys
        900                 905                 910

Glu Lys Gln Met Leu Lys Ile Ile Arg Asp Val Asp Leu Glu Ser Ile
    915                 920                 925

Glu Asp Gly Ser Leu Glu Leu Glu Lys Gly Glu Phe Leu Leu Gly Asn
930                 935                 940

Val Ile Asn Ala Val Val Ser Gln Val Met Leu Leu Leu Arg Glu Arg
945                 950                 955                 960

Asn Leu Gln Leu Ile Arg Asp Ile Pro Glu Glu Ile Lys Thr Leu Ala
            965                 970                 975

Val Tyr Gly Asp Gln Leu Arg Ile Gln Gln Val Leu Ser Asp Phe Leu
```

```
                    980             985             990
Leu Asn Ile Val Arg Tyr Ala Pro Ser Pro Asp Gly Trp Val Glu Ile
            995                 1000                1005

His Val Arg Pro Arg Ile Lys Gln Ile Ser Asp Gly Leu Thr Leu Leu
        1010                1015                1020

His Ala Glu Phe Arg Met Val Cys Pro Gly Glu Gly Leu Pro Pro Glu
1025                1030                1035                1040

Leu Ile Gln Asp Met Phe Asn Asn Ser Arg Trp Gly Thr Gln Glu Gly
            1045                1050                1055

Leu Gly Leu Ser Met Ser Arg Lys Ile Leu Lys Leu Met Asn Gly Glu
        1060                1065                1070

Val Gln Tyr Ile Arg Glu Ala Glu Arg Cys Tyr Phe Tyr Val Leu Leu
        1075                1080                1085

Glu Leu Pro Val Thr Arg Arg Ser Ser Lys Lys Cys
        1090                1095                1100

<210> SEQ ID NO 37
<211> LENGTH: 1171
<212> TYPE: PRT
<213> ORGANISM: Oryza sativa

<400> SEQUENCE: 37

Met Ala Ser Gly Ser Arg Ala Thr Pro Thr Arg Ser Pro Ser Ser Ala
1               5                   10                  15

Arg Pro Ala Ala Pro Arg His Gln His His Ser Gln Ser Ser Gly
                20                  25                  30

Gly Ser Thr Ser Arg Ala Gly Gly Gly Gly Gly Gly Gly Gly
            35                  40                  45

Gly Gly Gly Ala Ala Ala Glu Ser Val Ser Lys Ala Val Ala Gln
        50                  55                  60

Tyr Thr Leu Asp Ala Arg Leu His Ala Val Phe Glu Gln Ser Gly Ala
65                  70                  75                  80

Ser Gly Arg Ser Phe Asp Tyr Thr Gln Ser Leu Arg Ala Ser Pro Thr
                85                  90                  95

Pro Ser Ser Glu Gln Gln Ile Ala Ala Tyr Leu Ser Arg Ile Gln Arg
            100                 105                 110

Gly Gly His Ile Gln Pro Phe Gly Cys Thr Leu Ala Val Ala Asp Asp
        115                 120                 125

Ser Ser Phe Arg Leu Leu Ala Tyr Ser Glu Asn Thr Ala Asp Leu Leu
130                 135                 140

Asp Leu Ser Pro His His Ser Val Pro Ser Leu Asp Ser Ser Ala Val
145                 150                 155                 160

Pro Pro Pro Val Ser Leu Gly Ala Asp Ala Arg Leu Leu Phe Ala Pro
                165                 170                 175

Ser Ser Ala Val Leu Leu Glu Arg Ala Phe Ala Ala Arg Glu Ile Ser
            180                 185                 190

Leu Leu Asn Pro Leu Trp Ile His Ser Arg Val Ser Ser Lys Pro Phe
        195                 200                 205

Tyr Ala Ile Leu His Arg Ile Asp Val Gly Val Ile Asp Leu Glu
        210                 215                 220

Pro Ala Arg Thr Glu Asp Pro Ala Leu Ser Ile Ala Gly Ala Val Gln
225                 230                 235                 240

Ser Gln Lys Leu Ala Val Arg Ala Ile Ser Arg Leu Gln Ala Leu Pro
                245                 250                 255
```

```
Gly Gly Asp Val Lys Leu Leu Cys Asp Thr Val Val Glu His Val Arg
            260                 265                 270

Glu Leu Thr Gly Tyr Asp Arg Val Met Val Tyr Arg Phe His Glu Asp
        275                 280                 285

Glu His Gly Glu Val Val Ala Glu Ser Arg Arg Asn Asn Leu Glu Pro
    290                 295                 300

Tyr Ile Gly Leu His Tyr Pro Ala Thr Asp Ile Pro Gln Ala Ser Arg
305                 310                 315                 320

Phe Leu Phe Arg Gln Asn Arg Val Arg Met Ile Ala Asp Cys His Ala
                325                 330                 335

Ala Pro Val Arg Val Ile Gln Asp Pro Ala Leu Thr Gln Pro Leu Cys
            340                 345                 350

Leu Val Gly Ser Thr Leu Arg Ser Pro His Gly Cys His Ala Gln Tyr
        355                 360                 365

Met Ala Asn Met Gly Ser Ile Ala Ser Leu Val Met Ala Val Ile Ile
    370                 375                 380

Ser Ser Gly Gly Asp Asp His Asn Ile Ala Arg Gly Ser Ile Pro
385                 390                 395                 400

Ser Ala Met Lys Leu Trp Gly Leu Val Val Cys His His Thr Ser Pro
                405                 410                 415

Arg Cys Ile Pro Phe Pro Leu Arg Tyr Ala Cys Glu Phe Leu Met Gln
            420                 425                 430

Ala Phe Gly Leu Gln Leu Asn Met Glu Leu Gln Leu Ala His Gln Leu
        435                 440                 445

Ser Glu Lys His Ile Leu Arg Thr Gln Thr Leu Leu Cys Asp Met Leu
    450                 455                 460

Leu Arg Asp Ser Pro Thr Gly Ile Val Thr Gln Ser Pro Ser Ile Met
465                 470                 475                 480

Asp Leu Val Lys Cys Asp Gly Ala Ala Leu Tyr Tyr His Gly Lys Tyr
                485                 490                 495

Tyr Pro Leu Gly Val Thr Pro Thr Glu Val Gln Ile Lys Asp Ile Ile
            500                 505                 510

Glu Trp Leu Thr Met Cys His Gly Asp Ser Thr Gly Leu Ser Thr Asp
        515                 520                 525

Ser Leu Ala Asp Ala Gly Tyr Pro Gly Ala Ala Ala Leu Gly Asp Ala
    530                 535                 540

Val Ser Gly Met Ala Val Ala Tyr Ile Thr Pro Ser Asp Tyr Leu Phe
545                 550                 555                 560

Trp Phe Arg Ser His Thr Ala Lys Glu Ile Lys Trp Gly Gly Ala Lys
                565                 570                 575

His His Pro Glu Asp Lys Asp Gly Gln Arg Met His Pro Arg Ser
            580                 585                 590

Ser Phe Lys Ala Phe Leu Glu Val Val Lys Ser Arg Ser Leu Pro Trp
        595                 600                 605

Glu Asn Ala Glu Met Asp Ala Ile His Ser Leu Gln Leu Ile Leu Arg
    610                 615                 620

Asp Ser Phe Arg Asp Ser Ala Glu Gly Thr Ser Asn Ser Lys Ala Ile
625                 630                 635                 640

Val Asn Gly Gln Val Gln Leu Gly Glu Leu Leu Arg Gly Ile Asp
                645                 650                 655

Glu Leu Ser Ser Val Ala Arg Glu Met Val Arg Leu Ile Glu Thr Ala
            660                 665                 670

Thr Val Pro Ile Phe Ala Val Asp Thr Asp Gly Cys Ile Asn Gly Trp
```

```
                675                 680                 685
Asn Ala Lys Val Ala Glu Leu Thr Gly Leu Ser Val Glu Glu Ala Met
690                 695                 700
Gly Lys Ser Leu Val Asn Asp Leu Ile Phe Lys Glu Ser Glu Glu Thr
705                 710                 715                 720
Val Asn Lys Leu Leu Ser Arg Ala Leu Arg Gly Asp Glu Asp Lys Asn
                725                 730                 735
Val Glu Ile Lys Leu Lys Thr Phe Gly Pro Glu Gln Ser Lys Gly Pro
            740                 745                 750
Ile Phe Val Ile Val Asn Ala Cys Ser Ser Arg Asp Tyr Thr Lys Asn
        755                 760                 765
Ile Val Gly Val Cys Phe Val Gly Gln Asp Val Thr Gly Gln Lys Val
    770                 775                 780
Val Met Asp Lys Phe Ile Asn Ile Gln Gly Asp Tyr Lys Ala Ile Val
785                 790                 795                 800
His Asn Pro Asn Pro Leu Ile Pro Pro Ile Phe Ala Ser Asp Glu Asn
                805                 810                 815
Thr Cys Cys Ser Glu Trp Asn Thr Ala Met Glu Lys Leu Thr Gly Trp
            820                 825                 830
Ser Arg Gly Glu Val Val Gly Lys Leu Leu Val Gly Glu Val Phe Gly
        835                 840                 845
Asn Cys Cys Arg Leu Lys Gly Pro Asp Ala Leu Thr Lys Phe Met Ile
    850                 855                 860
Val Leu His Asn Ala Ile Gly Gly Gln Asp Cys Glu Lys Phe Pro Phe
865                 870                 875                 880
Ser Phe Phe Asp Lys Asn Gly Lys Tyr Val Gln Ala Leu Leu Thr Ala
                885                 890                 895
Asn Thr Arg Ser Arg Met Asp Gly Glu Ala Ile Gly Ala Phe Cys Phe
            900                 905                 910
Leu Gln Ile Ala Ser Pro Glu Leu Gln Gln Ala Phe Glu Ile Gln Arg
        915                 920                 925
His His Glu Lys Lys Cys Tyr Ala Arg Met Lys Glu Leu Ala Tyr Ile
    930                 935                 940
Tyr Gln Glu Ile Lys Asn Pro Leu Asn Gly Ile Arg Phe Thr Asn Ser
945                 950                 955                 960
Leu Leu Glu Met Thr Asp Leu Lys Asp Asp Gln Arg Gln Phe Leu Glu
                965                 970                 975
Thr Ser Thr Ala Cys Glu Lys Gln Met Ser Lys Ile Val Lys Asp Ala
            980                 985                 990
Ser Leu Gln Ser Ile Glu Asp Gly Ser Leu Val Leu Glu Lys Gly Glu
        995                 1000                1005
Phe Ser Leu Gly Ser Val Met Asn Ala Val Val Ser Gln Val Met Ile
    1010                1015                1020
Gln Leu Arg Glu Arg Asp Leu Gln Leu Ile Arg Asp Ile Pro Asp Glu
1025                1030                1035                1040
Ile Lys Glu Ala Ser Ala Tyr Gly Asp Gln Tyr Arg Ile Gln Gln Val
                1045                1050                1055
Leu Cys Asp Phe Leu Leu Ser Met Val Arg Phe Ala Pro Ala Glu Asn
            1060                1065                1070
Gly Trp Val Glu Ile Gln Val Arg Pro Asn Ile Lys Gln Asn Ser Asp
        1075                1080                1085
Gly Thr Asp Thr Met Leu Phe Leu Phe Arg Phe Ala Cys Pro Gly Glu
    1090                1095                1100
```

Gly Leu Pro Pro Glu Ile Val Gln Asp Met Phe Ser Asn Ser Arg Trp
1105                1110                1115                1120

Thr Thr Gln Glu Gly Ile Gly Leu Ser Ile Cys Arg Lys Ile Leu Lys
            1125                1130                1135

Leu Met Gly Gly Glu Val Gln Tyr Ile Arg Glu Ser Gly Arg Ser Phe
        1140                1145                1150

Phe His Ile Val Leu Glu Leu Pro Gln Pro Gln Gln Ala Ala Ser Arg
    1155                1160                1165

Gly Thr Ser
    1170

<210> SEQ ID NO 38
<211> LENGTH: 428
<212> TYPE: PRT
<213> ORGANISM: Arabidopsis thaliana

<400> SEQUENCE: 38

Met Glu His Gln Gly Trp Ser Phe Glu Glu Asn Tyr Ser Leu Ser Thr
1               5                   10                  15

Asn Arg Arg Ser Ile Arg Pro Gln Asp Glu Leu Val Glu Leu Leu Trp
            20                  25                  30

Arg Asp Gly Gln Val Val Leu Gln Ser Gln Thr His Arg Glu Gln Thr
        35                  40                  45

Gln Thr Gln Lys Gln Asp His His Glu Glu Ala Leu Arg Ser Ser Thr
    50                  55                  60

Phe Leu Glu Asp Gln Glu Thr Val Ser Trp Ile Gln Tyr Pro Pro Asp
65                  70                  75                  80

Glu Asp Pro Phe Glu Pro Asp Asp Phe Ser Ser His Phe Phe Ser Thr
                85                  90                  95

Met Asp Pro Leu Gln Arg Pro Thr Ser Glu Thr Val Lys Pro Lys Ser
            100                 105                 110

Ser Pro Glu Pro Pro Gln Val Met Val Lys Pro Lys Ala Cys Pro Asp
        115                 120                 125

Pro Pro Pro Gln Val Met Pro Pro Lys Phe Arg Leu Thr Asn Ser
    130                 135                 140

Ser Ser Gly Ile Arg Glu Thr Glu Met Glu Gln Tyr Ser Val Thr Thr
145                 150                 155                 160

Val Gly Pro Ser His Cys Gly Ser Asn Pro Ser Gln Asn Asp Leu Asp
                165                 170                 175

Val Ser Met Ser His Asp Arg Ser Lys Asn Ile Glu Glu Lys Leu Asn
            180                 185                 190

Pro Asn Ala Ser Ser Ser Ser Gly Gly Ser Ser Gly Cys Ser Phe Gly
        195                 200                 205

Lys Asp Ile Lys Glu Met Ala Ser Gly Arg Cys Ile Thr Thr Asp Arg
    210                 215                 220

Lys Arg Lys Arg Ile Asn His Thr Asp Glu Ser Val Ser Leu Ser Asp
225                 230                 235                 240

Ala Ile Gly Asn Lys Ser Asn Gln Arg Ser Gly Ser Asn Arg Arg Ser
                245                 250                 255

Arg Ala Ala Glu Val His Asn Leu Ser Glu Arg Arg Arg Arg Asp Arg
            260                 265                 270

Ile Asn Glu Arg Met Lys Ala Leu Gln Glu Leu Ile Pro His Cys Ser
        275                 280                 285

Lys Thr Asp Lys Ala Ser Ile Leu Asp Glu Ala Ile Asp Tyr Leu Lys

|  |  |  |  |  | 290 |  |  |  | 295 |  |  |  | 300 |  |  |
|---|---|---|---|---|---|---|---|---|---|---|---|---|---|---|---|

Ser Leu Gln Leu Gln Leu Gln Val Met Trp Met Gly Ser Gly Met Ala
305                 310                 315                 320

Ala Ala Ala Ala Ser Ala Pro Met Met Phe Pro Gly Val Gln Pro Gln
            325                 330                 335

Gln Phe Ile Arg Gln Ile Gln Ser Pro Val Gln Leu Pro Arg Phe Pro
            340                 345                 350

Val Met Asp Gln Ser Ala Ile Gln Asn Asn Pro Gly Leu Val Cys Gln
        355                 360                 365

Asn Pro Val Gln Asn Gln Ile Ile Ser Asp Arg Phe Ala Arg Tyr Ile
    370                 375                 380

Gly Gly Phe Pro His Met Gln Ala Ala Thr Gln Pro Met Glu Met Leu
385                 390                 395                 400

Arg Phe Ser Ser Pro Ala Gly Gln Gln Ser Gln Gln Pro Ser Ser Val
                405                 410                 415

Pro Thr Lys Thr Thr Asp Gly Ser Arg Leu Asp His
            420                 425

<210> SEQ ID NO 39
<211> LENGTH: 1747
<212> TYPE: DNA
<213> ORGANISM: Arabidopsis thaliana

<400> SEQUENCE: 39

```
actttctgtc tgtacccaaa agaagtaatg aacctctctc atcttcttct tctctgtttc      60
tttcatgttt tgtgagttgt ttctcaacaa ttttctggtc tcttagagtg agaggagaga     120
gatagagagt tgtgttgggc gtggaacttg actagttcc  acatatcagg ttatatagat     180
cttctctttc aacttctgat tcgtccagaa gctttcctaa tctgagatct gacatggaac     240
accaaggttg gagttttgag gagaattata gtttgtccac taatagaaga tctatcaggc     300
cacaagatga actagtggag ttattatggc gagatggaca gtggttctg  cagagccaaa     360
ctcatagaga acaaacccaa acccagaaac aagatcatca tgaagaagcc taagatcca     420
gcacctttct tgaagatcaa gaaactgtct cttggatcca ataccctcca gatgaagacc     480
cattcgaacc cgacgacttc tcctcccact tcttctcaac catggatccc ctccagagac     540
caacctcaga gacggttaag cctaagtcca gtcctgaacc tcctcaagtc atggttaagc     600
ctaaggcctg tcctgaccct cctcctcaag tcatgcctcc tccaaaattt aggttaacaa     660
attcatcatc ggggattagg gaaacagaaa tggaacagta ctcggtaacg accgttggac     720
ctagccattg cggaagcaac ccatcacaga acgatctcga tgtctcaatg agtcatgatc     780
gaagcaaaaa catagaagaa aagcttaatc cgaacgcaag ttcctcatca ggtggctcct     840
ctggttgcag ctttggcaaa gatatcaaag aaatggctag tggaagatgc atcacaaccg     900
accgtaagag aaaacgtata atcacactg  acgaatctgt atctctatca gatgcaatcg     960
gtaacaagtc gaaccaacga tcaggatcaa accgaaggag tcgagcagct gaagttcata    1020
atctctccga aggaggagg  agagatagga tcaatgagag aatgaaggct ttgcaagaac    1080
taataccca  ctgcagtaaa actgataaag cttcgatttt agacgaagcc atagattatt    1140
tgaaatcact tcagttacag cttcaagtga tgtggatggg gagtggaatg gcggcggcgg    1200
cggcttcggc tccgatgatg ttccccggag ttcaacctca gcagttcata cgtcagatac    1260
agagcccggt acagttacct cgatttccgg ttatggatca gtctgcaatt cagaacaatc    1320
ccggtttagt ttgccaaaac ccggtacaaa accagatcat ctccgaccgg tttgctagat    1380
```

```
acatcggtgg gttcccacac atgcaggccg cgactcagcc gatggagatg ttgagattta   1440
gttcaccggc gggacagcaa agtcaacaac cgtcgtctgt gccgacgaag accaccgacg   1500
gttctcgttt ggaccactag gttggtgagc cactttttta cttccttatt tttggtatgt   1560 ttcttttta tatctatctt tctgaacata cttaaaacgt tcaaggatgt attattatag    1620
agtaaacgtg caacttcatt acgttatttt ctgtatatgt gagtttatgt atgtcaaaat   1680
gacatgatga gatttttgt aaacaacatc ttaaaaacag gacatgtgat ttttgtaatc   1740
gtaaaaa                                                             1747
```

<210> SEQ ID NO 40
<211> LENGTH: 397
<212> TYPE: PRT
<213> ORGANISM: Zea mays

<400> SEQUENCE: 40

```
Met Gln Thr Ala Ile Glu His Ala Cys Ser Val Val Glu Cys Ala Ala
1               5                   10                  15

Thr Ala Arg Ala Ala Met Asp Met Ser His Tyr Ile Pro Asp Trp Ser
            20                  25                  30

Ser Ser Met Gly Asp Thr Phe Ala Pro Leu Gly Gly Glu Asp Asp
        35                  40                  45

Gly Leu Ile Glu Leu Met Trp Arg Asn Gly His Val Val Met Gln Ala
    50                  55                  60

Gln Ala Pro Arg Lys Pro Pro Arg Pro Asp Asp Glu Ala Ala Ala
65                  70                  75                  80

Ala Gln Ala Gln Ala Trp Phe Gln Tyr Pro Val Glu Arg Ala Asp
                85                  90                  95

Leu Phe Ser Glu Leu Phe Gly Glu Ala Gln Ala Ala Val Gly Gly Ala
            100                 105                 110

Arg Gly Glu Ala Ala Arg Gln Ser Ile Arg Met Met Pro Pro Pro
        115                 120                 125

Pro Pro Pro Arg Pro Ala Gln Ala Pro Arg Glu Glu Lys Ala Cys Pro
    130                 135                 140

Gly Asp Gly Gly Thr Ala Thr Ala Thr Asp Gly Ala Gly Ser Ser Val
145                 150                 155                 160

Leu Thr Val Val Ser Ser Leu Cys Gly Ser Asn Gly Asn His Val Gln
                165                 170                 175

Ala Thr Ala Pro Gly Asp Val Ala Arg Ala Arg Asp Val Leu Met Val
            180                 185                 190

Thr Ser Ser Ser Thr Thr Arg Ser Arg Ser Cys Thr Thr Lys Ser Glu
        195                 200                 205

Gln Pro Gly Pro Gly Pro Gly Ala Ala Arg Arg Ser Gly Lys Arg Lys
    210                 215                 220

His Asn Asp Ala Thr Asp Ala Glu Asp Val Gly Leu Glu Cys Glu Pro
225                 230                 235                 240

Ala Gln Arg Thr Thr Thr Ala Lys Arg Arg Ala Ala Gln Val His
                245                 250                 255

Asn Leu Ser Glu Arg Arg Arg Arg Asp Arg Ile Asn Glu Lys Met Lys
            260                 265                 270

Ala Leu Gln Glu Leu Ile Pro His Cys Asn Lys Ala Asp Lys Ala Ser
        275                 280                 285

Met Leu Asp Glu Ala Ile Glu Tyr Leu Lys Ser Leu Gln Leu Gln Leu
    290                 295                 300
```

```
Gln Val Val Trp Met Gly Gly Ile Ala Ala Gly Val His Gln
305                 310                 315                 320

Arg Thr Met Val Ala Pro Gly Arg Pro His Val Ala Ser Leu
                325                 330                 335

Pro Ala Ser Ala Pro Asp Leu Tyr Thr Arg Tyr Leu Ala Val Asp His
            340                 345                 350

Leu Pro Pro Pro Leu Val Pro Pro Arg Thr Ala Ala Ala Met
        355                 360                 365

Gly Leu Tyr Pro Arg Gln Asn Pro Val Pro Ala Thr Ser Ser Pro Ser
    370                 375                 380

Phe Arg Thr Thr Glu Asn Thr Arg Lys Leu Trp Gln Ala
385                 390                 395

<210> SEQ ID NO 41
<211> LENGTH: 1492
<212> TYPE: DNA
<213> ORGANISM: Zea mays

<400> SEQUENCE: 41
```

| | | | | | |
|---|---|---|---|---|---|
| ccttgccctg | ctgcaacttg | aacctcctgg | cagctcctgt | ttcaggcagg | cagcaagtag | 60 |
| ggaagaggct | ctgcagatca | gttccatgca | gacagcgatc | gagcacgcct | gctcggtggt | 120 |
| ggaatgcgct | gcgacagccc | gagccgccat | ggacatgagc | cactacatcc | ccgattggag | 180 |
| cagcagcatg | ggagacacct | tcgcgccact | gggcggcgag | gacgacgacg | ggctcatcga | 240 |
| gctcatgtgg | cgcaacggcc | acgtggtcat | gcaggcccag | gcgccgcgga | agccgccgag | 300 |
| acccgacgac | gacgaggcgg | cggcggcgca | ggcgcaggcg | tggttccagt | acccggtgga | 360 |
| ggagagggcc | gacctcttct | cggagctctt | cggggaggcg | caggcggccg | tcggcggcgc | 420 |
| gcgcggggag | gccgcgcgcc | agagtatccg | gatgatgccg | ccgccgccgc | cgccgccgag | 480 |
| gcccgcgcaa | gcgccgcggg | aggagaaggc | gtgcccggga | gacggcggca | cggcgacggc | 540 |
| gacggacggc | gccggctcgt | ccgtgctcac | ggtcgtgtcc | agcctctgcg | ggagcaacgg | 600 |
| caaccacgtg | caggcgacgg | cgccggggga | cgtcgccagg | gcccgcgacg | tgctgatggt | 660 |
| gacctcgtcg | tcgacgacgc | gttccaggtc | atgcaccacc | aagagcgagc | agcccgggtcc | 720 |
| cgggcccggc | gctgcccgcc | ggagcggcaa | gaggaagcat | aacgacgcca | ccgatgccga | 780 |
| ggacgtgggg | ctggagtgcg | agccggcgca | gaggacgacg | actgccaagc | ggcgccgcgc | 840 |
| cgcgcaagtc | cacaacctct | cggagcggag | gagacgggac | aggatcaacg | agaagatgaa | 900 |
| ggccctgcag | gaactcatac | cccactgcaa | caaagcggac | aaggcgtcga | tgctggacga | 960 |
| ggcgatcgag | tacctcaagt | cgctgcagct | ccagctgcag | gtggtgtgga | tgggcggcgg | 1020 |
| catcgcggcg | gcggggtgc | accagcggac | gatggtggcc | gcgcccgggc | gtcctcccca | 1080 |
| cgtggcttcc | ctgccggcgt | cggcgcccga | cctctatacg | cgctacctcg | ccgtcgacca | 1140 |
| cctgccgcca | ccgcccttgg | tgccaccgcc | acgcacggcg | gcggcgatgg | gcttgtaccc | 1200 |
| gcgccagaac | cccgtgccgg | cgacgtcgtc | tccttccttc | cgaacgaccg | aaaatacgcg | 1260 |
| aaaactatgg | caagcctgag | attcagatcc | ggggtatggt | gaccagctga | tgggtcatct | 1320 |
| agctgcatgc | atgtgtgtat | gtgttggtag | tatggttaag | ccttgacaga | gacttgtgat | 1380 |
| cgagaccgag | atcgaccgat | aggccgtcac | ttctttttc | ttccatcttt | cagttttgg | 1440 |
| ttgataggcc | ggagtgtaat | ttgaccagtg | gtcgagattt | gtcaagcgac | ac | 1492 |

<210> SEQ ID NO 42

<211> LENGTH: 562
<212> TYPE: PRT
<213> ORGANISM: Glycine max

<400> SEQUENCE: 42

Met Asn Ser Ile Pro Gly Trp Asp Phe Glu Ser Asp Thr Cys Leu
1               5                   10                  15

Thr Asn Gln Arg Lys Leu Ile Gly Pro Asp Gln Glu Leu Val Glu Leu
            20                  25                  30

Leu Trp Lys Asn Gly Gln Val Val Met His Asn Gln Thr His Arg Lys
        35                  40                  45

Thr Leu Gly Asn Ser Ser Asn Leu Arg Gln Val Gln Lys Ser Asp Gln
    50                  55                  60

Ser Val Leu Arg Ser Ser Gly Pro Tyr Gly Asn Ser Ser Asn Leu Asp
65                  70                  75                  80

Gln Glu Asp Ala Ala Pro Trp Val Gln Phe Pro Leu Glu Asp Pro Leu
                85                  90                  95

Glu Gln Asp Phe Cys Ser Asn Leu Leu Ser Glu Leu Pro Thr Cys Glu
            100                 105                 110

Phe Glu Ser Tyr Lys Pro Ile Arg Gln Leu Glu Glu Glu Lys Phe Ala
        115                 120                 125

Lys Phe Phe Ala Ser Gly Thr Pro His His Pro Thr Thr Ser Ser Ser
    130                 135                 140

Gln Pro Leu Pro Pro Asn Met Lys Pro Ser Cys Ile Gln Gly Leu Gln
145                 150                 155                 160

Gly Asn Pro Ile Pro Met Pro Ala Pro Arg Phe His Gly Pro Asp Ser
                165                 170                 175

Ser Gln Lys Ile His Asp Phe Gly Ala Ser Arg Lys Val Leu Asn Phe
            180                 185                 190

Pro Gln Phe Ser Thr Pro Arg Asn Asn Val Pro Ser Ala Pro Gly Ile
        195                 200                 205

Thr Gln Phe Arg Glu Lys Thr Thr Ala Asn Met Ser Gln Ser Glu Ala
    210                 215                 220

Arg Glu Tyr Ser Val Ile Thr Val Gly Ser Ser His Cys Gly Ser Asn
225                 230                 235                 240

His Ile Pro Gln Glu Gln Asp Val Ser Arg Ile Ser Thr Gly Val
                245                 250                 255

Trp Ala Thr Thr Asn Asn Asn Thr Thr Leu Ser Ala Glu Pro Glu Ala
            260                 265                 270

Val Arg Asp Tyr Val Gln Arg Pro Ile Cys Pro Lys Ser Gly Gln Gly
        275                 280                 285

Lys Ser Glu Met Ile Glu Leu Thr Val Thr Ser Ser Ser Gly Gly Ser
    290                 295                 300

Gly Ser Thr Gly Ile Gly Arg Thr Cys Ser Leu Ser Thr Arg Asp His
305                 310                 315                 320

Gly Gln Lys Arg Lys Gly Thr Glu Glu Glu Ala Leu Glu Glu Gln Ser
                325                 330                 335

Glu Asp Thr Glu Leu Lys Ser Ala Asp Gly Asn Lys Ala Ser Gln Arg
            340                 345                 350

Thr Arg Ser Ser Arg Arg Asn Arg Ala Ala Glu Val His Asn Gln Ser
        355                 360                 365

Glu Arg Arg Arg Arg Asp Arg Ile Asn Glu Lys Met Arg Thr Leu Gln
    370                 375                 380

Gln Leu Ile Pro Asn Ser Asn Lys Thr Asp Lys Ala Ser Met Leu Glu

```
                385                 390                 395                 400
        Glu Ala Ile Glu Tyr Leu Lys Ser Leu Gln Phe Gln Leu Gln Val Met
                        405                 410                 415

Trp Met Gly Gly Gly Met Thr Pro Val Met Phe Pro Gly Ile Gln His
                        420                 425                 430

Tyr Met Ser Gln Met Gly Met Gly Met Gly Ala Pro Ser Leu Pro Ser
                        435                 440                 445

Ile His Asn Pro Met Gln Leu Pro Lys Val Pro His Asp Gln Ala Met
        450                 455                 460

Ser Val Leu Gln Ile Pro Asn Gln Asn Leu Met Cys Gln Asn Pro Val
        465                 470                 475                 480

Leu Gly Ala Phe Asn Tyr Gln Asn Gln Met Gln Asn Pro Cys Leu Pro
                        485                 490                 495

Glu Gln Tyr Ala Arg Tyr Met Gly Tyr His Leu Met Gln Asn Ala Ser
                        500                 505                 510

Gln Pro Met Asn Val Phe Arg Tyr Gly Ser Gln Ala Val Gln His Ser
                        515                 520                 525

Gln Thr Met Ile Ala Pro Gly Asn Asn Ser Ser Gly Pro Met Ser Gly
                        530                 535                 540

Thr Ala Asn Ile Asp Asp Ala Asp Ser Gly Lys Ala Gly Ser Ser Thr
        545                 550                 555                 560

Phe Asn

<210> SEQ ID NO 43
<211> LENGTH: 2161
<212> TYPE: DNA
<213> ORGANISM: Glycine max

<400> SEQUENCE: 43
gaccccgttt tcaactggtc ccgtgttcct tcatttgatg ccacatgtgc agctacccat      60 gttttctcg ctgttgacga gcacaatata taataaatac catttttttc atgccatatt     120
tgctctcttc tctctttgta ctaataactt ggatctatgc cactgtcctt ctccttgtta    180
aaaactgtgc cacacgtctg tcaccaaact ccctaagcag aagaagcaca tgttcagagg    240
gagttttgtt tcatcagtct ctagctagca tatatttcta gcttctattc aacaagttgc    300
aaaaaacaga ctttgcctta accaaaagaa aatctgtttt taccttaact cagacaactc    360
gtttggtgaa ccatgaacaa cagtattcct ggttgggatt ttgagagtga tacatgtctc    420
accaaccaaa gaaagctcat agggccggac caagaacttg tagagctcct atggaaaaat    480
gggcaagtag ttatgcacaa ccaaacacat aggaagacac ttgggaattc atctaacttg    540
agacaggtgc agaaaagtga tcaatcagta ttaaggtcta gcggtcccta tggaaactca    600
agcaacttgg atcaagaaga tgccgcccca tgggtccaat tcccacttga ggacccattg    660
gaacaagatt tttgttcaaa cctttttatct gaactaccaa cttgtgaatt tgaatcttac    720
aagccaatca ggcaattgga agaggaaaag tttgccaaat ttttgcttc cggtaccccc    780 catcatccta caacttcaag ttcacaacca ctaccaccta acatgaaacc ctcatgtatt    840
cagggactcc aagggaatcc tattcctatg ccagctccaa gatttcatgg tcctgattca    900
tctcagaaaa tccatgactt tggagcatca cgaaaggttc taaatttttcc tcagttttca    960 acacccgta ataatgttcc atcagcacct ggtattacac agtttagaga gaaaactact   1020
gctaacatgt cacaaagtga ggctagagag tactcagtga tcacagttgg ttcaagtcac   1080
tgtggcagca atcacatccc tcaggagcaa gatgtaagca ggatttcaag cactggtgtt   1140
```

```
tgggccacta ctaataataa tactacttta tctgctgagc ctgaagctgt cagagattat    1200
gtccaaagac cgatttgtcc taagagtggc caaggaaaat cagagatgat tgaactaact    1260
gtgacttcat cttccggtgg ctcgggaagt actggtatcg gaagaacctg ttccctatca    1320
acaagagatc atggccaaaa gagaaaaggg acagaagaag aagcgttaga ggaacaaagt    1380
gaggacacag aacttaaatc agctgatgga acaaggcttc tcagcggac gaggtcttcc     1440 agaaggaacc gtgcagcaga agtgcataat caatcagaaa ggagaagaag agataggatc    1500
aacgagaaga tgaggacatt gcagcaactg atacctaata gtaacaagac agacaaagca    1560
tcaatgttag aagaggcaat cgaatacttg aaatcacttc agtttcagct tcaggttatg    1620
tggatggggg gtggcatgac accagtgatg ttcccaggaa ttcagcacta tatgtcacaa    1680
atgggtatgg gaatgggtgc accttctttg ccttccattc acaacccgat gcaattgcca    1740
aaagtgccac atgatcaagc catgtctgtg cttcagatac caaaccagaa tttaatgtgt    1800
caaaatccag ttttgggtgc ctttaactac caaaaccaga tgcagaaccc gtgccttcca    1860
gaacaatatg cacgttacat gggttaccat cttatgcaaa atgcctctca gcctatgaat    1920
gtgttcagat atggttccca agcagtgcaa cacagtcaaa cgatgattgc accaggcaat    1980
aatagcagcg gacccatgag tggaacagct aatattgatg atgctgacag tggcaaagcg    2040
ggttcttcca cctttaattg aatagtgaat agcaatacct taaaattact caattggggg    2100
aattacctaa tggagtacgt caatcctcac aagcaccaat atgtgctcca attttatgta    2160
g                                                                    2161
```

<210> SEQ ID NO 44
<211> LENGTH: 409
<212> TYPE: PRT
<213> ORGANISM: Oryza sativa

<400> SEQUENCE: 44

```
Met Asn Gln Phe Val Pro Asp Trp Asn Thr Thr Ser Met Gly Asp Gly
1               5                   10                  15

Phe Ala Pro Leu Gly Glu Asp Asp Gly Leu Val Glu Leu Leu Trp Cys
            20                  25                  30

Asn Gly His Val Val Met Gln Ser Gln Ala Pro Arg Lys Pro Pro Arg
        35                  40                  45

Pro Glu Lys Thr Thr Ala Ala Ala Ala Ala Met Ala Glu Asp Glu
    50                  55                  60

Ser Ala Ser Trp Phe Gln Tyr Pro Val Asp Asp Val Leu Glu Lys Asp
65                  70                  75                  80

Leu Phe Thr Glu Leu Phe Gly Glu Met Thr Ala Ala Gly Gly Gly Gly
                85                  90                  95

Gly Asp Val Arg Arg Ala Ala Cys Lys Glu Glu Arg Gly Ala Val Ala
            100                 105                 110

Ala Phe Gln Ser Arg Met Met Pro Pro Trp Pro Ala Arg Gly Lys
        115                 120                 125

Ala Glu Phe Gly Asp Val Asp Asp Val Cys Gly Val Ser Glu Val Val
130                 135                 140

Met Ala Lys Met Asp Gly Ala Ala Ala Ala Glu Thr Val Gly Glu Ser
145                 150                 155                 160

Ser Met Leu Thr Ile Gly Ser Ser Ile Cys Gly Ser Asn His Val Gln
                165                 170                 175

Thr Pro Pro Val Gly Asn Gly Lys Ala Gly Ala Gly Thr Ala Gly Ala
```

```
                    180                 185                 190
Ala Arg Arg Ala His Asp Thr Ala Thr Val Ala Ser Ser Ser Met Arg
                195                 200                 205

Ser Arg Ser Cys Thr Ala Lys Ala Glu Pro Arg Asp Val Ala Ala Ala
            210                 215                 220

Gly Val Gly Gly Lys Arg Lys Gln Arg Gly Ala Ala Met Glu Ser
225                 230                 235                 240

Gly Ser Pro Ser Glu Asp Val Glu Phe Glu Ser Ala Ala Ala Thr Cys
                245                 250                 255

Ser Pro Ala Gln Lys Thr Thr Thr Ala Lys Arg Arg Ala Ala Glu
            260                 265                 270

Val His Asn Leu Ser Glu Arg Arg Arg Asp Arg Ile Asn Glu Lys
        275                 280                 285

Met Lys Ala Leu Gln Glu Leu Ile Pro His Cys Asn Lys Thr Asp Lys
    290                 295                 300

Ala Ser Met Leu Asp Glu Ala Ile Glu Tyr Leu Lys Ser Leu Gln Leu
305                 310                 315                 320

Gln Leu Gln Met Met Trp Met Gly Gly Met Ala Pro Ala Val
                325                 330                 335

Met Phe Pro Ala Ala Gly Val His Gln Tyr Met Gln Arg Met Gly Ala
                340                 345                 350

Val Gly Met Gly Pro Pro His Met Ala Ser Leu Pro Arg Met Pro Pro
            355                 360                 365

Phe Met Ala Pro Pro Pro Ala Ala Val Gln Ser Ser Pro Val Val Ser
    370                 375                 380

Met Ala Asp Pro Tyr Ala Arg Cys Leu Ala Val Asp His Leu Gln Pro
385                 390                 395                 400

Pro Pro Pro Met Phe Arg Arg Glu Tyr
                405

<210> SEQ ID NO 45
<211> LENGTH: 1749
<212> TYPE: DNA
<213> ORGANISM: Oryza sativa

<400> SEQUENCE: 45
gcgagtcctc ttcctgccct gccctgccct gccctgcatt ctttctttct ccaccagggg      60
aatccagttc accccccagtg ctgcttctgc tgctgcttct gcatcatctt gccctgttaa    120
aaagacacag tgcccttgtt ctttcgcagt tgcaactagc atctcctcct ctacttgtac    180
tcacttcaca cctcagctca gctcagctca tctcctgtca tctcagctca aagagaaaga    240
gctgaaggtg taagctgatc accaggaagc agaggctttt tttcagatta cagttatctg    300
aaacaaccaa cttcagaatc aatcagcaaa ggtagaaaca agacagagct gctgtgcttc    360
tgtgattaat tagggttgtt aatgccatga accagttcgt ccctgattgg aacaccacca    420
gcatgggcga cggctttgcg ccattaggcg aagacgacgg gctcgtcgag ctgctatggt    480
gcaatggcca cgtcgtcatg cagagccagg cgccgcggaa gccgccgagg ccggagaaga    540
cgacggcggc ggcggcggcg gcgatggcgg aggatgagtc ggcgtcgtgg tttcagtacc    600
cggtcgacga cgtgcttgag aaggacctgt tcaccgagct gttcggcgaa atgacggcgg    660
ccggcggcgg cggcggcgac gtccgcaggg cggcgtgcaa ggaggagcgc ggcgcggtcg    720
ccgcgttcca gagcaggatg atgccgccgc cgtggccggc gagggggaag gcggagttcg    780
gtgacgtcga cgacgtgtgc ggcgtctcgg aggtcgtcat ggcgaagatg acggggcgg     840
```

```
cggcggcgga gacggtcggc gagtcatcga tgctgacaat cgggtcgagc atctgcggga   900
gcaaccacgt ccagacgccg ccggtgggga acgggaaggc cggcgccggc accgccggcg   960
ccgccagaag ggcgcacgac acggcgacgg tggcgtcgtc gtcgatgagg tcgaggtcct  1020
gcaccgccaa ggccgagccg cgcgacgtcg cagccgccgg cgtcggcggc aagcggaagc  1080
agcgcggcgg cgccgccatg gagtccggga ccccagcga ggacgtggag ttcgagtccg  1140
ccgccgcaac gtgctcgccg gcgcagaaga cgacgacggc gaagcggcgg cgcgccgccg  1200
aggtgcacaa cctctccgag aggaggagaa gagataggat caatgagaag atgaaagcat  1260
tacaggagct cataccctcac tgcaacaaaa cggacaaagc atcgatgctg atgaagcga  1320
tcgagtatct caagtcactg cagctccagc tacagatgat gtggatgggc ggcggaatgg  1380
cgccgccggc ggtgatgttc ccggcggccg gcgtgcacca gtacatgcag cggatgggcg  1440
ccgtcgggat gggcccacca cacatggcgt ccctgccgag gatgccgccg ttcatggcgc  1500
cgccgcccgc cgccgtgcag agctcgccgg tggtcagcat ggccgacccc tacgcccgct  1560
gcctcgccgt cgaccacctc cagccaccgc ctccgatgtt tcgacgcgaa tactagggaa  1620
ggaactaata tcaaataata gaaggggtga gccttcgaat cgagatcgtc tagcccacca  1680
ccttatagag ctagccggaa ggccctcgag cgtttctcat attttcagtt tcctaagagt  1740
tttttttt                                                           1749
```

<210> SEQ ID NO 46

<400> SEQUENCE: 46

000

<210> SEQ ID NO 47

<400> SEQUENCE: 47

000

<210> SEQ ID NO 48
<211> LENGTH: 187
<212> TYPE: PRT
<213> ORGANISM: Arabidopsis thaliana

<400> SEQUENCE: 48

```
Met Ser Leu Phe Pro Cys Glu Ala Ser Asn Met Asp Ser Met Val Gln
1               5                   10                  15

Asp Val Lys Pro Thr Asn Leu Phe Pro Arg Gln Pro Ser Phe Ser Ser
            20                  25                  30

Ser Ser Ser Leu Pro Lys Glu Asp Val Leu Lys Met Thr Gln Thr
        35                  40                  45

Thr Arg Ser Val Lys Pro Glu Ser Gln Thr Ala Pro Leu Thr Ile Phe
    50                  55                  60

Tyr Ala Gly Gln Val Ile Val Phe Asn Asp Phe Ser Ala Glu Lys Ala
65                  70                  75                  80

Lys Glu Val Ile Asn Leu Ala Ser Lys Gly Thr Ala Asn Ser Leu Ala
                85                  90                  95

Lys Asn Gln Thr Asp Ile Arg Ser Asn Ile Ala Thr Ile Ala Asn Gln
            100                 105                 110

Val Pro His Pro Arg Lys Thr Thr Gln Glu Pro Ile Gln Ser Ser
        115                 120                 125
```

Pro Thr Pro Leu Thr Glu Leu Pro Ile Ala Arg Arg Ala Ser Leu His
            130                 135                 140

Arg Phe Leu Glu Lys Arg Lys Asp Arg Val Thr Ser Lys Ala Pro Tyr
145                 150                 155                 160

Gln Leu Cys Asp Pro Ala Lys Ala Ser Ser Asn Pro Gln Thr Thr Gly
                165                 170                 175

Asn Met Ser Trp Leu Gly Leu Ala Ala Glu Ile
            180                 185

<210> SEQ ID NO 49
<211> LENGTH: 1527
<212> TYPE: DNA
<213> ORGANISM: Arabidopsis thaliana

<400> SEQUENCE: 49

| | | | | | |
|---|---|---|---|---|---|
| atattggagg | taggaagaag | aactctgcaa | ccaaaccaac | caaccccaaa | gccaaacaaa | 60 |
| gttttataga | gaccttccat | ttctccctct | cgtgacaaac | gcaatttgca | gagaagcaac | 120 |
| agcaacaaca | agaagaagaa | gaaaaagatt | tgagattact | ttgtatcgat | ttagctattc | 180 |
| gagaaactct | tgccgtttga | aagttttaat | tgttaaagat | gtcgagttct | atggaatgtt | 240 |
| ctgagttcgt | cggtagccgg | agatttactg | ggaagaagcc | tagcttctca | cagacgtgta | 300 |
| gtcgattgag | tcagtatcta | aaagagaacg | gtagctttgg | agatctgagc | ttaggaatgg | 360 |
| catgcaagcc | tgatgtcaat | ggtaagaaac | cttctctttc | tcctagatcc | acttcttttt | 420 |
| tcgttttctc | tgttttttat | ttcttgaatc | ttgatcttga | aaactttttca | agaaaatttt | 480 |
| gaatcgattt | caaagaaatt | agggagagtt | agtttgctaa | attttgacat | agaaaatgat | 540 |
| tggagagagt | tctaactttt | ggatcatata | tatttgcagg | aactttaggc | aactcacgtc | 600 |
| agccgacaac | aaccatgagt | ttattccctt | gtgaagcttc | taacatggat | tccatggttc | 660 |
| aagatgttaa | accgacgaat | ctgtttccta | ggcaaccaag | cttttcttcc | tcatcttcct | 720 |
| ctcttccaaa | ggaagatgtt | ttgaaaatga | cacagactac | cagatctgtg | aaaccagagt | 780 |
| ctcaaactgc | accattgact | atattctacg | ccgggcaagt | gattgtattc | aatgacttt | 840 |
| ctgctgagaa | agccaaagaa | gtgatcaact | tggcgagcaa | aggcaccgct | aatagcttag | 900 |
| ccaagaatca | aaccgatatc | agaagcaaca | tcgctactat | cgcaaaccaa | gttcctcatc | 960 |
| caagaaaaac | cacaacacaa | gagccaatcc | aatcctcccc | aacaccattg | acagaacttc | 1020 |
| ctattgctag | aagagcttca | cttcaccggt | tcttggagaa | gagaaaggac | agagttacgt | 1080 |
| caaaggcacc | ataccaatta | tgcgatccag | ccaaagcgtc | ttcaaaccct | caaaccacag | 1140 |
| gcaacatgtc | gtggctcggt | ttagcagctg | aaatatgaat | gctaaccacc | ctcaagccgt | 1200 |
| accaagaaat | tcttttgacg | acgttgcttc | aagacaagat | ataaaagctc | ctatcttcat | 1260 |
| gcttttgat | ttaagataca | aactactcaa | tgattaggaa | acttcatata | tttgtatgta | 1320 |
| ttgattagtg | atcaattatt | gttagtattc | gttatagtct | gttttttctac | tagttattgt | 1380 |
| cgcctgtcta | aatccccttg | ctatgggtta | tctcaaaatt | agtttcgtat | gtaactaatt | 1440 |
| ttgtaagaac | aataattttt | gttgacgaac | catactatca | aatactctaa | attatatctt | 1500 |
| gataaatcta | cctatcaggt | aagtagg | | | | 1527 |

<210> SEQ ID NO 50
<211> LENGTH: 352
<212> TYPE: PRT
<213> ORGANISM: Arabidopsis thaliana

<400> SEQUENCE: 50

| | | | | | | | | | | | | |
|---|---|---|---|---|---|---|---|---|---|---|---|---|
|Met|Glu|Arg|Asp|Phe|Leu|Gly|Leu|Gly|Ser|Lys|Asn|Ser|Pro|Ile|Thr|
|1| | | |5| | | |10| | | |15| | | |

Met Glu Arg Asp Phe Leu Gly Leu Gly Ser Lys Asn Ser Pro Ile Thr
1               5                   10                  15

Val Lys Glu Glu Thr Ser Glu Ser Ser Arg Asp Ser Ala Pro Asn Arg
            20                  25                  30

Gly Met Asn Trp Ser Phe Ser Asn Lys Val Ser Ala Ser Ser Ser Gln
        35                  40                  45

Phe Leu Ser Phe Arg Pro Thr Gln Glu Asp Arg His Arg Lys Ser Gly
50                  55                  60

Asn Tyr His Leu Pro His Ser Gly Ser Phe Met Pro Ser Ser Val Ala
65                  70                  75                  80

Asp Val Tyr Asp Ser Thr Arg Lys Ala Pro Tyr Ser Ser Val Gln Gly
                85                  90                  95

Val Arg Met Phe Pro Asn Ser Asn Gln His Glu Glu Thr Asn Ala Val
            100                 105                 110

Ser Met Ser Met Pro Gly Phe Gln Ser His His Tyr Ala Pro Gly Gly
        115                 120                 125

Arg Ser Phe Met Asn Asn Asn Asn Ser Gln Pro Leu Val Gly Val
    130                 135                 140

Pro Ile Met Ala Pro Pro Ile Ser Ile Leu Pro Pro Gly Ser Ile
145                 150                 155                 160

Val Gly Thr Thr Asp Ile Arg Ser Ser Lys Pro Ile Gly Ser Pro
                165                 170                 175

Ala Gln Leu Thr Ile Phe Tyr Ala Gly Ser Val Cys Val Tyr Asp Asp
            180                 185                 190

Ile Ser Pro Glu Lys Ala Lys Ala Ile Met Leu Leu Ala Gly Asn Gly
        195                 200                 205

Ser Ser Met Pro Gln Val Phe Ser Pro Pro Gln Thr His Gln Gln Val
    210                 215                 220

Val His His Thr Arg Ala Ser Val Asp Ser Ser Ala Met Pro Pro Ser
225                 230                 235                 240

Phe Met Pro Thr Ile Ser Tyr Leu Ser Pro Glu Ala Gly Ser Ser Thr
                245                 250                 255

Asn Gly Leu Gly Ala Thr Lys Ala Thr Arg Gly Leu Thr Ser Thr Tyr
            260                 265                 270

His Asn Asn Gln Ala Asn Gly Ser Asn Ile Asn Cys Pro Val Pro Val
        275                 280                 285

Ser Cys Ser Thr Asn Val Met Ala Pro Thr Val Ala Leu Pro Leu Ala
    290                 295                 300

Arg Lys Ala Ser Leu Ala Arg Phe Leu Glu Lys Arg Lys Glu Arg Val
305                 310                 315                 320

Thr Ser Val Ser Pro Tyr Cys Leu Asp Lys Lys Ser Ser Thr Asp Cys
                325                 330                 335

Arg Arg Ser Met Ser Glu Cys Ile Ser Ser Leu Ser Ser Ala Thr
            340                 345                 350

<210> SEQ ID NO 51
<211> LENGTH: 3253
<212> TYPE: DNA
<213> ORGANISM: Arabidopsis thaliana

<400> SEQUENCE: 51
gcgatttgtt aataaaacta gaaattgcgg tgaattaact tcattccacg ttttttcatt    60
ttctccctca aaagtctctg ttttttttcc ttttccggc gaagctctat ttagcttgat   120

-continued

| | | | | |
|---|---|---|---|---|
| tccggcgttt | aacacgcgtt | ttaatcgaaa | cagacatttg | agatcgaatt | aattttgtag | 180 |
| cgggctgtgt | ctttattata | gatggagaga | gattttctcg | ggttgggttc | gaaaaattct | 240 |
| ccgatcactg | tcaaggagga | aaccagcgaa | agctctagag | attcaggtta | tttattactc | 300 |
| ttctcaattt | ttctgattct | gattgttttt | aaatcgtaga | tttgtttgat | tgattaggag | 360 |
| ttattaggac | tacttgtagt | atggaatttg | ttttggata | gctgatttta | tggcttgctc | 420 |
| gggaactgga | attgtcagtt | tgttgcttgg | agcagaacat | tgtcctttgc | ttttctcggg | 480 |
| agatgtagaa | tttggatttg | gaaaaactag | tgttcttttc | caaagccttg | tcttaaacat | 540 |
| gctttcggtc | ggagaaatta | acgagaacta | atctcaagct | tctaacataa | ttaaactcgg | 600 |
| taaactttt | tttactagag | taaatttttt | tgttttgttt | gaagagtctt | ataattgaga | 660 |
| aatactttat | tagtttatac | taaaaaaaaa | acgaatacgt | aaaatgttgg | aaaagagggg | 720 |
| atgtatagag | actgatacaa | aaatgataaa | atagagacgg | ttggtagtag | gtagaaagat | 780 |
| taaatatact | caaagagtg | agttggatta | gtttataaga | tgattaactt | cttgattgtg | 840 |
| tgagttggat | tagtttatga | gattattaaa | atattgattg | tgtatttgtg | ttgtgtgttg | 900 |
| attaagcgga | acttgcgtta | gaatattgtt | caaggtacaa | tgtggaaata | atagttttct | 960 |
| caccacgagg | aatataatta | tttcaacttt | gttttcttat | cagccaaaac | gtgccacacc | 1020 |
| ataaaagtag | tgcatcaaca | tgtggtgtgg | tgtggtgggg | ttaaagtttg | aatctctctt | 1080 |
| taatttaaac | tattaaaaca | aacttaaatt | attggagttt | cgtacaatga | ctttcaatca | 1140 |
| aatgttttag | aattagacac | ggttttcgaa | agtggttttc | cctcgttgaa | tttgtcaaca | 1200 |
| gtatcagatt | ctacattgtt | ggttactaat | cttttccttg | aagtaggtgt | tgaattaatc | 1260 |
| ctctgttgtt | tatgtaagga | gatctcgaga | catttatggt | taacagttaa | cactacatgt | 1320 |
| ttgactttaa | actgattatc | ttttattctt | tttcttttgt | agctcccaac | agaggaatga | 1380 |
| actggtcttt | ctcaaacaaa | gtatcagctt | cttcttctca | gtttctatcc | ttcaggccaa | 1440 |
| ctcaagaaga | tagacataga | aagtctggaa | attatcatct | tcctcactct | ggttccttca | 1500 |
| tgccatcatc | agtagctgat | gtttatgatt | caacccgcaa | agctccttac | agttctgtac | 1560 |
| aggtatttgt | catcaaaacc | tatgttaacc | aagacccttg | tgttttttt | atccttcgca | 1620 |
| agatagcttt | aaaagtgagc | cctgttttat | gagcatatag | taattggttt | tgagtctagt | 1680 |
| ttagcacaag | ttcatggcaa | ttagtttgtg | gatctaatct | tggtttaata | ctgattcatt | 1740 |
| ttaagtgtaa | gctaagcttc | tcatttttga | taagttagtt | catacaatgc | ctcacaccta | 1800 |
| ctttatggct | tgttactctc | agggagtgag | gatgttccct | aattccaatc | aacacgaaga | 1860 |
| aactaacgca | gtttccatgt | cgatgccggg | tttccagtct | catcattatg | caccaggagg | 1920 |
| aagaagcttc | atgaacaata | acaataactc | acaaccttg | gtaggagttc | ctatcatggc | 1980 |
| acctccaatt | tcaatccttc | ctcctccagg | ttccattgta | gggactactg | atattaggta | 2040 |
| cccactagtc | atcatatcat | acagaaactc | tttctacatt | ttcatagttg | actaaagact | 2100 |
| tattttgtc | agatcttctt | ccaagccaat | aggttcacct | gcgcagttga | cgatcttta | 2160 |
| tgccggttca | gtttgtgttt | acgatgacat | atctcctgaa | aaggtatctc | aatcattttc | 2220 |
| ttccatatat | gcatctcttt | tactcgtaag | gtatggtact | catttgcttt | ctttcatttc | 2280 |
| tcaggcaaag | gcgataatgt | tgctagctgg | gaacggttcc | tctatgcctc | aagtctttc | 2340 |
| gccgcctcaa | actcatcaac | aagtggtcca | tcatactcgt | gcctctgtcg | attcttcagc | 2400 |
| tatgcctcct | agcttcatgc | ctacaatatc | ttatcttagc | cctgaagctg | gaagtagcac | 2460 |
| aaacggactc | ggagccacaa | aagcgacaag | aggcttgacg | tcaacatatc | acaacaacca | 2520 |

```
agctaatgga tccaatatta actgcccagt accagtttct tgttctacca atgtaatggc   2580
tccaacaggt aaaaaacaaa gtcagagacc tgatactaca ttcgccatct aacttactag   2640
tattttcatg gatgtaactt cattctcgtt ctgtttctta tgcagtggca ttacctctgg   2700
ctcgcaaagc atccctggct aggttttttag agaaacgcaa agaaaggtac gcaacacttc   2760
tttagaatac accattcaat agtttcttgg gctaactctc tttctcgctg tgggtttctc   2820
agggtcacga gcgtatcccc atattgctta gacaagaagt catcgacaga ttgtcgcaga   2880
tcaatgtctg aatgcattag ttcttctctc agctctgcaa cctaatttca tctacagtaa   2940
gaaggttgct ttagaccact ccacatccat atttgcattt caatggcggt cttttcaatg   3000
tctcagttaa ttttttcctca ctcgccacac tgagtttctc cttagcttta tatatacgat   3060
agtgtatact ttgtttacat gttttttggt ggaatggaac ttatgagagc atatcagata   3120
tgtacttggg aaaattagta gaaactgttt gtttcttttt ttttaactct gttctttttgt   3180 atatatcact gaagctcgca tatgtataat tcatgtaatg gaattgcatc gcttctgttt   3240
ccctaagtta ttt                                                     3253
```

<210> SEQ ID NO 52
<211> LENGTH: 310
<212> TYPE: PRT
<213> ORGANISM: Arabidopsis thaliana

<400> SEQUENCE: 52

```
Met Glu Arg Asp Phe Leu Gly Leu Gly Ser Lys Leu Ser Pro Ile Thr
1               5                   10                  15

Val Lys Glu Glu Thr Asn Glu Asp Ser Ala Pro Ser Arg Gly Met Met
                20                  25                  30

Asp Trp Ser Phe Ser Ser Lys Val Gly Ser Gly Pro Gln Phe Leu Ser
            35                  40                  45

Phe Gly Thr Ser Gln Gln Glu Thr Arg Val Asn Thr Val Asn Asp His
        50                  55                  60

Leu Leu Ser Ser Ala Ala Met Asp Gln Asn Gln Arg Thr Tyr Phe Ser
65                  70                  75                  80

Ser Leu Gln Glu Asp Arg Val Phe Pro Gly Ser Ser Gln Asp Gln
                85                  90                  95

Thr Thr Ile Thr Val Ser Met Ser Glu Pro Asn Tyr Ile Asn Ser Phe
            100                 105                 110

Ile Asn His Gln His Leu Gly Gly Ser Pro Ile Met Ala Pro Pro Val
        115                 120                 125

Ser Val Phe Pro Ala Pro Thr Thr Ile Arg Ser Ser Lys Pro Leu
    130                 135                 140

Pro Pro Gln Leu Thr Ile Phe Tyr Ala Gly Ser Val Leu Val Tyr Gln
145                 150                 155                 160

Asp Ile Ala Pro Glu Lys Ala Gln Ala Ile Met Leu Leu Ala Gly Asn
                165                 170                 175

Gly Pro His Ala Lys Pro Val Ser Gln Pro Lys Pro Gln Lys Leu Val
            180                 185                 190

His His Ser Leu Pro Thr Thr Asp Pro Pro Thr Met Pro Ser Phe
        195                 200                 205

Leu Pro Ser Ile Ser Tyr Ile Val Ser Glu Thr Arg Ser Ser Gly Ser
    210                 215                 220

Asn Gly Val Thr Gly Leu Gly Pro Thr Lys Thr Lys Ala Ser Leu Ala
225                 230                 235                 240
```

```
Ser Thr Arg Asn Asn Gln Thr Ala Ala Phe Ser Met Ala Pro Thr Val
            245                 250                 255

Gly Leu Pro Gln Thr Arg Lys Ala Ser Leu Ala Arg Phe Leu Glu Lys
        260                 265                 270

Arg Lys Glu Arg Val Ile Asn Val Ser Pro Tyr Tyr Val Asp Asn Lys
        275                 280                 285

Ser Ser Ile Asp Cys Arg Thr Leu Met Ser Glu Cys Val Ser Cys Pro
        290                 295                 300

Pro Ala His His Leu His
305                 310

<210> SEQ ID NO 53
<211> LENGTH: 3187
<212> TYPE: DNA
<213> ORGANISM: Arabidopsis thaliana

<400> SEQUENCE: 53
```

| | | | | | |
|---|---|---|---|---|---|
| attagaggaa | tcataaatcg | gcggtgtgtg | taacttcaac | tcacgttttt | catttctctc | 60 |
| caaagtcctt | caattgttac | taattctctc | tgatctctca | tttcttctct | ctccggtga | 120 |
| cattttttt | ctcccccgcg | aaagctaaac | cgttttgta | ttctcaacga | ttgataagcc | 180 |
| tgatggagag | agattttctc | gggctgggat | caaagttatc | tccgataact | gtgaaggagg | 240 |
| aaactaacga | agattcaggt | aattcatctt | caacatcttc | cattatgatc | tgatgattgt | 300 |
| gttttcatc | tcacttttt | ttgtttctat | ttttgtaatc | tcttttttg | tttattgttc | 360 |
| aagtacatat | atattgtttt | tctagcttga | ttgggagtcc | tactgtctgg | ttttttcttg | 420 |
| aacaagaaat | ttttcttcg | ttttctcggg | aagagaaaaa | ataaattagg | gtttcttttt | 480 |
| tcttgatata | tatttaagaa | attaggtttt | agtactatag | acagaaattt | agctactcga | 540 |
| atttgtttga | cgtagccgat | gaaaaacac | gttttgggac | tcgatagtta | gaaaattcat | 600 |
| acgttcacga | tctactttg | aagttttttt | cattaaatat | tttttgcaaa | ctacaaatgt | 660 |
| acaagtatac | aactatacaa | gcaaacacca | aacttgttga | cgttagtaat | taacaagtg | 720 |
| ttagtattat | ctttgaaaaa | taatattcag | agaacaaact | tgattttcta | ggtgactagg | 780 |
| tgatgcatgt | ttctaaagct | gttggtaatg | ttgagtgttt | tcaaaataat | ttcgtttttt | 840 |
| tcttcaaaca | gccgacaccg | acagaacaaa | aatgctatat | tttttttgtt | gcttacaaaa | 900 |
| ttgatcaatt | ggtttcaata | caatagtatc | ttctttagaa | aagattgttt | ttttcaaagc | 960 |
| cggattgaat | attgagaatt | agaacattgg | ctggttattc | tttttgaaaa | gtttatgcca | 1020 |
| ttttttaagg | tttattaagc | aacttgaatt | ctatcagtat | tatttaaaaa | cgaagacgtg | 1080 |
| aaatgttggg | aaaagaatgc | gttatatagc | gaccggctga | cgattagaga | tttaacaaca | 1140 |
| aatgcaagtt | gaattatata | aaagcaagat | tgattgtgac | ttgattaagt | tttatttcta | 1200 |
| tccaagtaga | ctcattgatt | aagttaggat | catgttgggt | attaaattta | gatcaagtta | 1260 |
| caatttggat | gaataattta | cttacccacg | aggaattaa | tagttagttc | ttgtcttttt | 1320 |
| atattccgaa | acgtgccatt | tcttgaaagt | atttgtatga | tcactatttt | ccccagtgtg | 1380 |
| tttggcttta | tgcagatttg | ttcattgttg | atgaatctaa | tgttaagagt | cgtccacttt | 1440 |
| agcatagcta | gatctgagtg | tttcctagtt | tgataaaatc | taaagacatt | tgctcatgtt | 1500 |
| tcagccccaa | gtagaggtat | gatggattgg | tcattctcaa | gcaaagtcgg | ttctggtcct | 1560 |
| cagtttcttt | cttttgggac | atcccaacaa | gaaacgcgtg | taaacacagt | caatgatcat | 1620 |
| ttgctttctt | ctgctgcaat | ggatcaaaac | cagagaactt | acttcagctc | actacaggtt | 1680 |

```
aggctatttc ttgaaaagaa aaaaagtagt gataaagtgt gatttagtga ccttgtaaga    1740
aagcttggca attggtttag tttcttctgg tctcaaaatt gatacaaaat gatctcagga    1800
agacagagtg ttcccaggtt ccagtcagca agaccaaaca accatcacag tctccatgtc    1860
cgaaccaaac tacatcaaca gtttcataaa ccaccaacat ttaggaggat ctcctatcat    1920
ggcacctcca gtttcagtat ttcctgctcc aaccactatt aggcatgcac tgcattctat    1980
cttcttctgt ttaacatcag atacagaacc tctttacttc tatagttgac tcgagctcct    2040
ttatgttcat ctccagatct tcttcaaaac cacttccccc tcagttgaca atcttttatg    2100
ccggttcagt attagtttac caagacatag ctcctgaaaa ggtaaccaaa tttccttcaa    2160
tatgtgttac attacagtcc aagctatcca ctgactaagt attcaatcaa agaaataagt    2220
ttcacgtata gacatgctga agttatagaa agttactaac ctggtttcaa catacagtat    2280
gttaatgatt catagatatg ataaatcttt gtccttactt cttcatttat tttgtattca    2340
taggcccaag ctatcatgtt gctagccgga aatggacctc atgctaaacc ggtttcacaa    2400
cctaaacctc aaaaactggt tcatcactct cttccaacca ctgatcctcc aactatgcct    2460
cctagtttcc tgccttccat ctcttacatt gtctctgaaa ccagaagtag tggatccaac    2520
ggggttactg gacttggacc aacaaaaaca aaggcgagtt tagcatccac gcgcaacaac    2580
caaactgctg ccttctctat ggctccaaca ggttatataat gaagtcttaa ctcctattaa    2640
tgttttgtca tcaaacttct atcttaggtt tagtttgtta taaccaaaaa atcttgctat    2700
gatttaatac agtgggttta ccacaaacac gcaaagcatc cttggctcgg ttcttagaga    2760
aacgcaaaga aaggtactga gctacaagat tattcactta ttcacaatat caaaacacag    2820
gtttgctgta tattggcttc gttttcttgc agggtcatta acgtatcacc ttattacgta    2880
gacaacaagt catcaataga ctgtagaaca ctgatgtctg aatgtgtaag ctgtcctcca    2940
gctcatcatc tgcactaaaa ccaatttaga cccctcattg ttctaaaggc ttttttcttt    3000
ttctctggct ctgtatccta tagactatag tatagttgtt atagcttttg tttattcaga    3060
ttttagtaca ctgggcttgt aaaagcaagt tatttatata tatcctataa atttaatttg    3120
gatactgtat gttttgtctt tactcttgca tgtgtataaa aacataaaaa gtaagactat    3180
tcaagct                                                              3187
```

<210> SEQ ID NO 54
<211> LENGTH: 267
<212> TYPE: PRT
<213> ORGANISM: Arabidopsis thaliana

<400> SEQUENCE: 54

```
Met Glu Arg Asp Phe Leu Gly Leu Ser Asp Lys Gln Tyr Leu Ser Asn
1               5                   10                  15

Asn Val Lys His Glu Val Asn Asp Asp Ala Val Glu Glu Arg Gly Leu
            20                  25                  30

Ser Thr Lys Ala Ala Arg Glu Trp Gly Lys Ser Lys Val Phe Ala Thr
        35                  40                  45

Ser Ser Phe Met Pro Ser Ser Asp Phe Gln Glu Ala Lys Ala Phe Pro
    50                  55                  60

Gly Ala Tyr Gln Trp Gly Ser Val Ser Ala Ala Asn Val Phe Arg Arg
65                  70                  75                  80

Cys Gln Phe Gly Gly Ala Phe Gln Asn Ala Thr Pro Leu Leu Leu Gly
                85                  90                  95
```

```
Gly Ser Val Pro Leu Pro Thr His Pro Ser Leu Val Pro Arg Val Ala
            100                 105                 110

Ser Ser Gly Ser Ser Pro Gln Leu Thr Ile Phe Tyr Gly Gly Thr Ile
        115                 120                 125

Ser Val Phe Asn Asp Ile Ser Pro Asp Lys Ala Gln Ala Ile Met Leu
    130                 135                 140

Cys Ala Gly Asn Gly Leu Lys Gly Glu Thr Gly Asp Ser Lys Pro Val
145                 150                 155                 160

Arg Glu Ala Glu Arg Met Tyr Gly Lys Gln Ile His Asn Thr Ala Ala
                165                 170                 175

Thr Ser Ser Ser Ala Thr His Thr Asp Asn Phe Ser Arg Cys Arg
            180                 185                 190

Asp Thr Pro Val Ala Ala Thr Asn Ala Met Ser Met Ile Glu Ser Phe
            195                 200                 205

Asn Ala Ala Pro Arg Asn Met Ile Pro Ser Val Pro Gln Ala Arg Lys
    210                 215                 220

Ala Ser Leu Ala Arg Phe Leu Glu Lys Arg Lys Glu Arg Leu Met Ser
225                 230                 235                 240

Ala Met Pro Tyr Lys Lys Met Leu Leu Asp Leu Ser Thr Gly Glu Ser
                245                 250                 255

Ser Gly Met Asn Tyr Ser Ser Thr Ser Pro Thr
            260                 265
```

<210> SEQ ID NO 55
<211> LENGTH: 2297
<212> TYPE: DNA
<213> ORGANISM: Arabidopsis thaliana

<400> SEQUENCE: 55

```
gcaaagagtt aaataagcct ctccaaaagt gtgtctgtaa cattaccaaa acgaaacctt    60
ccttgtggat tcccacttct ttcttctgtt tccttcttcc tcttctttaa attggatgtt   120
ttgggcaaga aacagagaga aacacgttaa tttgagagtt tgtcattgaa tatttggttt   180
gcaatggaaa gagattttct gggtttgagc gacaagcagt atctaagtaa taacgttaag   240
catgaggtta acgatgatgc tgtcgaagaa cgaggtttgt gttcttgtct cgagaatctt   300
ttattttaat gtttcaagaa gagatcagtt ttcactttta acatagccgt ataaagttgt   360
ttatttaaat ataattttc agattccaaa acttgaaaaa aaaagattc cattaaatct     420
tttataaaaa tgagattgga tagattagtc aaattgacga ccataaaaaa tgatacttat   480
agggttaagt acgaaggcag ctagagaatg ggggaagtca aaggttttg ctacttcaag    540
tttcatgcct tcttcagatt tccaggttgg ttcatcttaa aatttaactt actctgtatc   600
agtttcagat gttatggcta atctaatggt tctataagct accgcataat catggtcgtc   660
ttttagcatg tgcaagagga gtactcaatt atggtcttga ttaaaaagaa gaatttactt   720
tcaaattatg ttaaacacat caatcacata tttatgagaa aagttgtttt cgtaagagat   780
agccaccgga aaatggtcgg ataaatggcc gaactttatc atttttgtgt atgtggccaa   840
tcattaacca gggaaaaaaa attgttggat aagtgctagt taagagctgg tagggtcggt   900
cgtctgccag ccgcaaagtt agggaaaaaa taatttaata ttttgtggcg tttggtgttt   960
ggcgtttgga tcacgtttat ttcttggcat ttttctaaat ttagaatgta caaaaaattt  1020
aaagacgttg acgattaaaa tttgaattta acaaattagg aggctaaggc gtttccgggt  1080
gcataccagt ggggatcagt ttctgcggcc aatgttttcc gcagatgcca atttggtggt  1140
```

-continued

```
gcgtttcaaa acgcgacgcc gcttttacta ggcggttcag ttcctttacc aactcatcct   1200
tctcttgttc cacggtaatt tccatattat gatgcaaaaa cattcaacaa ttttttttgct  1260
cttttcatat tttgatttgg ttatgtgggt ttgtggaaac agagtggctt cctccggatc   1320
atctcctcag ctcacaatct tttatggcgg aactataagc gtctttaatg acatatctcc   1380
cgataaggta tatataatca agattcatac aaataacatt tacataacat ttacatgttc   1440
taaaacggac tattcatgat atgtgagtag gctcaagcca tcatgttatg cgccgggaac   1500
ggtttgaaag gtgaaactgg agatagcaaa ccggttcgag aagctgaaag aatgtatgga   1560
aaacaaatcc ataacactgc tgctacctca tcaagctctg ccactcacac tgataaattc   1620
tcaaggtgta gggacacacc cgttgctgcg actaatgcaa tgagcatgat cgaatcattc   1680
aatgcagctc ctcgtaacat gattccttca ggtatgtgtg tctaatatca acatcaaaac   1740
aaaatataat caagattttt gcttcctcaa atcatatgtc taaactcgaa aattgctttt   1800
ttccagtccc tcaagctcgg aaagcatcct tggctcggtt cttggagaag cgcaaagaga   1860
ggtttgattt tgtatttttt ttctttatag aaaattttga ggttttcaa ttgaatctaa    1920
aagaattgat gttgttggtg caggcttatg agtgcaatgc catacaagaa gatgcttctt   1980
gatttgtcga ccggagaatc cagtggaatg aattactctt ctacttctcc tacataaaac   2040
ctacactttt tttttttttt tttacaatgg taatttgtaa ttgtaatcat tagattatga   2100
ttatatagtt accatttata ttcttacgag caggagaaga cgttagggcg tctctgtatt   2160
tgatcattgt ttgtaatgct ttggtctgtt tattgtagga ttacattata actttaagaa   2220
ctaacagata tatgtttgtc atggactcat gtctgtcaag aatttaatat caaataaaat   2280
tcactataat tttttt                                                   2297
```

<210> SEQ ID NO 56
<211> LENGTH: 197
<212> TYPE: PRT
<213> ORGANISM: Arabidopsis thaliana

<400> SEQUENCE: 56

```
Met Ser Lys Ala Thr Ile Glu Leu Asp Phe Leu Gly Leu Glu Lys Lys
1               5                   10                  15

Gln Thr Asn Asn Ala Pro Lys Pro Lys Phe Gln Lys Phe Leu Asp Arg
            20                  25                  30

Arg Arg Ser Phe Arg Asp Ile Gln Gly Ala Ile Ser Lys Ile Asp Pro
        35                  40                  45

Glu Ile Ile Lys Ser Leu Leu Ala Ser Thr Gly Asn Asn Ser Asp Ser
    50                  55                  60

Ser Ala Lys Ser Arg Ser Val Pro Ser Thr Pro Arg Glu Asp Gln Pro
65                  70                  75                  80

Gln Ile Pro Ile Ser Pro Val His Ala Ser Leu Ala Arg Ser Thr
            85                  90                  95

Glu Leu Val Ser Gly Thr Val Pro Met Thr Ile Phe Tyr Asn Gly Ser
            100                 105                 110

Val Ser Val Phe Gln Val Ser Arg Asn Lys Ala Gly Glu Ile Met Lys
        115                 120                 125

Val Ala Asn Glu Ala Ala Ser Lys Lys Asp Glu Ser Ser Met Glu Thr
    130                 135                 140

Asp Leu Ser Val Ile Leu Pro Thr Thr Leu Arg Pro Lys Leu Phe Gly
145                 150                 155                 160

Gln Asn Leu Glu Gly Asp Leu Pro Ile Ala Arg Arg Lys Ser Leu Gln
```

165                 170                 175
Arg Phe Leu Glu Lys Arg Lys Glu Arg Leu Val Ser Thr Ser Pro Tyr
            180                 185                 190
Tyr Pro Thr Ser Ala
        195

<210> SEQ ID NO 57
<211> LENGTH: 1927
<212> TYPE: DNA
<213> ORGANISM: Arabidopsis thaliana

<400> SEQUENCE: 57

| | | | | | |
|---|---|---|---|---|---|
| aaaaactctc | acatgagaaa | tcagaatccg | ttattattcc | tccatttatt | catctcaaaa | 60 |
| cccatatctc | tctgtcttga | tctctctctc | actttctaat | aagatcaaag | aagatgtcga | 120 |
| aagctaccat | agaactcgat | tcctcggac | ttgagaagaa | acaaaccaac | aacgctccta | 180 |
| agcctaagtt | ccagaaattt | ctcgatcgcc | gtcgtagttt | ccgaggttcg | tttggtttt | 240 |
| agtcgctctc | tctttttttt | ttcttgcgat | aaatcgaatt | tattcatatg | gaactcctgc | 300 |
| agatattcaa | ggtgcgattt | cgaaaatcga | tccggagatt | atcaaatcgc | tgttagcttc | 360 |
| cactggaaac | aattccgatt | catcggctaa | atctcgttcg | gttccgtcta | ctccgaggga | 420 |
| agatcagcct | cagatcccga | tttctccggt | ccacgcgtct | ctcgccaggt | attttttgtct | 480 |
| ttccggtaaa | gttttttttt | tctttctaac | ttttttggcg | ctaccagaaa | agacgaaaaa | 540 |
| atttgaaatt | caaatttca | aaacattcat | tttcctcagg | tctagtaccg | aactcgtttc | 600 |
| gggaactgtt | cctatgacga | ttttctacaa | tggaagtgtt | tcagttttcc | aagtgtctcg | 660 |
| taacaaagct | ggtgaaatta | tgaaggtcgc | taatgaagca | gcatctaaga | aagacgagtc | 720 |
| gtcgatggag | acagatcttt | cggtaattct | tccgaccact | ctaagaccaa | agctcttttgg | 780 |
| ccagaatcta | gaaggaggtt | agtataataa | aaataaaaat | cacttagtgc | tggattcttc | 840 |
| tagaattta | gttacatatt | attgcatgta | gagatctaag | aagagtttgt | tgttagagag | 900 |
| gaattggttg | ctaattagtt | tggaattaga | tatcaaagag | ttaaagacta | tagtttatgt | 960 |
| ctatacgtat | taatatacgt | tattaataaa | agtataaaca | tgttgtttaa | tttctgataa | 1020 |
| gaaactggtt | tatgcgtgtg | tatgcagatc | ttcccatcgc | aaggagaaag | tcactgcaac | 1080 |
| gttttctcga | gaagcgcaag | gagaggtaat | gattcttcaa | caatccaagg | attttttaccc | 1140 |
| ccaaataatt | aaagaaaggt | ttttattttt | ctctctctcg | accttttttt | tactataagt | 1200 |
| tatttaagat | agtaattatg | ggtcctgcct | cttttactct | cacatacaac | ttaagattca | 1260 |
| actagttttg | ttcaacaacg | cacatgctta | tacgtagata | gataatggag | atcagtagta | 1320 |
| atatcggtat | acgtaggtta | ctattgtaat | ggaacttta | aaaagcgcgt | tgactttgag | 1380 |
| tctttgactc | tagttctgtt | tgctacaccg | acaagttata | ttttcaaaa | tgatgagaaa | 1440 |
| acgaggagaa | acaccggaaa | aaaatttgaa | cttttacttt | tatcagacca | tacgccaaa | 1500 |
| gaaagatctg | tatattatat | aagttatcac | aaaacgcggt | ttcacatttt | ctttttcgtc | 1560 |
| ttgttgtgtt | tgcagattag | tatcaacatc | tccttactat | ccgacatcgg | cctaaacgat | 1620 |
| ctctttttag | attgggacat | ggaccaaatt | tgtcttttc | aatcggaaga | catccatgtt | 1680 |
| cgttttttgga | tttggcttat | ttccaatctt | cttttgaagc | cttcttcgtc | gttgctaaat | 1740 |
| cgtatactat | tcacgacaaa | cgttttttagg | agattacgtt | acctactaag | attatatata | 1800 |
| ttggtttgtt | tttaaaaatg | tctattatct | ttattgtcat | tgatagcttg | atttaagaag | 1860 |
| ctctctctta | tcccgtgacc | ttctactttt | gttttatttt | ttagtatatg | gtaaagaaaa | 1920 | ttataac 1927

<210> SEQ ID NO 58
<211> LENGTH: 273
<212> TYPE: PRT
<213> ORGANISM: Brassica rapa

<400> SEQUENCE: 58

Met Ser Ser Pro Met Glu Ser Ser Asp Phe Ala Ala Thr Arg Arg Phe
1               5                   10                  15

Ser Arg Lys Pro Ser Phe Ser Gln Thr Cys Ser Arg Leu Ser Gln Tyr
            20                  25                  30

Leu Lys Glu Asn Gly Ser Phe Gly Asp Leu Ser Leu Gly Met Ala Cys
        35                  40                  45

Lys Pro Glu Val Asn Gly Ile Ser Arg Gln Pro Thr Thr Thr Met Ser
    50                  55                  60

Leu Phe Pro Cys Glu Ala Ser Asn Met Glu Pro Ile Gly Gln Asp Val
65                  70                  75                  80

Lys Pro Lys Asn Leu Phe Pro Arg Gln Pro Ser Phe Ser Ser Ser
                85                  90                  95

Ser Ser Leu Pro Lys Glu Asp Ile Leu Lys Met Thr Gln Ala Thr Ser
            100                 105                 110

Ser Thr Arg Ser Val Lys Pro Glu Pro Gln Thr Ala Pro Leu Thr Ile
        115                 120                 125

Phe Tyr Gly Gly Gln Val Ile Val Phe Asn Asp Phe Ser Ala Glu Lys
    130                 135                 140

Ala Lys Glu Val Met Asp Leu Ala Ser Lys Gly Thr Ala Asn Thr Phe
145                 150                 155                 160

Thr Gly Phe Thr Ser Asn Val Asn Asn Ile Gln Ser Val Tyr Thr
                165                 170                 175

Thr Asn Leu Ala Asn Asn Gln Thr Glu Met Arg Ser Asn Ile Ala Pro
            180                 185                 190

Ile Pro Asn Gln Leu Pro His Leu Met Lys Thr Thr Thr Gln Asn Pro
        195                 200                 205

Val Gln Ser Ser Ser Thr Ala Met Ala Cys Glu Leu Pro Ile Ala Arg
    210                 215                 220

Arg Ala Ser Leu His Arg Phe Leu Ala Lys Arg Lys Asp Arg Val Thr
225                 230                 235                 240

Ser Lys Ala Pro Tyr Gln Leu Asn Asp Pro Ala Lys Ala Ser Ser Lys
                245                 250                 255

Pro Gln Thr Gly Asp Asn Thr Thr Ser Trp Leu Gly Leu Ala Ala Glu
            260                 265                 270

Met

<210> SEQ ID NO 59
<211> LENGTH: 252
<212> TYPE: PRT
<213> ORGANISM: Brassica oleracea

<400> SEQUENCE: 59

Met Ser Ser Ser Met Glu Cys Ser Thr Thr Arg Arg Ser Ser Ser Gly
1               5                   10                  15

Lys Pro Ser Phe Ser Leu Thr Cys Ser Arg Leu Ser Gln Tyr Leu Lys
            20                  25                  30

Glu Asn Gly Ser Phe Gly Asp Leu Ser Leu Gly Met Ser Cys Lys Pro

```
                35                  40                  45
Asp Thr Asn Gly Met Ser Arg Lys Pro Thr Thr Met Ser Leu Phe
 50                  55                  60
Pro Cys Glu Ala Ser Asn Val Gly Ser Met Ala Ala Gln Asp Val
 65                  70                  75                  80
Lys Pro Lys Asn Leu Phe Pro Arg Gln Pro Ser Phe Ser Ser Ser
                 85                  90                  95
Ser Ser Ile Pro Lys Glu Asp Val Pro Lys Met Thr Gln Thr Thr
            100                 105                 110
Arg Ser Leu Lys Pro Glu Pro Gln Thr Ala Pro Leu Thr Ile Phe Tyr
            115                 120                 125
Gly Gly Gln Val Ile Val Phe Asn Asp Phe Ser Ala Glu Lys Ala Lys
130                 135                 140
Glu Val Met Asn Leu Ala Asn Lys Gly Thr Ala Asn Thr Phe Thr Gly
145                 150                 155                 160
Phe Thr Ser Thr Leu Asn Asn Asn Ile Ala Pro Thr Pro Asn Gln Val
                165                 170                 175
Pro His Leu Met Lys Ala Ala Thr Gln Asp Pro Lys Gln Thr Ser Ser
                180                 185                 190
Ala Ala Met Ala Cys Glu Leu Pro Ile Ala Arg Arg Ala Ser Leu His
            195                 200                 205
Arg Phe Leu Ala Lys Arg Lys Asp Arg Val Thr Ser Lys Ala Pro Tyr
210                 215                 220
Gln Leu Asn Asp Pro Ala Lys Ala Tyr Ser Lys Pro Gln Thr Gly Asn
225                 230                 235                 240
Thr Thr Thr Ser Trp Leu Gly Leu Ala Ala Asp Met
                245                 250

<210> SEQ ID NO 60
<211> LENGTH: 233
<212> TYPE: PRT
<213> ORGANISM: Zea mays

<400> SEQUENCE: 60

Met Ala Ala Ser Ala Arg Pro Gly Glu Arg Ala Thr Ser Phe Ala Val
 1               5                  10                  15
Ala Cys Ser Leu Leu Ser Arg Phe Val Arg Gln Asn Gly Val Ala Ala
                 20                  25                  30
Ala Asp Leu Gly Leu Arg Ile Lys Gly Glu Val Glu Gln Gln Arg Thr
             35                  40                  45
Pro Ala Thr Thr Asn Ser Leu Pro Gly Ala Glu Gly Glu Val Glu
 50                  55                  60
Arg Arg Lys Glu Thr Met Glu Leu Phe Pro Gln Ser Val Gly Phe Ser
 65                  70                  75                  80
Ile Lys Asp Ala Ala Pro Arg Glu Glu Gln Gly Asp Lys Glu Lys
                 85                  90                  95
Pro Lys Gln Leu Thr Ile Phe Tyr Gly Gly Lys Val Leu Val Phe Asp
            100                 105                 110
Asp Phe Pro Ala Asp Lys Ala Lys Asp Leu Met Gln Leu Ala Ser Lys
            115                 120                 125
Gly Ser Pro Val Val Gln Asn Val Ala Leu Pro Gln Pro Ser Ala Ala
        130                 135                 140
Ala Ala Val Thr Thr Asp Lys Ala Val Leu Asp Pro Val Ile Ser Leu
145                 150                 155                 160
```

Ala Ala Ala Lys Lys Pro Ala Arg Thr Asn Ala Ser Asp Met Pro Ile
            165                 170                 175

Met Arg Lys Ala Ser Leu His Arg Phe Leu Glu Lys Arg Lys Asp Arg
        180                 185                 190

Leu Asn Ala Lys Thr Pro Tyr Gln Thr Ala Pro Ser Asp Ala Ala Pro
            195                 200                 205

Val Lys Lys Glu Pro Glu Ser Gln Pro Trp Leu Gly Leu Gly Pro Asn
    210                 215                 220

Ala Val Asp Ser Ser Leu Asn Leu Ser
225                 230

<210> SEQ ID NO 61
<211> LENGTH: 240
<212> TYPE: PRT
<213> ORGANISM: Glycine max

<400> SEQUENCE: 61

Met Ser Ser Ser Glu Tyr Leu Val Phe Ser Ser His His Pro Ala
1               5                   10                  15

Asn Ser Pro Ala Glu Lys Ser Thr Phe Ser Gln Thr Cys Ser Leu Leu
            20                  25                  30

Ser Gln Tyr Ile Lys Glu Lys Gly Thr Phe Gly Asp Leu Thr Leu Gly
        35                  40                  45

Met Thr Cys Thr Ala Glu Thr Asn Gly Ser Pro Glu Thr Ser Cys His
    50                  55                  60

Ser Ala Thr Thr Met Glu Leu Phe Pro Thr Ile Ile Thr Gln Arg Asn
65                  70                  75                  80

Pro Thr Thr Val Asp Phe Leu Ser Pro Gln Thr Ala Tyr Pro His His
                85                  90                  95

Ser Glu Val Pro Ile Met Val Lys Ser Ser Ala Phe Lys Ser Met Glu
            100                 105                 110

Lys Glu Pro Lys Ala Ala Gln Leu Thr Ile Phe Tyr Ala Gly Gln Val
        115                 120                 125

Val Val Phe Asp Asp Phe Pro Ala Glu Lys Leu Glu Glu Ile Thr Ser
    130                 135                 140

Leu Ala Gly Lys Gly Ile Ser Gln Ser Gln Asn Thr Ser Ala Tyr Ala
145                 150                 155                 160

His Thr His Asn Gln Gln Val Asn His Pro Ser Phe Val Pro Asn Ile
                165                 170                 175

Ser Pro Gln Ala Pro Ser Arg Pro Leu Val Cys Asp Leu Pro Ile Ala
            180                 185                 190

Arg Lys Ala Ser Leu His Arg Phe Leu Ser Lys Arg Lys Asp Arg Ile
        195                 200                 205

Ala Ala Lys Ala Pro Tyr Gln Ile Asn Asn Pro Asn Ser Ala Ser Ser
    210                 215                 220

Lys Pro Ala Glu Ser Met Ser Trp Leu Gly Leu Gly Ala Gln Ser Thr
225                 230                 235                 240

<210> SEQ ID NO 62
<211> LENGTH: 244
<212> TYPE: PRT
<213> ORGANISM: Oryza sativa

<400> SEQUENCE: 62

Met Ala Ala Ser Ala Arg Pro Val Gly Val Gly Gly Glu Arg Ala Thr
1               5                   10                  15

```
Ser Phe Ala Met Ala Cys Ser Leu Leu Ser Arg Tyr Val Arg Gln Asn
             20                  25                  30

Gly Ala Ala Ala Ala Glu Leu Gly Leu Gly Ile Arg Gly Glu Gly Glu
         35                  40                  45

Ala Pro Arg Ala Ala Pro Ala Thr Met Ser Leu Leu Pro Gly Glu Ala
     50                  55                  60

Glu Arg Lys Lys Glu Thr Met Glu Leu Phe Pro Gln Ser Ala Gly Phe
 65                  70                  75                  80

Gly Gln Gln Asp Ala Ile Thr Ala Asp Ser Ala Ala Asp Ala Arg Glu
                 85                  90                  95

Gln Glu Pro Glu Lys Arg Gln Leu Thr Ile Phe Tyr Gly Gly Lys Val
            100                 105                 110

Leu Val Phe Asn Asp Phe Pro Ala Asp Lys Ala Lys Gly Leu Met Gln
        115                 120                 125

Leu Ala Ser Lys Gly Ser Pro Val Ala Pro Gln Asn Ala Ala Ala Pro
    130                 135                 140

Ala Pro Ala Ala Val Thr Asp Asn Thr Lys Ala Pro Met Ala Val Pro
145                 150                 155                 160

Ala Pro Val Ser Ser Leu Pro Thr Ala Gln Ala Asp Ala Gln Lys Pro
                165                 170                 175

Ala Arg Ala Asn Ala Ser Asp Met Pro Ile Ala Arg Lys Ala Ser Leu
            180                 185                 190

His Arg Phe Leu Glu Lys Arg Lys Asp Arg Leu Asn Ala Lys Thr Pro
        195                 200                 205

Tyr Gln Ala Ser Pro Ser Asp Ala Thr Pro Val Lys Lys Glu Pro Glu
    210                 215                 220

Ser Gln Pro Trp Leu Gly Leu Gly Pro Asn Ala Val Val Lys Pro Ile
225                 230                 235                 240

Glu Arg Gly Gln

<210> SEQ ID NO 63
<211> LENGTH: 391
<212> TYPE: PRT
<213> ORGANISM: Zea mays

<400> SEQUENCE: 63

Met Glu Arg Asp Phe Leu Ala Ala Ile Gly Lys Glu Gln Gln His Pro
 1               5                  10                  15

Arg Lys Glu Lys Ala Gly Gly Gly Ala Glu Glu Ser Ala Tyr Phe Gly
             20                  25                  30

Ala Ala Ala Val Pro Ala Met Asp Trp Ser Phe Ala Ser Lys Pro Cys
         35                  40                  45

Ala Ala Pro Ala Leu Met Ser Phe Arg Ser Ala Ala Arg Glu Glu Pro
     50                  55                  60

Ser Phe Pro Gln Phe Ser Ala Leu Asp Gly Thr Lys Asn Thr Ala Pro
 65                  70                  75                  80

Arg Met Leu Thr His Gln Arg Ser Phe Gly Pro Asp Ser Thr Gln Tyr
                 85                  90                  95

Ala Ala Leu His Arg Ala Gln Asn Gly Ala Arg Val Val Pro Val Ser
            100                 105                 110

Ser Pro Phe Ser Gln Ser Asn Pro Met Phe Arg Val Gln Ser Ser Pro
        115                 120                 125

Ser Leu Pro Asn Ser Thr Ala Phe Lys Gln Pro Pro Phe Ala Ile Ser
    130                 135                 140
```

```
Asn Ala Val Ala Ser Ser Thr Val Gly Ser Tyr Gly Gly Thr Arg Asp
145                 150                 155                 160

Ala Val Arg Pro Arg Thr Ala Gln Leu Thr Ile Phe Tyr Ala Gly Ser
            165                 170                 175

Val Asn Val Phe Asn Asn Val Ser Ala Glu Lys Ala Gln Glu Leu Met
        180                 185                 190

Phe Leu Ala Ser Arg Gly Ser Ser Ala Pro Val Ala Cys Lys Pro Glu
    195                 200                 205

Ala Pro Pro Thr Leu Ala Pro Ala Lys Val Thr Ala Pro Glu Val Leu
210                 215                 220

Leu Pro Ala Lys Gln Met Leu Phe Gln Lys Pro Gln His Leu Ser Pro
225                 230                 235                 240

Pro Pro Ser Ser Val Pro Gly Ile Leu Gln Ser Ala Ala Leu Pro Arg
            245                 250                 255

Ser Ala Ser Ser Ser Asn Leu Asp Ser Pro Ala Pro Lys Ser Ser
        260                 265                 270

Val Pro Leu Ala Val Pro Val Ser Gln Ala Pro Pro Ala Thr Leu
    275                 280                 285

Ile Ala Thr Thr Thr Ala Ala Ile Met Pro Arg Ala Val Pro Gln
290                 295                 300

Ala Arg Lys Ala Ser Leu Ala Arg Phe Leu Glu Lys Arg Lys Glu Arg
305                 310                 315                 320

Val Thr Thr Ala Ala Pro Tyr Pro Ser Ala Lys Ser Pro Leu Glu Ser
            325                 330                 335

Ser Asp Thr Phe Gly Ser Gly Ser Ala Ser Ala Asn Ala Asn Asp Lys
        340                 345                 350

Ser Ser Cys Thr Asp Ile Ala Leu Ser Ser Asn His Glu Glu Ser Leu
    355                 360                 365

Cys Leu Gly Gly Gln Pro Arg Ser Ile Ile Ser Phe Ser Glu Glu Ser
370                 375                 380

Pro Ser Thr Lys Leu Gln Ile
385                 390

<210> SEQ ID NO 64
<211> LENGTH: 386
<212> TYPE: PRT
<213> ORGANISM: Glycine max

<400> SEQUENCE: 64

Met Glu Arg Glu Phe Gly Leu Ser Ser Lys Asn Gly Ala Trp Thr
1               5                   10                  15

Thr Met Lys Asp Asp Ala Val Asn Lys Ser Arg Asp Gln Val Arg Ser
            20                  25                  30

Ser Gly Met Gln Trp Ser Phe Pro Asn Lys Val Ser Ala Leu Pro Gln
        35                  40                  45

Phe Leu Ser Phe Lys Thr Asn Gln Glu Asp Lys Pro Arg Lys Thr Ile
    50                  55                  60

Leu Glu Pro Leu Ala Ser Ser Gly Tyr Met Ala Met Ser Thr Gln Tyr
65                  70                  75                  80

Ala Phe Asp Ser Asn Gln Lys Ser Phe Leu Gly Leu Thr Asn Arg Asn
                85                  90                  95

Leu Ser Ile Ser Lys His Ala Ala Gly Asn Lys Gln Gly Met Thr Val
            100                 105                 110

Tyr Pro Leu Gln Cys Cys Asp Ala Gln Ser Glu Glu Ala Arg Ile Phe
        115                 120                 125
```

```
Ser Val Ser Asn Gln Ser Asn Gln Val Ser Pro Val Leu Gln Ser Asn
130                 135                 140

Leu Ala Ser Thr Gly Leu Asn Met Val Asn Ser Val Ile Lys Pro Gln
145                 150                 155                 160

Pro Phe Gly Ser Lys Ser Ser Gly Thr Pro Leu Ser Ile Leu Pro Ser
                165                 170                 175

Ile Gly Ser Ile Val Gly Ser Thr Asp Leu Arg Asn Asn Ser Lys Ser
            180                 185                 190

Ser Thr Met Pro Thr Gln Leu Thr Ile Phe Tyr Ala Gly Ser Val Cys
        195                 200                 205

Val Tyr Asp Asp Ile Ser Pro Glu Lys Ala Lys Ala Ile Met Leu Met
210                 215                 220

Ala Gly Asn Gly Tyr Thr Pro Thr Glu Lys Met Glu Leu Pro Thr Val
225                 230                 235                 240

Lys Leu Gln Pro Ala Ile Ser Ile Pro Ser Lys Asp Asp Gly Phe Met
                245                 250                 255

Ile Ser Gln Ser Tyr Pro Pro Ser Thr Phe Pro Thr Pro Leu Pro Leu
            260                 265                 270

Thr Ser His Val Asn Ser Gln Pro Gly Gly Ser Ser Asn Lys
        275                 280                 285

Glu Ile Ser Ile Ile Arg Gln Val Gly Pro Ser Thr Ala Pro Thr Asn
290                 295                 300

His Leu Glu Ser Pro Ile Ile Gly Ser Ile Gly Ser Ala Ser Lys Glu
305                 310                 315                 320

Lys Ala Gln Pro Val Cys Leu Pro Gln Ala Arg Lys Ala Ser Leu Ala
                325                 330                 335

Arg Phe Leu Glu Lys Arg Lys Gly Arg Met Met Arg Thr Ser Pro Tyr
            340                 345                 350

Leu Tyr Met Ser Lys Lys Ser Pro Glu Cys Ser Ser Ser Gly Ser Asp
        355                 360                 365

Ser Val Ser Phe Ser Leu Asn Phe Ser Gly Ser Cys Ser Leu Pro Ala
370                 375                 380

Thr Asn
385

<210> SEQ ID NO 65
<211> LENGTH: 416
<212> TYPE: PRT
<213> ORGANISM: Oryza sativa

<400> SEQUENCE: 65

Met Glu Arg Asp Phe Leu Gly Ala Ile Gly Lys Asp Glu Glu Gln Arg
1               5                   10                  15

Arg His Ala Glu Glu Arg Lys Glu Ser Asp Tyr Phe Gly Ala Gly Gly
                20                  25                  30

Gly Ala Ala Ala Ala Met Asp Trp Ser Phe Ala Ser Arg Ala Ala
            35                  40                  45

Leu Met Ser Phe Arg Ser Ser Ser Ala Ala Ala Ala Ala Arg
50                  55                  60

Glu Glu Thr Arg Glu Leu Ala Phe Pro His Phe Ser Ala Leu Asp Gly
65                  70                  75                  80

Ala Lys Met Gln Gln Ala Ser His Val Leu Ala Arg Gln Lys Ser Phe
                85                  90                  95

Gly Ala Glu Ser His Gly Ile Pro Gln Tyr Ala Ala Ala Ala Ala Val
```

```
            100                 105                 110
His Gly Ala His Arg Gly Gln Pro Pro His Val Leu Asn Gly Ala Arg
            115                 120             125
Val Ile Pro Ala Ser Ser Pro Phe Asn Pro Asn Asn Pro Met Phe Arg
130                 135                 140
Val Gln Ser Ser Pro Asn Leu Pro Asn Ala Val Gly Ala Gly Gly Gly
145                 150                 155                 160
Ala Phe Lys Gln Pro Pro Phe Ala Met Gly Asn Ala Val Ala Gly Ser
                165                 170                 175
Thr Val Gly Val Tyr Gly Thr Arg Asp Met Pro Lys Ala Lys Ala Ala
                180                 185                 190
Gln Leu Thr Ile Phe Tyr Ala Gly Ser Val Asn Val Phe Asn Asn Val
                195                 200                 205
Ser Pro Glu Lys Ala Gln Glu Leu Met Phe Leu Ala Ser Arg Gly Ser
    210                 215                 220
Leu Pro Ser Ala Pro Thr Thr Val Ala Arg Met Pro Glu Ala His Val
225                 230                 235                 240
Phe Pro Pro Ala Lys Val Thr Val Pro Glu Val Ser Pro Thr Lys Pro
                245                 250                 255
Met Met Leu Gln Lys Pro Gln Leu Val Ser Ser Pro Val Pro Ala Ile
                260                 265                 270
Ser Lys Pro Ile Ser Val Val Ser Gln Ala Thr Ser Leu Pro Arg Ser
                275                 280                 285
Ala Ser Ser Ser Asn Val Asp Ser Asn Val Thr Lys Ser Ser Gly Pro
    290                 295                 300
Leu Val Val Pro Pro Thr Ser Leu Pro Pro Ala Gln Pro Glu Thr
305                 310                 315                 320
Leu Ala Thr Thr Thr Ala Ala Ile Met Pro Arg Ala Val Pro Gln
                325                 330                 335
Ala Arg Lys Ala Ser Leu Ala Arg Phe Leu Glu Lys Arg Lys Glu Arg
                340                 345                 350
Val Thr Thr Val Ala Pro Tyr Pro Leu Ala Lys Ser Pro Leu Glu Ser
                355                 360                 365
Ser Asp Thr Met Gly Ser Ala Asn Asp Asn Lys Ser Ser Cys Thr Asp
    370                 375                 380
Ile Ala Leu Ser Ser Asn Arg Asp Glu Ser Leu Ser Leu Gly Gln Pro
385                 390                 395                 400
Arg Thr Ile Ser Phe Cys Glu Glu Ser Pro Ser Thr Lys Leu Gln Ile
                405                 410                 415

<210> SEQ ID NO 66
<211> LENGTH: 404
<212> TYPE: PRT
<213> ORGANISM: Zea mays

<400> SEQUENCE: 66

Met Ala Lys Ser Gly Ala Ser Phe Pro Glu Ser Ser Trp Met Glu Arg
1               5                   10                  15
Asp Phe Leu Ala Ala Ile Gly Lys Glu Gln Gln His Pro His Lys Glu
                20                  25                  30
Glu Ala Gly Ala Glu Glu Ser Ala Tyr Phe Gly Gly Ala Gly Ala Ala
            35                  40                  45
Ala Ala Ala Pro Ala Met Asp Trp Ser Phe Ala Ser Lys Pro Gly Ala
    50                  55                  60
```

Ala Pro Ala Leu Met Ser Phe Arg Ser Ala Ser Phe Pro Gln Phe Ser
65                  70                  75                  80

Ser Phe Asp Gly Ala Lys Asn Pro Ala Pro Arg Ile Leu Thr His Gln
            85                  90                  95

Arg Ser Phe Gly Pro Asp Ser Thr His Tyr Ala Ala His Arg Thr
        100                 105                 110

Gln His Ala Leu Asn Gly Ala Arg Val Thr Pro Val Ser Ser Pro Phe
            115                 120                 125

Asn Gln Asn Ser Pro Met Phe Arg Val Gln Ser Ser Pro Ser Leu Pro
130                 135                 140

Asn Gly Thr Ala Phe Lys Gln Pro Pro Phe Ala Ile Asn Asn Ala
145                 150                 155                 160

Ala Ala Ser Ser Thr Val Gly Phe Tyr Gly Thr Arg Asp Val Val Arg
                165                 170                 175

Pro Lys Thr Ala Gln Leu Thr Ile Phe Tyr Ala Gly Ser Val Asn Val
                180                 185                 190

Phe Asp Asn Val Ser Ala Glu Lys Ala Gln Glu Leu Met Leu Leu Ala
        195                 200                 205

Ser Arg Gly Ser Leu Pro Ser Ser Ala Pro Val Ala Arg Lys Pro Glu
210                 215                 220

Ala Pro Ile Leu Ala Pro Ala Lys Val Thr Ala Pro Glu Val Leu His
225                 230                 235                 240

Ala Thr Gln Met Leu Phe Gln Lys Pro Gln His Val Ser Pro Pro Ser
                245                 250                 255

Ser Ala Ile Ser Lys Pro Ile Pro Gly Ile Leu Gln Ala Ala Ser Leu
                260                 265                 270

Pro Arg Ser Ala Ser Ser Ser Asn Leu Asp Ser Pro Phe Pro Lys Ser
            275                 280                 285

Ser Val Pro Phe Pro Val Ser Pro Val Ser Gln Ala Pro Arg Ala Gln
            290                 295                 300

Pro Ala Thr Ile Ala Ala Thr Thr Ala Ala Ile Met Pro Arg Ala
305                 310                 315                 320

Val Pro Gln Ala Arg Lys Ala Ser Leu Ala Arg Phe Leu Glu Lys Arg
                325                 330                 335

Lys Glu Arg Val Thr Thr Ala Ala Pro Tyr Pro Ser Ala Lys Ser Pro
            340                 345                 350

Met Glu Ser Ser Asp Thr Phe Gly Ser Gly Ser Ala Asn Asp Lys Ser
            355                 360                 365

Ser Cys Thr Asp Ile Ala Leu Ser Ser Asn His Glu Glu Ser Leu Cys
        370                 375                 380

Leu Gly Gln Pro Arg Asn Ile Ser Phe Ile Gln Glu Ser Pro Ser Thr
385                 390                 395                 400

Lys Leu Gln Ile

<210> SEQ ID NO 67
<211> LENGTH: 340
<212> TYPE: PRT
<213> ORGANISM: Glycine max

<400> SEQUENCE: 67

Met Glu Arg Asp Phe Met Gly Leu Asn Leu Lys Glu Pro Leu Ala Val
1               5                   10                  15

Val Lys Glu Glu Met Asn Asn Asp Gly Cys Lys Asn Ser Gly Phe Lys
            20                  25                  30

Lys Gly Arg Ile Ala Gln Trp Pro Phe Ser Asn Lys Val Ser Ala Leu
            35                  40                  45

Pro His Leu Met Ser Phe Lys Ala Ser Gln Asp Asp Lys Thr Lys Asn
        50                  55                  60

Thr Val Ser Asp Thr Leu Ser Ser Ser Gly Phe Met Ser Ile Leu Ser
65                  70                  75                  80

Gln Glu Ala Phe Asp Thr Ser Gln Lys Arg Ser Ala Gly Glu Pro Gln
                85                  90                  95

Met Phe Ser Val Pro Asn Gln Ala Ile Ser Val Ser Leu Gly Asn Pro
            100                 105                 110

Phe Leu Lys Asn His Phe Ala Ala Ala Gly Gln Lys Pro Leu Leu Gly
            115                 120                 125

Gly Ile Pro Val Thr Thr Ser His Ser Val Leu Pro Ser Ala Val Ala
        130                 135                 140

Val Ala Gly Met Thr Glu Ser Cys Asn Ser Val Lys Pro Ser Ala Gln
145                 150                 155                 160

Leu Thr Ile Phe Tyr Ala Gly Thr Val Asn Ile Phe Asp Asp Ile Ser
                165                 170                 175

Ala Glu Lys Ala Gln Ala Ile Met Leu Leu Ala Gly Asn Ser Leu Ser
            180                 185                 190

Ala Ala Ser Asn Met Ala Gln Pro Asn Val Gln Val Pro Ile Ser Lys
        195                 200                 205

Leu Gly Ala Gly Ala Gly Val Pro Ser Gln Pro Ala Asn Thr Ser
        210                 215                 220

Pro Gly Ser Gly Leu Ser Ser Pro Leu Ser Val Ser Ser His Thr Gly
225                 230                 235                 240

Val Gln Ser Gly Ser Gly Leu Thr Ser Thr Asp Glu Phe Leu Ala Ala
                245                 250                 255

Lys Thr Thr Gly Val Pro Asn Thr Pro Ile Cys Asn Val Glu Pro Pro
            260                 265                 270

Lys Val Val Ser Ala Thr Thr Met Leu Thr Ser Ala Val Pro Gln Ala
        275                 280                 285

Arg Lys Ala Ser Leu Ala Arg Phe Leu Glu Lys Arg Lys Glu Arg Val
        290                 295                 300

Met Ser Ala Ala Pro Tyr Asn Leu Asn Lys Lys Ser Glu Glu Cys Ala
305                 310                 315                 320

Thr Ala Glu Tyr Ala Gly Val Asn Phe Ser Ala Thr Asn Thr Val Leu
                325                 330                 335

Ala Lys Gln Gly
            340

<210> SEQ ID NO 68
<211> LENGTH: 427
<212> TYPE: PRT
<213> ORGANISM: Oryza sativa

<400> SEQUENCE: 68

Met Glu Arg Asp Phe Leu Gly Ala Ile Trp Arg Lys Glu Glu Ala Ala
1               5                   10                  15

Gly Lys Pro Glu Glu His Ser Asp Tyr Arg Gly Gly Gly Gly Gly Ala
            20                  25                  30

Ser Ala Ala Met Gln Trp Gln Phe Pro Ala Thr Lys Val Gly Ala Ala
        35                  40                  45

Ser Ser Ala Phe Met Ser Phe Arg Ser Ser Ala Ala Ala Ala Arg Glu
        50                  55                  60

```
Glu Asp Pro Lys Glu Ala Ala Val Phe Asp Arg Phe Ser Leu Ser Gly
 65                  70                  75                  80

Phe Arg Pro Pro Arg Pro Ser Pro Gly Asp Ala Phe Asp Gly Ala
                 85                  90                  95

Ala Ala Met Lys Gln Arg Gln Phe Gly Phe Asn Gly Arg Gln Gln Tyr
            100                 105                 110

Ala Ala Ala Ala Gln His Gly His Arg Glu Gln Gly Val Asp Ser Tyr
            115                 120                 125

Gly Val Ala Ala Pro His His Phe Pro Ser Pro Ser Pro Ser Pro Arg
            130                 135                 140

His Pro Val Pro Phe Gly His Ala Asn Pro Met Leu Arg Val His Ser
145                 150                 155                 160

Leu Pro Asn Val Ala Gly Gly Ser Pro Tyr Arg Asn Gln Ser Phe Ser
                165                 170                 175

Val Gly Asn Ser Val Ala Gly Ser Thr Val Gly Val Tyr Gly Gly Pro
            180                 185                 190

Arg Asp Leu Gln Asn Pro Lys Val Thr Gln Met Thr Ile Phe Tyr Asp
            195                 200                 205

Gly Leu Val Asn Val Phe Asp Asn Ile Pro Val Glu Lys Ala Gln Glu
        210                 215                 220

Leu Met Leu Leu Ala Ser Arg Ala Ser Ile Pro Ser Pro Ser Ala
225                 230                 235                 240

Ala Arg Lys Ser Asp Ser Pro Ile Ser Ala Ala Lys Leu Thr Val
                245                 250                 255

Pro Glu Ala Leu Pro Ala Arg Gln Ile Val Val Gln Lys Pro Glu Ala
            260                 265                 270

Ser Val Pro Leu Val Ser Gly Val Ser Asn Pro Ile Thr Ile Val Ser
            275                 280                 285

Gln Ala Val Thr Leu Pro Lys Ser Phe Ser Ser Asn Asp Ser Ala
        290                 295                 300

Gly Pro Lys Ser Gly Gly Leu Pro Leu Ala Val Thr Pro Leu Ser Gln
305                 310                 315                 320

Ala Ser Pro Ser Gln Pro Ile Pro Val Ala Thr Thr Asn Ala Ser Ala
                325                 330                 335

Ile Met Pro Arg Ala Val Pro Gln Ala Arg Lys Ala Ser Leu Ala Arg
            340                 345                 350

Phe Leu Glu Lys Arg Lys Glu Arg Val Ser Ser Val Ala Pro Tyr Pro
            355                 360                 365

Ser Ser Lys Ser Pro Leu Glu Ser Ser Asp Thr Ile Gly Ser Pro Ser
        370                 375                 380

Thr Pro Ser Lys Ser Ser Cys Thr Asp Ile Thr Pro Ser Thr Asn Asn
385                 390                 395                 400

Cys Glu Asp Ser Leu Cys Leu Gly Gln Pro Arg Asn Ile Ser Phe Ser
                405                 410                 415

Ser Gln Glu Pro Pro Ser Thr Lys Leu Gln Ile
            420                 425

<210> SEQ ID NO 69
<211> LENGTH: 353
<212> TYPE: PRT
<213> ORGANISM: Zea mays

<400> SEQUENCE: 69

Met Asp Trp Ser Phe Ala Ser Lys Pro Cys Ala Ala Pro Ala Leu Met
```

```
                1               5                       10                      15
        Ser Phe Arg Ser Ala Arg Glu Glu Pro Ser Phe Pro Gln Phe Ser
                        20                      25                      30
        Ala Leu Asp Gly Thr Lys Asn Thr Ala Pro Arg Met Leu Thr His Gln
                        35                      40                      45
        Arg Ser Phe Gly Pro Asp Ser Thr Gln Tyr Ala Ala Leu His Arg Ala
                        50                      55                      60
        Gln Asn Gly Ala Arg Val Val Pro Val Ser Ser Pro Phe Ser Gln Ser
        65                      70                      75                      80
        Asn Pro Met Phe Arg Val Gln Ser Ser Pro Ser Leu Pro Asn Ser Thr
                        85                      90                      95
        Ala Phe Lys Gln Pro Pro Phe Ala Ile Ser Asn Ala Val Ala Ser Ser
                        100                     105                     110
        Thr Val Gly Ser Tyr Gly Gly Thr Arg Asp Ala Val Arg Pro Arg Thr
                        115                     120                     125
        Ala Gln Leu Thr Ile Phe Tyr Ala Gly Ser Val Asn Val Phe Asn Asn
                        130                     135                     140
        Val Ser Ala Glu Lys Ala Gln Glu Leu Met Phe Leu Ala Ser Arg Gly
        145                     150                     155                     160
        Ser Ser Ala Pro Val Ala Cys Lys Pro Glu Ala Pro Thr Leu Ala
                        165                     170                     175
        Pro Ala Lys Val Thr Ala Pro Glu Val Leu Leu Pro Ala Lys Gln Met
                        180                     185                     190
        Leu Phe Gln Lys Pro Gln His Leu Ser Pro Pro Ser Ser Val Pro
                        195                     200                     205
        Gly Ile Leu Gln Ser Ala Ala Leu Pro Arg Ser Ala Ser Ser Ser Ser
                210                     215                     220
        Asn Leu Asp Ser Pro Ala Pro Lys Ser Ser Val Pro Leu Ala Val Pro
        225                     230                     235                     240
        Pro Val Ser Gln Ala Pro Pro Ala Thr Leu Ile Ala Thr Thr Ala
                        245                     250                     255
        Ala Ala Ile Met Pro Arg Ala Val Pro Gln Ala Arg Lys Ala Ser Leu
                        260                     265                     270
        Ala Arg Phe Leu Glu Lys Arg Lys Glu Arg Val Thr Thr Ala Ala Pro
                        275                     280                     285
        Tyr Pro Ser Ala Lys Ser Pro Leu Glu Ser Ser Asp Thr Phe Gly Ser
                        290                     295                     300
        Gly Ser Ala Ser Ala Asn Ala Asn Asp Lys Ser Ser Cys Thr Asp Ile
        305                     310                     315                     320
        Ala Leu Ser Ser Asn His Glu Glu Ser Leu Cys Leu Gly Gly Gln Pro
                        325                     330                     335
        Arg Ser Ile Ile Ser Phe Ser Glu Glu Ser Pro Ser Thr Lys Leu Gln
                        340                     345                     350
        Ile

<210> SEQ ID NO 70
<211> LENGTH: 338
<212> TYPE: PRT
<213> ORGANISM: Glycine max

<400> SEQUENCE: 70

Met Glu Arg Asp Phe Met Gly Leu Asn Leu Lys Glu Pro Leu Ala Val
1               5                       10                      15

Val Lys Glu Glu Met Asn Asn Asp Gly Cys Lys Asn Ser Gly Phe Lys
```

```
            20                  25                  30
Lys Gly Arg Ile Ala Gln Trp Pro Phe Ser Asn Lys Val Ser Ala Leu
            35                  40                  45

Pro His Leu Met Ser Phe Lys Ala Ser Gln Asp Asp Lys Thr Lys Asn
        50                  55                  60

Thr Val Ser Asp Thr Leu Ser Ser Ser Gly Phe Met Ser Ile Leu Ser
65                  70                  75                  80

Gln Glu Ala Phe Asp Thr Ser Gln Lys Arg Ser Ala Gly Glu Pro Gln
                85                  90                  95

Met Phe Ser Val Pro Asn Gln Ala Ile Ser Val Ser Leu Gly Asn Pro
            100                 105                 110

Phe Leu Lys Asn His Phe Ala Ala Gly Gln Lys Pro Leu Leu Gly
            115                 120                 125

Gly Ile Pro Val Thr Thr Ser His Ser Val Leu Pro Ser Ala Val Ala
        130                 135                 140

Val Ala Gly Met Thr Glu Ser Cys Val Lys Pro Ser Ala Gln Leu Thr
145                 150                 155                 160

Ile Phe Tyr Ala Gly Thr Val Asn Ile Phe Asp Asp Ile Ser Ala Glu
                165                 170                 175

Lys Ala Gln Ala Ile Met Leu Leu Ala Gly Asn Ser Leu Ser Ala Ala
            180                 185                 190

Ser Asn Met Ala Gln Pro Asn Val Gln Val Pro Ile Ser Lys Leu Gly
            195                 200                 205

Ala Gly Ala Gly Val Pro Val Ser Gln Pro Ala Asn Thr Ser Pro Gly
        210                 215                 220

Ser Gly Leu Ser Ser Pro Leu Ser Val Ser Ser His Thr Gly Val Gln
225                 230                 235                 240

Ser Gly Ser Gly Leu Thr Ser Thr Asp Glu Phe Leu Ala Ala Lys Thr
                245                 250                 255

Thr Gly Val Pro Asn Thr Pro Ile Cys Asn Val Glu Pro Pro Lys Val
            260                 265                 270

Val Ser Ala Thr Thr Met Leu Thr Ser Ala Val Pro Gln Ala Arg Lys
            275                 280                 285

Ala Ser Leu Ala Arg Phe Leu Glu Lys Arg Lys Glu Arg Val Met Ser
        290                 295                 300

Ala Ala Pro Tyr Asn Leu Asn Lys Lys Ser Glu Glu Cys Ala Thr Ala
305                 310                 315                 320

Glu Tyr Ala Gly Val Asn Phe Ser Ala Thr Asn Thr Val Leu Ala Lys
                325                 330                 335

Gln Gly

<210> SEQ ID NO 71
<211> LENGTH: 308
<212> TYPE: PRT
<213> ORGANISM: Oryza sativa

<400> SEQUENCE: 71

Met Gln Gln Ala Ser His Val Leu Ala Arg Gln Pro Pro His Val Leu
1               5                   10                  15

Asn Gly Ala Arg Val Ile Pro Ala Ser Ser Pro Phe Asn Pro Asn Asn
            20                  25                  30

Pro Met Phe Arg Val Gln Ser Ser Pro Asn Leu Pro Asn Ala Val Gly
            35                  40                  45

Ala Gly Gly Gly Ala Phe Lys Gln Pro Pro Phe Ala Met Gly Asn Ala
```

```
            50                  55                  60
Val Ala Gly Ser Thr Val Gly Val Tyr Gly Thr Arg Asp Met Pro Lys
 65                  70                  75                  80

Ala Lys Ala Ala Gln Leu Thr Ile Phe Tyr Ala Gly Ser Val Asn Val
                 85                  90                  95

Phe Asn Asn Val Ser Pro Glu Lys Ala Gln Glu Leu Met Phe Leu Ala
            100                 105                 110

Ser Arg Gly Ser Leu Pro Ser Ala Pro Thr Thr Val Ala Arg Met Pro
        115                 120                 125

Glu Ala His Val Phe Pro Pro Ala Lys Val Thr Val Pro Glu Val Ser
    130                 135                 140

Pro Thr Lys Pro Met Met Leu Gln Lys Pro Gln Leu Val Ser Ser Pro
145                 150                 155                 160

Val Pro Ala Ile Ser Lys Pro Ile Ser Val Val Ser Gln Ala Thr Ser
                165                 170                 175

Leu Pro Arg Ser Ala Ser Ser Ser Asn Val Asp Ser Asn Val Thr Lys
            180                 185                 190

Ser Ser Gly Pro Leu Val Val Pro Pro Thr Ser Leu Pro Pro Pro Ala
        195                 200                 205

Gln Pro Glu Thr Leu Ala Thr Thr Ala Ala Ala Ile Met Pro Arg
    210                 215                 220

Ala Val Pro Gln Ala Arg Lys Ala Ser Leu Ala Arg Phe Leu Glu Lys
225                 230                 235                 240

Arg Lys Glu Arg Val Thr Thr Val Ala Pro Tyr Pro Leu Ala Lys Ser
                245                 250                 255

Pro Leu Glu Ser Ser Asp Thr Met Gly Ser Ala Asn Asp Asn Lys Ser
            260                 265                 270

Ser Cys Thr Asp Ile Ala Leu Ser Ser Asn Arg Asp Glu Ser Leu Ser
        275                 280                 285

Leu Gly Gln Pro Arg Thr Ile Ser Phe Cys Glu Glu Ser Pro Ser Thr
    290                 295                 300

Lys Leu Gln Ile
305

<210> SEQ ID NO 72
<211> LENGTH: 218
<212> TYPE: PRT
<213> ORGANISM: Zea mays

<400> SEQUENCE: 72

Met Ala Gly His Ala Pro Ala Arg Asp Lys Thr Thr Thr Gly Phe Ala
 1               5                  10                  15

Ala Thr Cys Ser Leu Leu Ser Gln Phe Leu Lys Glu Lys Lys Gly Gly
                 20                  25                  30

Leu Gln Gly Leu Gly Gly Leu Ala Met Ala Pro Ala Pro Ala Ala Gly
            35                  40                  45

Ala Gly Ala Phe Arg Pro Pro Thr Thr Met Asn Leu Leu Ser Ala Leu
        50                  55                  60

Asp Ala Ala Lys Ala Thr Val Gly Glu Pro Glu Gly His Gly Gln Arg
 65                  70                  75                  80

Thr Gly Gly Asn Pro Arg Glu Ala Ala Gly Glu Glu Ala Gln Gln Leu
                 85                  90                  95

Thr Ile Phe Tyr Gly Gly Lys Val Val Val Phe Asp Arg Phe Pro Ser
            100                 105                 110
```

```
Ala Lys Val Lys Asp Leu Leu Gln Ile Val Ser Pro Pro Gly Ala Asp
            115                 120                 125

Ala Val Val Asp Gly Ala Gly Ala Ala Val Pro Thr Gln Asn
    130                 135                 140

Leu Pro Arg Pro Ser His Asp Ser Leu Ser Ala Asp Leu Pro Ile Ala
145                 150                 155                 160

Arg Arg Asn Ser Leu His Arg Phe Leu Glu Lys Arg Lys Asp Arg Ile
                165                 170                 175

Thr Ala Lys Ala Pro Tyr Gln Val Asn Ser Ser Val Gly Ala Glu Ala
            180                 185                 190

Ser Lys Ala Glu Lys Pro Trp Leu Gly Leu Gly Gln Glu Gln Glu Gly
        195                 200                 205

Ser Asp Gly Arg Gln Ala Gly Glu Glu Met
    210                 215
```

<210> SEQ ID NO 73
<211> LENGTH: 201
<212> TYPE: PRT
<213> ORGANISM: Glycine max

<400> SEQUENCE: 73

```
Met Ala Ala Gly Val Thr Val Lys Ser Glu Val Leu Glu Ser Ser Pro
1               5                   10                  15

Pro Glu Gly Val Cys Ser Asn Thr Val Glu Asn His Leu Val Gln Thr
            20                  25                  30

Asn Leu Ser Asp Gly Ser Pro Asn Lys Ser Val Pro Ala Ser Gly Leu
        35                  40                  45

Asp Ala Val Ile Pro Ser Ala Asn Gln Leu Thr Ile Phe Tyr Asn Gly
    50                  55                  60

Ser Val Cys Val Tyr Asp Gly Ile Pro Ala Glu Lys Val His Glu Ile
65                  70                  75                  80

Met Leu Ile Ala Ala Ala Ala Lys Ser Thr Glu Met Lys Lys Ile
                85                  90                  95

Gly Thr Gln Thr Thr Leu Ile Ser Pro Ala Pro Ser Arg Pro Ser Ser
            100                 105                 110

Pro His Gly Ile Thr Asn Asn Ile Gly Ser Ser Gln Lys Ser Ser Ile
        115                 120                 125

Cys Arg Leu Gln Ala Glu Phe Pro Ile Ala Arg Arg His Ser Leu Gln
    130                 135                 140

Arg Phe Leu Glu Lys Arg Arg Asp Arg Leu Gly Ser Lys Thr Pro Tyr
145                 150                 155                 160

Pro Ser Ser Pro Thr Thr Lys Val Ala Asp Asn Ile Glu Asn Asn Phe
                165                 170                 175

Cys Ala Asp Asn Ala Pro Glu Leu Ile Ser Leu Asn Arg Ser Glu Glu
                180                 185                 190

Glu Phe Gln Pro Thr Val Ser Ala Ser
            195                 200
```

<210> SEQ ID NO 74
<211> LENGTH: 188
<212> TYPE: PRT
<213> ORGANISM: Oryza sativa

<400> SEQUENCE: 74

```
Met Ser Thr Arg Ala Pro Val Glu Leu Asp Phe Leu Gly Leu Arg Ala
1               5                   10                  15
```

```
Ala Ala Ala Asp Ala Asp Asp Arg His Ala Lys Ser Gly Gly Ser Ser
             20                  25                  30

Ala Ser Ser Ser Ser Ser Ile Arg Gly Met Glu Thr Ser Ala Ile Ala
         35                  40                  45

Arg Ile Gly Pro His Leu Leu Arg Arg Val Ile Ala Ala Ala Gly Pro
     50                  55                  60

Pro Pro Pro Pro Ser Thr Ala Pro Val Pro Glu Glu Met Pro Gly Ala
 65                  70                  75                  80

Ala Ala Ala Ala Ala Pro Met Thr Leu Phe Tyr Asn Gly Ser Val Ala
                 85                  90                  95

Val Phe Asp Val Ser His Asp Lys Ala Glu Ala Ile Met Arg Met Ala
            100                 105                 110

Thr Glu Ala Thr Lys Ala Lys Gly Leu Ala Arg Gly Asn Ala Ile Val
        115                 120                 125

Gly Asn Phe Ala Lys Glu Pro Leu Thr Arg Thr Lys Ser Leu Gln Arg
    130                 135                 140

Phe Leu Ser Lys Arg Lys Glu Arg Leu Thr Ser Leu Gly Pro Tyr Gln
145                 150                 155                 160

Val Gly Gly Pro Ala Ala Val Gly Ala Thr Thr Ser Thr Thr Thr Lys
                165                 170                 175

Ser Phe Leu Ala Lys Glu Glu Glu His Thr Ala Ser
            180                 185

<210> SEQ ID NO 75
<211> LENGTH: 20
<212> TYPE: DNA
<213> ORGANISM: Artificial Sequence
<220> FEATURE:
<223> OTHER INFORMATION: A synthetic primer

<400> SEQUENCE: 75
accgagacac attcccgatt                                          20

<210> SEQ ID NO 76
<211> LENGTH: 20
<212> TYPE: DNA
<213> ORGANISM: Artificial Sequence
<220> FEATURE:
<223> OTHER INFORMATION: A synthetic primer

<400> SEQUENCE: 76
catcaggctt gcatgccatt                                          20

<210> SEQ ID NO 77
<211> LENGTH: 25
<212> TYPE: DNA
<213> ORGANISM: Artificial Sequence
<220> FEATURE:
<223> OTHER INFORMATION: A synthetic primer

<400> SEQUENCE: 77
acgaataaga gcgtccattt tagag                                    25

<210> SEQ ID NO 78
<211> LENGTH: 24
<212> TYPE: DNA
<213> ORGANISM: Artificial Sequence
<220> FEATURE:
<223> OTHER INFORMATION: A synthetic primer

<400> SEQUENCE: 78
```
gtggagtggt ctaaagcaac cttc                          24

<210> SEQ ID NO 79
<211> LENGTH: 23
<212> TYPE: DNA
<213> ORGANISM: Artificial Sequence
<220> FEATURE:
<223> OTHER INFORMATION: A synthetic primer

<400> SEQUENCE: 79
ataacgctgc ggacatctac att                           23

<210> SEQ ID NO 80
<211> LENGTH: 21
<212> TYPE: DNA
<213> ORGANISM: Artificial Sequence
<220> FEATURE:
<223> OTHER INFORMATION: A synthetic primer

<400> SEQUENCE: 80
tcaggaagac agagtgttcc c                             21

<210> SEQ ID NO 81
<211> LENGTH: 21
<212> TYPE: DNA
<213> ORGANISM: Artificial Sequence
<220> FEATURE:
<223> OTHER INFORMATION: A synthetic primer

<400> SEQUENCE: 81
tgcgtttctc taagaaccga g                             21

<210> SEQ ID NO 82

<400> SEQUENCE: 82

000

<210> SEQ ID NO 83
<211> LENGTH: 20
<212> TYPE: DNA
<213> ORGANISM: Artificial Sequence
<220> FEATURE:
<223> OTHER INFORMATION: A synthetic primer

<400> SEQUENCE: 83
ttgggtgatg gttcacgtag                               20

<210> SEQ ID NO 84
<211> LENGTH: 21
<212> TYPE: DNA
<213> ORGANISM: Artificial Sequence
<220> FEATURE:
<223> OTHER INFORMATION: A synthetic primer

<400> SEQUENCE: 84
taccgcataa tcatggtcgt c                             21

<210> SEQ ID NO 85
<211> LENGTH: 21
<212> TYPE: DNA
<213> ORGANISM: Artificial Sequence
<220> FEATURE:
<223> OTHER INFORMATION: A synthetic primer

<400> SEQUENCE: 85
tcatgctcat tgcattagtc g                                   21

<210> SEQ ID NO 86
<211> LENGTH: 22
<212> TYPE: DNA
<213> ORGANISM: Artificial Sequence
<220> FEATURE:
<223> OTHER INFORMATION: A synthetic primer

<400> SEQUENCE: 86
ctttgaagac gtggttggaa cg                                  22

<210> SEQ ID NO 87
<211> LENGTH: 22
<212> TYPE: DNA
<213> ORGANISM: Artificial Sequence
<220> FEATURE:
<223> OTHER INFORMATION: A synthetic primer

<400> SEQUENCE: 87
atttctcgat cgccgtcgta gt                                  22

<210> SEQ ID NO 88
<211> LENGTH: 25
<212> TYPE: DNA
<213> ORGANISM: Artificial Sequence
<220> FEATURE:
<223> OTHER INFORMATION: A synthetic primer

<400> SEQUENCE: 88
gccaaagagc tttggtctta gagtg                               25

<210> SEQ ID NO 89
<211> LENGTH: 25
<212> TYPE: DNA
<213> ORGANISM: Artificial Sequence
<220> FEATURE:
<223> OTHER INFORMATION: A synthetic primer

<400> SEQUENCE: 89
gtctaagcgt caatttgttt acacc                               25

<210> SEQ ID NO 90
<211> LENGTH: 25
<212> TYPE: DNA
<213> ORGANISM: Artificial Sequence
<220> FEATURE:
<223> OTHER INFORMATION: A synthetic primer

<400> SEQUENCE: 90
atgtcgagtt ctatggaatg ttctg                               25

<210> SEQ ID NO 91
<211> LENGTH: 26
<212> TYPE: DNA
<213> ORGANISM: Artificial Sequence
<220> FEATURE:
<223> OTHER INFORMATION: A synthetic primer

<400> SEQUENCE: 91
tcatatttca gctgctaaac cgagcc                              26

<210> SEQ ID NO 92
<211> LENGTH: 21
<212> TYPE: DNA
<213> ORGANISM: Artificial Sequence

```
<220> FEATURE:
<223> OTHER INFORMATION: A synthetic primer

<400> SEQUENCE: 92
atggagagag attttctcgg g                                            21

<210> SEQ ID NO 93
<211> LENGTH: 23
<212> TYPE: DNA
<213> ORGANISM: Artificial Sequence
<220> FEATURE:
<223> OTHER INFORMATION: A synthetic primer

<400> SEQUENCE: 93
ttaggttgca gagctgagag aag                                          23

<210> SEQ ID NO 94
<211> LENGTH: 20
<212> TYPE: DNA
<213> ORGANISM: Artificial Sequence
<220> FEATURE:
<223> OTHER INFORMATION: A synthetic primer

<400> SEQUENCE: 94
atggagagag attttctcgg                                              20

<210> SEQ ID NO 95
<211> LENGTH: 20
<212> TYPE: DNA
<213> ORGANISM: Artificial Sequence
<220> FEATURE:
<223> OTHER INFORMATION: A synthetic primer

<400> SEQUENCE: 95
cagatgatga gctggaggac                                              20

<210> SEQ ID NO 96
<211> LENGTH: 24
<212> TYPE: DNA
<213> ORGANISM: Artificial Sequence
<220> FEATURE:
<223> OTHER INFORMATION: A synthetic primer

<400> SEQUENCE: 96
atggaaagag attttctggg tttg                                         24

<210> SEQ ID NO 97
<211> LENGTH: 29
<212> TYPE: DNA
<213> ORGANISM: Artificial Sequence
<220> FEATURE:
<223> OTHER INFORMATION: A synthetic primer

<400> SEQUENCE: 97
ttatgtagga gaagtagaag agtaattca                                    29

<210> SEQ ID NO 98
<211> LENGTH: 22
<212> TYPE: DNA
<213> ORGANISM: Artificial Sequence
<220> FEATURE:
<223> OTHER INFORMATION: A synthetic primer

<400> SEQUENCE: 98
atgtcgaaag ctaccataga ac                                           22
```

<210> SEQ ID NO 99
<211> LENGTH: 30
<212> TYPE: DNA
<213> ORGANISM: Artificial Sequence
<220> FEATURE:
<223> OTHER INFORMATION: A synthetic primer

<400> SEQUENCE: 99
gatagtaagg agatgttgat actaatctct                                      30

<210> SEQ ID NO 100
<211> LENGTH: 24
<212> TYPE: DNA
<213> ORGANISM: Artificial Sequence
<220> FEATURE:
<223> OTHER INFORMATION: A synthetic primer

<400> SEQUENCE: 100
atggctgatg gtgaagacat tcaa                                            24

<210> SEQ ID NO 101
<211> LENGTH: 24
<212> TYPE: DNA
<213> ORGANISM: Artificial Sequence
<220> FEATURE:
<223> OTHER INFORMATION: A synthetic primer

<400> SEQUENCE: 101
tcagaagcac ttcctgtgaa caat                                            24

<210> SEQ ID NO 102
<211> LENGTH: 19
<212> TYPE: DNA
<213> ORGANISM: Artificial Sequence
<220> FEATURE:
<223> OTHER INFORMATION: A synthetic primer

<400> SEQUENCE: 102
aagcagcgta atcggtagg                                                  19

<210> SEQ ID NO 103
<211> LENGTH: 21
<212> TYPE: DNA
<213> ORGANISM: Artificial Sequence
<220> FEATURE:
<223> OTHER INFORMATION: A synthetic primer

<400> SEQUENCE: 103
gcacagcaat cgggtataaa g                                               21

<210> SEQ ID NO 104
<211> LENGTH: 24
<212> TYPE: DNA
<213> ORGANISM: Artificial Sequence
<220> FEATURE:
<223> OTHER INFORMATION: A synthetic primer

<400> SEQUENCE: 104
ggagaactca cgatgggagc gatt                                            24

<210> SEQ ID NO 105
<211> LENGTH: 24
<212> TYPE: DNA
<213> ORGANISM: Artificial Sequence
<220> FEATURE:
<223> OTHER INFORMATION: A synthetic primer

<400> SEQUENCE: 105
gcgtcgtggc tttcgataac caga                                              24

<210> SEQ ID NO 106
<211> LENGTH: 17
<212> TYPE: DNA
<213> ORGANISM: Artificial Sequence
<220> FEATURE:
<223> OTHER INFORMATION: A synthetic primer

<400> SEQUENCE: 106
gctggcggtt cgacatg                                                      17

<210> SEQ ID NO 107
<211> LENGTH: 21
<212> TYPE: DNA
<213> ORGANISM: Artificial Sequence
<220> FEATURE:
<223> OTHER INFORMATION: A synthetic primer

<400> SEQUENCE: 107
gccattcctc tgcgaattag a                                                 21

<210> SEQ ID NO 108
<211> LENGTH: 26
<212> TYPE: DNA
<213> ORGANISM: Artificial Sequence
<220> FEATURE:
<223> OTHER INFORMATION: A synthetic primer

<400> SEQUENCE: 108
agaaactcca aatcaagaac cagctc                                            26

<210> SEQ ID NO 109
<211> LENGTH: 26
<212> TYPE: DNA
<213> ORGANISM: Artificial Sequence
<220> FEATURE:
<223> OTHER INFORMATION: A synthetic primer

<400> SEQUENCE: 109
ccggtttaat cgaagaacac gaagac                                            26

<210> SEQ ID NO 110
<211> LENGTH: 4
<212> TYPE: PRT
<213> ORGANISM: Artificial Sequence
<220> FEATURE:
<223> OTHER INFORMATION: A synthetic protein

<400> SEQUENCE: 110

Gly Trp Gly Asp
1

<210> SEQ ID NO 111
<211> LENGTH: 4
<212> TYPE: PRT
<213> ORGANISM: Artificial Sequence
<220> FEATURE:
<223> OTHER INFORMATION: A synthetic protein

<400> SEQUENCE: 111

Asp Phe Ser Gly
1

```
<210> SEQ ID NO 112
<211> LENGTH: 11
<212> TYPE: PRT
<213> ORGANISM: Artificial Sequence
<220> FEATURE:
<223> OTHER INFORMATION: A synthetic protein

<400> SEQUENCE: 112

Arg Glu Leu Asn Ser Leu Ile Ser Gly Gly Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: A synthetic protein

<400> SEQUENCE: 113

Asp Thr Glu Trp Phe Phe Leu Val Ser Met
1               5                   10

<210> SEQ ID NO 114
<211> LENGTH: 15
<212> TYPE: PRT
<213> ORGANISM: Artificial Sequence
<220> FEATURE:
<223> OTHER INFORMATION: A synthetic protein

<400> SEQUENCE: 114

Val Val Asn Asp Leu Met Ile Gln Gln Ala Thr Val Lys Met Gly
1               5                   10                  15

<210> SEQ ID NO 115
<211> LENGTH: 32
<212> TYPE: PRT
<213> ORGANISM: Artificial Sequence
<220> FEATURE:
<223> OTHER INFORMATION: A synthetic protein

<400> SEQUENCE: 115

Lys Arg Gly Arg Lys Pro Ala Asn Gly Arg Glu Glu Pro Leu Asn His
1               5                   10                  15

Val Glu Ala Glu Arg Gln Arg Arg Glu Lys Leu Asn Gln Arg Phe Tyr
            20                  25                  30

<210> SEQ ID NO 116
<211> LENGTH: 49
<212> TYPE: PRT
<213> ORGANISM: Artificial Sequence
<220> FEATURE:
<223> OTHER INFORMATION: A synthetic protein

<400> SEQUENCE: 116

Gly Asp Asn Thr Val Ile Leu Gly Trp Gly Asp Gly Tyr Tyr Lys Gly
1               5                   10                  15

Glu Glu Asp Lys Glu Lys Lys Asn Asn Thr Asn Thr Ala Glu Gln
            20                  25                  30

Glu His Arg Lys Arg Val Ile Arg Glu Leu Asn Ser Leu Ile Ser Gly
        35                  40                  45

Gly

<210> SEQ ID NO 117
<211> LENGTH: 51
```

```
<212> TYPE: PRT
<213> ORGANISM: Artificial Sequence
<220> FEATURE:
<223> OTHER INFORMATION: A synthetic protein

<400> SEQUENCE: 117

Asn Asn Asn Thr Val Leu Leu Gly Trp Gly Asp Gly Tyr Tyr Lys Gly
1               5                   10                  15
Glu Glu Glu Lys Ser Arg Lys Lys Ser Asn Pro Ala Ser Ala Ala
            20                  25                  30
Glu Gln Glu His Arg Lys Arg Val Ile Arg Glu Leu Asn Ser Leu Ile
        35                  40                  45
Ser Gly Gly
    50

<210> SEQ ID NO 118
<211> LENGTH: 52
<212> TYPE: PRT
<213> ORGANISM: Artificial Sequence
<220> FEATURE:
<223> OTHER INFORMATION: A synthetic protein

<400> SEQUENCE: 118

Gly Ala Gly Ala Ser Leu Leu Gly Trp Gly Asp Gly Tyr Tyr Lys Gly
1               5                   10                  15
Cys Asp Asp Ala Asp Lys Arg Ala Arg Gln Gln Pro Thr Pro Ala Ser
            20                  25                  30
Ala Ala Glu Gln His Arg Lys Arg Val Leu Arg Glu Leu Asn Ser Leu
        35                  40                  45
Ile Ala Gly Gly
    50

<210> SEQ ID NO 119
<211> LENGTH: 53
<212> TYPE: PRT
<213> ORGANISM: Artificial Sequence
<220> FEATURE:
<223> OTHER INFORMATION: A synthetic protein

<400> SEQUENCE: 119

Ala Thr Gly Ala Ser Leu Leu Gly Trp Gly Asp Gly Tyr Tyr Lys Gly
1               5                   10                  15
Cys Asp Asp Asp Lys Arg Arg His Arg Pro Pro Leu Thr Pro Ala Ala
            20                  25                  30
Gln Ala Glu Gln Glu His Arg Lys Arg Val Leu Arg Glu Leu Asn Ser
        35                  40                  45
Leu Ile Ser Gly Gly
    50

<210> SEQ ID NO 120
<211> LENGTH: 53
<212> TYPE: PRT
<213> ORGANISM: Artificial Sequence
<220> FEATURE:
<223> OTHER INFORMATION: A synthetic protein

<400> SEQUENCE: 120

Ser Thr Gly Ala Ser Leu Leu Gly Trp Gly Asp Gly Tyr Tyr Lys Gly
1               5                   10                  15
Cys Asp Asp Asp Lys Arg Lys Gln Arg Ser Ser Thr Pro Ala Ala Ala
            20                  25                  30
```

Ala Glu Gln Glu His Arg Lys Arg Val Leu Arg Glu Leu Asn Ser
         35                  40                  45

Leu Ile Ala Gly Ala
    50

<210> SEQ ID NO 121
<211> LENGTH: 52
<212> TYPE: PRT
<213> ORGANISM: Artificial Sequence
<220> FEATURE:
<223> OTHER INFORMATION: A synthetic protein

<400> SEQUENCE: 121

Ala Thr Gly Ala Ser Leu Leu Gly Trp Gly Asp Gly Tyr Tyr Lys Gly
1               5                   10                  15

Cys Asp Glu Asp Lys Arg Lys Gln Lys Pro Leu Thr Pro Ser Ala Gln
            20                  25                  30

Ala Glu Gln Glu His Arg Lys Arg Val Leu Arg Glu Leu Asn Ser Leu
        35                  40                  45

Ile Ser Gly Ala
    50

<210> SEQ ID NO 122
<211> LENGTH: 52
<212> TYPE: PRT
<213> ORGANISM: Artificial Sequence
<220> FEATURE:
<223> OTHER INFORMATION: A synthetic protein

<400> SEQUENCE: 122

Ala Thr Gly Ala Ser Leu Leu Gly Trp Gly Asp Gly Tyr Tyr Lys Gly
1               5                   10                  15

Cys Asp Asp Asp Lys Arg Lys Gln Arg Pro Leu Thr Pro Ala Ala Gln
            20                  25                  30

Ala Glu Gln Glu His Arg Lys Arg Val Leu Arg Glu Leu Asn Ser Leu
        35                  40                  45

Ile Ser Gly Ala
    50

<210> SEQ ID NO 123
<211> LENGTH: 55
<212> TYPE: PRT
<213> ORGANISM: Artificial Sequence
<220> FEATURE:
<223> OTHER INFORMATION: A synthetic protein

<400> SEQUENCE: 123

Phe Ser Gly Ala Ser Val Leu Gly Trp Gly Asp His Tyr Tyr Lys Gly
1               5                   10                  15

Glu Glu Asp Lys Ala Lys Pro Arg Gln Arg Ser Ser Ser Pro Pro Phe
            20                  25                  30

Ser Thr Pro Ala Asp Gln Glu Tyr Arg Lys Lys Val Leu Arg Glu Leu
        35                  40                  45

Asn Ser Leu Ile Ser Gly Gly
    50                  55

<210> SEQ ID NO 124
<211> LENGTH: 55
<212> TYPE: PRT
<213> ORGANISM: Artificial Sequence
<220> FEATURE:
<223> OTHER INFORMATION: A synthetic protein

<400> SEQUENCE: 124

Phe Ser Gly Ala Ser Val Leu Gly Trp Gly Asp Gly Tyr Tyr Lys Gly
1               5                   10                  15

Glu Glu Asp Lys Ala Asn Pro Arg Arg Arg Ser Ser Ser Pro Pro Phe
            20                  25                  30

Ser Thr Pro Ala Asp Gln Glu Tyr Arg Lys Lys Val Leu Arg Glu Leu
        35                  40                  45

Asn Ser Leu Ile Ser Gly Gly
    50                  55

<210> SEQ ID NO 125
<211> LENGTH: 53
<212> TYPE: PRT
<213> ORGANISM: Artificial Sequence
<220> FEATURE:
<223> OTHER INFORMATION: A synthetic protein

<400> SEQUENCE: 125

Phe Ser Ser Pro Ser Val Leu Gly Trp Gly Asp Gly Tyr Tyr Lys Gly
1               5                   10                  15

Glu Glu Asp Lys Ala Lys Arg Lys Leu Ser Val Ser Ser Pro Ala Tyr
            20                  25                  30

Ile Ala Glu Gln Glu His Arg Lys Lys Val Leu Arg Glu Leu Asn Ser
        35                  40                  45

Leu Ile Ser Gly Ala
    50

<210> SEQ ID NO 126
<211> LENGTH: 54
<212> TYPE: PRT
<213> ORGANISM: Artificial Sequence
<220> FEATURE:
<223> OTHER INFORMATION: A synthetic protein

<400> SEQUENCE: 126

Phe Ala Ser Gln Thr Val Leu Gly Trp Gly Asp Gly Tyr Tyr Lys Gly
1               5                   10                  15

Glu Glu Asp Lys Asn Lys Arg Arg Gly Ser Ser Ser Ala Ala Asn
            20                  25                  30

Phe Cys Ala Glu Gln Glu His Arg Lys Lys Val Leu Arg Glu Leu Asn
        35                  40                  45

Ser Leu Ile Ser Gly Val
    50

<210> SEQ ID NO 127
<211> LENGTH: 55
<212> TYPE: PRT
<213> ORGANISM: Artificial Sequence
<220> FEATURE:
<223> OTHER INFORMATION: A synthetic protein

<400> SEQUENCE: 127

Arg Ser Gly Gln Gln Val Leu Gly Trp Gly Asp Gly Cys Cys Arg Glu
1               5                   10                  15

Pro Asn Glu Glu Glu Glu Ser Lys Val Val Arg Ser Tyr Asn Phe Asn
            20                  25                  30

Asn Met Gly Ala Glu Glu Glu Thr Trp Gln Asp Met Arg Lys Arg Val
        35                  40                  45

Leu Gln Lys Leu His Arg Leu

-continued

```
<210> SEQ ID NO 128
<211> LENGTH: 55
<212> TYPE: PRT
<213> ORGANISM: Artificial Sequence
<220> FEATURE:
<223> OTHER INFORMATION: A synthetic protein

<400> SEQUENCE: 128

Lys Ala Gly Asp Leu Val Leu Cys Trp Gly Asp Gly Tyr Cys Arg Glu
1               5                   10                  15

Pro Lys Glu Gly Glu Lys Ser Glu Ile Val Arg Ile Leu Ser Met Gly
            20                  25                  30

Arg Glu Glu Glu Thr His Gln Thr Met Arg Lys Arg Val Leu Gln Lys
        35                  40                  45

Leu His Asp Leu Phe Gly Gly
    50                  55

<210> SEQ ID NO 129
<211> LENGTH: 23
<212> TYPE: DNA
<213> ORGANISM: Artificial Sequence
<220> FEATURE:
<223> OTHER INFORMATION: A synthetic primer

<400> SEQUENCE: 129
acggttcctc tatgcctcaa gtc                                           23
```